US009306179B2

(12) United States Patent
Tsai et al.

(10) Patent No.: US 9,306,179 B2
(45) Date of Patent: Apr. 5, 2016

(54) ORGANIC ELECTROLUMINESCENT MATERIALS AND DEVICES

(71) Applicant: Universal Display Corporation, Ewing, NJ (US)

(72) Inventors: Jui-Yi Tsai, Newtown, PA (US); Chuanjun Xia, Lawrenceville, NJ (US); Miguel A. Esteruelas, Zaragoza (ES); Enrique Oñate Rodriguez, Zaragoza (ES); Tamara Bolano, Zaragoza (ES); Adrian U. Palacios, Zaragoza (ES)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 19 days.

(21) Appl. No.: 14/075,527

(22) Filed: Nov. 8, 2013

(65) Prior Publication Data
US 2015/0129840 A1    May 14, 2015

(51) Int. Cl.
| C07F 15/00 | (2006.01) |
| H01L 51/54 | (2006.01) |
| C09K 11/06 | (2006.01) |
| H01L 51/00 | (2006.01) |
| H01L 51/50 | (2006.01) |

(52) U.S. Cl.
CPC .......... *H01L 51/0088* (2013.01); *C07F 15/002* (2013.01); *C09K 11/06* (2013.01); *C09K 2211/1044* (2013.01); *C09K 2211/185* (2013.01); *H01L 51/5016* (2013.01)

(58) Field of Classification Search
CPC H01L 51/0088; C07F 15/002; C07F 15/0026
See application file for complete search history.

(56) References Cited

U.S. PATENT DOCUMENTS

| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,916,606 | B2 * | 7/2005 | Massey et al. .............. 435/5 |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0151042 | A1 | 8/2003 | Hueschen et al. |

(Continued)

FOREIGN PATENT DOCUMENTS

| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al.,"Highly Efficient Phosphorescent Emission from Organic Electroluminescent Devices," Nature, vol. 395, 151-154, (1998).

(Continued)

*Primary Examiner* — Marie R. Yamnitzky
(74) *Attorney, Agent, or Firm* — Duane Morris LLP

(57) ABSTRACT

A novel emitter compound having the formula $Os(L^1)(L^2)(L^3)$ and a novel method of making such compounds are disclosed. In the formula $Os(L^1)(L^2)(L^3)$, each of $L^1$, $L^2$, and $L^3$ is independently a bidentate ligand. The method includes (a) reacting a precursor of ligand $L^1$ with an osmium precursor to form a first intermediate product that has the ligand $L^1$ coordinated to the osmium, wherein the osmium precursor has the formula $OsH_x(PR_3)_y$, wherein x is an integer from 2 to 6 and y is an integer from 2 to 5, and R is selected from the group consisting of aryl, alkyl and cycloalkyl; (b) reacting the first intermediate product with a reducing agent to form a Os(II) second intermediate product; (c) reacting the second intermediate product with a coordinating solvent to form a third intermediate product; and (d) reacting a mixture of ligands $L^2$ and $L^3$ with said third intermediate product.

17 Claims, 4 Drawing Sheets

(56) References Cited

U.S. PATENT DOCUMENTS

| | | |
|---|---|---|
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0001875 A1 | 1/2009 | Chi et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2011/0155238 A1* | 6/2011 | Shen et al. ............ 136/256 |
| 2012/0012790 A1* | 1/2012 | Nazeeruddin et al. ... 252/301.35 |
| 2012/0215000 A1 | 8/2012 | Tsai |

FOREIGN PATENT DOCUMENTS

| | | |
|---|---|---|
| EP | 2034538 | 3/2009 |
| JP | 2005011610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009046266 A1 | 4/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Baldo et al."Very high-efficiency green organic light-emitting devices based on electrophosphorescence," Appl. Phys. Lett, vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater, 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., "1,2,4-Triazole Derivative as an Electron Transport Layer in Organic Electroluminescent Devices," Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

(56) References Cited

OTHER PUBLICATIONS

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto,Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91:209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^ C^ N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69 (15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al."A Novel Class of Phosphorescent Gold(III) Alkynyl-Based Organic Light-Emitting Devices with Tunable Colour," Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Hwang, Kwun-Chi et al., Luminescent Osmium(II) Complexes with Functionalized 2-Phenylpyridine Chelating Ligands: Preparation, Structural Analyses, and Photophysical Properties, Inorg. Chem. 2008, 47, pp. 3307-3317.

Tung, Yung-Liang et al., Highly Efficient Red Phosphorescent Osmium(II) Complexes for OLED Applications, Organometallics, 2004, 23, pp. 3745-3748.

Chou, Pi-Tai and Chi, Yun, Osmium- and Ruthenium-Based Phosphorescent Materials: Design, Photophysics, and Utilization in OLED Fabrication, Eur. J. Inorg. Chem., 2006, pp. 3319-3332.

\* cited by examiner

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same. More particularly, the compounds disclosed herein are novel phosphorus containing tris(bidentate) osmium complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

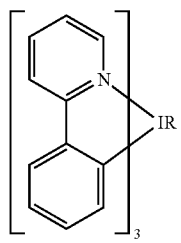

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an embodiment, a method of making a compound having the formula $Os(L^1)(L^2)(L^3)$, wherein each of $L^1$, $L^2$, and $L^3$ is independently a bidentate ligand is disclosed. The method comprises: (a) reacting a precursor of ligand $L^1$ with an osmium precursor to form a first intermediate product that has the ligand $L^1$ coordinated to the osmium, wherein the osmium precursor has the formula $OsH_x(PR_3)_y$, wherein x is an integer from 2 to 6 and y is an integer from 2 to 5, and R is selected from the group consisting of aryl, alkyl and cycloalkyl; (b) reacting the first intermediate product with a reducing agent to form a Os(II) second intermediate product; (c) reacting the second intermediate product with a coordinating solvent to form a third intermediate product; and (d) reacting a mixture of ligands $L^2$ and $L^3$ with said third intermediate product.

According to another aspect of the present disclosure, a compound having the formula $Os(L^1)(L^2)(L^3)$ is disclosed, wherein $L^1$, $L^2$ and $L^3$ are independently a bidentate ligand; and wherein each of $L^1$, $L^2$, and $L^3$ is different from each other.

According to another aspect, a first device comprising a first organic light emitting device is provided. The first organic light emitting device can comprise an anode, a cathode, and an organic layer, disposed between the anode and the cathode. The organic layer can include a compound having the formula $Os(L^1)(L^2)(L^3)$, wherein $L^1$, $L^2$, and $L^3$ are independently a bidentate ligand, and wherein each of $L^1$, $L^2$, and $L^3$ is different from each other. The first device can be a consumer product, an organic light-emitting device, and/or a lighting panel.

The compounds disclosed herein are novel ancillary ligands for metal complexes. The incorporation of these ligands can narrow the emission spectrum, decrease evaporation temperature, and improve device efficiency. The inventors have discovered that incorporating these novel ancillary ligands in iridium complexes improved sublimation of the resulting iridium complexes, color spectrum of phosphorescence by these iridium complexes, and their EQE.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
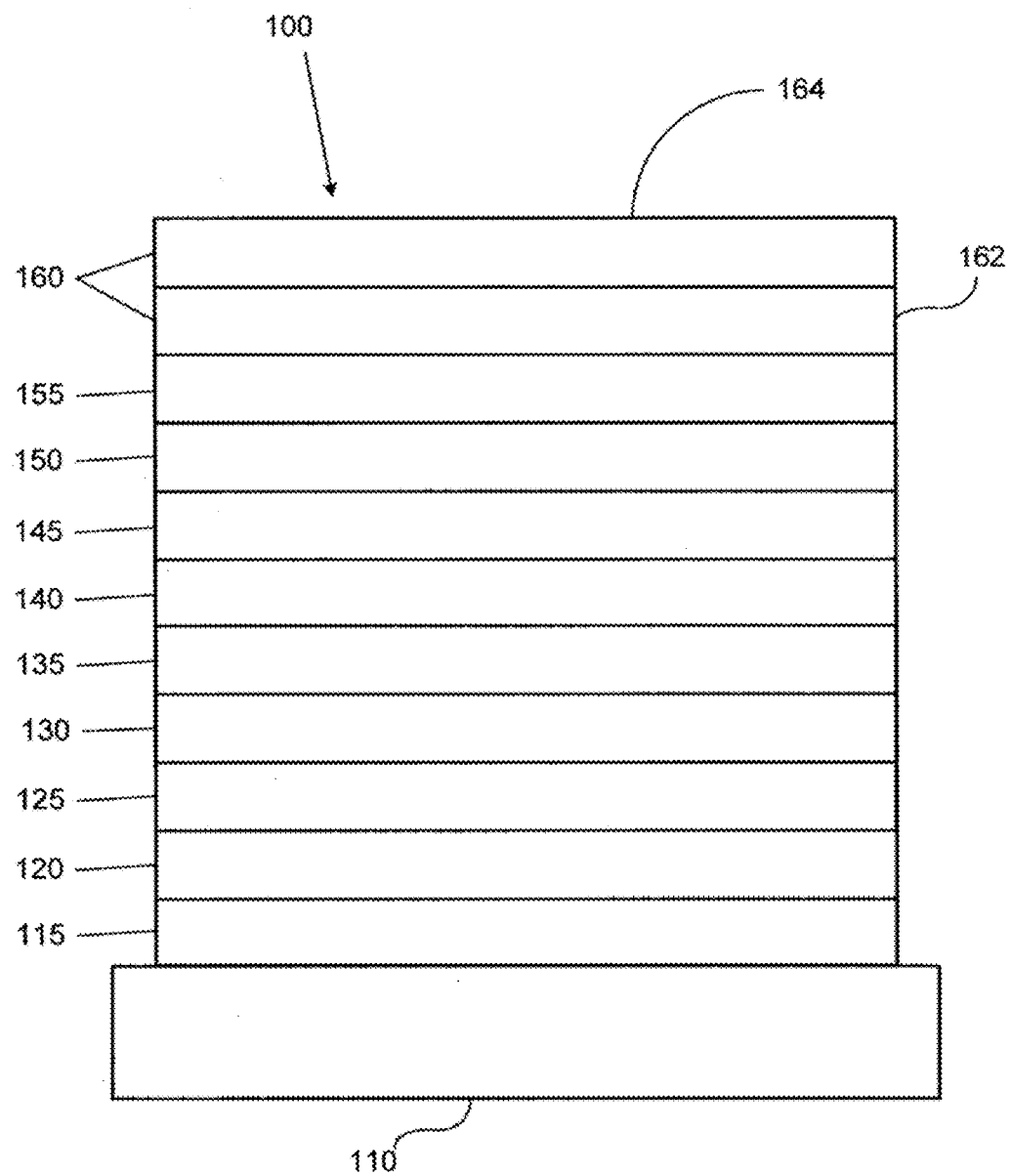
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
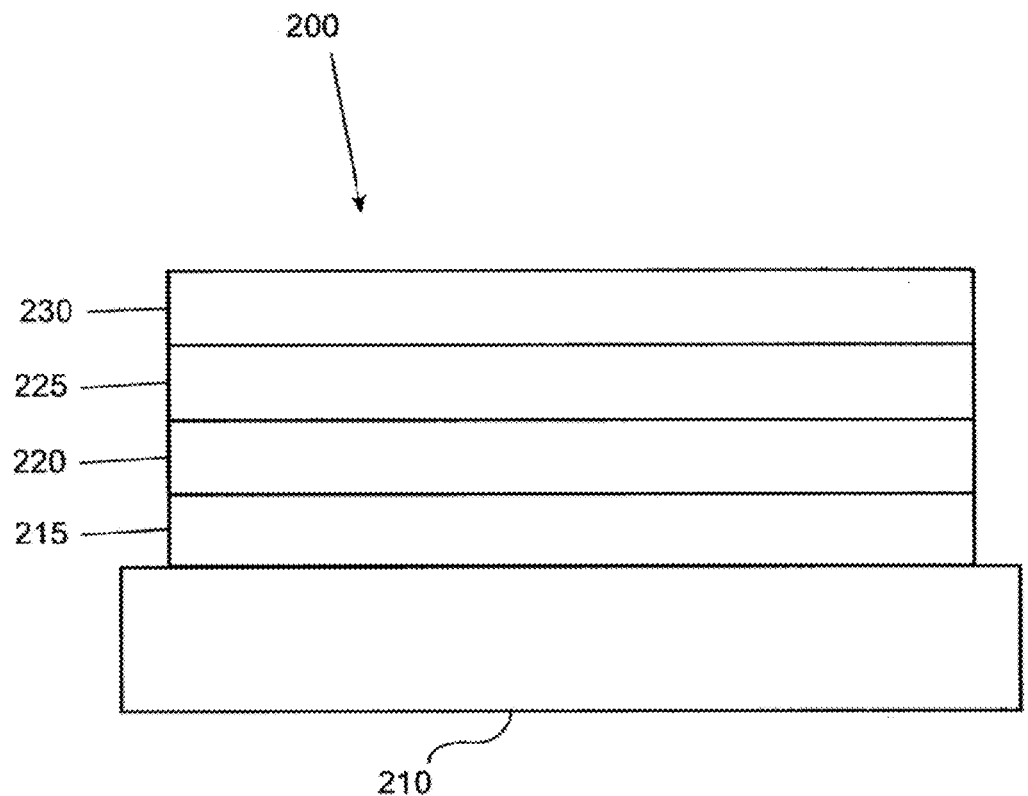
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting.

For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aralkyl, heterocyclic group, aryl, aromatic group, and heteroaryl are known to the art, and are defined in U.S. Pat. No. 7,279,704 at cols. 31-32, which are incorporated herein by reference.

As used herein, "substituted" indicates that a substituent other than H is bonded to the relevant carbon. Thus, where $R^2$ is monosubstituted, then one $R^2$ must be other than H. Similarly, where $R^3$ is disubstituted, then two of $R^3$ must be other than H. Similarly, where $R^2$ is unsubstituted $R^2$ is hydrogen for all available positions.

According to an aspect of the present disclosure, a novel osmium(II) complexes comprising three different bidentate ligands are disclosed. According to another aspect, a synthetic method for making such Os(II) complexes is provided.

Osmium (II) complexes have been investigated for OLED applications. The octahedral ligand arrangement of the Os(II) complexes resembles that of Ir(III) complexes. Os(II) complexes generally exhibit low oxidation potential, i.e. shallow HOMO energy level than Ir(III) complexes. Tris-bidentate Os(II) carbene complexes offer unique advantages for OLED applications. It offers a great deal of flexibility for color tuning and bring the HOMO level to proper alignment with the device.

Although US 2009/0001875 disclosed tris-bidentate Os(II) complexes, in those tris-bidentate Os(II) complexes, two of the bidentate ligands binding to Os(II) metal are identical. The inventors have discovered that further benefits are achieved when three different bidentate ligands are coordinated to Os(II) metal to form a heteroleptic complex. For example, the thermal properties, electrochemical properties, and photophysical properties can be tuned by selecting three proper ligands. It offers more flexibility for materials design than two identical ligands.

Such osmium complexes comprising three different bidentate ligands have never been synthesized before the invention disclosed herein. These novel complexes are useful compounds for phosphorescent emitters. One aspect of the present disclosure also provides a new method developed by the inventors for synthesizing such tris-bidentate Os(II) complexes where the Os(II) complexes comprise three different bidentate ligands. This method is, however, suitable for making both heteroleptic and homoleptic tris-bidentate Os(II) complexes.

As shown in the scheme below, (a) an osmium precursor is first reacted with a precursor of bidentate ligand $L^1$ to form a first intermediate product that has the bidentate ligand $L^1$ coordinated to the osmium atom, wherein the osmium precursor has the formula $OsH_x(PR_3)_y$, wherein x is an integer from 2 to 6 and y is an integer from 2 to 5, and R is selected from the group consisting of aryl, alkyl and cycloalkyl. Then, (b) the first intermediate product is reacted with a reducing agent to form a Os(II) second intermediate product. Then, (c) the second with a reducing agent to form a Os(II) second intermediate product. Then, (c) the second intermediate product is reacted with a coordinating solvent to form a third intermediate product. Next, (d) a mixture of precursors of bidentate ligands $L^2$ and $L^3$ is reacted with the third intermediate product to obtain the final complex.

In one embodiment of the method, R is selected from the group consisting of methyl, ethyl, propyl, 1-methylethyl, butyl, 1-methylpropyl, 2-methylpropyl, 1,1-dimethylethyl, cyclohexyl, phenyl, 2,6-dimethylphenyl, and 2-methylphenyl. In another embodiment, R is 1-methylethyl.

In one embodiment of the method, the osmium precursor has the formula $OsH_6(P^iPr_3)_2$.

In one embodiment of the method, the ligand $L^1$ has at least one coordinating atom of carbene. In another embodiment, the ligand $L^1$ is a monoanionic bidentate ligand, $L^2$ is a monoanionic bidentate ligand, and $L^3$ is a neutral bidentate ligand.

In one embodiment of the method, the ligands $L^1$, $L^2$, and $L^3$ are independently selected from the group LIST-A consisting of:

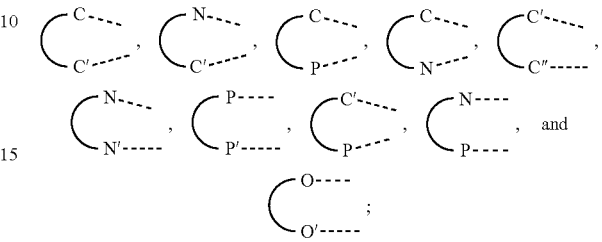

wherein C is a monoanionic carbon coordinating atom, C' and C" are each a neutral carbene coordinating atom, N is a neutral nitrogen coordinating atom, N' is an anionic nitrogen coordinating atom, P and P' are each a neutral phosphorus coordinating atom, O is a monoanionic oxygen coordinating atom, and O' is a neutral oxygen coordinating atom.

According to another aspect, the ligands $L^1$, $L^2$, and $L^3$ are independently selected from the group LIST-B consisting of:

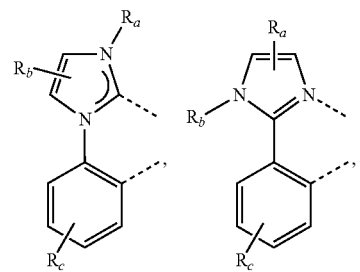

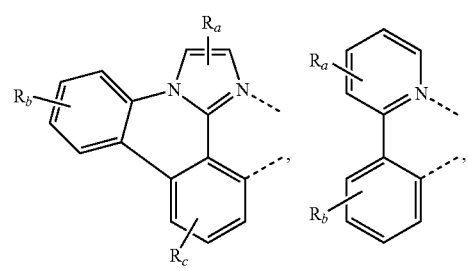

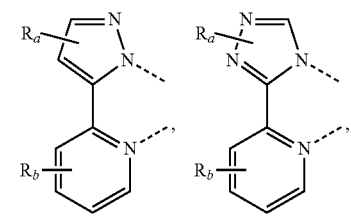

-continued
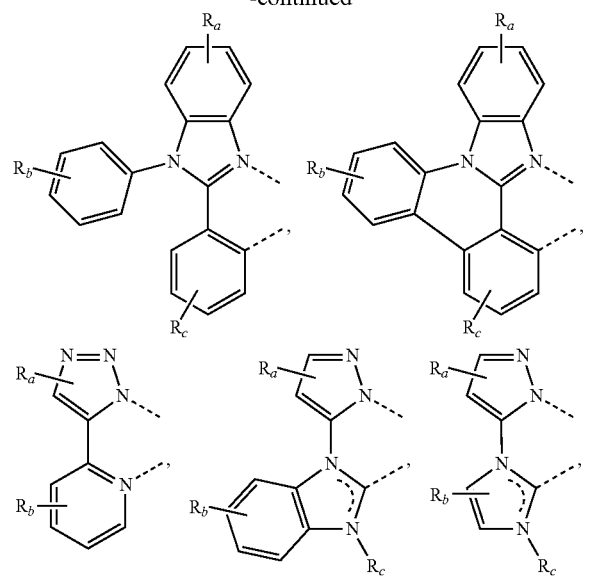
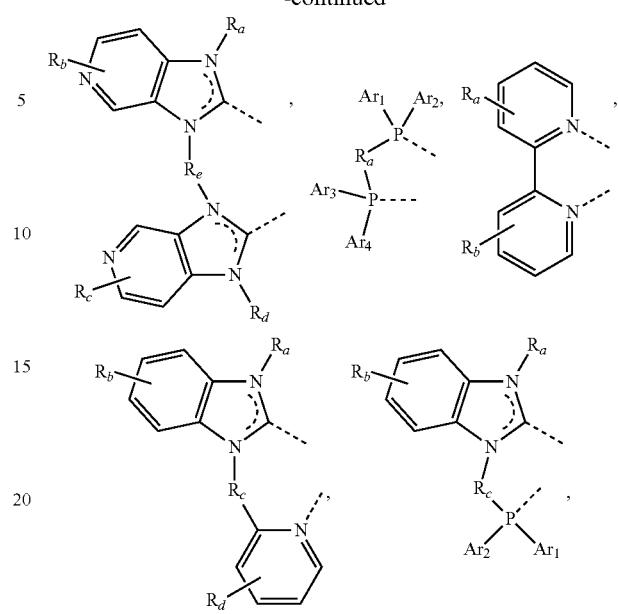
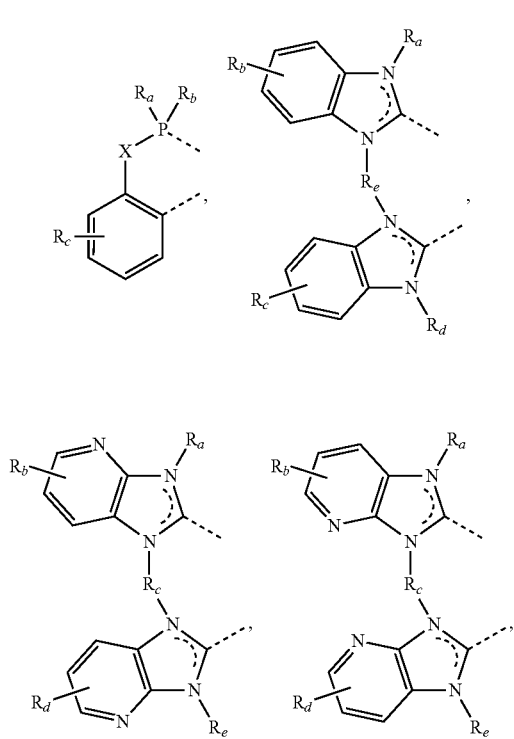
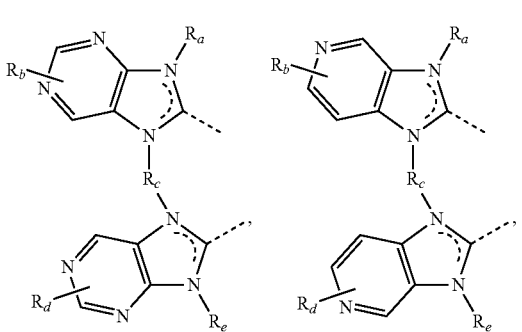
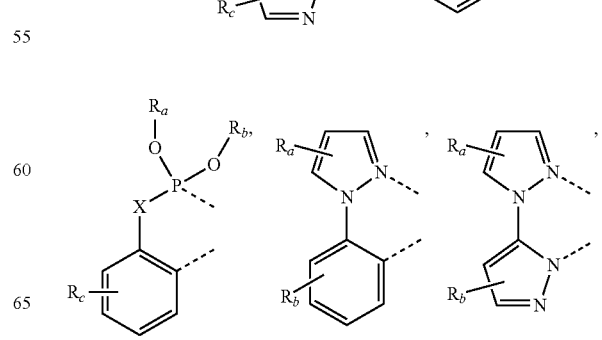

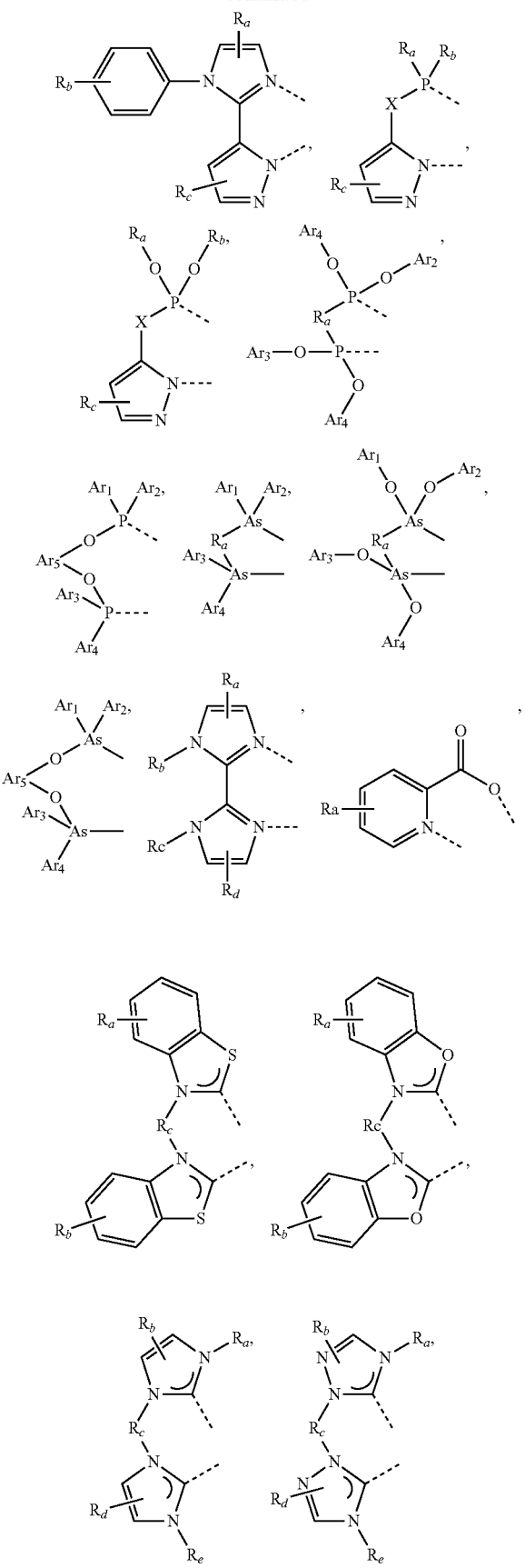

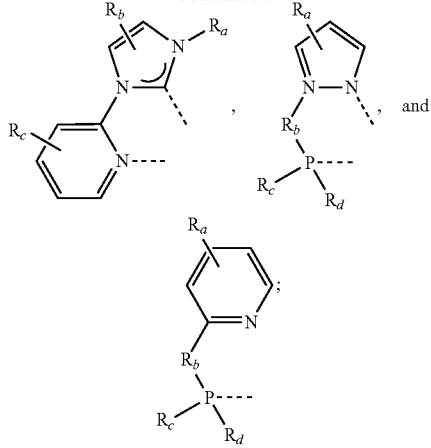

wherein $R_a$, $R_b$, $R_c$, $R_d$, and $R_e$ are each independently mono, di, tri, or tetra substitutions;

wherein $R_a$, $R_b$, $R_c$, $R_d$, and $R_e$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, $R_d$, and $R_e$ are optionally joined to form a fused ring and may be further substituted, wherein the dash lines show the connection points to osmium.

According to another aspect, the ligands $L^1$, $L^2$, and $L^3$ are independently selected from the group LIST-C consisting of:

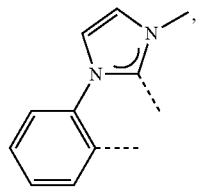

$L^{101}$

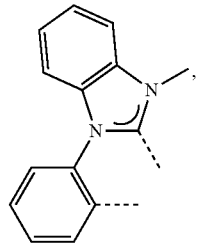

$L^{102}$

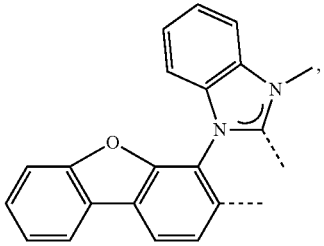

$L^{103}$

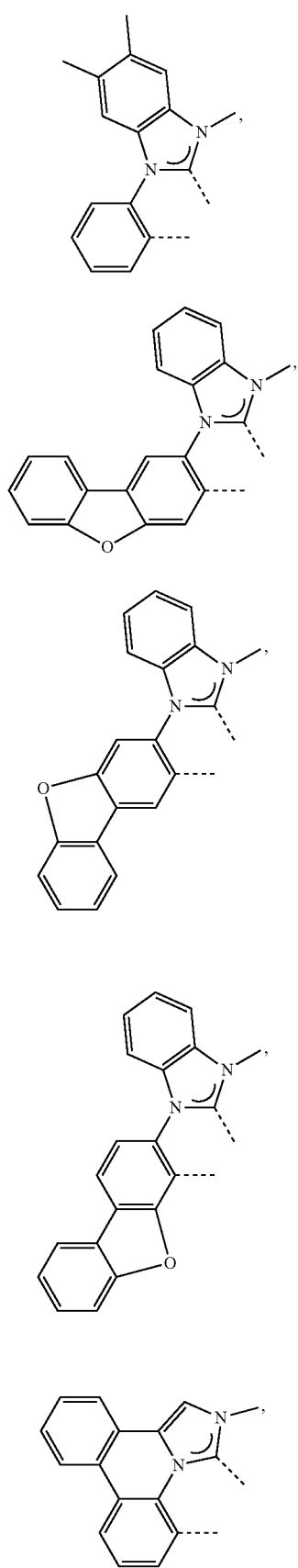
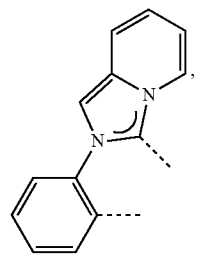
L[109]
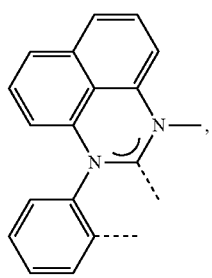
L[110]
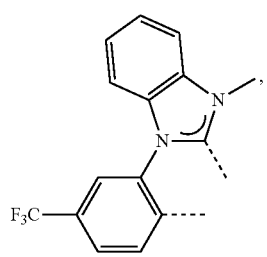
L[111]
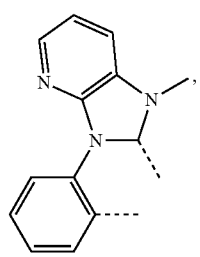
L[112]
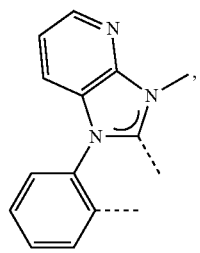
L[113]
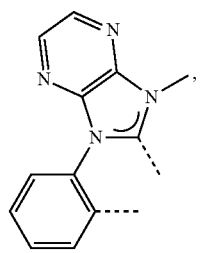
L[114]

| | |
|---|---|
| 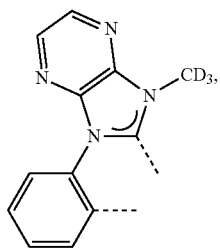 | L115 |
| 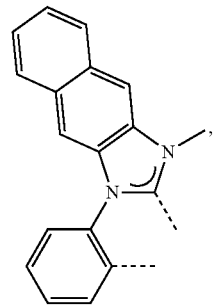 | L116 |
| 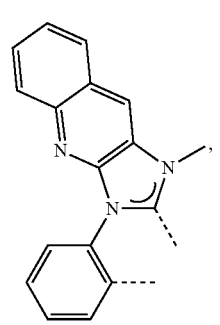 | L117 |
| 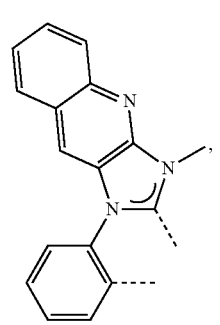 | L118 |
| 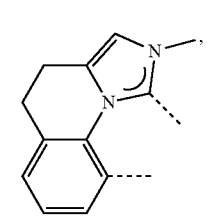 | L119 |
| 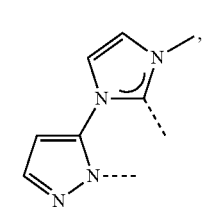 | L120 |
| | |
|---|---|
| 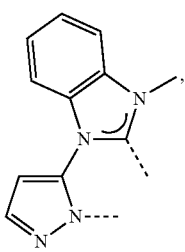 | L121 |
| 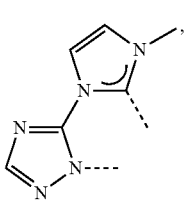 | L122 |
| 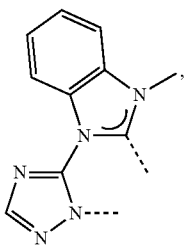 | L123 |
| 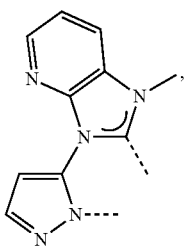 | L124 |
| 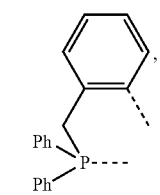 | L125 |
| 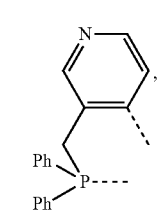 | L126 |
| 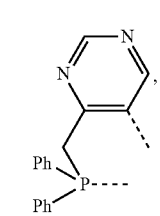 | L127 |

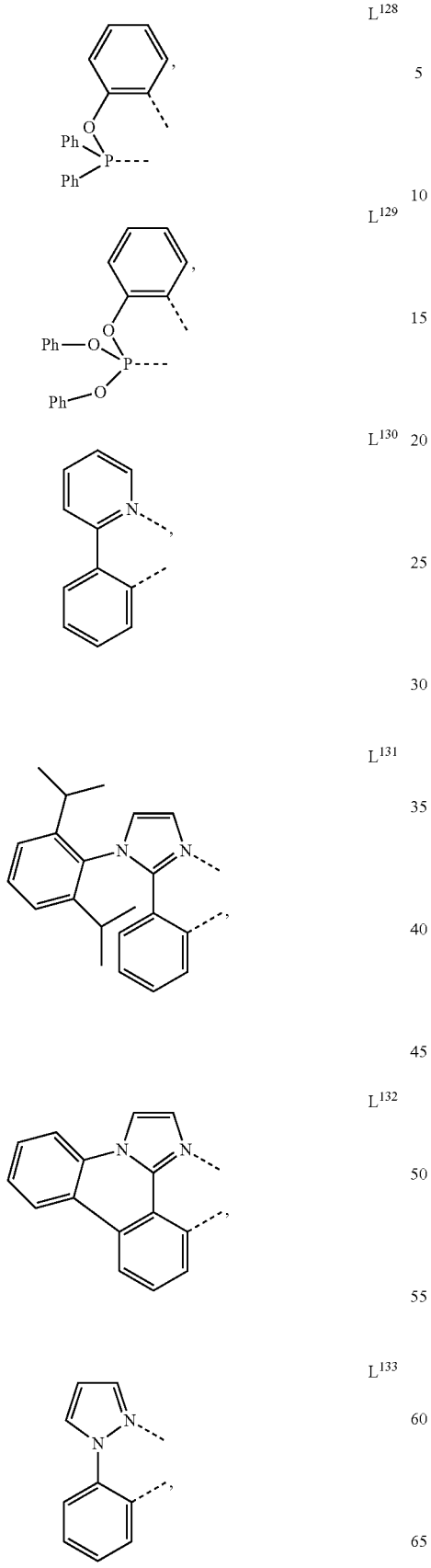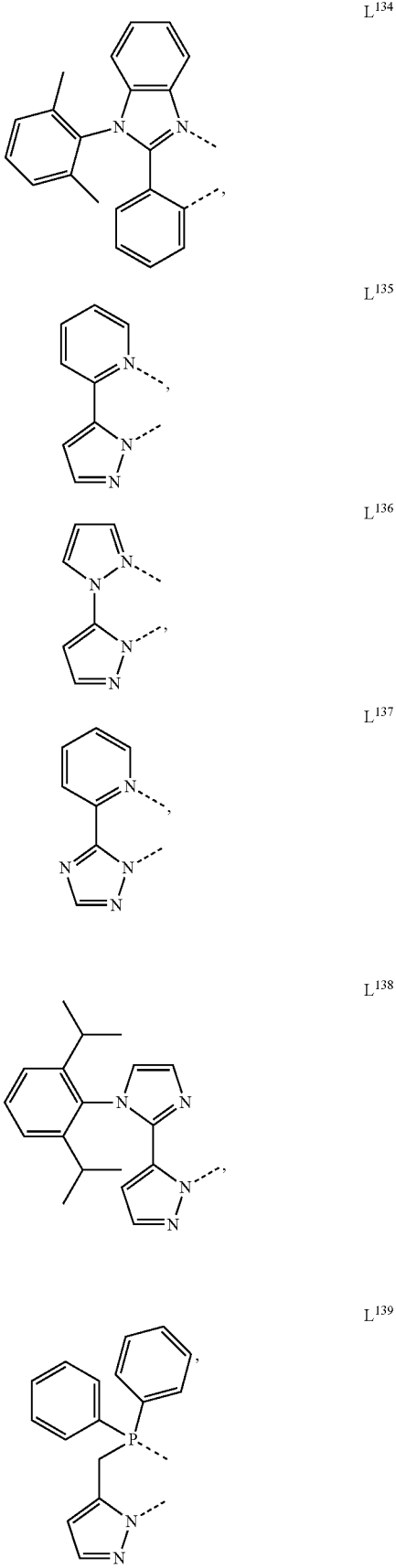

L¹⁴⁰
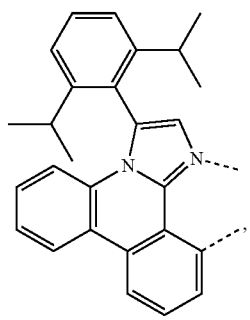
L¹⁴¹
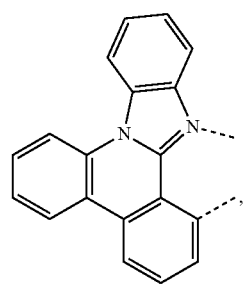
L¹⁴²
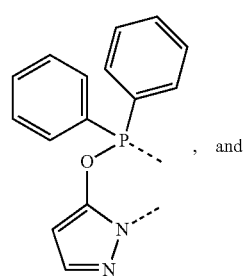, and
L¹⁴³
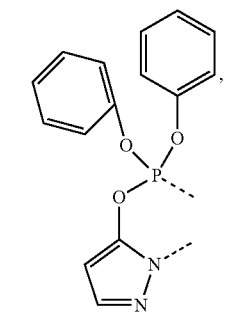
wherein the dash lines show the connection points to osmium.
According to another aspect, the ligands L¹, L², and L³ are independently selected from the group LIST-D consisting of:
L¹⁴⁴
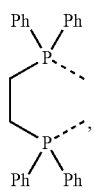
L¹⁴⁵
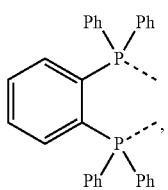
L¹⁴⁶
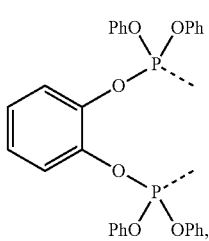
L¹⁴⁷
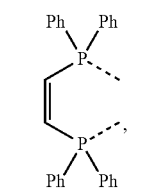
L¹⁴⁸
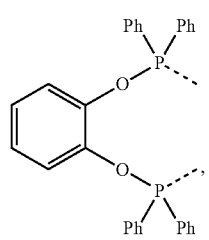
L¹⁴⁹
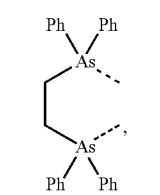
L¹⁵⁰
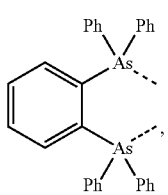
L¹⁵¹
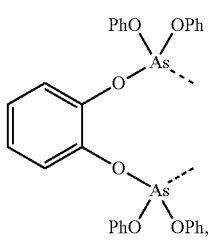

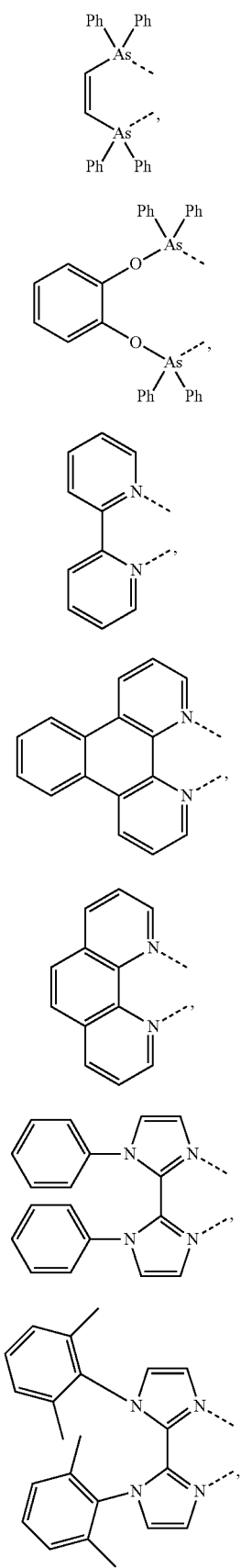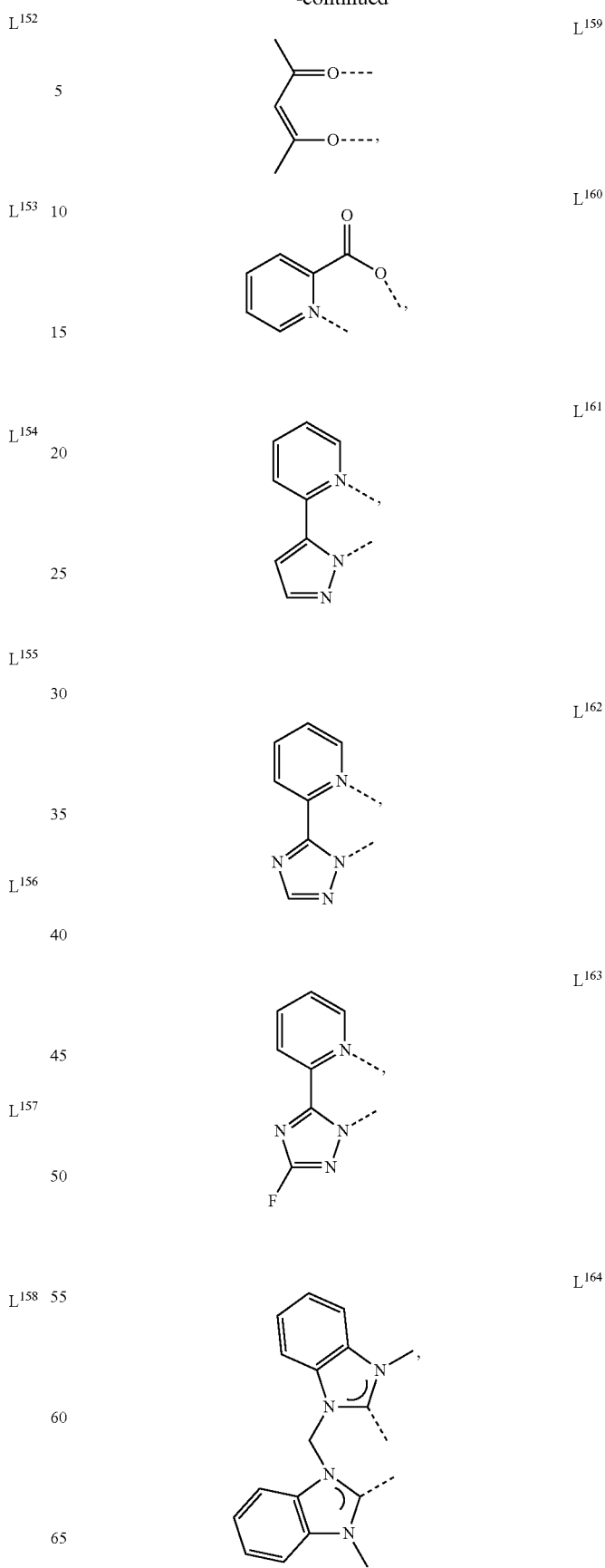

| | |
|---|---|
| 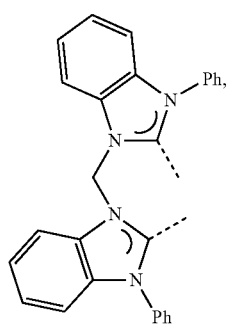 | L165 |
| 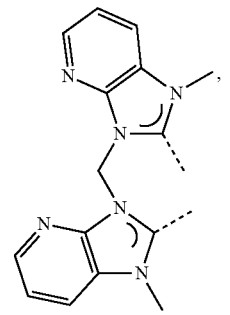 | L166 |
| 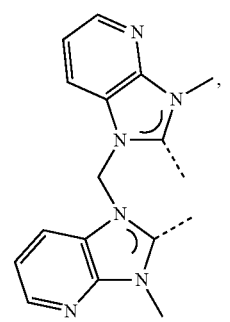 | L167 |
| 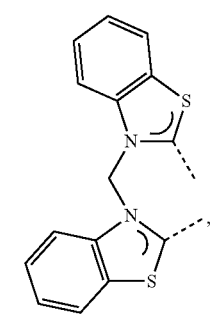 | L168 |
| 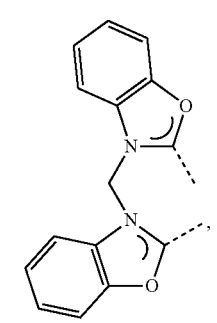 | L169 |
| | |
|---|---|
| 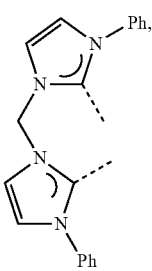 | L170 |
| 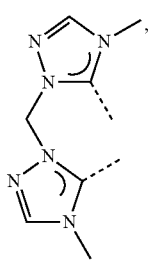 | L171 |
| 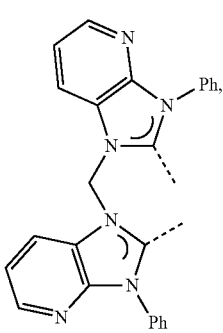 | L172 |
| 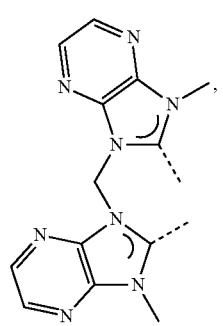 | L173 |
| 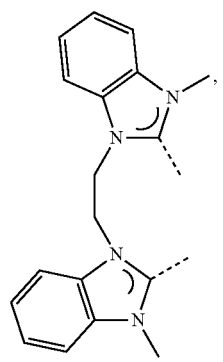 | L174 |

L¹⁷⁵ 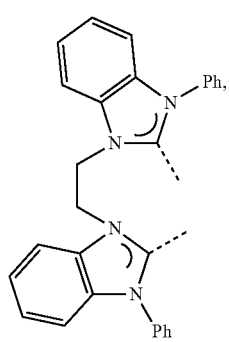

L¹⁷⁶ 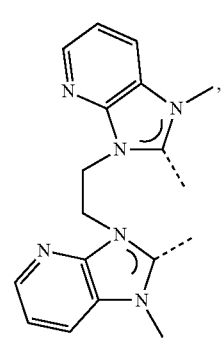

L¹⁷⁷ 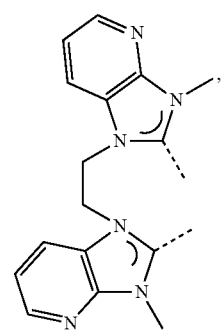

L¹⁷⁸ 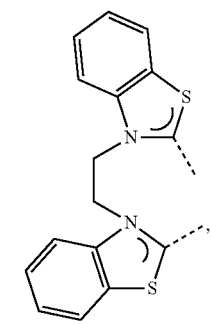

L¹⁷⁹ 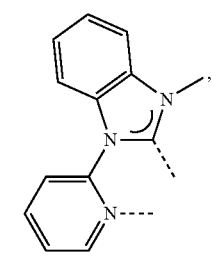

L¹⁸⁰ 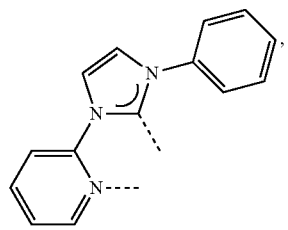

L¹⁸¹ 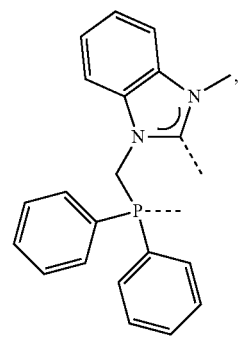

L¹⁸² 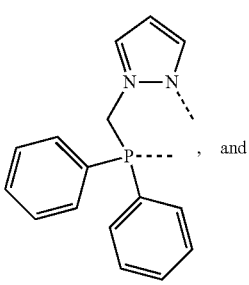, and

L¹⁸³ 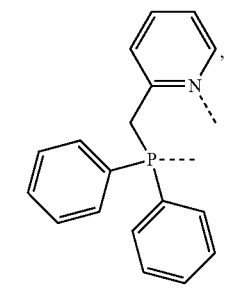

wherein the dash lines show the connection points to osmium.

According to another aspect, the compound having the formula $Os(L^1)(L^2)(L^3)$ is selected from the group consisting of Compounds 1 to 4176 defined in Table 1 below:

TABLE 1

| Compound number | $L_1$ | $L_2$ | $L_3$ |
|---|---|---|---|
| 1. | $L^{101}$ | $L^{102}$ | $L^{102}$ |
| 2. | $L^{101}$ | $L^{103}$ | $L^{144}$ |
| 3. | $L^{101}$ | $L^{104}$ | $L^{144}$ |
| 4. | $L^{101}$ | $L^{105}$ | $L^{144}$ |
| 5. | $L^{101}$ | $L^{106}$ | $L^{144}$ |
| 6. | $L^{101}$ | $L^{107}$ | $L^{144}$ |
| 7. | $L^{101}$ | $L^{108}$ | $L^{144}$ |
| 8. | $L^{101}$ | $L^{109}$ | $L^{144}$ |
| 9. | $L^{101}$ | $L^{110}$ | $L^{144}$ |
| 10. | $L^{101}$ | $L^{111}$ | $L^{144}$ |
| 11. | $L^{101}$ | $L^{112}$ | $L^{144}$ |

TABLE 1-continued

| Compound number | $L_1$ | $L_2$ | $L_3$ |
|---|---|---|---|
| 12. | $L^{101}$ | $L^{113}$ | $L^{144}$ |
| 13. | $L^{101}$ | $L^{114}$ | $L^{144}$ |
| 14. | $L^{101}$ | $L^{115}$ | $L^{144}$ |
| 15. | $L^{101}$ | $L^{116}$ | $L^{144}$ |
| 16. | $L^{101}$ | $L^{117}$ | $L^{144}$ |
| 17. | $L^{101}$ | $L^{118}$ | $L^{144}$ |
| 18. | $L^{101}$ | $L^{119}$ | $L^{144}$ |
| 19. | $L^{101}$ | $L^{130}$ | $L^{144}$ |
| 20. | $L^{101}$ | $L^{131}$ | $L^{144}$ |
| 21. | $L^{101}$ | $L^{132}$ | $L^{144}$ |
| 22. | $L^{101}$ | $L^{133}$ | $L^{144}$ |
| 23. | $L^{101}$ | $L^{134}$ | $L^{144}$ |
| 24. | $L^{101}$ | $L^{140}$ | $L^{144}$ |
| 25. | $L^{101}$ | $L^{141}$ | $L^{144}$ |
| 26. | $L^{101}$ | $L^{159}$ | $L^{144}$ |
| 27. | $L^{101}$ | $L^{160}$ | $L^{144}$ |
| 28. | $L^{101}$ | $L^{102}$ | $L^{145}$ |
| 29. | $L^{101}$ | $L^{103}$ | $L^{145}$ |
| 30. | $L^{101}$ | $L^{104}$ | $L^{145}$ |
| 31. | $L^{101}$ | $L^{105}$ | $L^{145}$ |
| 32. | $L^{101}$ | $L^{106}$ | $L^{145}$ |
| 33. | $L^{101}$ | $L^{107}$ | $L^{145}$ |
| 34. | $L^{101}$ | $L^{108}$ | $L^{145}$ |
| 35. | $L^{101}$ | $L^{109}$ | $L^{145}$ |
| 36. | $L^{101}$ | $L^{110}$ | $L^{145}$ |
| 37. | $L^{101}$ | $L^{111}$ | $L^{145}$ |
| 38. | $L^{101}$ | $L^{112}$ | $L^{145}$ |
| 39. | $L^{101}$ | $L^{113}$ | $L^{145}$ |
| 40. | $L^{101}$ | $L^{114}$ | $L^{145}$ |
| 41. | $L^{101}$ | $L^{115}$ | $L^{145}$ |
| 42. | $L^{101}$ | $L^{116}$ | $L^{145}$ |
| 43. | $L^{101}$ | $L^{117}$ | $L^{145}$ |
| 44. | $L^{101}$ | $L^{118}$ | $L^{145}$ |
| 45. | $L^{101}$ | $L^{119}$ | $L^{145}$ |
| 46. | $L^{101}$ | $L^{130}$ | $L^{145}$ |
| 47. | $L^{101}$ | $L^{131}$ | $L^{145}$ |
| 48. | $L^{101}$ | $L^{132}$ | $L^{145}$ |
| 49. | $L^{101}$ | $L^{133}$ | $L^{145}$ |
| 50. | $L^{101}$ | $L^{134}$ | $L^{145}$ |
| 51. | $L^{101}$ | $L^{140}$ | $L^{145}$ |
| 52. | $L^{101}$ | $L^{141}$ | $L^{145}$ |
| 53. | $L^{101}$ | $L^{159}$ | $L^{145}$ |
| 54. | $L^{101}$ | $L^{160}$ | $L^{145}$ |
| 55. | $L^{101}$ | $L^{102}$ | $L^{147}$ |
| 56. | $L^{101}$ | $L^{103}$ | $L^{147}$ |
| 57. | $L^{101}$ | $L^{104}$ | $L^{147}$ |
| 58. | $L^{101}$ | $L^{105}$ | $L^{147}$ |
| 59. | $L^{101}$ | $L^{106}$ | $L^{147}$ |
| 60. | $L^{101}$ | $L^{107}$ | $L^{147}$ |
| 61. | $L^{101}$ | $L^{108}$ | $L^{147}$ |
| 62. | $L^{101}$ | $L^{109}$ | $L^{147}$ |
| 63. | $L^{101}$ | $L^{110}$ | $L^{147}$ |
| 64. | $L^{101}$ | $L^{111}$ | $L^{147}$ |
| 65. | $L^{101}$ | $L^{112}$ | $L^{147}$ |
| 66. | $L^{101}$ | $L^{113}$ | $L^{147}$ |
| 67. | $L^{101}$ | $L^{114}$ | $L^{147}$ |
| 68. | $L^{101}$ | $L^{115}$ | $L^{147}$ |
| 69. | $L^{101}$ | $L^{116}$ | $L^{147}$ |
| 70. | $L^{101}$ | $L^{117}$ | $L^{147}$ |
| 71. | $L^{101}$ | $L^{118}$ | $L^{147}$ |
| 72. | $L^{101}$ | $L^{119}$ | $L^{147}$ |
| 73. | $L^{101}$ | $L^{130}$ | $L^{147}$ |
| 74. | $L^{101}$ | $L^{131}$ | $L^{147}$ |
| 75. | $L^{101}$ | $L^{132}$ | $L^{147}$ |
| 76. | $L^{101}$ | $L^{133}$ | $L^{147}$ |
| 77. | $L^{101}$ | $L^{134}$ | $L^{147}$ |
| 78. | $L^{101}$ | $L^{140}$ | $L^{147}$ |
| 79. | $L^{101}$ | $L^{141}$ | $L^{147}$ |
| 80. | $L^{101}$ | $L^{159}$ | $L^{147}$ |
| 81. | $L^{101}$ | $L^{160}$ | $L^{147}$ |
| 82. | $L^{101}$ | $L^{102}$ | $L^{149}$ |
| 83. | $L^{101}$ | $L^{103}$ | $L^{149}$ |
| 84. | $L^{101}$ | $L^{104}$ | $L^{149}$ |
| 85. | $L^{101}$ | $L^{105}$ | $L^{149}$ |
| 86. | $L^{101}$ | $L^{106}$ | $L^{149}$ |
| 87. | $L^{101}$ | $L^{107}$ | $L^{149}$ |
| 88. | $L^{101}$ | $L^{108}$ | $L^{149}$ |
| 89. | $L^{101}$ | $L^{109}$ | $L^{149}$ |
| 90. | $L^{101}$ | $L^{110}$ | $L^{149}$ |
| 91. | $L^{101}$ | $L^{111}$ | $L^{149}$ |
| 92. | $L^{101}$ | $L^{112}$ | $L^{149}$ |
| 93. | $L^{101}$ | $L^{113}$ | $L^{149}$ |
| 94. | $L^{101}$ | $L^{114}$ | $L^{149}$ |
| 95. | $L^{101}$ | $L^{115}$ | $L^{149}$ |
| 96. | $L^{101}$ | $L^{116}$ | $L^{149}$ |
| 97. | $L^{101}$ | $L^{117}$ | $L^{149}$ |
| 98. | $L^{101}$ | $L^{118}$ | $L^{149}$ |
| 99. | $L^{101}$ | $L^{119}$ | $L^{149}$ |
| 100. | $L^{101}$ | $L^{130}$ | $L^{149}$ |
| 101. | $L^{101}$ | $L^{131}$ | $L^{149}$ |
| 102. | $L^{101}$ | $L^{132}$ | $L^{149}$ |
| 103. | $L^{101}$ | $L^{133}$ | $L^{149}$ |
| 104. | $L^{101}$ | $L^{134}$ | $L^{149}$ |
| 105. | $L^{101}$ | $L^{140}$ | $L^{149}$ |
| 106. | $L^{101}$ | $L^{141}$ | $L^{149}$ |
| 107. | $L^{101}$ | $L^{159}$ | $L^{149}$ |
| 108. | $L^{101}$ | $L^{160}$ | $L^{149}$ |
| 109. | $L^{101}$ | $L^{102}$ | $L^{152}$ |
| 110. | $L^{101}$ | $L^{103}$ | $L^{152}$ |
| 111. | $L^{101}$ | $L^{104}$ | $L^{152}$ |
| 112. | $L^{101}$ | $L^{105}$ | $L^{152}$ |
| 113. | $L^{101}$ | $L^{106}$ | $L^{152}$ |
| 114. | $L^{101}$ | $L^{107}$ | $L^{152}$ |
| 115. | $L^{101}$ | $L^{108}$ | $L^{152}$ |
| 116. | $L^{101}$ | $L^{109}$ | $L^{152}$ |
| 117. | $L^{101}$ | $L^{110}$ | $L^{152}$ |
| 118. | $L^{101}$ | $L^{111}$ | $L^{152}$ |
| 119. | $L^{101}$ | $L^{112}$ | $L^{152}$ |
| 120. | $L^{101}$ | $L^{113}$ | $L^{152}$ |
| 121. | $L^{101}$ | $L^{114}$ | $L^{152}$ |
| 122. | $L^{101}$ | $L^{115}$ | $L^{152}$ |
| 123. | $L^{101}$ | $L^{116}$ | $L^{152}$ |
| 124. | $L^{101}$ | $L^{117}$ | $L^{152}$ |
| 125. | $L^{101}$ | $L^{118}$ | $L^{152}$ |
| 126. | $L^{101}$ | $L^{119}$ | $L^{152}$ |
| 127. | $L^{101}$ | $L^{130}$ | $L^{152}$ |
| 128. | $L^{101}$ | $L^{131}$ | $L^{152}$ |
| 129. | $L^{101}$ | $L^{132}$ | $L^{152}$ |
| 130. | $L^{101}$ | $L^{133}$ | $L^{152}$ |
| 131. | $L^{101}$ | $L^{134}$ | $L^{152}$ |
| 132. | $L^{101}$ | $L^{140}$ | $L^{152}$ |
| 133. | $L^{101}$ | $L^{141}$ | $L^{152}$ |
| 134. | $L^{101}$ | $L^{159}$ | $L^{152}$ |
| 135. | $L^{101}$ | $L^{160}$ | $L^{152}$ |
| 136. | $L^{101}$ | $L^{102}$ | $L^{164}$ |
| 137. | $L^{101}$ | $L^{103}$ | $L^{164}$ |
| 138. | $L^{101}$ | $L^{104}$ | $L^{164}$ |
| 139. | $L^{101}$ | $L^{105}$ | $L^{164}$ |
| 140. | $L^{101}$ | $L^{106}$ | $L^{164}$ |
| 141. | $L^{101}$ | $L^{107}$ | $L^{164}$ |
| 142. | $L^{101}$ | $L^{108}$ | $L^{164}$ |
| 143. | $L^{101}$ | $L^{109}$ | $L^{164}$ |
| 144. | $L^{101}$ | $L^{110}$ | $L^{164}$ |
| 145. | $L^{101}$ | $L^{111}$ | $L^{164}$ |
| 146. | $L^{101}$ | $L^{112}$ | $L^{164}$ |
| 147. | $L^{101}$ | $L^{113}$ | $L^{164}$ |
| 148. | $L^{101}$ | $L^{114}$ | $L^{164}$ |
| 149. | $L^{101}$ | $L^{115}$ | $L^{164}$ |
| 150. | $L^{101}$ | $L^{116}$ | $L^{164}$ |
| 151. | $L^{101}$ | $L^{117}$ | $L^{164}$ |
| 152. | $L^{101}$ | $L^{118}$ | $L^{164}$ |
| 153. | $L^{101}$ | $L^{119}$ | $L^{164}$ |
| 154. | $L^{101}$ | $L^{130}$ | $L^{164}$ |
| 155. | $L^{101}$ | $L^{131}$ | $L^{164}$ |
| 156. | $L^{101}$ | $L^{132}$ | $L^{164}$ |
| 157. | $L^{101}$ | $L^{133}$ | $L^{164}$ |
| 158. | $L^{101}$ | $L^{134}$ | $L^{164}$ |
| 159. | $L^{101}$ | $L^{140}$ | $L^{164}$ |
| 160. | $L^{101}$ | $L^{141}$ | $L^{164}$ |
| 161. | $L^{101}$ | $L^{159}$ | $L^{164}$ |
| 162. | $L^{101}$ | $L^{160}$ | $L^{164}$ |
| 163. | $L^{101}$ | $L^{102}$ | $L^{165}$ |
| 164. | $L^{101}$ | $L^{103}$ | $L^{165}$ |
| 165. | $L^{101}$ | $L^{104}$ | $L^{165}$ |

TABLE 1-continued

| Compound number | L₁ | L₂ | L₃ |
|---|---|---|---|
| 166. | L¹⁰¹ | L¹⁰⁵ | L¹⁶⁵ |
| 167. | L¹⁰¹ | L¹⁰⁶ | L¹⁶⁵ |
| 168. | L¹⁰¹ | L¹⁰⁷ | L¹⁶⁵ |
| 169. | L¹⁰¹ | L¹⁰⁸ | L¹⁶⁵ |
| 170. | L¹⁰¹ | L¹⁰⁹ | L¹⁶⁵ |
| 171. | L¹⁰¹ | L¹¹⁰ | L¹⁶⁵ |
| 172. | L¹⁰¹ | L¹¹¹ | L¹⁶⁵ |
| 173. | L¹⁰¹ | L¹¹² | L¹⁶⁵ |
| 174. | L¹⁰¹ | L¹¹³ | L¹⁶⁵ |
| 175. | L¹⁰¹ | L¹¹⁴ | L¹⁶⁵ |
| 176. | L¹⁰¹ | L¹¹⁵ | L¹⁶⁵ |
| 177. | L¹⁰¹ | L¹¹⁶ | L¹⁶⁵ |
| 178. | L¹⁰¹ | L¹¹⁷ | L¹⁶⁵ |
| 179. | L¹⁰¹ | L¹¹⁸ | L¹⁶⁵ |
| 180. | L¹⁰¹ | L¹¹⁹ | L¹⁶⁵ |
| 181. | L¹⁰¹ | L¹³⁰ | L¹⁶⁵ |
| 182. | L¹⁰¹ | L¹³¹ | L¹⁶⁵ |
| 183. | L¹⁰¹ | L¹³² | L¹⁶⁵ |
| 184. | L¹⁰¹ | L¹³³ | L¹⁶⁵ |
| 185. | L¹⁰¹ | L¹³⁴ | L¹⁶⁵ |
| 186. | L¹⁰¹ | L¹⁴⁰ | L¹⁶⁵ |
| 187. | L¹⁰¹ | L¹⁴¹ | L¹⁶⁵ |
| 188. | L¹⁰¹ | L¹⁵⁹ | L¹⁶⁵ |
| 189. | L¹⁰¹ | L¹⁶⁰ | L¹⁶⁵ |
| 190. | L¹⁰¹ | L¹⁰² | L¹⁶⁶ |
| 191. | L¹⁰¹ | L¹⁰³ | L¹⁶⁶ |
| 192. | L¹⁰¹ | L¹⁰⁴ | L¹⁶⁶ |
| 193. | L¹⁰¹ | L¹⁰⁵ | L¹⁶⁶ |
| 194. | L¹⁰¹ | L¹⁰⁶ | L¹⁶⁶ |
| 195. | L¹⁰¹ | L¹⁰⁷ | L¹⁶⁶ |
| 196. | L¹⁰¹ | L¹⁰⁸ | L¹⁶⁶ |
| 197. | L¹⁰¹ | L¹⁰⁹ | L¹⁶⁶ |
| 198. | L¹⁰¹ | L¹¹⁰ | L¹⁶⁶ |
| 199. | L¹⁰¹ | L¹¹¹ | L¹⁶⁶ |
| 200. | L¹⁰¹ | L¹¹² | L¹⁶⁶ |
| 201. | L¹⁰¹ | L¹¹³ | L¹⁶⁶ |
| 202. | L¹⁰¹ | L¹¹⁴ | L¹⁶⁶ |
| 203. | L¹⁰¹ | L¹¹⁵ | L¹⁶⁶ |
| 204. | L¹⁰¹ | L¹¹⁶ | L¹⁶⁶ |
| 205. | L¹⁰¹ | L¹¹⁷ | L¹⁶⁶ |
| 206. | L¹⁰¹ | L¹¹⁸ | L¹⁶⁶ |
| 207. | L¹⁰¹ | L¹¹⁹ | L¹⁶⁶ |
| 208. | L¹⁰¹ | L¹³⁰ | L¹⁶⁶ |
| 209. | L¹⁰¹ | L¹³¹ | L¹⁶⁶ |
| 210. | L¹⁰¹ | L¹³² | L¹⁶⁶ |
| 211. | L¹⁰¹ | L¹³³ | L¹⁶⁶ |
| 212. | L¹⁰¹ | L¹³⁴ | L¹⁶⁶ |
| 213. | L¹⁰¹ | L¹⁴⁰ | L¹⁶⁶ |
| 214. | L¹⁰¹ | L¹⁴¹ | L¹⁶⁶ |
| 215. | L¹⁰¹ | L¹⁵⁹ | L¹⁶⁶ |
| 216. | L¹⁰¹ | L¹⁶⁰ | L¹⁶⁶ |
| 217. | L¹⁰¹ | L¹⁰² | L¹⁷⁰ |
| 218. | L¹⁰¹ | L¹⁰³ | L¹⁷⁰ |
| 219. | L¹⁰¹ | L¹⁰⁴ | L¹⁷⁰ |
| 220. | L¹⁰¹ | L¹⁰⁵ | L¹⁷⁰ |
| 221. | L¹⁰¹ | L¹⁰⁶ | L¹⁷⁰ |
| 222. | L¹⁰¹ | L¹⁰⁷ | L¹⁷⁰ |
| 223. | L¹⁰¹ | L¹⁰⁸ | L¹⁷⁰ |
| 224. | L¹⁰¹ | L¹⁰⁹ | L¹⁷⁰ |
| 225. | L¹⁰¹ | L¹¹⁰ | L¹⁷⁰ |
| 226. | L¹⁰¹ | L¹¹¹ | L¹⁷⁰ |
| 227. | L¹⁰¹ | L¹¹² | L¹⁷⁰ |
| 228. | L¹⁰¹ | L¹¹³ | L¹⁷⁰ |
| 229. | L¹⁰¹ | L¹¹⁴ | L¹⁷⁰ |
| 230. | L¹⁰¹ | L¹¹⁵ | L¹⁷⁰ |
| 231. | L¹⁰¹ | L¹¹⁶ | L¹⁷⁰ |
| 232. | L¹⁰¹ | L¹¹⁷ | L¹⁷⁰ |
| 233. | L¹⁰¹ | L¹¹⁸ | L¹⁷⁰ |
| 234. | L¹⁰¹ | L¹¹⁹ | L¹⁷⁰ |
| 235. | L¹⁰¹ | L¹³⁰ | L¹⁷⁰ |
| 236. | L¹⁰¹ | L¹³¹ | L¹⁷⁰ |
| 237. | L¹⁰¹ | L¹³² | L¹⁷⁰ |
| 238. | L¹⁰¹ | L¹³³ | L¹⁷⁰ |
| 239. | L¹⁰¹ | L¹³⁴ | L¹⁷⁰ |
| 240. | L¹⁰¹ | L¹⁴⁰ | L¹⁷⁰ |
| 241. | L¹⁰¹ | L¹⁴¹ | L¹⁷⁰ |
| 242. | L¹⁰¹ | L¹⁵⁹ | L¹⁷⁰ |
| 243. | L¹⁰¹ | L¹⁶⁰ | L¹⁷⁰ |
| 244. | L¹⁰¹ | L¹⁰² | L¹⁷⁴ |
| 245. | L¹⁰¹ | L¹⁰³ | L¹⁷⁴ |
| 246. | L¹⁰¹ | L¹⁰⁴ | L¹⁷⁴ |
| 247. | L¹⁰¹ | L¹⁰⁵ | L¹⁷⁴ |
| 248. | L¹⁰¹ | L¹⁰⁶ | L¹⁷⁴ |
| 249. | L¹⁰¹ | L¹⁰⁷ | L¹⁷⁴ |
| 250. | L¹⁰¹ | L¹⁰⁸ | L¹⁷⁴ |
| 251. | L¹⁰¹ | L¹⁰⁹ | L¹⁷⁴ |
| 252. | L¹⁰¹ | L¹¹⁰ | L¹⁷⁴ |
| 253. | L¹⁰¹ | L¹¹¹ | L¹⁷⁴ |
| 254. | L¹⁰¹ | L¹¹² | L¹⁷⁴ |
| 255. | L¹⁰¹ | L¹¹³ | L¹⁷⁴ |
| 256. | L¹⁰¹ | L¹¹⁴ | L¹⁷⁴ |
| 257. | L¹⁰¹ | L¹¹⁵ | L¹⁷⁴ |
| 258. | L¹⁰¹ | L¹¹⁶ | L¹⁷⁴ |
| 259. | L¹⁰¹ | L¹¹⁷ | L¹⁷⁴ |
| 260. | L¹⁰¹ | L¹¹⁸ | L¹⁷⁴ |
| 261. | L¹⁰¹ | L¹¹⁹ | L¹⁷⁴ |
| 262. | L¹⁰¹ | L¹³⁰ | L¹⁷⁴ |
| 263. | L¹⁰¹ | L¹³¹ | L¹⁷⁴ |
| 264. | L¹⁰¹ | L¹³² | L¹⁷⁴ |
| 265. | L¹⁰¹ | L¹³³ | L¹⁷⁴ |
| 266. | L¹⁰¹ | L¹³⁴ | L¹⁷⁴ |
| 267. | L¹⁰¹ | L¹⁴⁰ | L¹⁷⁴ |
| 268. | L¹⁰¹ | L¹⁴¹ | L¹⁷⁴ |
| 269. | L¹⁰¹ | L¹⁵⁹ | L¹⁷⁴ |
| 270. | L¹⁰¹ | L¹⁶⁰ | L¹⁷⁴ |
| 271. | L¹⁰¹ | L¹⁰² | L¹⁷⁶ |
| 272. | L¹⁰¹ | L¹⁰³ | L¹⁷⁶ |
| 273. | L¹⁰¹ | L¹⁰⁴ | L¹⁷⁶ |
| 274. | L¹⁰¹ | L¹⁰⁵ | L¹⁷⁶ |
| 275. | L¹⁰¹ | L¹⁰⁶ | L¹⁷⁶ |
| 276. | L¹⁰¹ | L¹⁰⁷ | L¹⁷⁶ |
| 277. | L¹⁰¹ | L¹⁰⁸ | L¹⁷⁶ |
| 278. | L¹⁰¹ | L¹⁰⁹ | L¹⁷⁶ |
| 279. | L¹⁰¹ | L¹¹⁰ | L¹⁷⁶ |
| 280. | L¹⁰¹ | L¹¹¹ | L¹⁷⁶ |
| 281. | L¹⁰¹ | L¹¹² | L¹⁷⁶ |
| 282. | L¹⁰¹ | L¹¹³ | L¹⁷⁶ |
| 283. | L¹⁰¹ | L¹¹⁴ | L¹⁷⁶ |
| 284. | L¹⁰¹ | L¹¹⁵ | L¹⁷⁶ |
| 285. | L¹⁰¹ | L¹¹⁶ | L¹⁷⁶ |
| 286. | L¹⁰¹ | L¹¹⁷ | L¹⁷⁶ |
| 287. | L¹⁰¹ | L¹¹⁸ | L¹⁷⁶ |
| 288. | L¹⁰¹ | L¹¹⁹ | L¹⁷⁶ |
| 289. | L¹⁰¹ | L¹³⁰ | L¹⁷⁶ |
| 290. | L¹⁰¹ | L¹³¹ | L¹⁷⁶ |
| 291. | L¹⁰¹ | L¹³² | L¹⁷⁶ |
| 292. | L¹⁰¹ | L¹³³ | L¹⁷⁶ |
| 293. | L¹⁰¹ | L¹³⁴ | L¹⁷⁶ |
| 294. | L¹⁰¹ | L¹⁴⁰ | L¹⁷⁶ |
| 295. | L¹⁰¹ | L¹⁴¹ | L¹⁷⁶ |
| 296. | L¹⁰¹ | L¹⁵⁹ | L¹⁷⁶ |
| 297. | L¹⁰¹ | L¹⁶⁰ | L¹⁷⁶ |
| 298. | L¹⁰¹ | L¹⁰² | L¹⁷⁹ |
| 299. | L¹⁰¹ | L¹⁰³ | L¹⁷⁹ |
| 300. | L¹⁰¹ | L¹⁰⁴ | L¹⁷⁹ |
| 301. | L¹⁰¹ | L¹⁰⁵ | L¹⁷⁹ |
| 302. | L¹⁰¹ | L¹⁰⁶ | L¹⁷⁹ |
| 303. | L¹⁰¹ | L¹⁰⁷ | L¹⁷⁹ |
| 304. | L¹⁰¹ | L¹⁰⁸ | L¹⁷⁹ |
| 305. | L¹⁰¹ | L¹⁰⁹ | L¹⁷⁹ |
| 306. | L¹⁰¹ | L¹¹⁰ | L¹⁷⁹ |
| 307. | L¹⁰¹ | L¹¹¹ | L¹⁷⁹ |
| 308. | L¹⁰¹ | L¹¹² | L¹⁷⁹ |
| 309. | L¹⁰¹ | L¹¹³ | L¹⁷⁹ |
| 310. | L¹⁰¹ | L¹¹⁴ | L¹⁷⁹ |
| 311. | L¹⁰¹ | L¹¹⁵ | L¹⁷⁹ |
| 312. | L¹⁰¹ | L¹¹⁶ | L¹⁷⁹ |
| 313. | L¹⁰¹ | L¹¹⁷ | L¹⁷⁹ |
| 314. | L¹⁰¹ | L¹¹⁸ | L¹⁷⁹ |
| 315. | L¹⁰¹ | L¹¹⁹ | L¹⁷⁹ |
| 316. | L¹⁰¹ | L¹³⁰ | L¹⁷⁹ |
| 317. | L¹⁰¹ | L¹³¹ | L¹⁷⁹ |
| 318. | L¹⁰¹ | L¹³² | L¹⁷⁹ |
| 319. | L¹⁰¹ | L¹³³ | L¹⁷⁹ |

TABLE 1-continued

| Compound number | L₁ | L₂ | L₃ |
|---|---|---|---|
| 320. | L¹⁰¹ | L¹³⁴ | L¹⁷⁹ |
| 321. | L¹⁰¹ | L¹⁴⁰ | L¹⁷⁹ |
| 322. | L¹⁰¹ | L¹⁴¹ | L¹⁷⁹ |
| 323. | L¹⁰¹ | L¹⁵⁹ | L¹⁷⁹ |
| 324. | L¹⁰¹ | L¹⁶⁰ | L¹⁷⁹ |
| 325. | L¹⁰¹ | L¹⁰² | L¹⁸⁰ |
| 326. | L¹⁰¹ | L¹⁰³ | L¹⁸⁰ |
| 327. | L¹⁰¹ | L¹⁰⁴ | L¹⁸⁰ |
| 328. | L¹⁰¹ | L¹⁰⁵ | L¹⁸⁰ |
| 329. | L¹⁰¹ | L¹⁰⁶ | L¹⁸⁰ |
| 330. | L¹⁰¹ | L¹⁰⁷ | L¹⁸⁰ |
| 331. | L¹⁰¹ | L¹⁰⁸ | L¹⁸⁰ |
| 332. | L¹⁰¹ | L¹⁰⁹ | L¹⁸⁰ |
| 333. | L¹⁰¹ | L¹¹⁰ | L¹⁸⁰ |
| 334. | L¹⁰¹ | L¹¹¹ | L¹⁸⁰ |
| 335. | L¹⁰¹ | L¹¹² | L¹⁸⁰ |
| 336. | L¹⁰¹ | L¹¹³ | L¹⁸⁰ |
| 337. | L¹⁰¹ | L¹¹⁴ | L¹⁸⁰ |
| 338. | L¹⁰¹ | L¹¹⁵ | L¹⁸⁰ |
| 339. | L¹⁰¹ | L¹¹⁶ | L¹⁸⁰ |
| 340. | L¹⁰¹ | L¹¹⁷ | L¹⁸⁰ |
| 341. | L¹⁰¹ | L¹¹⁸ | L¹⁸⁰ |
| 342. | L¹⁰¹ | L¹¹⁹ | L¹⁸⁰ |
| 343. | L¹⁰¹ | L¹³⁰ | L¹⁸⁰ |
| 344. | L¹⁰¹ | L¹³¹ | L¹⁸⁰ |
| 345. | L¹⁰¹ | L¹³² | L¹⁸⁰ |
| 346. | L¹⁰¹ | L¹³³ | L¹⁸⁰ |
| 347. | L¹⁰¹ | L¹³⁴ | L¹⁸⁰ |
| 348. | L¹⁰¹ | L¹⁴⁰ | L¹⁸⁰ |
| 349. | L¹⁰¹ | L¹⁴¹ | L¹⁸⁰ |
| 350. | L¹⁰¹ | L¹⁵⁹ | L¹⁸⁰ |
| 351. | L¹⁰¹ | L¹⁶⁰ | L¹⁸⁰ |
| 352. | L¹⁰² | L¹⁰³ | L¹⁴⁴ |
| 353. | L¹⁰² | L¹⁰⁴ | L¹⁴⁴ |
| 354. | L¹⁰² | L¹⁰⁵ | L¹⁴⁴ |
| 355. | L¹⁰² | L¹⁰⁶ | L¹⁴⁴ |
| 356. | L¹⁰² | L¹⁰⁷ | L¹⁴⁴ |
| 357. | L¹⁰² | L¹⁰⁸ | L¹⁴⁴ |
| 358. | L¹⁰² | L¹⁰⁹ | L¹⁴⁴ |
| 359. | L¹⁰² | L¹¹⁰ | L¹⁴⁴ |
| 360. | L¹⁰² | L¹¹¹ | L¹⁴⁴ |
| 361. | L¹⁰² | L¹¹² | L¹⁴⁴ |
| 362. | L¹⁰² | L¹¹³ | L¹⁴⁴ |
| 363. | L¹⁰² | L¹¹⁴ | L¹⁴⁴ |
| 364. | L¹⁰² | L¹¹⁵ | L¹⁴⁴ |
| 365. | L¹⁰² | L¹¹⁶ | L¹⁴⁴ |
| 366. | L¹⁰² | L¹¹⁷ | L¹⁴⁴ |
| 367. | L¹⁰² | L¹¹⁸ | L¹⁴⁴ |
| 368. | L¹⁰² | L¹¹⁹ | L¹⁴⁴ |
| 369. | L¹⁰² | L¹³⁰ | L¹⁴⁴ |
| 370. | L¹⁰² | L¹³¹ | L¹⁴⁴ |
| 371. | L¹⁰² | L¹³² | L¹⁴⁴ |
| 372. | L¹⁰² | L¹³³ | L¹⁴⁴ |
| 373. | L¹⁰² | L¹³⁴ | L¹⁴⁴ |
| 374. | L¹⁰² | L¹⁴⁰ | L¹⁴⁴ |
| 375. | L¹⁰² | L¹⁴¹ | L¹⁴⁴ |
| 376. | L¹⁰² | L¹⁵⁹ | L¹⁴⁴ |
| 377. | L¹⁰² | L¹⁶⁰ | L¹⁴⁴ |
| 378. | L¹⁰² | L¹⁰³ | L¹⁴⁵ |
| 379. | L¹⁰² | L¹⁰⁴ | L¹⁴⁵ |
| 380. | L¹⁰² | L¹⁰⁵ | L¹⁴⁵ |
| 381. | L¹⁰² | L¹⁰⁶ | L¹⁴⁵ |
| 382. | L¹⁰² | L¹⁰⁷ | L¹⁴⁵ |
| 383. | L¹⁰² | L¹⁰⁸ | L¹⁴⁵ |
| 384. | L¹⁰² | L¹⁰⁹ | L¹⁴⁵ |
| 385. | L¹⁰² | L¹¹⁰ | L¹⁴⁵ |
| 386. | L¹⁰² | L¹¹¹ | L¹⁴⁵ |
| 387. | L¹⁰² | L¹¹² | L¹⁴⁵ |
| 388. | L¹⁰² | L¹¹³ | L¹⁴⁵ |
| 389. | L¹⁰² | L¹¹⁴ | L¹⁴⁵ |
| 390. | L¹⁰² | L¹¹⁵ | L¹⁴⁵ |
| 391. | L¹⁰² | L¹¹⁶ | L¹⁴⁵ |
| 392. | L¹⁰² | L¹¹⁷ | L¹⁴⁵ |
| 393. | L¹⁰² | L¹¹⁸ | L¹⁴⁵ |
| 394. | L¹⁰² | L¹¹⁹ | L¹⁴⁵ |
| 395. | L¹⁰² | L¹³⁰ | L¹⁴⁵ |
| 396. | L¹⁰² | L¹³¹ | L¹⁴⁵ |
| 397. | L¹⁰² | L¹³² | L¹⁴⁵ |
| 398. | L¹⁰² | L¹³³ | L¹⁴⁵ |
| 399. | L¹⁰² | L¹³⁴ | L¹⁴⁵ |
| 400. | L¹⁰² | L¹⁴⁰ | L¹⁴⁵ |
| 401. | L¹⁰² | L¹⁴¹ | L¹⁴⁵ |
| 402. | L¹⁰² | L¹⁵⁹ | L¹⁴⁵ |
| 403. | L¹⁰² | L¹⁶⁰ | L¹⁴⁵ |
| 404. | L¹⁰² | L¹⁰³ | L¹⁴⁷ |
| 405. | L¹⁰² | L¹⁰⁴ | L¹⁴⁷ |
| 406. | L¹⁰² | L¹⁰⁵ | L¹⁴⁷ |
| 407. | L¹⁰² | L¹⁰⁶ | L¹⁴⁷ |
| 408. | L¹⁰² | L¹⁰⁷ | L¹⁴⁷ |
| 409. | L¹⁰² | L¹⁰⁸ | L¹⁴⁷ |
| 410. | L¹⁰² | L¹⁰⁹ | L¹⁴⁷ |
| 411. | L¹⁰² | L¹¹⁰ | L¹⁴⁷ |
| 412. | L¹⁰² | L¹¹¹ | L¹⁴⁷ |
| 413. | L¹⁰² | L¹¹² | L¹⁴⁷ |
| 414. | L¹⁰² | L¹¹³ | L¹⁴⁷ |
| 415. | L¹⁰² | L¹¹⁴ | L¹⁴⁷ |
| 416. | L¹⁰² | L¹¹⁵ | L¹⁴⁷ |
| 417. | L¹⁰² | L¹¹⁶ | L¹⁴⁷ |
| 418. | L¹⁰² | L¹¹⁷ | L¹⁴⁷ |
| 419. | L¹⁰² | L¹¹⁸ | L¹⁴⁷ |
| 420. | L¹⁰² | L¹¹⁹ | L¹⁴⁷ |
| 421. | L¹⁰² | L¹³⁰ | L¹⁴⁷ |
| 422. | L¹⁰² | L¹³¹ | L¹⁴⁷ |
| 423. | L¹⁰² | L¹³² | L¹⁴⁷ |
| 424. | L¹⁰² | L¹³³ | L¹⁴⁷ |
| 425. | L¹⁰² | L¹³⁴ | L¹⁴⁷ |
| 426. | L¹⁰² | L¹⁴⁰ | L¹⁴⁷ |
| 427. | L¹⁰² | L¹⁴¹ | L¹⁴⁷ |
| 428. | L¹⁰² | L¹⁵⁹ | L¹⁴⁷ |
| 429. | L¹⁰² | L¹⁶⁰ | L¹⁴⁷ |
| 430. | L¹⁰² | L¹⁰³ | L¹⁴⁹ |
| 431. | L¹⁰² | L¹⁰⁴ | L¹⁴⁹ |
| 432. | L¹⁰² | L¹⁰⁵ | L¹⁴⁹ |
| 433. | L¹⁰² | L¹⁰⁶ | L¹⁴⁹ |
| 434. | L¹⁰² | L¹⁰⁷ | L¹⁴⁹ |
| 435. | L¹⁰² | L¹⁰⁸ | L¹⁴⁹ |
| 436. | L¹⁰² | L¹⁰⁹ | L¹⁴⁹ |
| 437. | L¹⁰² | L¹¹⁰ | L¹⁴⁹ |
| 438. | L¹⁰² | L¹¹¹ | L¹⁴⁹ |
| 439. | L¹⁰² | L¹¹² | L¹⁴⁹ |
| 440. | L¹⁰² | L¹¹³ | L¹⁴⁹ |
| 441. | L¹⁰² | L¹¹⁴ | L¹⁴⁹ |
| 442. | L¹⁰² | L¹¹⁵ | L¹⁴⁹ |
| 443. | L¹⁰² | L¹¹⁶ | L¹⁴⁹ |
| 444. | L¹⁰² | L¹¹⁷ | L¹⁴⁹ |
| 445. | L¹⁰² | L¹¹⁸ | L¹⁴⁹ |
| 446. | L¹⁰² | L¹¹⁹ | L¹⁴⁹ |
| 447. | L¹⁰² | L¹³⁰ | L¹⁴⁹ |
| 448. | L¹⁰² | L¹³¹ | L¹⁴⁹ |
| 449. | L¹⁰² | L¹³² | L¹⁴⁹ |
| 450. | L¹⁰² | L¹³³ | L¹⁴⁹ |
| 451. | L¹⁰² | L¹³⁴ | L¹⁴⁹ |
| 452. | L¹⁰² | L¹⁴⁰ | L¹⁴⁹ |
| 453. | L¹⁰² | L¹⁴¹ | L¹⁴⁹ |
| 454. | L¹⁰² | L¹⁵⁹ | L¹⁴⁹ |
| 455. | L¹⁰² | L¹⁶⁰ | L¹⁴⁹ |
| 456. | L¹⁰² | L¹⁰³ | L¹⁵² |
| 457. | L¹⁰² | L¹⁰⁴ | L¹⁵² |
| 458. | L¹⁰² | L¹⁰⁵ | L¹⁵² |
| 459. | L¹⁰² | L¹⁰⁶ | L¹⁵² |
| 460. | L¹⁰² | L¹⁰⁷ | L¹⁵² |
| 461. | L¹⁰² | L¹⁰⁸ | L¹⁵² |
| 462. | L¹⁰² | L¹⁰⁹ | L¹⁵² |
| 463. | L¹⁰² | L¹¹⁰ | L¹⁵² |
| 464. | L¹⁰² | L¹¹¹ | L¹⁵² |
| 465. | L¹⁰² | L¹¹² | L¹⁵² |
| 466. | L¹⁰² | L¹¹³ | L¹⁵² |
| 467. | L¹⁰² | L¹¹⁴ | L¹⁵² |
| 468. | L¹⁰² | L¹¹⁵ | L¹⁵² |
| 469. | L¹⁰² | L¹¹⁶ | L¹⁵² |
| 470. | L¹⁰² | L¹¹⁷ | L¹⁵² |
| 471. | L¹⁰² | L¹¹⁸ | L¹⁵² |
| 472. | L¹⁰² | L¹¹⁹ | L¹⁵² |
| 473. | L¹⁰² | L¹³⁰ | L¹⁵² |

TABLE 1-continued

| Compound number | $L_1$ | $L_2$ | $L_3$ |
|---|---|---|---|
| 474. | $L^{102}$ | $L^{131}$ | $L^{152}$ |
| 475. | $L^{102}$ | $L^{132}$ | $L^{152}$ |
| 476. | $L^{102}$ | $L^{133}$ | $L^{152}$ |
| 477. | $L^{102}$ | $L^{134}$ | $L^{152}$ |
| 478. | $L^{102}$ | $L^{140}$ | $L^{152}$ |
| 479. | $L^{102}$ | $L^{141}$ | $L^{152}$ |
| 480. | $L^{102}$ | $L^{159}$ | $L^{152}$ |
| 481. | $L^{102}$ | $L^{160}$ | $L^{152}$ |
| 482. | $L^{102}$ | $L^{103}$ | $L^{164}$ |
| 483. | $L^{102}$ | $L^{104}$ | $L^{164}$ |
| 484. | $L^{102}$ | $L^{105}$ | $L^{164}$ |
| 485. | $L^{102}$ | $L^{106}$ | $L^{164}$ |
| 486. | $L^{102}$ | $L^{107}$ | $L^{164}$ |
| 487. | $L^{102}$ | $L^{108}$ | $L^{164}$ |
| 488. | $L^{102}$ | $L^{109}$ | $L^{164}$ |
| 489. | $L^{102}$ | $L^{110}$ | $L^{164}$ |
| 490. | $L^{102}$ | $L^{111}$ | $L^{164}$ |
| 491. | $L^{102}$ | $L^{112}$ | $L^{164}$ |
| 492. | $L^{102}$ | $L^{113}$ | $L^{164}$ |
| 493. | $L^{102}$ | $L^{114}$ | $L^{164}$ |
| 494. | $L^{102}$ | $L^{115}$ | $L^{164}$ |
| 495. | $L^{102}$ | $L^{116}$ | $L^{164}$ |
| 496. | $L^{102}$ | $L^{117}$ | $L^{164}$ |
| 497. | $L^{102}$ | $L^{118}$ | $L^{164}$ |
| 498. | $L^{102}$ | $L^{119}$ | $L^{164}$ |
| 499. | $L^{102}$ | $L^{130}$ | $L^{164}$ |
| 500. | $L^{102}$ | $L^{131}$ | $L^{164}$ |
| 501. | $L^{102}$ | $L^{132}$ | $L^{164}$ |
| 502. | $L^{102}$ | $L^{133}$ | $L^{164}$ |
| 503. | $L^{102}$ | $L^{134}$ | $L^{164}$ |
| 504. | $L^{102}$ | $L^{140}$ | $L^{164}$ |
| 505. | $L^{102}$ | $L^{141}$ | $L^{164}$ |
| 506. | $L^{102}$ | $L^{159}$ | $L^{164}$ |
| 507. | $L^{102}$ | $L^{160}$ | $L^{164}$ |
| 508. | $L^{102}$ | $L^{103}$ | $L^{165}$ |
| 509. | $L^{102}$ | $L^{104}$ | $L^{165}$ |
| 510. | $L^{102}$ | $L^{105}$ | $L^{165}$ |
| 511. | $L^{102}$ | $L^{106}$ | $L^{165}$ |
| 512. | $L^{102}$ | $L^{107}$ | $L^{165}$ |
| 513. | $L^{102}$ | $L^{108}$ | $L^{165}$ |
| 514. | $L^{102}$ | $L^{109}$ | $L^{165}$ |
| 515. | $L^{102}$ | $L^{110}$ | $L^{165}$ |
| 516. | $L^{102}$ | $L^{111}$ | $L^{165}$ |
| 517. | $L^{102}$ | $L^{112}$ | $L^{165}$ |
| 518. | $L^{102}$ | $L^{113}$ | $L^{165}$ |
| 519. | $L^{102}$ | $L^{114}$ | $L^{165}$ |
| 520. | $L^{102}$ | $L^{115}$ | $L^{165}$ |
| 521. | $L^{102}$ | $L^{116}$ | $L^{165}$ |
| 522. | $L^{102}$ | $L^{117}$ | $L^{165}$ |
| 523. | $L^{102}$ | $L^{118}$ | $L^{165}$ |
| 524. | $L^{102}$ | $L^{119}$ | $L^{165}$ |
| 525. | $L^{102}$ | $L^{130}$ | $L^{165}$ |
| 526. | $L^{102}$ | $L^{131}$ | $L^{165}$ |
| 527. | $L^{102}$ | $L^{132}$ | $L^{165}$ |
| 528. | $L^{102}$ | $L^{133}$ | $L^{165}$ |
| 529. | $L^{102}$ | $L^{134}$ | $L^{165}$ |
| 530. | $L^{102}$ | $L^{140}$ | $L^{165}$ |
| 531. | $L^{102}$ | $L^{141}$ | $L^{165}$ |
| 532. | $L^{102}$ | $L^{159}$ | $L^{165}$ |
| 533. | $L^{102}$ | $L^{160}$ | $L^{165}$ |
| 534. | $L^{102}$ | $L^{103}$ | $L^{166}$ |
| 535. | $L^{102}$ | $L^{104}$ | $L^{166}$ |
| 536. | $L^{102}$ | $L^{105}$ | $L^{166}$ |
| 537. | $L^{102}$ | $L^{106}$ | $L^{166}$ |
| 538. | $L^{102}$ | $L^{107}$ | $L^{166}$ |
| 539. | $L^{102}$ | $L^{108}$ | $L^{166}$ |
| 540. | $L^{102}$ | $L^{109}$ | $L^{166}$ |
| 541. | $L^{102}$ | $L^{110}$ | $L^{166}$ |
| 542. | $L^{102}$ | $L^{111}$ | $L^{166}$ |
| 543. | $L^{102}$ | $L^{112}$ | $L^{166}$ |
| 544. | $L^{102}$ | $L^{113}$ | $L^{166}$ |
| 545. | $L^{102}$ | $L^{114}$ | $L^{166}$ |
| 546. | $L^{102}$ | $L^{115}$ | $L^{166}$ |
| 547. | $L^{102}$ | $L^{116}$ | $L^{166}$ |
| 548. | $L^{102}$ | $L^{117}$ | $L^{166}$ |
| 549. | $L^{102}$ | $L^{118}$ | $L^{166}$ |
| 550. | $L^{102}$ | $L^{119}$ | $L^{166}$ |
| 551. | $L^{102}$ | $L^{130}$ | $L^{166}$ |
| 552. | $L^{102}$ | $L^{131}$ | $L^{166}$ |
| 553. | $L^{102}$ | $L^{132}$ | $L^{166}$ |
| 554. | $L^{102}$ | $L^{133}$ | $L^{166}$ |
| 555. | $L^{102}$ | $L^{134}$ | $L^{166}$ |
| 556. | $L^{102}$ | $L^{140}$ | $L^{166}$ |
| 557. | $L^{102}$ | $L^{141}$ | $L^{166}$ |
| 558. | $L^{102}$ | $L^{159}$ | $L^{166}$ |
| 559. | $L^{102}$ | $L^{160}$ | $L^{166}$ |
| 560. | $L^{102}$ | $L^{103}$ | $L^{170}$ |
| 561. | $L^{102}$ | $L^{104}$ | $L^{170}$ |
| 562. | $L^{102}$ | $L^{105}$ | $L^{170}$ |
| 563. | $L^{102}$ | $L^{106}$ | $L^{170}$ |
| 564. | $L^{102}$ | $L^{107}$ | $L^{170}$ |
| 565. | $L^{102}$ | $L^{108}$ | $L^{170}$ |
| 566. | $L^{102}$ | $L^{109}$ | $L^{170}$ |
| 567. | $L^{102}$ | $L^{110}$ | $L^{170}$ |
| 568. | $L^{102}$ | $L^{111}$ | $L^{170}$ |
| 569. | $L^{102}$ | $L^{112}$ | $L^{170}$ |
| 570. | $L^{102}$ | $L^{113}$ | $L^{170}$ |
| 571. | $L^{102}$ | $L^{114}$ | $L^{170}$ |
| 572. | $L^{102}$ | $L^{115}$ | $L^{170}$ |
| 573. | $L^{102}$ | $L^{116}$ | $L^{170}$ |
| 574. | $L^{102}$ | $L^{117}$ | $L^{170}$ |
| 575. | $L^{102}$ | $L^{118}$ | $L^{170}$ |
| 576. | $L^{102}$ | $L^{119}$ | $L^{170}$ |
| 577. | $L^{102}$ | $L^{130}$ | $L^{170}$ |
| 578. | $L^{102}$ | $L^{131}$ | $L^{170}$ |
| 579. | $L^{102}$ | $L^{132}$ | $L^{170}$ |
| 580. | $L^{102}$ | $L^{133}$ | $L^{170}$ |
| 581. | $L^{102}$ | $L^{134}$ | $L^{170}$ |
| 582. | $L^{102}$ | $L^{140}$ | $L^{170}$ |
| 583. | $L^{102}$ | $L^{141}$ | $L^{170}$ |
| 584. | $L^{102}$ | $L^{159}$ | $L^{170}$ |
| 585. | $L^{102}$ | $L^{160}$ | $L^{170}$ |
| 586. | $L^{102}$ | $L^{103}$ | $L^{174}$ |
| 587. | $L^{102}$ | $L^{104}$ | $L^{174}$ |
| 588. | $L^{102}$ | $L^{105}$ | $L^{174}$ |
| 589. | $L^{102}$ | $L^{106}$ | $L^{174}$ |
| 590. | $L^{102}$ | $L^{107}$ | $L^{174}$ |
| 591. | $L^{102}$ | $L^{108}$ | $L^{174}$ |
| 592. | $L^{102}$ | $L^{109}$ | $L^{174}$ |
| 593. | $L^{102}$ | $L^{110}$ | $L^{174}$ |
| 594. | $L^{102}$ | $L^{111}$ | $L^{174}$ |
| 595. | $L^{102}$ | $L^{112}$ | $L^{174}$ |
| 596. | $L^{102}$ | $L^{113}$ | $L^{174}$ |
| 597. | $L^{102}$ | $L^{114}$ | $L^{174}$ |
| 598. | $L^{102}$ | $L^{115}$ | $L^{174}$ |
| 599. | $L^{102}$ | $L^{116}$ | $L^{174}$ |
| 600. | $L^{102}$ | $L^{117}$ | $L^{174}$ |
| 601. | $L^{102}$ | $L^{118}$ | $L^{174}$ |
| 602. | $L^{102}$ | $L^{119}$ | $L^{174}$ |
| 603. | $L^{102}$ | $L^{130}$ | $L^{174}$ |
| 604. | $L^{102}$ | $L^{131}$ | $L^{174}$ |
| 605. | $L^{102}$ | $L^{132}$ | $L^{174}$ |
| 606. | $L^{102}$ | $L^{133}$ | $L^{174}$ |
| 607. | $L^{102}$ | $L^{134}$ | $L^{174}$ |
| 608. | $L^{102}$ | $L^{140}$ | $L^{174}$ |
| 609. | $L^{102}$ | $L^{141}$ | $L^{174}$ |
| 610. | $L^{102}$ | $L^{159}$ | $L^{174}$ |
| 611. | $L^{102}$ | $L^{160}$ | $L^{174}$ |
| 612. | $L^{102}$ | $L^{103}$ | $L^{176}$ |
| 613. | $L^{102}$ | $L^{104}$ | $L^{176}$ |
| 614. | $L^{102}$ | $L^{105}$ | $L^{176}$ |
| 615. | $L^{102}$ | $L^{106}$ | $L^{176}$ |
| 616. | $L^{102}$ | $L^{107}$ | $L^{176}$ |
| 617. | $L^{102}$ | $L^{108}$ | $L^{176}$ |
| 618. | $L^{102}$ | $L^{109}$ | $L^{176}$ |
| 619. | $L^{102}$ | $L^{110}$ | $L^{176}$ |
| 620. | $L^{102}$ | $L^{111}$ | $L^{176}$ |
| 621. | $L^{102}$ | $L^{112}$ | $L^{176}$ |
| 622. | $L^{102}$ | $L^{113}$ | $L^{176}$ |
| 623. | $L^{102}$ | $L^{114}$ | $L^{176}$ |
| 624. | $L^{102}$ | $L^{115}$ | $L^{176}$ |
| 625. | $L^{102}$ | $L^{116}$ | $L^{176}$ |
| 626. | $L^{102}$ | $L^{117}$ | $L^{176}$ |
| 627. | $L^{102}$ | $L^{118}$ | $L^{176}$ |

TABLE 1-continued

| Compound number | $L_1$ | $L_2$ | $L_3$ |
|---|---|---|---|
| 628. | $L^{102}$ | $L^{119}$ | $L^{176}$ |
| 629. | $L^{102}$ | $L^{130}$ | $L^{176}$ |
| 630. | $L^{102}$ | $L^{131}$ | $L^{176}$ |
| 631. | $L^{102}$ | $L^{132}$ | $L^{176}$ |
| 632. | $L^{102}$ | $L^{133}$ | $L^{176}$ |
| 633. | $L^{102}$ | $L^{134}$ | $L^{176}$ |
| 634. | $L^{102}$ | $L^{140}$ | $L^{176}$ |
| 635. | $L^{102}$ | $L^{141}$ | $L^{176}$ |
| 636. | $L^{102}$ | $L^{159}$ | $L^{176}$ |
| 637. | $L^{102}$ | $L^{160}$ | $L^{176}$ |
| 638. | $L^{102}$ | $L^{103}$ | $L^{179}$ |
| 639. | $L^{102}$ | $L^{104}$ | $L^{179}$ |
| 640. | $L^{102}$ | $L^{105}$ | $L^{179}$ |
| 641. | $L^{102}$ | $L^{106}$ | $L^{179}$ |
| 642. | $L^{102}$ | $L^{107}$ | $L^{179}$ |
| 643. | $L^{102}$ | $L^{108}$ | $L^{179}$ |
| 644. | $L^{102}$ | $L^{109}$ | $L^{179}$ |
| 645. | $L^{102}$ | $L^{110}$ | $L^{179}$ |
| 646. | $L^{102}$ | $L^{111}$ | $L^{179}$ |
| 647. | $L^{102}$ | $L^{112}$ | $L^{179}$ |
| 648. | $L^{102}$ | $L^{113}$ | $L^{179}$ |
| 649. | $L^{102}$ | $L^{114}$ | $L^{179}$ |
| 650. | $L^{102}$ | $L^{115}$ | $L^{179}$ |
| 651. | $L^{102}$ | $L^{116}$ | $L^{179}$ |
| 652. | $L^{102}$ | $L^{117}$ | $L^{179}$ |
| 653. | $L^{102}$ | $L^{118}$ | $L^{179}$ |
| 654. | $L^{102}$ | $L^{119}$ | $L^{179}$ |
| 655. | $L^{102}$ | $L^{130}$ | $L^{179}$ |
| 656. | $L^{102}$ | $L^{131}$ | $L^{179}$ |
| 657. | $L^{102}$ | $L^{132}$ | $L^{179}$ |
| 658. | $L^{102}$ | $L^{133}$ | $L^{179}$ |
| 659. | $L^{102}$ | $L^{134}$ | $L^{179}$ |
| 660. | $L^{102}$ | $L^{140}$ | $L^{179}$ |
| 661. | $L^{102}$ | $L^{141}$ | $L^{179}$ |
| 662. | $L^{102}$ | $L^{159}$ | $L^{179}$ |
| 663. | $L^{102}$ | $L^{160}$ | $L^{179}$ |
| 664. | $L^{102}$ | $L^{103}$ | $L^{180}$ |
| 665. | $L^{102}$ | $L^{104}$ | $L^{180}$ |
| 666. | $L^{102}$ | $L^{105}$ | $L^{180}$ |
| 667. | $L^{102}$ | $L^{106}$ | $L^{180}$ |
| 668. | $L^{102}$ | $L^{107}$ | $L^{180}$ |
| 669. | $L^{102}$ | $L^{108}$ | $L^{180}$ |
| 670. | $L^{102}$ | $L^{109}$ | $L^{180}$ |
| 671. | $L^{102}$ | $L^{110}$ | $L^{180}$ |
| 672. | $L^{102}$ | $L^{111}$ | $L^{180}$ |
| 673. | $L^{102}$ | $L^{112}$ | $L^{180}$ |
| 674. | $L^{102}$ | $L^{113}$ | $L^{180}$ |
| 675. | $L^{102}$ | $L^{114}$ | $L^{180}$ |
| 676. | $L^{102}$ | $L^{115}$ | $L^{180}$ |
| 677. | $L^{102}$ | $L^{116}$ | $L^{180}$ |
| 678. | $L^{102}$ | $L^{117}$ | $L^{180}$ |
| 679. | $L^{102}$ | $L^{118}$ | $L^{180}$ |
| 680. | $L^{102}$ | $L^{119}$ | $L^{180}$ |
| 681. | $L^{102}$ | $L^{130}$ | $L^{180}$ |
| 682. | $L^{102}$ | $L^{131}$ | $L^{180}$ |
| 683. | $L^{102}$ | $L^{132}$ | $L^{180}$ |
| 684. | $L^{102}$ | $L^{133}$ | $L^{180}$ |
| 685. | $L^{102}$ | $L^{134}$ | $L^{180}$ |
| 686. | $L^{102}$ | $L^{140}$ | $L^{180}$ |
| 687. | $L^{102}$ | $L^{141}$ | $L^{180}$ |
| 688. | $L^{102}$ | $L^{159}$ | $L^{180}$ |
| 689. | $L^{102}$ | $L^{160}$ | $L^{180}$ |
| 690. | $L^{103}$ | $L^{104}$ | $L^{144}$ |
| 691. | $L^{103}$ | $L^{105}$ | $L^{144}$ |
| 692. | $L^{103}$ | $L^{106}$ | $L^{144}$ |
| 693. | $L^{103}$ | $L^{107}$ | $L^{144}$ |
| 694. | $L^{103}$ | $L^{108}$ | $L^{144}$ |
| 695. | $L^{103}$ | $L^{109}$ | $L^{144}$ |
| 696. | $L^{103}$ | $L^{110}$ | $L^{144}$ |
| 697. | $L^{103}$ | $L^{111}$ | $L^{144}$ |
| 698. | $L^{103}$ | $L^{112}$ | $L^{144}$ |
| 699. | $L^{103}$ | $L^{113}$ | $L^{144}$ |
| 700. | $L^{103}$ | $L^{114}$ | $L^{144}$ |
| 701. | $L^{103}$ | $L^{115}$ | $L^{144}$ |
| 702. | $L^{103}$ | $L^{116}$ | $L^{144}$ |
| 703. | $L^{103}$ | $L^{117}$ | $L^{144}$ |
| 704. | $L^{103}$ | $L^{118}$ | $L^{144}$ |
| 705. | $L^{103}$ | $L^{119}$ | $L^{144}$ |
| 706. | $L^{103}$ | $L^{130}$ | $L^{144}$ |
| 707. | $L^{103}$ | $L^{131}$ | $L^{144}$ |
| 708. | $L^{103}$ | $L^{132}$ | $L^{144}$ |
| 709. | $L^{103}$ | $L^{133}$ | $L^{144}$ |
| 710. | $L^{103}$ | $L^{134}$ | $L^{144}$ |
| 711. | $L^{103}$ | $L^{140}$ | $L^{144}$ |
| 712. | $L^{103}$ | $L^{141}$ | $L^{144}$ |
| 713. | $L^{103}$ | $L^{159}$ | $L^{144}$ |
| 714. | $L^{103}$ | $L^{160}$ | $L^{144}$ |
| 715. | $L^{103}$ | $L^{104}$ | $L^{145}$ |
| 716. | $L^{103}$ | $L^{105}$ | $L^{145}$ |
| 717. | $L^{103}$ | $L^{106}$ | $L^{145}$ |
| 718. | $L^{103}$ | $L^{107}$ | $L^{145}$ |
| 719. | $L^{103}$ | $L^{108}$ | $L^{145}$ |
| 720. | $L^{103}$ | $L^{109}$ | $L^{145}$ |
| 721. | $L^{103}$ | $L^{110}$ | $L^{145}$ |
| 722. | $L^{103}$ | $L^{111}$ | $L^{145}$ |
| 723. | $L^{103}$ | $L^{112}$ | $L^{145}$ |
| 724. | $L^{103}$ | $L^{113}$ | $L^{145}$ |
| 725. | $L^{103}$ | $L^{114}$ | $L^{145}$ |
| 726. | $L^{103}$ | $L^{115}$ | $L^{145}$ |
| 727. | $L^{103}$ | $L^{116}$ | $L^{145}$ |
| 728. | $L^{103}$ | $L^{117}$ | $L^{145}$ |
| 729. | $L^{103}$ | $L^{118}$ | $L^{145}$ |
| 730. | $L^{103}$ | $L^{119}$ | $L^{145}$ |
| 731. | $L^{103}$ | $L^{130}$ | $L^{145}$ |
| 732. | $L^{103}$ | $L^{131}$ | $L^{145}$ |
| 733. | $L^{103}$ | $L^{132}$ | $L^{145}$ |
| 734. | $L^{103}$ | $L^{133}$ | $L^{145}$ |
| 735. | $L^{103}$ | $L^{134}$ | $L^{145}$ |
| 736. | $L^{103}$ | $L^{140}$ | $L^{145}$ |
| 737. | $L^{103}$ | $L^{141}$ | $L^{145}$ |
| 738. | $L^{103}$ | $L^{159}$ | $L^{145}$ |
| 739. | $L^{103}$ | $L^{160}$ | $L^{145}$ |
| 740. | $L^{103}$ | $L^{104}$ | $L^{147}$ |
| 741. | $L^{103}$ | $L^{105}$ | $L^{147}$ |
| 742. | $L^{103}$ | $L^{106}$ | $L^{147}$ |
| 743. | $L^{103}$ | $L^{107}$ | $L^{147}$ |
| 744. | $L^{103}$ | $L^{108}$ | $L^{147}$ |
| 745. | $L^{103}$ | $L^{109}$ | $L^{147}$ |
| 746. | $L^{103}$ | $L^{110}$ | $L^{147}$ |
| 747. | $L^{103}$ | $L^{111}$ | $L^{147}$ |
| 748. | $L^{103}$ | $L^{112}$ | $L^{147}$ |
| 749. | $L^{103}$ | $L^{113}$ | $L^{147}$ |
| 750. | $L^{103}$ | $L^{114}$ | $L^{147}$ |
| 751. | $L^{103}$ | $L^{115}$ | $L^{147}$ |
| 752. | $L^{103}$ | $L^{116}$ | $L^{147}$ |
| 753. | $L^{103}$ | $L^{117}$ | $L^{147}$ |
| 754. | $L^{103}$ | $L^{118}$ | $L^{147}$ |
| 755. | $L^{103}$ | $L^{119}$ | $L^{147}$ |
| 756. | $L^{103}$ | $L^{130}$ | $L^{147}$ |
| 757. | $L^{103}$ | $L^{131}$ | $L^{147}$ |
| 758. | $L^{103}$ | $L^{132}$ | $L^{147}$ |
| 759. | $L^{103}$ | $L^{133}$ | $L^{147}$ |
| 760. | $L^{103}$ | $L^{134}$ | $L^{147}$ |
| 761. | $L^{103}$ | $L^{140}$ | $L^{147}$ |
| 762. | $L^{103}$ | $L^{141}$ | $L^{147}$ |
| 763. | $L^{103}$ | $L^{159}$ | $L^{147}$ |
| 764. | $L^{103}$ | $L^{160}$ | $L^{147}$ |
| 765. | $L^{103}$ | $L^{104}$ | $L^{149}$ |
| 766. | $L^{103}$ | $L^{105}$ | $L^{149}$ |
| 767. | $L^{103}$ | $L^{106}$ | $L^{149}$ |
| 768. | $L^{103}$ | $L^{107}$ | $L^{149}$ |
| 769. | $L^{103}$ | $L^{108}$ | $L^{149}$ |
| 770. | $L^{103}$ | $L^{109}$ | $L^{149}$ |
| 771. | $L^{103}$ | $L^{110}$ | $L^{149}$ |
| 772. | $L^{103}$ | $L^{111}$ | $L^{149}$ |
| 773. | $L^{103}$ | $L^{112}$ | $L^{149}$ |
| 774. | $L^{103}$ | $L^{113}$ | $L^{149}$ |
| 775. | $L^{103}$ | $L^{114}$ | $L^{149}$ |
| 776. | $L^{103}$ | $L^{115}$ | $L^{149}$ |
| 777. | $L^{103}$ | $L^{116}$ | $L^{149}$ |
| 778. | $L^{103}$ | $L^{117}$ | $L^{149}$ |
| 779. | $L^{103}$ | $L^{118}$ | $L^{149}$ |
| 780. | $L^{103}$ | $L^{119}$ | $L^{149}$ |
| 781. | $L^{103}$ | $L^{130}$ | $L^{149}$ |

TABLE 1-continued

| Compound number | $L_1$ | $L_2$ | $L_3$ |
|---|---|---|---|
| 782. | $L^{103}$ | $L^{131}$ | $L^{149}$ |
| 783. | $L^{103}$ | $L^{132}$ | $L^{149}$ |
| 784. | $L^{103}$ | $L^{133}$ | $L^{149}$ |
| 785. | $L^{103}$ | $L^{134}$ | $L^{149}$ |
| 786. | $L^{103}$ | $L^{140}$ | $L^{149}$ |
| 787. | $L^{103}$ | $L^{141}$ | $L^{149}$ |
| 788. | $L^{103}$ | $L^{159}$ | $L^{149}$ |
| 789. | $L^{103}$ | $L^{160}$ | $L^{149}$ |
| 790. | $L^{103}$ | $L^{104}$ | $L^{152}$ |
| 791. | $L^{103}$ | $L^{105}$ | $L^{152}$ |
| 792. | $L^{103}$ | $L^{106}$ | $L^{152}$ |
| 793. | $L^{103}$ | $L^{107}$ | $L^{152}$ |
| 794. | $L^{103}$ | $L^{108}$ | $L^{152}$ |
| 795. | $L^{103}$ | $L^{109}$ | $L^{152}$ |
| 796. | $L^{103}$ | $L^{110}$ | $L^{152}$ |
| 797. | $L^{103}$ | $L^{111}$ | $L^{152}$ |
| 798. | $L^{103}$ | $L^{112}$ | $L^{152}$ |
| 799. | $L^{103}$ | $L^{113}$ | $L^{152}$ |
| 800. | $L^{103}$ | $L^{114}$ | $L^{152}$ |
| 801. | $L^{103}$ | $L^{115}$ | $L^{152}$ |
| 802. | $L^{103}$ | $L^{116}$ | $L^{152}$ |
| 803. | $L^{103}$ | $L^{117}$ | $L^{152}$ |
| 804. | $L^{103}$ | $L^{118}$ | $L^{152}$ |
| 805. | $L^{103}$ | $L^{119}$ | $L^{152}$ |
| 806. | $L^{103}$ | $L^{130}$ | $L^{152}$ |
| 807. | $L^{103}$ | $L^{131}$ | $L^{152}$ |
| 808. | $L^{103}$ | $L^{132}$ | $L^{152}$ |
| 809. | $L^{103}$ | $L^{133}$ | $L^{152}$ |
| 810. | $L^{103}$ | $L^{134}$ | $L^{152}$ |
| 811. | $L^{103}$ | $L^{140}$ | $L^{152}$ |
| 812. | $L^{103}$ | $L^{141}$ | $L^{152}$ |
| 813. | $L^{103}$ | $L^{159}$ | $L^{152}$ |
| 814. | $L^{103}$ | $L^{160}$ | $L^{152}$ |
| 815. | $L^{103}$ | $L^{104}$ | $L^{164}$ |
| 816. | $L^{103}$ | $L^{105}$ | $L^{164}$ |
| 817. | $L^{103}$ | $L^{106}$ | $L^{164}$ |
| 818. | $L^{103}$ | $L^{107}$ | $L^{164}$ |
| 819. | $L^{103}$ | $L^{108}$ | $L^{164}$ |
| 820. | $L^{103}$ | $L^{109}$ | $L^{164}$ |
| 821. | $L^{103}$ | $L^{110}$ | $L^{164}$ |
| 822. | $L^{103}$ | $L^{111}$ | $L^{164}$ |
| 823. | $L^{103}$ | $L^{112}$ | $L^{164}$ |
| 824. | $L^{103}$ | $L^{113}$ | $L^{164}$ |
| 825. | $L^{103}$ | $L^{114}$ | $L^{164}$ |
| 826. | $L^{103}$ | $L^{115}$ | $L^{164}$ |
| 827. | $L^{103}$ | $L^{116}$ | $L^{164}$ |
| 828. | $L^{103}$ | $L^{117}$ | $L^{164}$ |
| 829. | $L^{103}$ | $L^{118}$ | $L^{164}$ |
| 830. | $L^{103}$ | $L^{119}$ | $L^{164}$ |
| 831. | $L^{103}$ | $L^{130}$ | $L^{164}$ |
| 832. | $L^{103}$ | $L^{131}$ | $L^{164}$ |
| 833. | $L^{103}$ | $L^{132}$ | $L^{164}$ |
| 834. | $L^{103}$ | $L^{133}$ | $L^{164}$ |
| 835. | $L^{103}$ | $L^{134}$ | $L^{164}$ |
| 836. | $L^{103}$ | $L^{140}$ | $L^{164}$ |
| 837. | $L^{103}$ | $L^{141}$ | $L^{164}$ |
| 838. | $L^{103}$ | $L^{159}$ | $L^{164}$ |
| 839. | $L^{103}$ | $L^{160}$ | $L^{164}$ |
| 840. | $L^{103}$ | $L^{104}$ | $L^{165}$ |
| 841. | $L^{103}$ | $L^{105}$ | $L^{165}$ |
| 842. | $L^{103}$ | $L^{106}$ | $L^{165}$ |
| 843. | $L^{103}$ | $L^{107}$ | $L^{165}$ |
| 844. | $L^{103}$ | $L^{108}$ | $L^{165}$ |
| 845. | $L^{103}$ | $L^{109}$ | $L^{165}$ |
| 846. | $L^{103}$ | $L^{110}$ | $L^{165}$ |
| 847. | $L^{103}$ | $L^{111}$ | $L^{165}$ |
| 848. | $L^{103}$ | $L^{112}$ | $L^{165}$ |
| 849. | $L^{103}$ | $L^{113}$ | $L^{165}$ |
| 850. | $L^{103}$ | $L^{114}$ | $L^{165}$ |
| 851. | $L^{103}$ | $L^{115}$ | $L^{165}$ |
| 852. | $L^{103}$ | $L^{116}$ | $L^{165}$ |
| 853. | $L^{103}$ | $L^{117}$ | $L^{165}$ |
| 854. | $L^{103}$ | $L^{118}$ | $L^{165}$ |
| 855. | $L^{103}$ | $L^{119}$ | $L^{165}$ |
| 856. | $L^{103}$ | $L^{130}$ | $L^{165}$ |
| 857. | $L^{103}$ | $L^{131}$ | $L^{165}$ |
| 858. | $L^{103}$ | $L^{132}$ | $L^{165}$ |
| 859. | $L^{103}$ | $L^{133}$ | $L^{165}$ |
| 860. | $L^{103}$ | $L^{134}$ | $L^{165}$ |
| 861. | $L^{103}$ | $L^{140}$ | $L^{165}$ |
| 862. | $L^{103}$ | $L^{141}$ | $L^{165}$ |
| 863. | $L^{103}$ | $L^{159}$ | $L^{165}$ |
| 864. | $L^{103}$ | $L^{160}$ | $L^{165}$ |
| 865. | $L^{103}$ | $L^{104}$ | $L^{166}$ |
| 866. | $L^{103}$ | $L^{105}$ | $L^{166}$ |
| 867. | $L^{103}$ | $L^{106}$ | $L^{166}$ |
| 868. | $L^{103}$ | $L^{107}$ | $L^{166}$ |
| 869. | $L^{103}$ | $L^{108}$ | $L^{166}$ |
| 870. | $L^{103}$ | $L^{109}$ | $L^{166}$ |
| 871. | $L^{103}$ | $L^{110}$ | $L^{166}$ |
| 872. | $L^{103}$ | $L^{111}$ | $L^{166}$ |
| 873. | $L^{103}$ | $L^{112}$ | $L^{166}$ |
| 874. | $L^{103}$ | $L^{113}$ | $L^{166}$ |
| 875. | $L^{103}$ | $L^{114}$ | $L^{166}$ |
| 876. | $L^{103}$ | $L^{115}$ | $L^{166}$ |
| 877. | $L^{103}$ | $L^{116}$ | $L^{166}$ |
| 878. | $L^{103}$ | $L^{117}$ | $L^{166}$ |
| 879. | $L^{103}$ | $L^{118}$ | $L^{166}$ |
| 880. | $L^{103}$ | $L^{119}$ | $L^{166}$ |
| 881. | $L^{103}$ | $L^{130}$ | $L^{166}$ |
| 882. | $L^{103}$ | $L^{131}$ | $L^{166}$ |
| 883. | $L^{103}$ | $L^{132}$ | $L^{166}$ |
| 884. | $L^{103}$ | $L^{133}$ | $L^{166}$ |
| 885. | $L^{103}$ | $L^{134}$ | $L^{166}$ |
| 886. | $L^{103}$ | $L^{140}$ | $L^{166}$ |
| 887. | $L^{103}$ | $L^{141}$ | $L^{166}$ |
| 888. | $L^{103}$ | $L^{159}$ | $L^{166}$ |
| 889. | $L^{103}$ | $L^{160}$ | $L^{166}$ |
| 890. | $L^{103}$ | $L^{104}$ | $L^{170}$ |
| 891. | $L^{103}$ | $L^{105}$ | $L^{170}$ |
| 892. | $L^{103}$ | $L^{106}$ | $L^{170}$ |
| 893. | $L^{103}$ | $L^{107}$ | $L^{170}$ |
| 894. | $L^{103}$ | $L^{108}$ | $L^{170}$ |
| 895. | $L^{103}$ | $L^{109}$ | $L^{170}$ |
| 896. | $L^{103}$ | $L^{110}$ | $L^{170}$ |
| 897. | $L^{103}$ | $L^{111}$ | $L^{170}$ |
| 898. | $L^{103}$ | $L^{112}$ | $L^{170}$ |
| 899. | $L^{103}$ | $L^{113}$ | $L^{170}$ |
| 900. | $L^{103}$ | $L^{114}$ | $L^{170}$ |
| 901. | $L^{103}$ | $L^{115}$ | $L^{170}$ |
| 902. | $L^{103}$ | $L^{116}$ | $L^{170}$ |
| 903. | $L^{103}$ | $L^{117}$ | $L^{170}$ |
| 904. | $L^{103}$ | $L^{118}$ | $L^{170}$ |
| 905. | $L^{103}$ | $L^{119}$ | $L^{170}$ |
| 906. | $L^{103}$ | $L^{130}$ | $L^{170}$ |
| 907. | $L^{103}$ | $L^{131}$ | $L^{170}$ |
| 908. | $L^{103}$ | $L^{132}$ | $L^{170}$ |
| 909. | $L^{103}$ | $L^{133}$ | $L^{170}$ |
| 910. | $L^{103}$ | $L^{134}$ | $L^{170}$ |
| 911. | $L^{103}$ | $L^{140}$ | $L^{170}$ |
| 912. | $L^{103}$ | $L^{141}$ | $L^{170}$ |
| 913. | $L^{103}$ | $L^{159}$ | $L^{170}$ |
| 914. | $L^{103}$ | $L^{160}$ | $L^{170}$ |
| 915. | $L^{103}$ | $L^{104}$ | $L^{174}$ |
| 916. | $L^{103}$ | $L^{105}$ | $L^{174}$ |
| 917. | $L^{103}$ | $L^{106}$ | $L^{174}$ |
| 918. | $L^{103}$ | $L^{107}$ | $L^{174}$ |
| 919. | $L^{103}$ | $L^{108}$ | $L^{174}$ |
| 920. | $L^{103}$ | $L^{109}$ | $L^{174}$ |
| 921. | $L^{103}$ | $L^{110}$ | $L^{174}$ |
| 922. | $L^{103}$ | $L^{111}$ | $L^{174}$ |
| 923. | $L^{103}$ | $L^{112}$ | $L^{174}$ |
| 924. | $L^{103}$ | $L^{113}$ | $L^{174}$ |
| 925. | $L^{103}$ | $L^{114}$ | $L^{174}$ |
| 926. | $L^{103}$ | $L^{115}$ | $L^{174}$ |
| 927. | $L^{103}$ | $L^{116}$ | $L^{174}$ |
| 928. | $L^{103}$ | $L^{117}$ | $L^{174}$ |
| 929. | $L^{103}$ | $L^{118}$ | $L^{174}$ |
| 930. | $L^{103}$ | $L^{119}$ | $L^{174}$ |
| 931. | $L^{103}$ | $L^{130}$ | $L^{174}$ |
| 932. | $L^{103}$ | $L^{131}$ | $L^{174}$ |
| 933. | $L^{103}$ | $L^{132}$ | $L^{174}$ |
| 934. | $L^{103}$ | $L^{133}$ | $L^{174}$ |
| 935. | $L^{103}$ | $L^{134}$ | $L^{174}$ |

TABLE 1-continued

| Compound number | $L_1$ | $L_2$ | $L_3$ |
|---|---|---|---|
| 936. | $L^{103}$ | $L^{140}$ | $L^{174}$ |
| 937. | $L^{103}$ | $L^{141}$ | $L^{174}$ |
| 938. | $L^{103}$ | $L^{159}$ | $L^{174}$ |
| 939. | $L^{103}$ | $L^{160}$ | $L^{174}$ |
| 940. | $L^{103}$ | $L^{104}$ | $L^{176}$ |
| 941. | $L^{103}$ | $L^{105}$ | $L^{176}$ |
| 942. | $L^{103}$ | $L^{106}$ | $L^{176}$ |
| 943. | $L^{103}$ | $L^{107}$ | $L^{176}$ |
| 944. | $L^{103}$ | $L^{108}$ | $L^{176}$ |
| 945. | $L^{103}$ | $L^{109}$ | $L^{176}$ |
| 946. | $L^{103}$ | $L^{110}$ | $L^{176}$ |
| 947. | $L^{103}$ | $L^{111}$ | $L^{176}$ |
| 948. | $L^{103}$ | $L^{112}$ | $L^{176}$ |
| 949. | $L^{103}$ | $L^{113}$ | $L^{176}$ |
| 950. | $L^{103}$ | $L^{114}$ | $L^{176}$ |
| 951. | $L^{103}$ | $L^{115}$ | $L^{176}$ |
| 952. | $L^{103}$ | $L^{116}$ | $L^{176}$ |
| 953. | $L^{103}$ | $L^{117}$ | $L^{176}$ |
| 954. | $L^{103}$ | $L^{118}$ | $L^{176}$ |
| 955. | $L^{103}$ | $L^{119}$ | $L^{176}$ |
| 956. | $L^{103}$ | $L^{130}$ | $L^{176}$ |
| 957. | $L^{103}$ | $L^{131}$ | $L^{176}$ |
| 958. | $L^{103}$ | $L^{132}$ | $L^{176}$ |
| 959. | $L^{103}$ | $L^{133}$ | $L^{176}$ |
| 960. | $L^{103}$ | $L^{134}$ | $L^{176}$ |
| 961. | $L^{103}$ | $L^{140}$ | $L^{176}$ |
| 962. | $L^{103}$ | $L^{141}$ | $L^{176}$ |
| 963. | $L^{103}$ | $L^{159}$ | $L^{176}$ |
| 964. | $L^{103}$ | $L^{160}$ | $L^{176}$ |
| 965. | $L^{103}$ | $L^{104}$ | $L^{179}$ |
| 966. | $L^{103}$ | $L^{105}$ | $L^{179}$ |
| 967. | $L^{103}$ | $L^{106}$ | $L^{179}$ |
| 968. | $L^{103}$ | $L^{107}$ | $L^{179}$ |
| 969. | $L^{103}$ | $L^{108}$ | $L^{179}$ |
| 970. | $L^{103}$ | $L^{109}$ | $L^{179}$ |
| 971. | $L^{103}$ | $L^{110}$ | $L^{179}$ |
| 972. | $L^{103}$ | $L^{111}$ | $L^{179}$ |
| 973. | $L^{103}$ | $L^{112}$ | $L^{179}$ |
| 974. | $L^{103}$ | $L^{113}$ | $L^{179}$ |
| 975. | $L^{103}$ | $L^{114}$ | $L^{179}$ |
| 976. | $L^{103}$ | $L^{115}$ | $L^{179}$ |
| 977. | $L^{103}$ | $L^{116}$ | $L^{179}$ |
| 978. | $L^{103}$ | $L^{117}$ | $L^{179}$ |
| 979. | $L^{103}$ | $L^{118}$ | $L^{179}$ |
| 980. | $L^{103}$ | $L^{119}$ | $L^{179}$ |
| 981. | $L^{103}$ | $L^{130}$ | $L^{179}$ |
| 982. | $L^{103}$ | $L^{131}$ | $L^{179}$ |
| 983. | $L^{103}$ | $L^{132}$ | $L^{179}$ |
| 984. | $L^{103}$ | $L^{133}$ | $L^{179}$ |
| 985. | $L^{103}$ | $L^{134}$ | $L^{179}$ |
| 986. | $L^{103}$ | $L^{140}$ | $L^{179}$ |
| 987. | $L^{103}$ | $L^{141}$ | $L^{179}$ |
| 988. | $L^{103}$ | $L^{159}$ | $L^{179}$ |
| 989. | $L^{103}$ | $L^{160}$ | $L^{179}$ |
| 990. | $L^{103}$ | $L^{104}$ | $L^{180}$ |
| 991. | $L^{103}$ | $L^{105}$ | $L^{180}$ |
| 992. | $L^{103}$ | $L^{106}$ | $L^{180}$ |
| 993. | $L^{103}$ | $L^{107}$ | $L^{180}$ |
| 994. | $L^{103}$ | $L^{108}$ | $L^{180}$ |
| 995. | $L^{103}$ | $L^{109}$ | $L^{180}$ |
| 996. | $L^{103}$ | $L^{110}$ | $L^{180}$ |
| 997. | $L^{103}$ | $L^{111}$ | $L^{180}$ |
| 998. | $L^{103}$ | $L^{112}$ | $L^{180}$ |
| 999. | $L^{103}$ | $L^{113}$ | $L^{180}$ |
| 1000. | $L^{103}$ | $L^{114}$ | $L^{180}$ |
| 1001 | $L^{103}$ | $L^{115}$ | $L^{180}$ |
| 1002. | $L^{103}$ | $L^{116}$ | $L^{180}$ |
| 1003. | $L^{103}$ | $L^{117}$ | $L^{180}$ |
| 1004. | $L^{103}$ | $L^{118}$ | $L^{180}$ |
| 1005. | $L^{103}$ | $L^{119}$ | $L^{180}$ |
| 1006. | $L^{103}$ | $L^{130}$ | $L^{180}$ |
| 1007. | $L^{103}$ | $L^{131}$ | $L^{180}$ |
| 1008. | $L^{103}$ | $L^{132}$ | $L^{180}$ |
| 1009. | $L^{103}$ | $L^{133}$ | $L^{180}$ |
| 1010 | $L^{103}$ | $L^{134}$ | $L^{180}$ |
| 1011 | $L^{103}$ | $L^{140}$ | $L^{180}$ |
| 1012. | $L^{103}$ | $L^{141}$ | $L^{180}$ |
| 1013. | $L^{103}$ | $L^{159}$ | $L^{180}$ |
| 1014. | $L^{103}$ | $L^{160}$ | $L^{180}$ |
| 1015. | $L^{104}$ | $L^{105}$ | $L^{144}$ |
| 1016. | $L^{104}$ | $L^{106}$ | $L^{144}$ |
| 1017. | $L^{104}$ | $L^{107}$ | $L^{144}$ |
| 1018. | $L^{104}$ | $L^{108}$ | $L^{144}$ |
| 1019. | $L^{104}$ | $L^{109}$ | $L^{144}$ |
| 1020. | $L^{104}$ | $L^{110}$ | $L^{144}$ |
| 1021. | $L^{104}$ | $L^{111}$ | $L^{144}$ |
| 1022. | $L^{104}$ | $L^{112}$ | $L^{144}$ |
| 1023. | $L^{104}$ | $L^{113}$ | $L^{144}$ |
| 1024. | $L^{104}$ | $L^{114}$ | $L^{144}$ |
| 1025. | $L^{104}$ | $L^{115}$ | $L^{144}$ |
| 1026. | $L^{104}$ | $L^{116}$ | $L^{144}$ |
| 1027. | $L^{104}$ | $L^{117}$ | $L^{144}$ |
| 1028. | $L^{104}$ | $L^{118}$ | $L^{144}$ |
| 1029. | $L^{104}$ | $L^{119}$ | $L^{144}$ |
| 1030. | $L^{104}$ | $L^{130}$ | $L^{144}$ |
| 1031. | $L^{104}$ | $L^{131}$ | $L^{144}$ |
| 1032. | $L^{104}$ | $L^{132}$ | $L^{144}$ |
| 1033. | $L^{104}$ | $L^{133}$ | $L^{144}$ |
| 1034. | $L^{104}$ | $L^{134}$ | $L^{144}$ |
| 1035. | $L^{104}$ | $L^{140}$ | $L^{144}$ |
| 1036. | $L^{104}$ | $L^{141}$ | $L^{144}$ |
| 1037. | $L^{104}$ | $L^{159}$ | $L^{144}$ |
| 1038. | $L^{104}$ | $L^{160}$ | $L^{144}$ |
| 1039. | $L^{104}$ | $L^{105}$ | $L^{145}$ |
| 1040. | $L^{104}$ | $L^{106}$ | $L^{145}$ |
| 1041. | $L^{104}$ | $L^{107}$ | $L^{145}$ |
| 1042. | $L^{104}$ | $L^{108}$ | $L^{145}$ |
| 1043. | $L^{104}$ | $L^{109}$ | $L^{145}$ |
| 1044. | $L^{104}$ | $L^{110}$ | $L^{145}$ |
| 1045. | $L^{104}$ | $L^{111}$ | $L^{145}$ |
| 1046. | $L^{104}$ | $L^{112}$ | $L^{145}$ |
| 1047. | $L^{104}$ | $L^{113}$ | $L^{145}$ |
| 1048. | $L^{104}$ | $L^{114}$ | $L^{145}$ |
| 1049. | $L^{104}$ | $L^{115}$ | $L^{145}$ |
| 1050. | $L^{104}$ | $L^{116}$ | $L^{145}$ |
| 1051. | $L^{104}$ | $L^{117}$ | $L^{145}$ |
| 1052. | $L^{104}$ | $L^{118}$ | $L^{145}$ |
| 1053. | $L^{104}$ | $L^{119}$ | $L^{145}$ |
| 1054. | $L^{104}$ | $L^{130}$ | $L^{145}$ |
| 1055. | $L^{104}$ | $L^{131}$ | $L^{145}$ |
| 1056. | $L^{104}$ | $L^{132}$ | $L^{145}$ |
| 1057. | $L^{104}$ | $L^{133}$ | $L^{145}$ |
| 1058. | $L^{104}$ | $L^{134}$ | $L^{145}$ |
| 1059. | $L^{104}$ | $L^{140}$ | $L^{145}$ |
| 1060. | $L^{104}$ | $L^{141}$ | $L^{145}$ |
| 1061. | $L^{104}$ | $L^{159}$ | $L^{145}$ |
| 1062. | $L^{104}$ | $L^{160}$ | $L^{145}$ |
| 1063. | $L^{104}$ | $L^{105}$ | $L^{147}$ |
| 1064. | $L^{104}$ | $L^{106}$ | $L^{147}$ |
| 1065. | $L^{104}$ | $L^{107}$ | $L^{147}$ |
| 1066. | $L^{104}$ | $L^{108}$ | $L^{147}$ |
| 1067. | $L^{104}$ | $L^{109}$ | $L^{147}$ |
| 1068. | $L^{104}$ | $L^{110}$ | $L^{147}$ |
| 1069. | $L^{104}$ | $L^{111}$ | $L^{147}$ |
| 1070. | $L^{104}$ | $L^{112}$ | $L^{147}$ |
| 1071. | $L^{104}$ | $L^{113}$ | $L^{147}$ |
| 1072. | $L^{104}$ | $L^{114}$ | $L^{147}$ |
| 1073. | $L^{104}$ | $L^{115}$ | $L^{147}$ |
| 1074. | $L^{104}$ | $L^{116}$ | $L^{147}$ |
| 1075. | $L^{104}$ | $L^{117}$ | $L^{147}$ |
| 1076. | $L^{104}$ | $L^{118}$ | $L^{147}$ |
| 1077. | $L^{104}$ | $L^{119}$ | $L^{147}$ |
| 1078. | $L^{104}$ | $L^{130}$ | $L^{147}$ |
| 1079. | $L^{104}$ | $L^{131}$ | $L^{147}$ |
| 1080. | $L^{104}$ | $L^{132}$ | $L^{147}$ |
| 1081. | $L^{104}$ | $L^{133}$ | $L^{147}$ |
| 1082. | $L^{104}$ | $L^{134}$ | $L^{147}$ |
| 1083. | $L^{104}$ | $L^{140}$ | $L^{147}$ |
| 1084. | $L^{104}$ | $L^{141}$ | $L^{147}$ |
| 1085. | $L^{104}$ | $L^{159}$ | $L^{147}$ |
| 1086. | $L^{104}$ | $L^{160}$ | $L^{147}$ |
| 1087. | $L^{104}$ | $L^{105}$ | $L^{149}$ |
| 1088. | $L^{104}$ | $L^{106}$ | $L^{149}$ |
| 1089. | $L^{104}$ | $L^{107}$ | $L^{149}$ |

TABLE 1-continued

| Compound number | $L_1$ | $L_2$ | $L_3$ |
|---|---|---|---|
| 1090. | $L^{104}$ | $L^{108}$ | $L^{149}$ |
| 1091. | $L^{104}$ | $L^{109}$ | $L^{149}$ |
| 1092. | $L^{104}$ | $L^{110}$ | $L^{149}$ |
| 1093. | $L^{104}$ | $L^{111}$ | $L^{149}$ |
| 1094. | $L^{104}$ | $L^{112}$ | $L^{149}$ |
| 1095. | $L^{104}$ | $L^{113}$ | $L^{149}$ |
| 1096. | $L^{104}$ | $L^{114}$ | $L^{149}$ |
| 1097. | $L^{104}$ | $L^{115}$ | $L^{149}$ |
| 1098. | $L^{104}$ | $L^{116}$ | $L^{149}$ |
| 1099. | $L^{104}$ | $L^{117}$ | $L^{149}$ |
| 1100. | $L^{104}$ | $L^{118}$ | $L^{149}$ |
| 1101. | $L^{104}$ | $L^{119}$ | $L^{149}$ |
| 1102. | $L^{104}$ | $L^{130}$ | $L^{149}$ |
| 1103. | $L^{104}$ | $L^{131}$ | $L^{149}$ |
| 1104. | $L^{104}$ | $L^{132}$ | $L^{149}$ |
| 1105. | $L^{104}$ | $L^{133}$ | $L^{149}$ |
| 1106. | $L^{104}$ | $L^{134}$ | $L^{149}$ |
| 1107. | $L^{104}$ | $L^{140}$ | $L^{149}$ |
| 1108. | $L^{104}$ | $L^{141}$ | $L^{149}$ |
| 1109. | $L^{104}$ | $L^{159}$ | $L^{149}$ |
| 1110. | $L^{104}$ | $L^{160}$ | $L^{149}$ |
| 1111. | $L^{104}$ | $L^{105}$ | $L^{152}$ |
| 1112. | $L^{104}$ | $L^{106}$ | $L^{152}$ |
| 1113. | $L^{104}$ | $L^{107}$ | $L^{152}$ |
| 1114. | $L^{104}$ | $L^{108}$ | $L^{152}$ |
| 1115. | $L^{104}$ | $L^{109}$ | $L^{152}$ |
| 1116. | $L^{104}$ | $L^{110}$ | $L^{152}$ |
| 1117. | $L^{104}$ | $L^{111}$ | $L^{152}$ |
| 1118. | $L^{104}$ | $L^{112}$ | $L^{152}$ |
| 1119. | $L^{104}$ | $L^{113}$ | $L^{152}$ |
| 1120. | $L^{104}$ | $L^{114}$ | $L^{152}$ |
| 1121. | $L^{104}$ | $L^{115}$ | $L^{152}$ |
| 1122. | $L^{104}$ | $L^{116}$ | $L^{152}$ |
| 1123. | $L^{104}$ | $L^{117}$ | $L^{152}$ |
| 1124. | $L^{104}$ | $L^{118}$ | $L^{152}$ |
| 1125. | $L^{104}$ | $L^{119}$ | $L^{152}$ |
| 1126. | $L^{104}$ | $L^{130}$ | $L^{152}$ |
| 1127. | $L^{104}$ | $L^{131}$ | $L^{152}$ |
| 1128. | $L^{104}$ | $L^{132}$ | $L^{152}$ |
| 1129. | $L^{104}$ | $L^{133}$ | $L^{152}$ |
| 1130. | $L^{104}$ | $L^{134}$ | $L^{152}$ |
| 1131. | $L^{104}$ | $L^{140}$ | $L^{152}$ |
| 1132. | $L^{104}$ | $L^{141}$ | $L^{152}$ |
| 1133. | $L^{104}$ | $L^{159}$ | $L^{152}$ |
| 1134. | $L^{104}$ | $L^{160}$ | $L^{152}$ |
| 1135. | $L^{104}$ | $L^{105}$ | $L^{164}$ |
| 1136. | $L^{104}$ | $L^{106}$ | $L^{164}$ |
| 1137. | $L^{104}$ | $L^{107}$ | $L^{164}$ |
| 1138. | $L^{104}$ | $L^{108}$ | $L^{164}$ |
| 1139. | $L^{104}$ | $L^{109}$ | $L^{164}$ |
| 1140. | $L^{104}$ | $L^{110}$ | $L^{164}$ |
| 1141. | $L^{104}$ | $L^{111}$ | $L^{164}$ |
| 1142. | $L^{104}$ | $L^{112}$ | $L^{164}$ |
| 1143. | $L^{104}$ | $L^{113}$ | $L^{164}$ |
| 1144. | $L^{104}$ | $L^{114}$ | $L^{164}$ |
| 1145. | $L^{104}$ | $L^{115}$ | $L^{164}$ |
| 1146. | $L^{104}$ | $L^{116}$ | $L^{164}$ |
| 1147. | $L^{104}$ | $L^{117}$ | $L^{164}$ |
| 1148. | $L^{104}$ | $L^{118}$ | $L^{164}$ |
| 1149. | $L^{104}$ | $L^{119}$ | $L^{164}$ |
| 1150. | $L^{104}$ | $L^{130}$ | $L^{164}$ |
| 1151. | $L^{104}$ | $L^{131}$ | $L^{164}$ |
| 1152. | $L^{104}$ | $L^{132}$ | $L^{164}$ |
| 1153. | $L^{104}$ | $L^{133}$ | $L^{164}$ |
| 1154. | $L^{104}$ | $L^{134}$ | $L^{164}$ |
| 1155. | $L^{104}$ | $L^{140}$ | $L^{164}$ |
| 1156. | $L^{104}$ | $L^{141}$ | $L^{164}$ |
| 1157. | $L^{104}$ | $L^{159}$ | $L^{164}$ |
| 1158. | $L^{104}$ | $L^{160}$ | $L^{164}$ |
| 1159. | $L^{104}$ | $L^{105}$ | $L^{165}$ |
| 1160. | $L^{104}$ | $L^{106}$ | $L^{165}$ |
| 1161. | $L^{104}$ | $L^{107}$ | $L^{165}$ |
| 1162. | $L^{104}$ | $L^{108}$ | $L^{165}$ |
| 1163. | $L^{104}$ | $L^{109}$ | $L^{165}$ |
| 1164. | $L^{104}$ | $L^{110}$ | $L^{165}$ |
| 1165. | $L^{104}$ | $L^{111}$ | $L^{165}$ |
| 1166. | $L^{104}$ | $L^{112}$ | $L^{165}$ |
| 1167. | $L^{104}$ | $L^{113}$ | $L^{165}$ |
| 1168. | $L^{104}$ | $L^{114}$ | $L^{165}$ |
| 1169. | $L^{104}$ | $L^{115}$ | $L^{165}$ |
| 1170. | $L^{104}$ | $L^{116}$ | $L^{165}$ |
| 1171. | $L^{104}$ | $L^{117}$ | $L^{165}$ |
| 1172. | $L^{104}$ | $L^{118}$ | $L^{165}$ |
| 1173. | $L^{104}$ | $L^{119}$ | $L^{165}$ |
| 1174. | $L^{104}$ | $L^{130}$ | $L^{165}$ |
| 1175. | $L^{104}$ | $L^{131}$ | $L^{165}$ |
| 1176. | $L^{104}$ | $L^{132}$ | $L^{165}$ |
| 1177. | $L^{104}$ | $L^{133}$ | $L^{165}$ |
| 1178. | $L^{104}$ | $L^{134}$ | $L^{165}$ |
| 1179. | $L^{104}$ | $L^{140}$ | $L^{165}$ |
| 1180. | $L^{104}$ | $L^{141}$ | $L^{165}$ |
| 1181. | $L^{104}$ | $L^{159}$ | $L^{165}$ |
| 1182. | $L^{104}$ | $L^{160}$ | $L^{165}$ |
| 1183. | $L^{104}$ | $L^{105}$ | $L^{166}$ |
| 1184. | $L^{104}$ | $L^{106}$ | $L^{166}$ |
| 1185. | $L^{104}$ | $L^{107}$ | $L^{166}$ |
| 1186. | $L^{104}$ | $L^{108}$ | $L^{166}$ |
| 1187. | $L^{104}$ | $L^{109}$ | $L^{166}$ |
| 1188. | $L^{104}$ | $L^{110}$ | $L^{166}$ |
| 1189. | $L^{104}$ | $L^{111}$ | $L^{166}$ |
| 1190. | $L^{104}$ | $L^{112}$ | $L^{166}$ |
| 1191. | $L^{104}$ | $L^{113}$ | $L^{166}$ |
| 1192. | $L^{104}$ | $L^{114}$ | $L^{166}$ |
| 1193. | $L^{104}$ | $L^{115}$ | $L^{166}$ |
| 1194. | $L^{104}$ | $L^{116}$ | $L^{166}$ |
| 1195. | $L^{104}$ | $L^{117}$ | $L^{166}$ |
| 1196. | $L^{104}$ | $L^{118}$ | $L^{166}$ |
| 1197. | $L^{104}$ | $L^{119}$ | $L^{166}$ |
| 1198. | $L^{104}$ | $L^{130}$ | $L^{166}$ |
| 1199. | $L^{104}$ | $L^{131}$ | $L^{166}$ |
| 1200. | $L^{104}$ | $L^{132}$ | $L^{166}$ |
| 1201. | $L^{104}$ | $L^{133}$ | $L^{166}$ |
| 1202. | $L^{104}$ | $L^{134}$ | $L^{166}$ |
| 1203. | $L^{104}$ | $L^{140}$ | $L^{166}$ |
| 1204. | $L^{104}$ | $L^{141}$ | $L^{166}$ |
| 1205. | $L^{104}$ | $L^{159}$ | $L^{166}$ |
| 1206. | $L^{104}$ | $L^{160}$ | $L^{166}$ |
| 1207. | $L^{104}$ | $L^{105}$ | $L^{170}$ |
| 1208. | $L^{104}$ | $L^{106}$ | $L^{170}$ |
| 1209. | $L^{104}$ | $L^{107}$ | $L^{170}$ |
| 1210. | $L^{104}$ | $L^{108}$ | $L^{170}$ |
| 1211. | $L^{104}$ | $L^{109}$ | $L^{170}$ |
| 1212. | $L^{104}$ | $L^{110}$ | $L^{170}$ |
| 1213. | $L^{104}$ | $L^{111}$ | $L^{170}$ |
| 1214. | $L^{104}$ | $L^{112}$ | $L^{170}$ |
| 1215. | $L^{104}$ | $L^{113}$ | $L^{170}$ |
| 1216. | $L^{104}$ | $L^{114}$ | $L^{170}$ |
| 1217. | $L^{104}$ | $L^{115}$ | $L^{170}$ |
| 1218. | $L^{104}$ | $L^{116}$ | $L^{170}$ |
| 1219. | $L^{104}$ | $L^{117}$ | $L^{170}$ |
| 1220. | $L^{104}$ | $L^{118}$ | $L^{170}$ |
| 1221. | $L^{104}$ | $L^{119}$ | $L^{170}$ |
| 1222. | $L^{104}$ | $L^{130}$ | $L^{170}$ |
| 1223. | $L^{104}$ | $L^{131}$ | $L^{170}$ |
| 1224. | $L^{104}$ | $L^{132}$ | $L^{170}$ |
| 1225. | $L^{104}$ | $L^{133}$ | $L^{170}$ |
| 1226. | $L^{104}$ | $L^{134}$ | $L^{170}$ |
| 1227. | $L^{104}$ | $L^{140}$ | $L^{170}$ |
| 1228. | $L^{104}$ | $L^{141}$ | $L^{170}$ |
| 1229. | $L^{104}$ | $L^{159}$ | $L^{170}$ |
| 1230. | $L^{104}$ | $L^{160}$ | $L^{170}$ |
| 1231. | $L^{104}$ | $L^{105}$ | $L^{174}$ |
| 1232. | $L^{104}$ | $L^{106}$ | $L^{174}$ |
| 1233. | $L^{104}$ | $L^{107}$ | $L^{174}$ |
| 1234. | $L^{104}$ | $L^{108}$ | $L^{174}$ |
| 1235. | $L^{104}$ | $L^{109}$ | $L^{174}$ |
| 1236. | $L^{104}$ | $L^{110}$ | $L^{174}$ |
| 1237. | $L^{104}$ | $L^{111}$ | $L^{174}$ |
| 1238. | $L^{104}$ | $L^{112}$ | $L^{174}$ |
| 1239. | $L^{104}$ | $L^{113}$ | $L^{174}$ |
| 1240. | $L^{104}$ | $L^{114}$ | $L^{174}$ |
| 1241. | $L^{104}$ | $L^{115}$ | $L^{174}$ |
| 1242. | $L^{104}$ | $L^{116}$ | $L^{174}$ |
| 1243. | $L^{104}$ | $L^{117}$ | $L^{174}$ |

TABLE 1-continued

| Compound number | $L_1$ | $L_2$ | $L_3$ |
|---|---|---|---|
| 1244. | $L^{104}$ | $L^{118}$ | $L^{174}$ |
| 1245. | $L^{104}$ | $L^{119}$ | $L^{174}$ |
| 1246. | $L^{104}$ | $L^{130}$ | $L^{174}$ |
| 1247. | $L^{104}$ | $L^{131}$ | $L^{174}$ |
| 1248. | $L^{104}$ | $L^{132}$ | $L^{174}$ |
| 1249. | $L^{104}$ | $L^{133}$ | $L^{174}$ |
| 1250. | $L^{104}$ | $L^{134}$ | $L^{174}$ |
| 1251. | $L^{104}$ | $L^{140}$ | $L^{174}$ |
| 1252. | $L^{104}$ | $L^{141}$ | $L^{174}$ |
| 1253. | $L^{104}$ | $L^{159}$ | $L^{174}$ |
| 1254. | $L^{104}$ | $L^{160}$ | $L^{174}$ |
| 1255. | $L^{104}$ | $L^{105}$ | $L^{176}$ |
| 1256. | $L^{104}$ | $L^{106}$ | $L^{176}$ |
| 1257. | $L^{104}$ | $L^{107}$ | $L^{176}$ |
| 1258. | $L^{104}$ | $L^{108}$ | $L^{176}$ |
| 1259. | $L^{104}$ | $L^{109}$ | $L^{176}$ |
| 1260. | $L^{104}$ | $L^{110}$ | $L^{176}$ |
| 1261. | $L^{104}$ | $L^{111}$ | $L^{176}$ |
| 1262. | $L^{104}$ | $L^{112}$ | $L^{176}$ |
| 1263. | $L^{104}$ | $L^{113}$ | $L^{176}$ |
| 1264. | $L^{104}$ | $L^{114}$ | $L^{176}$ |
| 1265. | $L^{104}$ | $L^{115}$ | $L^{176}$ |
| 1266. | $L^{104}$ | $L^{116}$ | $L^{176}$ |
| 1267. | $L^{104}$ | $L^{117}$ | $L^{176}$ |
| 1268. | $L^{104}$ | $L^{118}$ | $L^{176}$ |
| 1269. | $L^{104}$ | $L^{119}$ | $L^{176}$ |
| 1270. | $L^{104}$ | $L^{130}$ | $L^{176}$ |
| 1271. | $L^{104}$ | $L^{131}$ | $L^{176}$ |
| 1272. | $L^{104}$ | $L^{132}$ | $L^{176}$ |
| 1273. | $L^{104}$ | $L^{133}$ | $L^{176}$ |
| 1274. | $L^{104}$ | $L^{134}$ | $L^{176}$ |
| 1275. | $L^{104}$ | $L^{140}$ | $L^{176}$ |
| 1276. | $L^{104}$ | $L^{141}$ | $L^{176}$ |
| 1277. | $L^{104}$ | $L^{159}$ | $L^{176}$ |
| 1278. | $L^{104}$ | $L^{160}$ | $L^{176}$ |
| 1279. | $L^{104}$ | $L^{105}$ | $L^{179}$ |
| 1280. | $L^{104}$ | $L^{106}$ | $L^{179}$ |
| 1281. | $L^{104}$ | $L^{107}$ | $L^{179}$ |
| 1282. | $L^{104}$ | $L^{108}$ | $L^{179}$ |
| 1283. | $L^{104}$ | $L^{109}$ | $L^{179}$ |
| 1284. | $L^{104}$ | $L^{110}$ | $L^{179}$ |
| 1285. | $L^{104}$ | $L^{111}$ | $L^{179}$ |
| 1286. | $L^{104}$ | $L^{112}$ | $L^{179}$ |
| 1287. | $L^{104}$ | $L^{113}$ | $L^{179}$ |
| 1288. | $L^{104}$ | $L^{114}$ | $L^{179}$ |
| 1289. | $L^{104}$ | $L^{115}$ | $L^{179}$ |
| 1290. | $L^{104}$ | $L^{116}$ | $L^{179}$ |
| 1291. | $L^{104}$ | $L^{117}$ | $L^{179}$ |
| 1292. | $L^{104}$ | $L^{118}$ | $L^{179}$ |
| 1293. | $L^{104}$ | $L^{119}$ | $L^{179}$ |
| 1294. | $L^{104}$ | $L^{130}$ | $L^{179}$ |
| 1295. | $L^{104}$ | $L^{131}$ | $L^{179}$ |
| 1296. | $L^{104}$ | $L^{132}$ | $L^{179}$ |
| 1297. | $L^{104}$ | $L^{133}$ | $L^{179}$ |
| 1298. | $L^{104}$ | $L^{134}$ | $L^{179}$ |
| 1299. | $L^{104}$ | $L^{140}$ | $L^{179}$ |
| 1300. | $L^{104}$ | $L^{141}$ | $L^{179}$ |
| 1301. | $L^{104}$ | $L^{159}$ | $L^{179}$ |
| 1302. | $L^{104}$ | $L^{160}$ | $L^{179}$ |
| 1303. | $L^{104}$ | $L^{105}$ | $L^{180}$ |
| 1304. | $L^{104}$ | $L^{106}$ | $L^{180}$ |
| 1305. | $L^{104}$ | $L^{107}$ | $L^{180}$ |
| 1306. | $L^{104}$ | $L^{108}$ | $L^{180}$ |
| 1307. | $L^{104}$ | $L^{109}$ | $L^{180}$ |
| 1308. | $L^{104}$ | $L^{110}$ | $L^{180}$ |
| 1309. | $L^{104}$ | $L^{111}$ | $L^{180}$ |
| 1310. | $L^{104}$ | $L^{112}$ | $L^{180}$ |
| 1311. | $L^{104}$ | $L^{113}$ | $L^{180}$ |
| 1312. | $L^{104}$ | $L^{114}$ | $L^{180}$ |
| 1313. | $L^{104}$ | $L^{115}$ | $L^{180}$ |
| 1314. | $L^{104}$ | $L^{116}$ | $L^{180}$ |
| 1315. | $L^{104}$ | $L^{117}$ | $L^{180}$ |
| 1316. | $L^{104}$ | $L^{118}$ | $L^{180}$ |
| 1317. | $L^{104}$ | $L^{119}$ | $L^{180}$ |
| 1318. | $L^{104}$ | $L^{130}$ | $L^{180}$ |
| 1319. | $L^{104}$ | $L^{131}$ | $L^{180}$ |
| 1320. | $L^{104}$ | $L^{132}$ | $L^{180}$ |
| 1321. | $L^{104}$ | $L^{133}$ | $L^{180}$ |
| 1322. | $L^{104}$ | $L^{134}$ | $L^{180}$ |
| 1323. | $L^{104}$ | $L^{140}$ | $L^{180}$ |
| 1324. | $L^{104}$ | $L^{141}$ | $L^{180}$ |
| 1325. | $L^{104}$ | $L^{159}$ | $L^{180}$ |
| 1326. | $L^{104}$ | $L^{160}$ | $L^{180}$ |
| 1327. | $L^{105}$ | $L^{106}$ | $L^{144}$ |
| 1328. | $L^{105}$ | $L^{107}$ | $L^{144}$ |
| 1329. | $L^{105}$ | $L^{108}$ | $L^{144}$ |
| 1330. | $L^{105}$ | $L^{109}$ | $L^{144}$ |
| 1331. | $L^{105}$ | $L^{110}$ | $L^{144}$ |
| 1332. | $L^{105}$ | $L^{111}$ | $L^{144}$ |
| 1333. | $L^{105}$ | $L^{112}$ | $L^{144}$ |
| 1334. | $L^{105}$ | $L^{113}$ | $L^{144}$ |
| 1335. | $L^{105}$ | $L^{114}$ | $L^{144}$ |
| 1336. | $L^{105}$ | $L^{115}$ | $L^{144}$ |
| 1337. | $L^{105}$ | $L^{116}$ | $L^{144}$ |
| 1338. | $L^{105}$ | $L^{117}$ | $L^{144}$ |
| 1339. | $L^{105}$ | $L^{118}$ | $L^{144}$ |
| 1340. | $L^{105}$ | $L^{119}$ | $L^{144}$ |
| 1341. | $L^{105}$ | $L^{130}$ | $L^{144}$ |
| 1342. | $L^{105}$ | $L^{131}$ | $L^{144}$ |
| 1343. | $L^{105}$ | $L^{132}$ | $L^{144}$ |
| 1344. | $L^{105}$ | $L^{133}$ | $L^{144}$ |
| 1345. | $L^{105}$ | $L^{134}$ | $L^{144}$ |
| 1346. | $L^{105}$ | $L^{140}$ | $L^{144}$ |
| 1347. | $L^{105}$ | $L^{141}$ | $L^{144}$ |
| 1348. | $L^{105}$ | $L^{159}$ | $L^{144}$ |
| 1349. | $L^{105}$ | $L^{160}$ | $L^{144}$ |
| 1350. | $L^{105}$ | $L^{106}$ | $L^{145}$ |
| 1351. | $L^{105}$ | $L^{107}$ | $L^{145}$ |
| 1352. | $L^{105}$ | $L^{108}$ | $L^{145}$ |
| 1353. | $L^{105}$ | $L^{109}$ | $L^{145}$ |
| 1354. | $L^{105}$ | $L^{110}$ | $L^{145}$ |
| 1355. | $L^{105}$ | $L^{111}$ | $L^{145}$ |
| 1356. | $L^{105}$ | $L^{112}$ | $L^{145}$ |
| 1357. | $L^{105}$ | $L^{113}$ | $L^{145}$ |
| 1358. | $L^{105}$ | $L^{114}$ | $L^{145}$ |
| 1359. | $L^{105}$ | $L^{115}$ | $L^{145}$ |
| 1360. | $L^{105}$ | $L^{116}$ | $L^{145}$ |
| 1361. | $L^{105}$ | $L^{117}$ | $L^{145}$ |
| 1362. | $L^{105}$ | $L^{118}$ | $L^{145}$ |
| 1363. | $L^{105}$ | $L^{119}$ | $L^{145}$ |
| 1364. | $L^{105}$ | $L^{130}$ | $L^{145}$ |
| 1365. | $L^{105}$ | $L^{131}$ | $L^{145}$ |
| 1366. | $L^{105}$ | $L^{132}$ | $L^{145}$ |
| 1367. | $L^{105}$ | $L^{133}$ | $L^{145}$ |
| 1368. | $L^{105}$ | $L^{134}$ | $L^{145}$ |
| 1369. | $L^{105}$ | $L^{140}$ | $L^{145}$ |
| 1370. | $L^{105}$ | $L^{141}$ | $L^{145}$ |
| 1371. | $L^{105}$ | $L^{159}$ | $L^{145}$ |
| 1372. | $L^{105}$ | $L^{160}$ | $L^{145}$ |
| 1373. | $L^{105}$ | $L^{106}$ | $L^{147}$ |
| 1374. | $L^{105}$ | $L^{107}$ | $L^{147}$ |
| 1375. | $L^{105}$ | $L^{108}$ | $L^{147}$ |
| 1376. | $L^{105}$ | $L^{109}$ | $L^{147}$ |
| 1377. | $L^{105}$ | $L^{110}$ | $L^{147}$ |
| 1378. | $L^{105}$ | $L^{111}$ | $L^{147}$ |
| 1379. | $L^{105}$ | $L^{112}$ | $L^{147}$ |
| 1380. | $L^{105}$ | $L^{113}$ | $L^{147}$ |
| 1381. | $L^{105}$ | $L^{114}$ | $L^{147}$ |
| 1382. | $L^{105}$ | $L^{115}$ | $L^{147}$ |
| 1383. | $L^{105}$ | $L^{116}$ | $L^{147}$ |
| 1384. | $L^{105}$ | $L^{117}$ | $L^{147}$ |
| 1385. | $L^{105}$ | $L^{118}$ | $L^{147}$ |
| 1386. | $L^{105}$ | $L^{119}$ | $L^{147}$ |
| 1387. | $L^{105}$ | $L^{130}$ | $L^{147}$ |
| 1388. | $L^{105}$ | $L^{131}$ | $L^{147}$ |
| 1389. | $L^{105}$ | $L^{132}$ | $L^{147}$ |
| 1390. | $L^{105}$ | $L^{133}$ | $L^{147}$ |
| 1391. | $L^{105}$ | $L^{134}$ | $L^{147}$ |
| 1392. | $L^{105}$ | $L^{140}$ | $L^{147}$ |
| 1393. | $L^{105}$ | $L^{141}$ | $L^{147}$ |
| 1394. | $L^{105}$ | $L^{159}$ | $L^{147}$ |
| 1395. | $L^{105}$ | $L^{160}$ | $L^{147}$ |
| 1396. | $L^{105}$ | $L^{106}$ | $L^{149}$ |
| 1397. | $L^{105}$ | $L^{107}$ | $L^{149}$ |

TABLE 1-continued

| Compound number | $L_1$ | $L_2$ | $L_3$ |
|---|---|---|---|
| 1398. | $L^{105}$ | $L^{108}$ | $L^{149}$ |
| 1399. | $L^{105}$ | $L^{109}$ | $L^{149}$ |
| 1400. | $L^{105}$ | $L^{110}$ | $L^{149}$ |
| 1401. | $L^{105}$ | $L^{111}$ | $L^{149}$ |
| 1402. | $L^{105}$ | $L^{112}$ | $L^{149}$ |
| 1403. | $L^{105}$ | $L^{113}$ | $L^{149}$ |
| 1404. | $L^{105}$ | $L^{114}$ | $L^{149}$ |
| 1405. | $L^{105}$ | $L^{115}$ | $L^{149}$ |
| 1406. | $L^{105}$ | $L^{116}$ | $L^{149}$ |
| 1407. | $L^{105}$ | $L^{117}$ | $L^{149}$ |
| 1408. | $L^{105}$ | $L^{118}$ | $L^{149}$ |
| 1409. | $L^{105}$ | $L^{119}$ | $L^{149}$ |
| 1410. | $L^{105}$ | $L^{130}$ | $L^{149}$ |
| 1411. | $L^{105}$ | $L^{131}$ | $L^{149}$ |
| 1412. | $L^{105}$ | $L^{132}$ | $L^{149}$ |
| 1413. | $L^{105}$ | $L^{133}$ | $L^{149}$ |
| 1414. | $L^{105}$ | $L^{134}$ | $L^{149}$ |
| 1415. | $L^{105}$ | $L^{140}$ | $L^{149}$ |
| 1416. | $L^{105}$ | $L^{141}$ | $L^{149}$ |
| 1417. | $L^{105}$ | $L^{159}$ | $L^{149}$ |
| 1418. | $L^{105}$ | $L^{160}$ | $L^{149}$ |
| 1419. | $L^{105}$ | $L^{106}$ | $L^{152}$ |
| 1420. | $L^{105}$ | $L^{107}$ | $L^{152}$ |
| 1421. | $L^{105}$ | $L^{108}$ | $L^{152}$ |
| 1422. | $L^{105}$ | $L^{109}$ | $L^{152}$ |
| 1423. | $L^{105}$ | $L^{110}$ | $L^{152}$ |
| 1424. | $L^{105}$ | $L^{111}$ | $L^{152}$ |
| 1425. | $L^{105}$ | $L^{112}$ | $L^{152}$ |
| 1426. | $L^{105}$ | $L^{113}$ | $L^{152}$ |
| 1427. | $L^{105}$ | $L^{114}$ | $L^{152}$ |
| 1428. | $L^{105}$ | $L^{115}$ | $L^{152}$ |
| 1429. | $L^{105}$ | $L^{116}$ | $L^{152}$ |
| 1430. | $L^{105}$ | $L^{117}$ | $L^{152}$ |
| 1431. | $L^{105}$ | $L^{118}$ | $L^{152}$ |
| 1432. | $L^{105}$ | $L^{119}$ | $L^{152}$ |
| 1433. | $L^{105}$ | $L^{130}$ | $L^{152}$ |
| 1434. | $L^{105}$ | $L^{131}$ | $L^{152}$ |
| 1435. | $L^{105}$ | $L^{132}$ | $L^{152}$ |
| 1436. | $L^{105}$ | $L^{133}$ | $L^{152}$ |
| 1437. | $L^{105}$ | $L^{134}$ | $L^{152}$ |
| 1438. | $L^{105}$ | $L^{140}$ | $L^{152}$ |
| 1439. | $L^{105}$ | $L^{141}$ | $L^{152}$ |
| 1440. | $L^{105}$ | $L^{159}$ | $L^{152}$ |
| 1441. | $L^{105}$ | $L^{160}$ | $L^{152}$ |
| 1442. | $L^{105}$ | $L^{106}$ | $L^{164}$ |
| 1443. | $L^{105}$ | $L^{107}$ | $L^{164}$ |
| 1444. | $L^{105}$ | $L^{108}$ | $L^{164}$ |
| 1445. | $L^{105}$ | $L^{109}$ | $L^{164}$ |
| 1446. | $L^{105}$ | $L^{110}$ | $L^{164}$ |
| 1447. | $L^{105}$ | $L^{111}$ | $L^{164}$ |
| 1448. | $L^{105}$ | $L^{112}$ | $L^{164}$ |
| 1449. | $L^{105}$ | $L^{113}$ | $L^{164}$ |
| 1450. | $L^{105}$ | $L^{114}$ | $L^{164}$ |
| 1451. | $L^{105}$ | $L^{115}$ | $L^{164}$ |
| 1452. | $L^{105}$ | $L^{116}$ | $L^{164}$ |
| 1453. | $L^{105}$ | $L^{117}$ | $L^{164}$ |
| 1454. | $L^{105}$ | $L^{118}$ | $L^{164}$ |
| 1455. | $L^{105}$ | $L^{119}$ | $L^{164}$ |
| 1456. | $L^{105}$ | $L^{130}$ | $L^{164}$ |
| 1457. | $L^{105}$ | $L^{131}$ | $L^{164}$ |
| 1458. | $L^{105}$ | $L^{132}$ | $L^{164}$ |
| 1459. | $L^{105}$ | $L^{133}$ | $L^{164}$ |
| 1460. | $L^{105}$ | $L^{134}$ | $L^{164}$ |
| 1461. | $L^{105}$ | $L^{140}$ | $L^{164}$ |
| 1462. | $L^{105}$ | $L^{141}$ | $L^{164}$ |
| 1463. | $L^{105}$ | $L^{159}$ | $L^{164}$ |
| 1464. | $L^{105}$ | $L^{160}$ | $L^{164}$ |
| 1465. | $L^{105}$ | $L^{106}$ | $L^{165}$ |
| 1466. | $L^{105}$ | $L^{107}$ | $L^{165}$ |
| 1467. | $L^{105}$ | $L^{108}$ | $L^{165}$ |
| 1468. | $L^{105}$ | $L^{109}$ | $L^{165}$ |
| 1469. | $L^{105}$ | $L^{110}$ | $L^{165}$ |
| 1470. | $L^{105}$ | $L^{111}$ | $L^{165}$ |
| 1471. | $L^{105}$ | $L^{112}$ | $L^{165}$ |
| 1472. | $L^{105}$ | $L^{113}$ | $L^{165}$ |
| 1473. | $L^{105}$ | $L^{114}$ | $L^{165}$ |
| 1474. | $L^{105}$ | $L^{115}$ | $L^{165}$ |
| 1475. | $L^{105}$ | $L^{116}$ | $L^{165}$ |
| 1476. | $L^{105}$ | $L^{117}$ | $L^{165}$ |
| 1477. | $L^{105}$ | $L^{118}$ | $L^{165}$ |
| 1478. | $L^{105}$ | $L^{119}$ | $L^{165}$ |
| 1479. | $L^{105}$ | $L^{130}$ | $L^{165}$ |
| 1480. | $L^{105}$ | $L^{131}$ | $L^{165}$ |
| 1481. | $L^{105}$ | $L^{132}$ | $L^{165}$ |
| 1482. | $L^{105}$ | $L^{133}$ | $L^{165}$ |
| 1483. | $L^{105}$ | $L^{134}$ | $L^{165}$ |
| 1484. | $L^{105}$ | $L^{140}$ | $L^{165}$ |
| 1485. | $L^{105}$ | $L^{141}$ | $L^{165}$ |
| 1486. | $L^{105}$ | $L^{159}$ | $L^{165}$ |
| 1487. | $L^{105}$ | $L^{160}$ | $L^{165}$ |
| 1488. | $L^{105}$ | $L^{106}$ | $L^{166}$ |
| 1489. | $L^{105}$ | $L^{107}$ | $L^{166}$ |
| 1490. | $L^{105}$ | $L^{108}$ | $L^{166}$ |
| 1491. | $L^{105}$ | $L^{109}$ | $L^{166}$ |
| 1492. | $L^{105}$ | $L^{110}$ | $L^{166}$ |
| 1493. | $L^{105}$ | $L^{111}$ | $L^{166}$ |
| 1494. | $L^{105}$ | $L^{112}$ | $L^{166}$ |
| 1495. | $L^{105}$ | $L^{113}$ | $L^{166}$ |
| 1496. | $L^{105}$ | $L^{114}$ | $L^{166}$ |
| 1497. | $L^{105}$ | $L^{115}$ | $L^{166}$ |
| 1498. | $L^{105}$ | $L^{116}$ | $L^{166}$ |
| 1499. | $L^{105}$ | $L^{117}$ | $L^{166}$ |
| 1500. | $L^{105}$ | $L^{118}$ | $L^{166}$ |
| 1501. | $L^{105}$ | $L^{119}$ | $L^{166}$ |
| 1502. | $L^{105}$ | $L^{130}$ | $L^{166}$ |
| 1503. | $L^{105}$ | $L^{131}$ | $L^{166}$ |
| 1504. | $L^{105}$ | $L^{132}$ | $L^{166}$ |
| 1505. | $L^{105}$ | $L^{133}$ | $L^{166}$ |
| 1506. | $L^{105}$ | $L^{134}$ | $L^{166}$ |
| 1507. | $L^{105}$ | $L^{140}$ | $L^{166}$ |
| 1508. | $L^{105}$ | $L^{141}$ | $L^{166}$ |
| 1509. | $L^{105}$ | $L^{159}$ | $L^{166}$ |
| 1510. | $L^{105}$ | $L^{160}$ | $L^{166}$ |
| 1511. | $L^{105}$ | $L^{106}$ | $L^{170}$ |
| 1512. | $L^{105}$ | $L^{107}$ | $L^{170}$ |
| 1513. | $L^{105}$ | $L^{108}$ | $L^{170}$ |
| 1514. | $L^{105}$ | $L^{109}$ | $L^{170}$ |
| 1515. | $L^{105}$ | $L^{110}$ | $L^{170}$ |
| 1516. | $L^{105}$ | $L^{111}$ | $L^{170}$ |
| 1517. | $L^{105}$ | $L^{112}$ | $L^{170}$ |
| 1518. | $L^{105}$ | $L^{113}$ | $L^{170}$ |
| 1519. | $L^{105}$ | $L^{114}$ | $L^{170}$ |
| 1520. | $L^{105}$ | $L^{115}$ | $L^{170}$ |
| 1521. | $L^{105}$ | $L^{116}$ | $L^{170}$ |
| 1522. | $L^{105}$ | $L^{117}$ | $L^{170}$ |
| 1523. | $L^{105}$ | $L^{118}$ | $L^{170}$ |
| 1524. | $L^{105}$ | $L^{119}$ | $L^{170}$ |
| 1525. | $L^{105}$ | $L^{130}$ | $L^{170}$ |
| 1526. | $L^{105}$ | $L^{131}$ | $L^{170}$ |
| 1527. | $L^{105}$ | $L^{132}$ | $L^{170}$ |
| 1528. | $L^{105}$ | $L^{133}$ | $L^{170}$ |
| 1529. | $L^{105}$ | $L^{134}$ | $L^{170}$ |
| 1530. | $L^{105}$ | $L^{140}$ | $L^{170}$ |
| 1531. | $L^{105}$ | $L^{141}$ | $L^{170}$ |
| 1532. | $L^{105}$ | $L^{159}$ | $L^{170}$ |
| 1533. | $L^{105}$ | $L^{160}$ | $L^{170}$ |
| 1534. | $L^{105}$ | $L^{106}$ | $L^{174}$ |
| 1535. | $L^{105}$ | $L^{107}$ | $L^{174}$ |
| 1536. | $L^{105}$ | $L^{108}$ | $L^{174}$ |
| 1537. | $L^{105}$ | $L^{109}$ | $L^{174}$ |
| 1538. | $L^{105}$ | $L^{110}$ | $L^{174}$ |
| 1539. | $L^{105}$ | $L^{111}$ | $L^{174}$ |
| 1540. | $L^{105}$ | $L^{112}$ | $L^{174}$ |
| 1541. | $L^{105}$ | $L^{113}$ | $L^{174}$ |
| 1542. | $L^{105}$ | $L^{114}$ | $L^{174}$ |
| 1543. | $L^{105}$ | $L^{115}$ | $L^{174}$ |
| 1544. | $L^{105}$ | $L^{116}$ | $L^{174}$ |
| 1545. | $L^{105}$ | $L^{117}$ | $L^{174}$ |
| 1546. | $L^{105}$ | $L^{118}$ | $L^{174}$ |
| 1547. | $L^{105}$ | $L^{119}$ | $L^{174}$ |
| 1548. | $L^{105}$ | $L^{130}$ | $L^{174}$ |
| 1549. | $L^{105}$ | $L^{131}$ | $L^{174}$ |
| 1550. | $L^{105}$ | $L^{132}$ | $L^{174}$ |
| 1551. | $L^{105}$ | $L^{133}$ | $L^{174}$ |

TABLE 1-continued

| Compound number | $L_1$ | $L_2$ | $L_3$ |
|---|---|---|---|
| 1552. | $L^{105}$ | $L^{134}$ | $L^{174}$ |
| 1553. | $L^{105}$ | $L^{140}$ | $L^{174}$ |
| 1554. | $L^{105}$ | $L^{141}$ | $L^{174}$ |
| 1555. | $L^{105}$ | $L^{159}$ | $L^{174}$ |
| 1556. | $L^{105}$ | $L^{160}$ | $L^{174}$ |
| 1557. | $L^{105}$ | $L^{106}$ | $L^{176}$ |
| 1558. | $L^{105}$ | $L^{107}$ | $L^{176}$ |
| 1559. | $L^{105}$ | $L^{108}$ | $L^{176}$ |
| 1560. | $L^{105}$ | $L^{109}$ | $L^{176}$ |
| 1561. | $L^{105}$ | $L^{110}$ | $L^{176}$ |
| 1562. | $L^{105}$ | $L^{111}$ | $L^{176}$ |
| 1563. | $L^{105}$ | $L^{112}$ | $L^{176}$ |
| 1564. | $L^{105}$ | $L^{113}$ | $L^{176}$ |
| 1565. | $L^{105}$ | $L^{114}$ | $L^{176}$ |
| 1566. | $L^{105}$ | $L^{115}$ | $L^{176}$ |
| 1567. | $L^{105}$ | $L^{116}$ | $L^{176}$ |
| 1568. | $L^{105}$ | $L^{117}$ | $L^{176}$ |
| 1569. | $L^{105}$ | $L^{118}$ | $L^{176}$ |
| 1570. | $L^{105}$ | $L^{119}$ | $L^{176}$ |
| 1571. | $L^{105}$ | $L^{130}$ | $L^{176}$ |
| 1572. | $L^{105}$ | $L^{131}$ | $L^{176}$ |
| 1573. | $L^{105}$ | $L^{132}$ | $L^{176}$ |
| 1574. | $L^{105}$ | $L^{133}$ | $L^{176}$ |
| 1575. | $L^{105}$ | $L^{134}$ | $L^{176}$ |
| 1576. | $L^{105}$ | $L^{140}$ | $L^{176}$ |
| 1577. | $L^{105}$ | $L^{141}$ | $L^{176}$ |
| 1578. | $L^{105}$ | $L^{159}$ | $L^{176}$ |
| 1579. | $L^{105}$ | $L^{160}$ | $L^{176}$ |
| 1580. | $L^{105}$ | $L^{106}$ | $L^{179}$ |
| 1581. | $L^{105}$ | $L^{107}$ | $L^{179}$ |
| 1582. | $L^{105}$ | $L^{108}$ | $L^{179}$ |
| 1583. | $L^{105}$ | $L^{109}$ | $L^{179}$ |
| 1584. | $L^{105}$ | $L^{110}$ | $L^{179}$ |
| 1585. | $L^{105}$ | $L^{111}$ | $L^{179}$ |
| 1586. | $L^{105}$ | $L^{112}$ | $L^{179}$ |
| 1587. | $L^{105}$ | $L^{113}$ | $L^{179}$ |
| 1588. | $L^{105}$ | $L^{114}$ | $L^{179}$ |
| 1589. | $L^{105}$ | $L^{115}$ | $L^{179}$ |
| 1590. | $L^{105}$ | $L^{116}$ | $L^{179}$ |
| 1591. | $L^{105}$ | $L^{117}$ | $L^{179}$ |
| 1592. | $L^{105}$ | $L^{118}$ | $L^{179}$ |
| 1593. | $L^{105}$ | $L^{119}$ | $L^{179}$ |
| 1594. | $L^{105}$ | $L^{130}$ | $L^{179}$ |
| 1595. | $L^{105}$ | $L^{131}$ | $L^{179}$ |
| 1596. | $L^{105}$ | $L^{132}$ | $L^{179}$ |
| 1597. | $L^{105}$ | $L^{133}$ | $L^{179}$ |
| 1598. | $L^{105}$ | $L^{134}$ | $L^{179}$ |
| 1599. | $L^{105}$ | $L^{140}$ | $L^{179}$ |
| 1600. | $L^{105}$ | $L^{141}$ | $L^{179}$ |
| 1601. | $L^{105}$ | $L^{159}$ | $L^{179}$ |
| 1602. | $L^{105}$ | $L^{160}$ | $L^{179}$ |
| 1603. | $L^{105}$ | $L^{106}$ | $L^{180}$ |
| 1604. | $L^{105}$ | $L^{107}$ | $L^{180}$ |
| 1605. | $L^{105}$ | $L^{108}$ | $L^{180}$ |
| 1606. | $L^{105}$ | $L^{109}$ | $L^{180}$ |
| 1607. | $L^{105}$ | $L^{110}$ | $L^{180}$ |
| 1608. | $L^{105}$ | $L^{111}$ | $L^{180}$ |
| 1609. | $L^{105}$ | $L^{112}$ | $L^{180}$ |
| 1610. | $L^{105}$ | $L^{113}$ | $L^{180}$ |
| 1611. | $L^{105}$ | $L^{114}$ | $L^{180}$ |
| 1612. | $L^{105}$ | $L^{115}$ | $L^{180}$ |
| 1613. | $L^{105}$ | $L^{116}$ | $L^{180}$ |
| 1614. | $L^{105}$ | $L^{117}$ | $L^{180}$ |
| 1615. | $L^{105}$ | $L^{118}$ | $L^{180}$ |
| 1616. | $L^{105}$ | $L^{119}$ | $L^{180}$ |
| 1617. | $L^{105}$ | $L^{130}$ | $L^{180}$ |
| 1618. | $L^{105}$ | $L^{131}$ | $L^{180}$ |
| 1619. | $L^{105}$ | $L^{132}$ | $L^{180}$ |
| 1620. | $L^{105}$ | $L^{133}$ | $L^{180}$ |
| 1621. | $L^{105}$ | $L^{134}$ | $L^{180}$ |
| 1622. | $L^{105}$ | $L^{140}$ | $L^{180}$ |
| 1623. | $L^{105}$ | $L^{141}$ | $L^{180}$ |
| 1624. | $L^{105}$ | $L^{159}$ | $L^{180}$ |
| 1625. | $L^{105}$ | $L^{160}$ | $L^{180}$ |
| 1626. | $L^{106}$ | $L^{107}$ | $L^{144}$ |
| 1627. | $L^{106}$ | $L^{108}$ | $L^{144}$ |
| 1628. | $L^{106}$ | $L^{109}$ | $L^{144}$ |
| 1629. | $L^{106}$ | $L^{110}$ | $L^{144}$ |
| 1630. | $L^{106}$ | $L^{111}$ | $L^{144}$ |
| 1631. | $L^{106}$ | $L^{112}$ | $L^{144}$ |
| 1632. | $L^{106}$ | $L^{113}$ | $L^{144}$ |
| 1633. | $L^{106}$ | $L^{114}$ | $L^{144}$ |
| 1634. | $L^{106}$ | $L^{115}$ | $L^{144}$ |
| 1635. | $L^{106}$ | $L^{116}$ | $L^{144}$ |
| 1636. | $L^{106}$ | $L^{117}$ | $L^{144}$ |
| 1637. | $L^{106}$ | $L^{118}$ | $L^{144}$ |
| 1638. | $L^{106}$ | $L^{119}$ | $L^{144}$ |
| 1639. | $L^{106}$ | $L^{130}$ | $L^{144}$ |
| 1640. | $L^{106}$ | $L^{131}$ | $L^{144}$ |
| 1641. | $L^{106}$ | $L^{132}$ | $L^{144}$ |
| 1642. | $L^{106}$ | $L^{133}$ | $L^{144}$ |
| 1643. | $L^{106}$ | $L^{134}$ | $L^{144}$ |
| 1644. | $L^{106}$ | $L^{140}$ | $L^{144}$ |
| 1645. | $L^{106}$ | $L^{141}$ | $L^{144}$ |
| 1646. | $L^{106}$ | $L^{159}$ | $L^{144}$ |
| 1647. | $L^{106}$ | $L^{160}$ | $L^{144}$ |
| 1648. | $L^{106}$ | $L^{107}$ | $L^{145}$ |
| 1649. | $L^{106}$ | $L^{108}$ | $L^{145}$ |
| 1650. | $L^{106}$ | $L^{109}$ | $L^{145}$ |
| 1651. | $L^{106}$ | $L^{110}$ | $L^{145}$ |
| 1652. | $L^{106}$ | $L^{111}$ | $L^{145}$ |
| 1653. | $L^{106}$ | $L^{112}$ | $L^{145}$ |
| 1654. | $L^{106}$ | $L^{113}$ | $L^{145}$ |
| 1655. | $L^{106}$ | $L^{114}$ | $L^{145}$ |
| 1656. | $L^{106}$ | $L^{115}$ | $L^{145}$ |
| 1657. | $L^{106}$ | $L^{116}$ | $L^{145}$ |
| 1658. | $L^{106}$ | $L^{117}$ | $L^{145}$ |
| 1659. | $L^{106}$ | $L^{118}$ | $L^{145}$ |
| 1660. | $L^{106}$ | $L^{119}$ | $L^{145}$ |
| 1661. | $L^{106}$ | $L^{130}$ | $L^{145}$ |
| 1662. | $L^{106}$ | $L^{131}$ | $L^{145}$ |
| 1663. | $L^{106}$ | $L^{132}$ | $L^{145}$ |
| 1664. | $L^{106}$ | $L^{133}$ | $L^{145}$ |
| 1665. | $L^{106}$ | $L^{134}$ | $L^{145}$ |
| 1666. | $L^{106}$ | $L^{140}$ | $L^{145}$ |
| 1667. | $L^{106}$ | $L^{141}$ | $L^{145}$ |
| 1668. | $L^{106}$ | $L^{159}$ | $L^{145}$ |
| 1669. | $L^{106}$ | $L^{160}$ | $L^{145}$ |
| 1670. | $L^{106}$ | $L^{107}$ | $L^{147}$ |
| 1671. | $L^{106}$ | $L^{108}$ | $L^{147}$ |
| 1672. | $L^{106}$ | $L^{109}$ | $L^{147}$ |
| 1673. | $L^{106}$ | $L^{110}$ | $L^{147}$ |
| 1674. | $L^{106}$ | $L^{111}$ | $L^{147}$ |
| 1675. | $L^{106}$ | $L^{112}$ | $L^{147}$ |
| 1676. | $L^{106}$ | $L^{113}$ | $L^{147}$ |
| 1677. | $L^{106}$ | $L^{114}$ | $L^{147}$ |
| 1678. | $L^{106}$ | $L^{115}$ | $L^{147}$ |
| 1679. | $L^{106}$ | $L^{116}$ | $L^{147}$ |
| 1680. | $L^{106}$ | $L^{117}$ | $L^{147}$ |
| 1681. | $L^{106}$ | $L^{118}$ | $L^{147}$ |
| 1682. | $L^{106}$ | $L^{119}$ | $L^{147}$ |
| 1683. | $L^{106}$ | $L^{130}$ | $L^{147}$ |
| 1684. | $L^{106}$ | $L^{131}$ | $L^{147}$ |
| 1685. | $L^{106}$ | $L^{132}$ | $L^{147}$ |
| 1686. | $L^{106}$ | $L^{133}$ | $L^{147}$ |
| 1687. | $L^{106}$ | $L^{134}$ | $L^{147}$ |
| 1688. | $L^{106}$ | $L^{140}$ | $L^{147}$ |
| 1689. | $L^{106}$ | $L^{141}$ | $L^{147}$ |
| 1690. | $L^{106}$ | $L^{159}$ | $L^{147}$ |
| 1691. | $L^{106}$ | $L^{160}$ | $L^{147}$ |
| 1692. | $L^{106}$ | $L^{107}$ | $L^{149}$ |
| 1693. | $L^{106}$ | $L^{108}$ | $L^{149}$ |
| 1694. | $L^{106}$ | $L^{109}$ | $L^{149}$ |
| 1695. | $L^{106}$ | $L^{110}$ | $L^{149}$ |
| 1696. | $L^{106}$ | $L^{111}$ | $L^{149}$ |
| 1697. | $L^{106}$ | $L^{112}$ | $L^{149}$ |
| 1698. | $L^{106}$ | $L^{113}$ | $L^{149}$ |
| 1699. | $L^{106}$ | $L^{114}$ | $L^{149}$ |
| 1700. | $L^{106}$ | $L^{115}$ | $L^{149}$ |
| 1701. | $L^{106}$ | $L^{116}$ | $L^{149}$ |
| 1702. | $L^{106}$ | $L^{117}$ | $L^{149}$ |
| 1703. | $L^{106}$ | $L^{118}$ | $L^{149}$ |
| 1704. | $L^{106}$ | $L^{119}$ | $L^{149}$ |
| 1705. | $L^{106}$ | $L^{130}$ | $L^{149}$ |

TABLE 1-continued

| Compound number | $L_1$ | $L_2$ | $L_3$ |
|---|---|---|---|
| 1706. | $L^{106}$ | $L^{131}$ | $L^{149}$ |
| 1707. | $L^{106}$ | $L^{132}$ | $L^{149}$ |
| 1708. | $L^{106}$ | $L^{133}$ | $L^{149}$ |
| 1709. | $L^{106}$ | $L^{134}$ | $L^{149}$ |
| 1710. | $L^{106}$ | $L^{140}$ | $L^{149}$ |
| 1711. | $L^{106}$ | $L^{141}$ | $L^{149}$ |
| 1712. | $L^{106}$ | $L^{159}$ | $L^{149}$ |
| 1713. | $L^{106}$ | $L^{160}$ | $L^{149}$ |
| 1714. | $L^{106}$ | $L^{107}$ | $L^{152}$ |
| 1715. | $L^{106}$ | $L^{108}$ | $L^{152}$ |
| 1716. | $L^{106}$ | $L^{109}$ | $L^{152}$ |
| 1717. | $L^{106}$ | $L^{110}$ | $L^{152}$ |
| 1718. | $L^{106}$ | $L^{111}$ | $L^{152}$ |
| 1719. | $L^{106}$ | $L^{112}$ | $L^{152}$ |
| 1720. | $L^{106}$ | $L^{113}$ | $L^{152}$ |
| 1721. | $L^{106}$ | $L^{114}$ | $L^{152}$ |
| 1722. | $L^{106}$ | $L^{115}$ | $L^{152}$ |
| 1723. | $L^{106}$ | $L^{116}$ | $L^{152}$ |
| 1724. | $L^{106}$ | $L^{117}$ | $L^{152}$ |
| 1725. | $L^{106}$ | $L^{118}$ | $L^{152}$ |
| 1726. | $L^{106}$ | $L^{119}$ | $L^{152}$ |
| 1727. | $L^{106}$ | $L^{130}$ | $L^{152}$ |
| 1728. | $L^{106}$ | $L^{131}$ | $L^{152}$ |
| 1729. | $L^{106}$ | $L^{132}$ | $L^{152}$ |
| 1730. | $L^{106}$ | $L^{133}$ | $L^{152}$ |
| 1731. | $L^{106}$ | $L^{134}$ | $L^{152}$ |
| 1732. | $L^{106}$ | $L^{140}$ | $L^{152}$ |
| 1733. | $L^{106}$ | $L^{141}$ | $L^{152}$ |
| 1734. | $L^{106}$ | $L^{159}$ | $L^{152}$ |
| 1735. | $L^{106}$ | $L^{160}$ | $L^{152}$ |
| 1736. | $L^{106}$ | $L^{107}$ | $L^{164}$ |
| 1737. | $L^{106}$ | $L^{108}$ | $L^{164}$ |
| 1738. | $L^{106}$ | $L^{109}$ | $L^{164}$ |
| 1739. | $L^{106}$ | $L^{110}$ | $L^{164}$ |
| 1740. | $L^{106}$ | $L^{111}$ | $L^{164}$ |
| 1741. | $L^{106}$ | $L^{112}$ | $L^{164}$ |
| 1742. | $L^{106}$ | $L^{113}$ | $L^{164}$ |
| 1743. | $L^{106}$ | $L^{114}$ | $L^{164}$ |
| 1744. | $L^{106}$ | $L^{115}$ | $L^{164}$ |
| 1745. | $L^{106}$ | $L^{116}$ | $L^{164}$ |
| 1746. | $L^{106}$ | $L^{117}$ | $L^{164}$ |
| 1747. | $L^{106}$ | $L^{118}$ | $L^{164}$ |
| 1748. | $L^{106}$ | $L^{119}$ | $L^{164}$ |
| 1749. | $L^{106}$ | $L^{130}$ | $L^{164}$ |
| 1750. | $L^{106}$ | $L^{131}$ | $L^{164}$ |
| 1751. | $L^{106}$ | $L^{132}$ | $L^{164}$ |
| 1752. | $L^{106}$ | $L^{133}$ | $L^{164}$ |
| 1753. | $L^{106}$ | $L^{134}$ | $L^{164}$ |
| 1754. | $L^{106}$ | $L^{140}$ | $L^{164}$ |
| 1755. | $L^{106}$ | $L^{141}$ | $L^{164}$ |
| 1756. | $L^{106}$ | $L^{159}$ | $L^{164}$ |
| 1757. | $L^{106}$ | $L^{160}$ | $L^{164}$ |
| 1758. | $L^{106}$ | $L^{107}$ | $L^{165}$ |
| 1759. | $L^{106}$ | $L^{108}$ | $L^{165}$ |
| 1760. | $L^{106}$ | $L^{109}$ | $L^{165}$ |
| 1761. | $L^{106}$ | $L^{110}$ | $L^{165}$ |
| 1762. | $L^{106}$ | $L^{111}$ | $L^{165}$ |
| 1763. | $L^{106}$ | $L^{112}$ | $L^{165}$ |
| 1764. | $L^{106}$ | $L^{113}$ | $L^{165}$ |
| 1765. | $L^{106}$ | $L^{114}$ | $L^{165}$ |
| 1766. | $L^{106}$ | $L^{115}$ | $L^{165}$ |
| 1767. | $L^{106}$ | $L^{116}$ | $L^{165}$ |
| 1768. | $L^{106}$ | $L^{117}$ | $L^{165}$ |
| 1769. | $L^{106}$ | $L^{118}$ | $L^{165}$ |
| 1770. | $L^{106}$ | $L^{119}$ | $L^{165}$ |
| 1771. | $L^{106}$ | $L^{130}$ | $L^{165}$ |
| 1772. | $L^{106}$ | $L^{131}$ | $L^{165}$ |
| 1773. | $L^{106}$ | $L^{132}$ | $L^{165}$ |
| 1774. | $L^{106}$ | $L^{133}$ | $L^{165}$ |
| 1775. | $L^{106}$ | $L^{134}$ | $L^{165}$ |
| 1776. | $L^{106}$ | $L^{140}$ | $L^{165}$ |
| 1777. | $L^{106}$ | $L^{141}$ | $L^{165}$ |
| 1778. | $L^{106}$ | $L^{159}$ | $L^{165}$ |
| 1779. | $L^{106}$ | $L^{160}$ | $L^{165}$ |
| 1780. | $L^{106}$ | $L^{107}$ | $L^{166}$ |
| 1781. | $L^{106}$ | $L^{108}$ | $L^{166}$ |
| 1782. | $L^{106}$ | $L^{109}$ | $L^{166}$ |
| 1783. | $L^{106}$ | $L^{110}$ | $L^{166}$ |
| 1784. | $L^{106}$ | $L^{111}$ | $L^{166}$ |
| 1785. | $L^{106}$ | $L^{112}$ | $L^{166}$ |
| 1786. | $L^{106}$ | $L^{113}$ | $L^{166}$ |
| 1787. | $L^{106}$ | $L^{114}$ | $L^{166}$ |
| 1788. | $L^{106}$ | $L^{115}$ | $L^{166}$ |
| 1789. | $L^{106}$ | $L^{116}$ | $L^{166}$ |
| 1790. | $L^{106}$ | $L^{117}$ | $L^{166}$ |
| 1791. | $L^{106}$ | $L^{118}$ | $L^{166}$ |
| 1792. | $L^{106}$ | $L^{119}$ | $L^{166}$ |
| 1793. | $L^{106}$ | $L^{130}$ | $L^{166}$ |
| 1794. | $L^{106}$ | $L^{131}$ | $L^{166}$ |
| 1795. | $L^{106}$ | $L^{132}$ | $L^{166}$ |
| 1796. | $L^{106}$ | $L^{133}$ | $L^{166}$ |
| 1797. | $L^{106}$ | $L^{134}$ | $L^{166}$ |
| 1798. | $L^{106}$ | $L^{140}$ | $L^{166}$ |
| 1799. | $L^{106}$ | $L^{141}$ | $L^{166}$ |
| 1800. | $L^{106}$ | $L^{159}$ | $L^{166}$ |
| 1801. | $L^{106}$ | $L^{160}$ | $L^{166}$ |
| 1802. | $L^{106}$ | $L^{107}$ | $L^{170}$ |
| 1803. | $L^{106}$ | $L^{108}$ | $L^{170}$ |
| 1804. | $L^{106}$ | $L^{109}$ | $L^{170}$ |
| 1805. | $L^{106}$ | $L^{110}$ | $L^{170}$ |
| 1806. | $L^{106}$ | $L^{111}$ | $L^{170}$ |
| 1807. | $L^{106}$ | $L^{112}$ | $L^{170}$ |
| 1808. | $L^{106}$ | $L^{113}$ | $L^{170}$ |
| 1809. | $L^{106}$ | $L^{114}$ | $L^{170}$ |
| 1810. | $L^{106}$ | $L^{115}$ | $L^{170}$ |
| 1811. | $L^{106}$ | $L^{116}$ | $L^{170}$ |
| 1812. | $L^{106}$ | $L^{117}$ | $L^{170}$ |
| 1813. | $L^{106}$ | $L^{118}$ | $L^{170}$ |
| 1814. | $L^{106}$ | $L^{119}$ | $L^{170}$ |
| 1815. | $L^{106}$ | $L^{130}$ | $L^{170}$ |
| 1816. | $L^{106}$ | $L^{131}$ | $L^{170}$ |
| 1817. | $L^{106}$ | $L^{132}$ | $L^{170}$ |
| 1818. | $L^{106}$ | $L^{133}$ | $L^{170}$ |
| 1819. | $L^{106}$ | $L^{134}$ | $L^{170}$ |
| 1820. | $L^{106}$ | $L^{140}$ | $L^{170}$ |
| 1821. | $L^{106}$ | $L^{141}$ | $L^{170}$ |
| 1822. | $L^{106}$ | $L^{159}$ | $L^{170}$ |
| 1823. | $L^{106}$ | $L^{160}$ | $L^{170}$ |
| 1824. | $L^{106}$ | $L^{107}$ | $L^{174}$ |
| 1825. | $L^{106}$ | $L^{108}$ | $L^{174}$ |
| 1826. | $L^{106}$ | $L^{109}$ | $L^{174}$ |
| 1827. | $L^{106}$ | $L^{110}$ | $L^{174}$ |
| 1828. | $L^{106}$ | $L^{111}$ | $L^{174}$ |
| 1829. | $L^{106}$ | $L^{112}$ | $L^{174}$ |
| 1830. | $L^{106}$ | $L^{113}$ | $L^{174}$ |
| 1831. | $L^{106}$ | $L^{114}$ | $L^{174}$ |
| 1832. | $L^{106}$ | $L^{115}$ | $L^{174}$ |
| 1833. | $L^{106}$ | $L^{116}$ | $L^{174}$ |
| 1834. | $L^{106}$ | $L^{117}$ | $L^{174}$ |
| 1835. | $L^{106}$ | $L^{118}$ | $L^{174}$ |
| 1836. | $L^{106}$ | $L^{119}$ | $L^{174}$ |
| 1837. | $L^{106}$ | $L^{130}$ | $L^{174}$ |
| 1838. | $L^{106}$ | $L^{131}$ | $L^{174}$ |
| 1839. | $L^{106}$ | $L^{132}$ | $L^{174}$ |
| 1840. | $L^{106}$ | $L^{133}$ | $L^{174}$ |
| 1841. | $L^{106}$ | $L^{134}$ | $L^{174}$ |
| 1842. | $L^{106}$ | $L^{140}$ | $L^{174}$ |
| 1843. | $L^{106}$ | $L^{141}$ | $L^{174}$ |
| 1844. | $L^{106}$ | $L^{159}$ | $L^{174}$ |
| 1845. | $L^{106}$ | $L^{160}$ | $L^{174}$ |
| 1846. | $L^{106}$ | $L^{107}$ | $L^{176}$ |
| 1847. | $L^{106}$ | $L^{108}$ | $L^{176}$ |
| 1848. | $L^{106}$ | $L^{109}$ | $L^{176}$ |
| 1849. | $L^{106}$ | $L^{110}$ | $L^{176}$ |
| 1850. | $L^{106}$ | $L^{111}$ | $L^{176}$ |
| 1851. | $L^{106}$ | $L^{112}$ | $L^{176}$ |
| 1852. | $L^{106}$ | $L^{113}$ | $L^{176}$ |
| 1853. | $L^{106}$ | $L^{114}$ | $L^{176}$ |
| 1854. | $L^{106}$ | $L^{115}$ | $L^{176}$ |
| 1855. | $L^{106}$ | $L^{116}$ | $L^{176}$ |
| 1856. | $L^{106}$ | $L^{117}$ | $L^{176}$ |
| 1857. | $L^{106}$ | $L^{118}$ | $L^{176}$ |
| 1858. | $L^{106}$ | $L^{119}$ | $L^{176}$ |
| 1859. | $L^{106}$ | $L^{130}$ | $L^{176}$ |

TABLE 1-continued

| Compound number | $L_1$ | $L_2$ | $L_3$ |
|---|---|---|---|
| 1860. | $L^{106}$ | $L^{131}$ | $L^{176}$ |
| 1861. | $L^{106}$ | $L^{132}$ | $L^{176}$ |
| 1862. | $L^{106}$ | $L^{133}$ | $L^{176}$ |
| 1863. | $L^{106}$ | $L^{134}$ | $L^{176}$ |
| 1864. | $L^{106}$ | $L^{140}$ | $L^{176}$ |
| 1865. | $L^{106}$ | $L^{141}$ | $L^{176}$ |
| 1866. | $L^{106}$ | $L^{159}$ | $L^{176}$ |
| 1867. | $L^{106}$ | $L^{160}$ | $L^{176}$ |
| 1868. | $L^{106}$ | $L^{107}$ | $L^{179}$ |
| 1869. | $L^{106}$ | $L^{108}$ | $L^{179}$ |
| 1870. | $L^{106}$ | $L^{109}$ | $L^{179}$ |
| 1871. | $L^{106}$ | $L^{110}$ | $L^{179}$ |
| 1872. | $L^{106}$ | $L^{111}$ | $L^{179}$ |
| 1873. | $L^{106}$ | $L^{112}$ | $L^{179}$ |
| 1874. | $L^{106}$ | $L^{113}$ | $L^{179}$ |
| 1875. | $L^{106}$ | $L^{114}$ | $L^{179}$ |
| 1876. | $L^{106}$ | $L^{115}$ | $L^{179}$ |
| 1877. | $L^{106}$ | $L^{116}$ | $L^{179}$ |
| 1878. | $L^{106}$ | $L^{117}$ | $L^{179}$ |
| 1879. | $L^{106}$ | $L^{118}$ | $L^{179}$ |
| 1880. | $L^{106}$ | $L^{119}$ | $L^{179}$ |
| 1881. | $L^{106}$ | $L^{130}$ | $L^{179}$ |
| 1882. | $L^{106}$ | $L^{131}$ | $L^{179}$ |
| 1883. | $L^{106}$ | $L^{132}$ | $L^{179}$ |
| 1884. | $L^{106}$ | $L^{133}$ | $L^{179}$ |
| 1885. | $L^{106}$ | $L^{134}$ | $L^{179}$ |
| 1886. | $L^{106}$ | $L^{140}$ | $L^{179}$ |
| 1887. | $L^{106}$ | $L^{141}$ | $L^{179}$ |
| 1888. | $L^{106}$ | $L^{159}$ | $L^{179}$ |
| 1889. | $L^{106}$ | $L^{160}$ | $L^{179}$ |
| 1890. | $L^{106}$ | $L^{107}$ | $L^{180}$ |
| 1891. | $L^{106}$ | $L^{108}$ | $L^{180}$ |
| 1892. | $L^{106}$ | $L^{109}$ | $L^{180}$ |
| 1893. | $L^{106}$ | $L^{110}$ | $L^{180}$ |
| 1894. | $L^{106}$ | $L^{111}$ | $L^{180}$ |
| 1895. | $L^{106}$ | $L^{112}$ | $L^{180}$ |
| 1896. | $L^{106}$ | $L^{113}$ | $L^{180}$ |
| 1897. | $L^{106}$ | $L^{114}$ | $L^{180}$ |
| 1898. | $L^{106}$ | $L^{115}$ | $L^{180}$ |
| 1899. | $L^{106}$ | $L^{116}$ | $L^{180}$ |
| 1900. | $L^{106}$ | $L^{117}$ | $L^{180}$ |
| 1901. | $L^{106}$ | $L^{118}$ | $L^{180}$ |
| 1902. | $L^{106}$ | $L^{119}$ | $L^{180}$ |
| 1903. | $L^{106}$ | $L^{130}$ | $L^{180}$ |
| 1904. | $L^{106}$ | $L^{131}$ | $L^{180}$ |
| 1905. | $L^{106}$ | $L^{132}$ | $L^{180}$ |
| 1906. | $L^{106}$ | $L^{133}$ | $L^{180}$ |
| 1907. | $L^{106}$ | $L^{134}$ | $L^{180}$ |
| 1908. | $L^{106}$ | $L^{140}$ | $L^{180}$ |
| 1909. | $L^{106}$ | $L^{141}$ | $L^{180}$ |
| 1910. | $L^{106}$ | $L^{159}$ | $L^{180}$ |
| 1911. | $L^{106}$ | $L^{160}$ | $L^{180}$ |
| 1912. | $L^{107}$ | $L^{108}$ | $L^{144}$ |
| 1913. | $L^{107}$ | $L^{109}$ | $L^{144}$ |
| 1914. | $L^{107}$ | $L^{110}$ | $L^{144}$ |
| 1915. | $L^{107}$ | $L^{111}$ | $L^{144}$ |
| 1916. | $L^{107}$ | $L^{112}$ | $L^{144}$ |
| 1917. | $L^{107}$ | $L^{113}$ | $L^{144}$ |
| 1918. | $L^{107}$ | $L^{114}$ | $L^{144}$ |
| 1919. | $L^{107}$ | $L^{115}$ | $L^{144}$ |
| 1920. | $L^{107}$ | $L^{116}$ | $L^{144}$ |
| 1921. | $L^{107}$ | $L^{117}$ | $L^{144}$ |
| 1922. | $L^{107}$ | $L^{118}$ | $L^{144}$ |
| 1923. | $L^{107}$ | $L^{119}$ | $L^{144}$ |
| 1924. | $L^{107}$ | $L^{130}$ | $L^{144}$ |
| 1925. | $L^{107}$ | $L^{131}$ | $L^{144}$ |
| 1926. | $L^{107}$ | $L^{132}$ | $L^{144}$ |
| 1927. | $L^{107}$ | $L^{133}$ | $L^{144}$ |
| 1928. | $L^{107}$ | $L^{134}$ | $L^{144}$ |
| 1929. | $L^{107}$ | $L^{140}$ | $L^{144}$ |
| 1930. | $L^{107}$ | $L^{141}$ | $L^{144}$ |
| 1931. | $L^{107}$ | $L^{159}$ | $L^{144}$ |
| 1932. | $L^{107}$ | $L^{160}$ | $L^{144}$ |
| 1933. | $L^{107}$ | $L^{108}$ | $L^{145}$ |
| 1934. | $L^{107}$ | $L^{109}$ | $L^{145}$ |
| 1935. | $L^{107}$ | $L^{110}$ | $L^{145}$ |
| 1936. | $L^{107}$ | $L^{111}$ | $L^{145}$ |
| 1937. | $L^{107}$ | $L^{112}$ | $L^{145}$ |
| 1938. | $L^{107}$ | $L^{113}$ | $L^{145}$ |
| 1939. | $L^{107}$ | $L^{114}$ | $L^{145}$ |
| 1940. | $L^{107}$ | $L^{115}$ | $L^{145}$ |
| 1941. | $L^{107}$ | $L^{116}$ | $L^{145}$ |
| 1942. | $L^{107}$ | $L^{117}$ | $L^{145}$ |
| 1943. | $L^{107}$ | $L^{118}$ | $L^{145}$ |
| 1944. | $L^{107}$ | $L^{119}$ | $L^{145}$ |
| 1945. | $L^{107}$ | $L^{130}$ | $L^{145}$ |
| 1946. | $L^{107}$ | $L^{131}$ | $L^{145}$ |
| 1947. | $L^{107}$ | $L^{132}$ | $L^{145}$ |
| 1948. | $L^{107}$ | $L^{133}$ | $L^{145}$ |
| 1949. | $L^{107}$ | $L^{134}$ | $L^{145}$ |
| 1950. | $L^{107}$ | $L^{140}$ | $L^{145}$ |
| 1951. | $L^{107}$ | $L^{141}$ | $L^{145}$ |
| 1952. | $L^{107}$ | $L^{159}$ | $L^{145}$ |
| 1953. | $L^{107}$ | $L^{160}$ | $L^{145}$ |
| 1954. | $L^{107}$ | $L^{108}$ | $L^{147}$ |
| 1955. | $L^{107}$ | $L^{109}$ | $L^{147}$ |
| 1956. | $L^{107}$ | $L^{110}$ | $L^{147}$ |
| 1957. | $L^{107}$ | $L^{111}$ | $L^{147}$ |
| 1958. | $L^{107}$ | $L^{112}$ | $L^{147}$ |
| 1959. | $L^{107}$ | $L^{113}$ | $L^{147}$ |
| 1960. | $L^{107}$ | $L^{114}$ | $L^{147}$ |
| 1961. | $L^{107}$ | $L^{115}$ | $L^{147}$ |
| 1962. | $L^{107}$ | $L^{116}$ | $L^{147}$ |
| 1963. | $L^{107}$ | $L^{117}$ | $L^{147}$ |
| 1964. | $L^{107}$ | $L^{118}$ | $L^{147}$ |
| 1965. | $L^{107}$ | $L^{119}$ | $L^{147}$ |
| 1966. | $L^{107}$ | $L^{130}$ | $L^{147}$ |
| 1967. | $L^{107}$ | $L^{131}$ | $L^{147}$ |
| 1968. | $L^{107}$ | $L^{132}$ | $L^{147}$ |
| 1969. | $L^{107}$ | $L^{133}$ | $L^{147}$ |
| 1970. | $L^{107}$ | $L^{134}$ | $L^{147}$ |
| 1971. | $L^{107}$ | $L^{140}$ | $L^{147}$ |
| 1972. | $L^{107}$ | $L^{141}$ | $L^{147}$ |
| 1973. | $L^{107}$ | $L^{159}$ | $L^{147}$ |
| 1974. | $L^{107}$ | $L^{160}$ | $L^{147}$ |
| 1975. | $L^{107}$ | $L^{108}$ | $L^{149}$ |
| 1976. | $L^{107}$ | $L^{109}$ | $L^{149}$ |
| 1977. | $L^{107}$ | $L^{110}$ | $L^{149}$ |
| 1978. | $L^{107}$ | $L^{111}$ | $L^{149}$ |
| 1979. | $L^{107}$ | $L^{112}$ | $L^{149}$ |
| 1980. | $L^{107}$ | $L^{113}$ | $L^{149}$ |
| 1981. | $L^{107}$ | $L^{114}$ | $L^{149}$ |
| 1982. | $L^{107}$ | $L^{115}$ | $L^{149}$ |
| 1983. | $L^{107}$ | $L^{116}$ | $L^{149}$ |
| 1984. | $L^{107}$ | $L^{117}$ | $L^{149}$ |
| 1985. | $L^{107}$ | $L^{118}$ | $L^{149}$ |
| 1986. | $L^{107}$ | $L^{119}$ | $L^{149}$ |
| 1987. | $L^{107}$ | $L^{130}$ | $L^{149}$ |
| 1988. | $L^{107}$ | $L^{131}$ | $L^{149}$ |
| 1989. | $L^{107}$ | $L^{132}$ | $L^{149}$ |
| 1990. | $L^{107}$ | $L^{133}$ | $L^{149}$ |
| 1991. | $L^{107}$ | $L^{134}$ | $L^{149}$ |
| 1992. | $L^{107}$ | $L^{140}$ | $L^{149}$ |
| 1993. | $L^{107}$ | $L^{141}$ | $L^{149}$ |
| 1994. | $L^{107}$ | $L^{159}$ | $L^{149}$ |
| 1995. | $L^{107}$ | $L^{160}$ | $L^{149}$ |
| 1996. | $L^{107}$ | $L^{108}$ | $L^{152}$ |
| 1997. | $L^{107}$ | $L^{109}$ | $L^{152}$ |
| 1998. | $L^{107}$ | $L^{110}$ | $L^{152}$ |
| 1999. | $L^{107}$ | $L^{111}$ | $L^{152}$ |
| 2000. | $L^{107}$ | $L^{112}$ | $L^{152}$ |
| 2001. | $L^{107}$ | $L^{113}$ | $L^{152}$ |
| 2002. | $L^{107}$ | $L^{114}$ | $L^{152}$ |
| 2003. | $L^{107}$ | $L^{115}$ | $L^{152}$ |
| 2004. | $L^{107}$ | $L^{116}$ | $L^{152}$ |
| 2005. | $L^{107}$ | $L^{117}$ | $L^{152}$ |
| 2006. | $L^{107}$ | $L^{118}$ | $L^{152}$ |
| 2007. | $L^{107}$ | $L^{119}$ | $L^{152}$ |
| 2008. | $L^{107}$ | $L^{130}$ | $L^{152}$ |
| 2009. | $L^{107}$ | $L^{131}$ | $L^{152}$ |
| 2010. | $L^{107}$ | $L^{132}$ | $L^{152}$ |
| 2011. | $L^{107}$ | $L^{133}$ | $L^{152}$ |
| 2012. | $L^{107}$ | $L^{134}$ | $L^{152}$ |
| 2013. | $L^{107}$ | $L^{140}$ | $L^{152}$ |

TABLE 1-continued

| Compound number | $L_1$ | $L_2$ | $L_3$ |
|---|---|---|---|
| 2014. | $L^{107}$ | $L^{141}$ | $L^{152}$ |
| 2015. | $L^{107}$ | $L^{159}$ | $L^{152}$ |
| 2016. | $L^{107}$ | $L^{160}$ | $L^{152}$ |
| 2017. | $L^{107}$ | $L^{108}$ | $L^{164}$ |
| 2018. | $L^{107}$ | $L^{109}$ | $L^{164}$ |
| 2019. | $L^{107}$ | $L^{110}$ | $L^{164}$ |
| 2020. | $L^{107}$ | $L^{111}$ | $L^{164}$ |
| 2021. | $L^{107}$ | $L^{112}$ | $L^{164}$ |
| 2022. | $L^{107}$ | $L^{113}$ | $L^{164}$ |
| 2023. | $L^{107}$ | $L^{114}$ | $L^{164}$ |
| 2024. | $L^{107}$ | $L^{115}$ | $L^{164}$ |
| 2025. | $L^{107}$ | $L^{116}$ | $L^{164}$ |
| 2026. | $L^{107}$ | $L^{117}$ | $L^{164}$ |
| 2027. | $L^{107}$ | $L^{118}$ | $L^{164}$ |
| 2028. | $L^{107}$ | $L^{119}$ | $L^{164}$ |
| 2029. | $L^{107}$ | $L^{130}$ | $L^{164}$ |
| 2030. | $L^{107}$ | $L^{131}$ | $L^{164}$ |
| 2031. | $L^{107}$ | $L^{132}$ | $L^{164}$ |
| 2032. | $L^{107}$ | 1:33 | $L^{164}$ |
| 2033. | $L^{107}$ | $L^{134}$ | $L^{164}$ |
| 2034. | $L^{107}$ | $L^{140}$ | $L^{164}$ |
| 2035. | $L^{107}$ | $L^{141}$ | $L^{164}$ |
| 2036. | $L^{107}$ | $L^{159}$ | $L^{164}$ |
| 2037. | $L^{107}$ | $L^{160}$ | $L^{164}$ |
| 2038. | $L^{107}$ | $L^{108}$ | $L^{165}$ |
| 2039. | $L^{107}$ | $L^{109}$ | $L^{165}$ |
| 2040. | $L^{107}$ | $L^{110}$ | $L^{165}$ |
| 2041. | $L^{107}$ | $L^{111}$ | $L^{165}$ |
| 2042. | $L^{107}$ | $L^{112}$ | $L^{165}$ |
| 2043. | $L^{107}$ | $L^{113}$ | $L^{165}$ |
| 2044. | $L^{107}$ | $L^{114}$ | $L^{165}$ |
| 2045. | $L^{107}$ | $L^{115}$ | $L^{165}$ |
| 2046. | $L^{107}$ | $L^{116}$ | $L^{165}$ |
| 2047. | $L^{107}$ | $L^{117}$ | $L^{165}$ |
| 2048. | $L^{107}$ | $L^{118}$ | $L^{165}$ |
| 2049. | $L^{107}$ | $L^{119}$ | $L^{165}$ |
| 2050. | $L^{107}$ | $L^{130}$ | $L^{165}$ |
| 2051. | $L^{107}$ | $L^{131}$ | $L^{165}$ |
| 2052. | $L^{107}$ | $L^{132}$ | $L^{165}$ |
| 2053. | $L^{107}$ | $L^{133}$ | $L^{165}$ |
| 2054. | $L^{107}$ | $L^{134}$ | $L^{165}$ |
| 2055. | $L^{107}$ | $L^{140}$ | $L^{165}$ |
| 2056. | $L^{107}$ | $L^{141}$ | $L^{165}$ |
| 2057. | $L^{107}$ | $L^{159}$ | $L^{165}$ |
| 2058. | $L^{107}$ | $L^{160}$ | $L^{165}$ |
| 2059. | $L^{107}$ | $L^{108}$ | $L^{166}$ |
| 2060. | $L^{107}$ | $L^{109}$ | $L^{166}$ |
| 2061. | $L^{107}$ | $L^{110}$ | $L^{166}$ |
| 2062. | $L^{107}$ | $L^{111}$ | $L^{166}$ |
| 2063. | $L^{107}$ | $L^{112}$ | $L^{166}$ |
| 2064. | $L^{107}$ | $L^{113}$ | $L^{166}$ |
| 2065. | $L^{107}$ | $L^{114}$ | $L^{166}$ |
| 2066. | $L^{107}$ | $L^{115}$ | $L^{166}$ |
| 2067. | $L^{107}$ | $L^{116}$ | $L^{166}$ |
| 2068. | $L^{107}$ | $L^{117}$ | $L^{166}$ |
| 2069. | $L^{107}$ | $L^{118}$ | $L^{166}$ |
| 2070. | $L^{107}$ | $L^{119}$ | $L^{166}$ |
| 2071. | $L^{107}$ | $L^{130}$ | $L^{166}$ |
| 2072. | $L^{107}$ | $L^{131}$ | $L^{166}$ |
| 2073. | $L^{107}$ | $L^{132}$ | $L^{166}$ |
| 2074. | $L^{107}$ | $L^{133}$ | $L^{166}$ |
| 2075. | $L^{107}$ | $L^{134}$ | $L^{166}$ |
| 2076. | $L^{107}$ | $L^{140}$ | $L^{166}$ |
| 2077. | $L^{107}$ | $L^{141}$ | $L^{166}$ |
| 2078. | $L^{107}$ | $L^{159}$ | $L^{166}$ |
| 2079. | $L^{107}$ | $L^{160}$ | $L^{166}$ |
| 2080. | $L^{107}$ | $L^{108}$ | $L^{170}$ |
| 2081. | $L^{107}$ | $L^{109}$ | $L^{170}$ |
| 2082. | $L^{107}$ | $L^{110}$ | $L^{170}$ |
| 2083. | $L^{107}$ | $L^{111}$ | $L^{170}$ |
| 2084. | $L^{107}$ | $L^{112}$ | $L^{170}$ |
| 2085. | $L^{107}$ | $L^{113}$ | $L^{170}$ |
| 2086. | $L^{107}$ | $L^{114}$ | $L^{170}$ |
| 2087. | $L^{107}$ | $L^{115}$ | $L^{170}$ |
| 2088. | $L^{107}$ | $L^{116}$ | $L^{170}$ |
| 2089. | $L^{107}$ | $L^{117}$ | $L^{170}$ |
| 2090. | $L^{107}$ | $L^{118}$ | $L^{170}$ |
| 2091. | $L^{107}$ | $L^{119}$ | $L^{170}$ |
| 2092. | $L^{107}$ | $L^{130}$ | $L^{170}$ |
| 2093. | $L^{107}$ | $L^{131}$ | $L^{170}$ |
| 2094. | $L^{107}$ | $L^{132}$ | $L^{170}$ |
| 2095. | $L^{107}$ | $L^{133}$ | $L^{170}$ |
| 2096. | $L^{107}$ | $L^{134}$ | $L^{170}$ |
| 2097. | $L^{107}$ | $L^{140}$ | $L^{170}$ |
| 2098. | $L^{107}$ | $L^{141}$ | $L^{170}$ |
| 2099. | $L^{107}$ | $L^{159}$ | $L^{170}$ |
| 2100. | $L^{107}$ | $L^{160}$ | $L^{170}$ |
| 2101. | $L^{107}$ | $L^{108}$ | $L^{174}$ |
| 2102. | $L^{107}$ | $L^{109}$ | $L^{174}$ |
| 2103. | $L^{107}$ | $L^{110}$ | $L^{174}$ |
| 2104. | $L^{107}$ | $L^{111}$ | $L^{174}$ |
| 2105. | $L^{107}$ | $L^{112}$ | $L^{174}$ |
| 2106. | $L^{107}$ | $L^{113}$ | $L^{174}$ |
| 2107. | $L^{107}$ | $L^{114}$ | $L^{174}$ |
| 2108. | $L^{107}$ | $L^{115}$ | $L^{174}$ |
| 2109. | $L^{107}$ | $L^{116}$ | $L^{174}$ |
| 2110. | $L^{107}$ | $L^{117}$ | $L^{174}$ |
| 2111. | $L^{107}$ | $L^{118}$ | $L^{174}$ |
| 2112. | $L^{107}$ | $L^{119}$ | $L^{174}$ |
| 2113. | $L^{107}$ | $L^{130}$ | $L^{174}$ |
| 2114. | $L^{107}$ | $L^{131}$ | $L^{174}$ |
| 2115. | $L^{107}$ | $L^{132}$ | $L^{174}$ |
| 2116. | $L^{107}$ | $L^{133}$ | $L^{174}$ |
| 2117. | $L^{107}$ | $L^{134}$ | $L^{174}$ |
| 2118. | $L^{107}$ | $L^{140}$ | $L^{174}$ |
| 2119. | $L^{107}$ | $L^{141}$ | $L^{174}$ |
| 2120. | $L^{107}$ | $L^{159}$ | $L^{174}$ |
| 2121. | $L^{107}$ | $L^{160}$ | $L^{174}$ |
| 2122. | $L^{107}$ | $L^{108}$ | $L^{176}$ |
| 2123. | $L^{107}$ | $L^{109}$ | $L^{176}$ |
| 2124. | $L^{107}$ | $L^{110}$ | $L^{176}$ |
| 2125. | $L^{107}$ | $L^{111}$ | $L^{176}$ |
| 2126. | $L^{107}$ | $L^{112}$ | $L^{176}$ |
| 2127. | $L^{107}$ | $L^{113}$ | $L^{176}$ |
| 2128. | $L^{107}$ | $L^{114}$ | $L^{176}$ |
| 2129. | $L^{107}$ | $L^{115}$ | $L^{176}$ |
| 2130. | $L^{107}$ | $L^{116}$ | $L^{176}$ |
| 2131. | $L^{107}$ | $L^{117}$ | $L^{176}$ |
| 2132. | $L^{107}$ | $L^{118}$ | $L^{176}$ |
| 2133. | $L^{107}$ | $L^{119}$ | $L^{176}$ |
| 2134. | $L^{107}$ | $L^{130}$ | $L^{176}$ |
| 2135. | $L^{107}$ | $L^{131}$ | $L^{176}$ |
| 2136. | $L^{107}$ | $L^{132}$ | $L^{176}$ |
| 2137. | $L^{107}$ | $L^{133}$ | $L^{176}$ |
| 2138. | $L^{107}$ | $L^{134}$ | $L^{176}$ |
| 2139. | $L^{107}$ | $L^{140}$ | $L^{176}$ |
| 2140. | $L^{107}$ | $L^{141}$ | $L^{176}$ |
| 2141. | $L^{107}$ | $L^{159}$ | $L^{176}$ |
| 2142. | $L^{107}$ | $L^{160}$ | $L^{176}$ |
| 2143. | $L^{107}$ | $L^{108}$ | $L^{179}$ |
| 2144. | $L^{107}$ | $L^{109}$ | $L^{179}$ |
| 2145. | $L^{107}$ | $L^{110}$ | $L^{179}$ |
| 2146. | $L^{107}$ | $L^{111}$ | $L^{179}$ |
| 2147. | $L^{107}$ | $L^{112}$ | $L^{179}$ |
| 2148. | $L^{107}$ | $L^{113}$ | $L^{179}$ |
| 2149. | $L^{107}$ | $L^{114}$ | $L^{179}$ |
| 2150. | $L^{107}$ | $L^{115}$ | $L^{179}$ |
| 2151. | $L^{107}$ | $L^{116}$ | $L^{179}$ |
| 2152. | $L^{107}$ | $L^{117}$ | $L^{179}$ |
| 2153. | $L^{107}$ | $L^{118}$ | $L^{179}$ |
| 2154. | $L^{107}$ | $L^{119}$ | $L^{179}$ |
| 2155. | $L^{107}$ | $L^{130}$ | $L^{179}$ |
| 2156. | $L^{107}$ | $L^{131}$ | $L^{179}$ |
| 2157. | $L^{107}$ | $L^{132}$ | $L^{179}$ |
| 2158. | $L^{107}$ | $L^{133}$ | $L^{179}$ |
| 2159. | $L^{107}$ | $L^{134}$ | $L^{179}$ |
| 2160. | $L^{107}$ | $L^{140}$ | $L^{179}$ |
| 2161. | $L^{107}$ | $L^{141}$ | $L^{179}$ |
| 2162. | $L^{107}$ | $L^{159}$ | $L^{179}$ |
| 2163. | $L^{107}$ | $L^{160}$ | $L^{179}$ |
| 2164. | $L^{107}$ | $L^{108}$ | $L^{180}$ |
| 2165. | $L^{107}$ | $L^{109}$ | $L^{180}$ |
| 2166. | $L^{107}$ | $L^{110}$ | $L^{180}$ |
| 2167. | $L^{107}$ | $L^{111}$ | $L^{180}$ |

TABLE 1-continued

| Compound number | $L_1$ | $L_2$ | $L_3$ |
|---|---|---|---|
| 2168. | $L^{107}$ | $L^{112}$ | $L^{180}$ |
| 2169. | $L^{107}$ | $L^{113}$ | $L^{180}$ |
| 2170. | $L^{107}$ | $L^{114}$ | $L^{180}$ |
| 2171. | $L^{107}$ | $L^{115}$ | $L^{180}$ |
| 2172. | $L^{107}$ | $L^{116}$ | $L^{180}$ |
| 2173. | $L^{107}$ | $L^{117}$ | $L^{180}$ |
| 2174. | $L^{107}$ | $L^{118}$ | $L^{180}$ |
| 2175. | $L^{107}$ | $L^{119}$ | $L^{180}$ |
| 2176. | $L^{107}$ | $L^{130}$ | $L^{180}$ |
| 2177. | $L^{107}$ | $L^{131}$ | $L^{180}$ |
| 2178. | $L^{107}$ | $L^{132}$ | $L^{180}$ |
| 2179. | $L^{107}$ | $L^{133}$ | $L^{180}$ |
| 2180. | $L^{107}$ | $L^{134}$ | $L^{180}$ |
| 2181. | $L^{107}$ | $L^{140}$ | $L^{180}$ |
| 2182. | $L^{107}$ | $L^{141}$ | $L^{180}$ |
| 2183. | $L^{107}$ | $L^{159}$ | $L^{180}$ |
| 2184. | $L^{107}$ | $L^{160}$ | $L^{180}$ |
| 2185. | $L^{108}$ | $L^{109}$ | $L^{144}$ |
| 2186. | $L^{108}$ | $L^{110}$ | $L^{144}$ |
| 2187. | $L^{108}$ | $L^{111}$ | $L^{144}$ |
| 2188. | $L^{108}$ | $L^{112}$ | $L^{144}$ |
| 2189. | $L^{108}$ | $L^{113}$ | $L^{144}$ |
| 2190. | $L^{108}$ | $L^{114}$ | $L^{144}$ |
| 2191. | $L^{108}$ | $L^{115}$ | $L^{144}$ |
| 2192. | $L^{108}$ | $L^{116}$ | $L^{144}$ |
| 2193. | $L^{108}$ | $L^{117}$ | $L^{144}$ |
| 2194. | $L^{108}$ | $L^{118}$ | $L^{144}$ |
| 2195. | $L^{108}$ | $L^{119}$ | $L^{144}$ |
| 2196. | $L^{108}$ | $L^{130}$ | $L^{144}$ |
| 2197. | $L^{108}$ | $L^{131}$ | $L^{144}$ |
| 2198. | $L^{108}$ | $L^{132}$ | $L^{144}$ |
| 2199. | $L^{108}$ | $L^{133}$ | $L^{144}$ |
| 2200. | $L^{108}$ | $L^{134}$ | $L^{144}$ |
| 2201. | $L^{108}$ | $L^{140}$ | $L^{144}$ |
| 2202. | $L^{108}$ | $L^{141}$ | $L^{144}$ |
| 2203. | $L^{108}$ | $L^{159}$ | $L^{144}$ |
| 2204. | $L^{108}$ | $L^{160}$ | $L^{144}$ |
| 2205. | $L^{108}$ | $L^{109}$ | $L^{145}$ |
| 2206. | $L^{108}$ | $L^{110}$ | $L^{145}$ |
| 2207. | $L^{108}$ | $L^{111}$ | $L^{145}$ |
| 2208. | $L^{108}$ | $L^{112}$ | $L^{145}$ |
| 2209. | $L^{108}$ | $L^{113}$ | $L^{145}$ |
| 2210. | $L^{108}$ | $L^{114}$ | $L^{145}$ |
| 2211. | $L^{108}$ | $L^{115}$ | $L^{145}$ |
| 2212. | $L^{108}$ | $L^{116}$ | $L^{145}$ |
| 2213. | $L^{108}$ | $L^{117}$ | $L^{145}$ |
| 2214. | $L^{108}$ | $L^{118}$ | $L^{145}$ |
| 2215. | $L^{108}$ | $L^{119}$ | $L^{145}$ |
| 2216. | $L^{108}$ | $L^{130}$ | $L^{145}$ |
| 2217. | $L^{108}$ | $L^{131}$ | $L^{145}$ |
| 2218. | $L^{108}$ | $L^{132}$ | $L^{145}$ |
| 2219. | $L^{108}$ | $L^{133}$ | $L^{145}$ |
| 2220. | $L^{108}$ | $L^{134}$ | $L^{145}$ |
| 2221. | $L^{108}$ | $L^{140}$ | $L^{145}$ |
| 2222. | $L^{108}$ | $L^{141}$ | $L^{145}$ |
| 2223. | $L^{108}$ | $L^{159}$ | $L^{145}$ |
| 2224. | $L^{108}$ | $L^{160}$ | $L^{145}$ |
| 2225. | $L^{108}$ | $L^{109}$ | $L^{147}$ |
| 2226. | $L^{108}$ | $L^{110}$ | $L^{147}$ |
| 2227. | $L^{108}$ | $L^{111}$ | $L^{147}$ |
| 2228. | $L^{108}$ | $L^{112}$ | $L^{147}$ |
| 2229. | $L^{108}$ | $L^{113}$ | $L^{147}$ |
| 2230. | $L^{108}$ | $L^{114}$ | $L^{147}$ |
| 2231. | $L^{108}$ | $L^{115}$ | $L^{147}$ |
| 2232. | $L^{108}$ | $L^{116}$ | $L^{147}$ |
| 2233. | $L^{108}$ | $L^{117}$ | $L^{147}$ |
| 2234. | $L^{108}$ | $L^{118}$ | $L^{147}$ |
| 2235. | $L^{108}$ | $L^{119}$ | $L^{147}$ |
| 2236. | $L^{108}$ | $L^{130}$ | $L^{147}$ |
| 2237. | $L^{108}$ | $L^{131}$ | $L^{147}$ |
| 2238. | $L^{108}$ | $L^{132}$ | $L^{147}$ |
| 2239. | $L^{108}$ | $L^{133}$ | $L^{147}$ |
| 2240. | $L^{108}$ | $L^{134}$ | $L^{147}$ |
| 2241. | $L^{108}$ | $L^{140}$ | $L^{147}$ |
| 2242. | $L^{108}$ | $L^{141}$ | $L^{147}$ |
| 2243. | $L^{108}$ | $L^{159}$ | $L^{147}$ |
| 2244. | $L^{108}$ | $L^{160}$ | $L^{147}$ |
| 2245. | $L^{108}$ | $L^{109}$ | $L^{149}$ |
| 2246. | $L^{108}$ | $L^{110}$ | $L^{149}$ |
| 2247. | $L^{108}$ | $L^{111}$ | $L^{149}$ |
| 2248. | $L^{108}$ | $L^{112}$ | $L^{149}$ |
| 2249. | $L^{108}$ | $L^{113}$ | $L^{149}$ |
| 2250. | $L^{108}$ | $L^{114}$ | $L^{149}$ |
| 2251. | $L^{108}$ | $L^{115}$ | $L^{149}$ |
| 2252. | $L^{108}$ | $L^{116}$ | $L^{149}$ |
| 2253. | $L^{108}$ | $L^{117}$ | $L^{149}$ |
| 2254. | $L^{108}$ | $L^{118}$ | $L^{149}$ |
| 2255. | $L^{108}$ | $L^{119}$ | $L^{149}$ |
| 2256. | $L^{108}$ | $L^{130}$ | $L^{149}$ |
| 2257. | $L^{108}$ | $L^{131}$ | $L^{149}$ |
| 2258. | $L^{108}$ | $L^{132}$ | $L^{149}$ |
| 2259. | $L^{108}$ | $L^{133}$ | $L^{149}$ |
| 2260. | $L^{108}$ | $L^{134}$ | $L^{149}$ |
| 2261. | $L^{108}$ | $L^{140}$ | $L^{149}$ |
| 2262. | $L^{118}$ | $L^{141}$ | $L^{149}$ |
| 2263. | $L^{108}$ | $L^{159}$ | $L^{149}$ |
| 2264. | $L^{108}$ | $L^{160}$ | $L^{149}$ |
| 2265. | $L^{108}$ | $L^{109}$ | $L^{152}$ |
| 2266. | $L^{108}$ | $L^{110}$ | $L^{152}$ |
| 2267. | $L^{108}$ | $L^{111}$ | $L^{152}$ |
| 2268. | $L^{108}$ | $L^{112}$ | $L^{152}$ |
| 2269. | $L^{108}$ | $L^{113}$ | $L^{152}$ |
| 2270. | $L^{108}$ | $L^{114}$ | $L^{152}$ |
| 2271. | $L^{108}$ | $L^{115}$ | $L^{152}$ |
| 2272. | $L^{108}$ | $L^{116}$ | $L^{152}$ |
| 2273. | $L^{108}$ | $L^{117}$ | $L^{152}$ |
| 2274. | $L^{108}$ | $L^{118}$ | $L^{152}$ |
| 2275. | $L^{108}$ | $L^{119}$ | $L^{152}$ |
| 2276. | $L^{108}$ | $L^{130}$ | $L^{152}$ |
| 2277. | $L^{108}$ | $L^{131}$ | $L^{152}$ |
| 2278. | $L^{108}$ | $L^{132}$ | $L^{152}$ |
| 2279. | $L^{108}$ | $L^{133}$ | $L^{152}$ |
| 2280. | $L^{108}$ | $L^{134}$ | $L^{152}$ |
| 2281. | $L^{108}$ | $L^{140}$ | $L^{152}$ |
| 2282. | $L^{108}$ | $L^{141}$ | $L^{152}$ |
| 2283. | $L^{108}$ | $L^{159}$ | $L^{152}$ |
| 2284. | $L^{108}$ | $L^{160}$ | $L^{152}$ |
| 2285. | $L^{108}$ | $L^{109}$ | $L^{164}$ |
| 2286. | $L^{108}$ | $L^{110}$ | $L^{164}$ |
| 2287. | $L^{108}$ | $L^{111}$ | $L^{164}$ |
| 2288. | $L^{108}$ | $L^{112}$ | $L^{164}$ |
| 2289. | $L^{108}$ | $L^{113}$ | $L^{164}$ |
| 2290. | $L^{108}$ | $L^{114}$ | $L^{164}$ |
| 2291. | $L^{108}$ | $L^{115}$ | $L^{164}$ |
| 2292. | $L^{108}$ | $L^{116}$ | $L^{164}$ |
| 2293. | $L^{108}$ | $L^{117}$ | $L^{164}$ |
| 2294. | $L^{108}$ | $L^{118}$ | $L^{164}$ |
| 2295. | $L^{108}$ | $L^{119}$ | $L^{164}$ |
| 2296. | $L^{108}$ | $L^{130}$ | $L^{164}$ |
| 2297. | $L^{108}$ | $L^{131}$ | $L^{164}$ |
| 2298. | $L^{108}$ | $L^{132}$ | $L^{164}$ |
| 2299. | $L^{108}$ | $L^{133}$ | $L^{164}$ |
| 2300. | $L^{108}$ | $L^{134}$ | $L^{164}$ |
| 2301. | $L^{108}$ | $L^{140}$ | $L^{164}$ |
| 2302. | $L^{108}$ | $L^{141}$ | $L^{164}$ |
| 2303. | $L^{108}$ | $L^{159}$ | $L^{164}$ |
| 2304. | $L^{108}$ | $L^{160}$ | $L^{164}$ |
| 2305. | $L^{108}$ | $L^{109}$ | $L^{165}$ |
| 2306. | $L^{108}$ | $L^{110}$ | $L^{165}$ |
| 2307. | $L^{108}$ | $L^{111}$ | $L^{165}$ |
| 2308. | $L^{108}$ | $L^{112}$ | $L^{165}$ |
| 2309. | $L^{108}$ | $L^{113}$ | $L^{165}$ |
| 2310. | $L^{108}$ | $L^{114}$ | $L^{165}$ |
| 2311. | $L^{108}$ | $L^{115}$ | $L^{165}$ |
| 2312. | $L^{108}$ | $L^{116}$ | $L^{165}$ |
| 2313. | $L^{108}$ | $L^{117}$ | $L^{165}$ |
| 2314. | $L^{108}$ | $L^{118}$ | $L^{165}$ |
| 2315. | $L^{108}$ | $L^{119}$ | $L^{165}$ |
| 2316. | $L^{108}$ | $L^{130}$ | $L^{165}$ |
| 2317. | $L^{108}$ | $L^{131}$ | $L^{165}$ |
| 2318. | $L^{108}$ | $L^{132}$ | $L^{165}$ |
| 2319. | $L^{108}$ | $L^{133}$ | $L^{165}$ |
| 2320. | $L^{108}$ | $L^{134}$ | $L^{165}$ |
| 2321. | $L^{108}$ | $L^{140}$ | $L^{165}$ |

TABLE 1-continued

| Compound number | L₁ | L₂ | L₃ |
|---|---|---|---|
| 2322. | L¹⁰⁸ | L¹⁴¹ | L¹⁶⁵ |
| 2323. | L¹⁰⁸ | L¹⁵⁹ | L¹⁶⁵ |
| 2324. | L¹⁰⁸ | L¹⁶⁰ | L¹⁶⁵ |
| 2325. | L¹⁰⁸ | L¹⁰⁹ | L¹⁶⁶ |
| 2326. | L¹⁰⁸ | L¹¹⁰ | L¹⁶⁶ |
| 2327. | L¹⁰⁸ | L¹¹¹ | L¹⁶⁶ |
| 2328. | L¹⁰⁸ | L¹¹² | L¹⁶⁶ |
| 2329. | L¹⁰⁸ | L¹¹³ | L¹⁶⁶ |
| 2330. | L¹⁰⁸ | L¹¹⁴ | L¹⁶⁶ |
| 2331. | L¹⁰⁸ | L¹¹⁵ | L¹⁶⁶ |
| 2332. | L¹⁰⁸ | L¹¹⁶ | L¹⁶⁶ |
| 2333. | L¹⁰⁸ | L¹¹⁷ | L¹⁶⁶ |
| 2334. | L¹⁰⁸ | L¹¹⁸ | L¹⁶⁶ |
| 2335. | L¹⁰⁸ | L¹¹⁹ | L¹⁶⁶ |
| 2336. | L¹⁰⁸ | L¹³⁰ | L¹⁶⁶ |
| 2337. | L¹⁰⁸ | L¹³¹ | L¹⁶⁶ |
| 2338. | L¹⁰⁸ | L¹³² | L¹⁶⁶ |
| 2339. | L¹⁰⁸ | L¹³³ | L¹⁶⁶ |
| 2340. | L¹⁰⁸ | L¹³⁴ | L¹⁶⁶ |
| 2341. | L¹⁰⁸ | L¹⁴⁰ | L¹⁶⁶ |
| 2342. | L¹⁰⁸ | L¹⁴¹ | L¹⁶⁶ |
| 2343. | L¹⁰⁸ | L¹⁵⁹ | L¹⁶⁶ |
| 2344. | L¹⁰⁸ | L¹⁶⁰ | L¹⁶⁶ |
| 2345. | L¹⁰⁸ | L¹⁰⁹ | L¹⁷⁰ |
| 2346. | L¹⁰⁸ | L¹¹⁰ | L¹⁷⁰ |
| 2347. | L¹⁰⁸ | L¹¹¹ | L¹⁷⁰ |
| 2348. | L¹⁰⁸ | L¹¹² | L¹⁷⁰ |
| 2349. | L¹⁰⁸ | L¹¹³ | L¹⁷⁰ |
| 2350. | L¹⁰⁸ | L¹¹⁴ | L¹⁷⁰ |
| 2351. | L¹⁰⁸ | L¹¹⁵ | L¹⁷⁰ |
| 2352. | L¹⁰⁸ | L¹¹⁶ | L¹⁷⁰ |
| 2353. | L¹⁰⁸ | L¹¹⁷ | L¹⁷⁰ |
| 2354. | L¹⁰⁸ | L¹¹⁸ | L¹⁷⁰ |
| 2355. | L¹⁰⁸ | L¹¹⁹ | L¹⁷⁰ |
| 2356. | L¹⁰⁸ | L¹³⁰ | L¹⁷⁰ |
| 2357. | L¹⁰⁸ | L¹³¹ | L¹⁷⁰ |
| 2358. | L¹⁰⁸ | L¹³² | L¹⁷⁰ |
| 2359. | L¹⁰⁸ | L¹³³ | L¹⁷⁰ |
| 2360. | L¹⁰⁸ | L¹³⁴ | L¹⁷⁰ |
| 2361. | L¹⁰⁸ | L¹⁴⁰ | L¹⁷⁰ |
| 2362. | L¹⁰⁸ | L¹⁴¹ | L¹⁷⁰ |
| 2363. | L¹⁰⁸ | L¹⁵⁹ | L¹⁷⁰ |
| 2364. | L¹⁰⁸ | L¹⁶⁰ | L¹⁷⁰ |
| 2365. | L¹⁰⁸ | L¹⁰⁹ | L¹⁷⁴ |
| 2366. | L¹⁰⁸ | L¹¹⁰ | L¹⁷⁴ |
| 2367. | L¹⁰⁸ | L¹¹¹ | L¹⁷⁴ |
| 2368. | L¹⁰⁸ | L¹¹² | L¹⁷⁴ |
| 2369. | L¹⁰⁸ | L¹¹³ | L¹⁷⁴ |
| 2370. | L¹⁰⁸ | L¹¹⁴ | L¹⁷⁴ |
| 2371. | L¹⁰⁸ | L¹¹⁵ | L¹⁷⁴ |
| 2372. | L¹⁰⁸ | L¹¹⁶ | L¹⁷⁴ |
| 2373. | L¹⁰⁸ | L¹¹⁷ | L¹⁷⁴ |
| 2374. | L¹⁰⁸ | L¹¹⁸ | L¹⁷⁴ |
| 2375. | L¹⁰⁸ | L¹¹⁹ | L¹⁷⁴ |
| 2376. | L¹⁰⁸ | L¹³⁰ | L¹⁷⁴ |
| 2377. | L¹⁰⁸ | L¹³¹ | L¹⁷⁴ |
| 2378. | L¹⁰⁸ | L¹³² | L¹⁷⁴ |
| 2379. | L¹⁰⁸ | L¹³³ | L¹⁷⁴ |
| 2380. | L¹⁰⁸ | L¹³⁴ | L¹⁷⁴ |
| 2381. | L¹⁰⁸ | L¹⁴⁰ | L¹⁷⁴ |
| 2382. | L¹⁰⁸ | L¹⁴¹ | L¹⁷⁴ |
| 2383. | L¹⁰⁸ | L¹⁵⁹ | L¹⁷⁴ |
| 2384. | L¹⁰⁸ | L¹⁶⁰ | L¹⁷⁴ |
| 2385. | L¹⁰⁸ | L¹⁰⁹ | L¹⁷⁶ |
| 2386. | L¹⁰⁸ | L¹¹⁰ | L¹⁷⁶ |
| 2387. | L¹⁰⁸ | L¹¹¹ | L¹⁷⁶ |
| 2388. | L¹⁰⁸ | L¹¹² | L¹⁷⁶ |
| 2389. | L¹⁰⁸ | L¹¹³ | L¹⁷⁶ |
| 2390. | L¹⁰⁸ | L¹¹⁴ | L¹⁷⁶ |
| 2391. | L¹⁰⁸ | L¹¹⁵ | L¹⁷⁶ |
| 2392. | L¹⁰⁸ | L¹¹⁶ | L¹⁷⁶ |
| 2393. | L¹⁰⁸ | L¹¹⁷ | L¹⁷⁶ |
| 2394. | L¹⁰⁸ | L¹¹⁸ | L¹⁷⁶ |
| 2395. | L¹⁰⁸ | L¹¹⁹ | L¹⁷⁶ |
| 2396. | L¹⁰⁸ | L¹³⁰ | L¹⁷⁶ |
| 2397. | L¹⁰⁸ | L¹³¹ | L¹⁷⁶ |
| 2398. | L¹⁰⁸ | L¹³² | L¹⁷⁶ |
| 2399. | L¹⁰⁸ | L¹³³ | L¹⁷⁶ |
| 2400. | L¹⁰⁸ | L¹³⁴ | L¹⁷⁶ |
| 2401. | L¹⁰⁸ | L¹⁴⁰ | L¹⁷⁶ |
| 2402. | L¹⁰⁸ | L¹⁴¹ | L¹⁷⁶ |
| 2403. | L¹⁰⁸ | L¹⁵⁹ | L¹⁷⁶ |
| 2404. | L¹⁰⁸ | L¹⁶⁰ | L¹⁷⁶ |
| 2405. | L¹⁰⁸ | L¹⁰⁹ | L¹⁷⁹ |
| 2406. | L¹⁰⁸ | L¹¹⁰ | L¹⁷⁹ |
| 2407. | L¹⁰⁸ | L¹¹¹ | L¹⁷⁹ |
| 2408. | L¹⁰⁸ | L¹¹² | L¹⁷⁹ |
| 2409. | L¹⁰⁸ | L¹¹³ | L¹⁷⁹ |
| 2410. | L¹⁰⁸ | L¹¹⁴ | L¹⁷⁹ |
| 2411. | L¹⁰⁸ | L¹¹⁵ | L¹⁷⁹ |
| 2412. | L¹⁰⁸ | L¹¹⁶ | L¹⁷⁹ |
| 2413. | L¹⁰⁸ | L¹¹⁷ | L¹⁷⁹ |
| 2414. | L¹⁰⁸ | L¹¹⁸ | L¹⁷⁹ |
| 2415. | L¹⁰⁸ | L¹¹⁹ | L¹⁷⁹ |
| 2416. | L¹⁰⁸ | L¹³⁰ | L¹⁷⁹ |
| 2417. | L¹⁰⁸ | L¹³¹ | L¹⁷⁹ |
| 2418. | L¹⁰⁸ | L¹³² | L¹⁷⁹ |
| 2419. | L¹⁰⁸ | L¹³³ | L¹⁷⁹ |
| 2420. | L¹⁰⁸ | L¹³⁴ | L¹⁷⁹ |
| 2421. | L¹⁰⁸ | L¹⁴⁰ | L¹⁷⁹ |
| 2422. | L¹⁰⁸ | L¹⁴¹ | L¹⁷⁹ |
| 2423. | L¹⁰⁸ | L¹⁵⁹ | L¹⁷⁹ |
| 2424. | L¹⁰⁸ | L¹⁶⁰ | L¹⁷⁹ |
| 2425. | L¹⁰⁸ | L¹⁰⁹ | L¹⁸⁰ |
| 2426. | L¹⁰⁸ | L¹¹⁰ | L¹⁸⁰ |
| 2427. | L¹⁰⁸ | L¹¹¹ | L¹⁸⁰ |
| 2428. | L¹⁰⁸ | L¹¹² | L¹⁸⁰ |
| 2429. | L¹⁰⁸ | L¹¹³ | L¹⁸⁰ |
| 2430. | L¹⁰⁸ | L¹¹⁴ | L¹⁸⁰ |
| 2431. | L¹⁰⁸ | L¹¹⁵ | L¹⁸⁰ |
| 2432. | L¹⁰⁸ | L¹¹⁶ | L¹⁸⁰ |
| 2433. | L¹⁰⁸ | L¹¹⁷ | L¹⁸⁰ |
| 2434. | L¹⁰⁸ | L¹¹⁸ | L¹⁸⁰ |
| 2435. | L¹⁰⁸ | L¹¹⁹ | L¹⁸⁰ |
| 2436. | L¹⁰⁸ | L¹³⁰ | L¹⁸⁰ |
| 2437. | L¹⁰⁸ | L¹³¹ | L¹⁸⁰ |
| 2438. | L¹⁰⁸ | L¹³² | L¹⁸⁰ |
| 2439. | L¹⁰⁸ | L¹³³ | L¹⁸⁰ |
| 2440. | L¹⁰⁸ | L¹³⁴ | L¹⁸⁰ |
| 2441. | L¹⁰⁸ | L¹⁴⁰ | L¹⁸⁰ |
| 2442. | L¹⁰⁸ | L¹⁴¹ | L¹⁸⁰ |
| 2443. | L¹⁰⁸ | L¹⁵⁹ | L¹⁸⁰ |
| 2444. | L¹⁰⁸ | L¹⁶⁰ | L¹⁸⁰ |
| 2445. | L¹⁰⁹ | L¹¹⁰ | L¹⁴⁴ |
| 2446. | L¹⁰⁹ | L¹¹¹ | L¹⁴⁴ |
| 2447. | L¹⁰⁹ | L¹¹² | L¹⁴⁴ |
| 2448. | L¹⁰⁹ | L¹¹³ | L¹⁴⁴ |
| 2449. | L¹⁰⁹ | L¹¹⁴ | L¹⁴⁴ |
| 2450. | L¹⁰⁹ | L¹¹⁵ | L¹⁴⁴ |
| 2451. | L¹⁰⁹ | L¹¹⁶ | L¹⁴⁴ |
| 2452. | L¹⁰⁹ | L¹¹⁷ | L¹⁴⁴ |
| 2453. | L¹⁰⁹ | L¹¹⁸ | L¹⁴⁴ |
| 2454. | L¹⁰⁹ | L¹¹⁹ | L¹⁴⁴ |
| 2455. | L¹⁰⁹ | L¹³⁰ | L¹⁴⁴ |
| 2456. | L¹⁰⁹ | L¹³¹ | L¹⁴⁴ |
| 2457. | L¹⁰⁹ | L¹³² | L¹⁴⁴ |
| 2458. | L¹⁰⁹ | L¹³³ | L¹⁴⁴ |
| 2459. | L¹⁰⁹ | L¹³⁴ | L¹⁴⁴ |
| 2460. | L¹⁰⁹ | L¹⁴⁰ | L¹⁴⁴ |
| 2461. | L¹⁰⁹ | L¹⁴¹ | L¹⁴⁴ |
| 2462. | L¹⁰⁹ | L¹⁵⁹ | L¹⁴⁴ |
| 2463. | L¹⁰⁹ | L¹⁶⁰ | L¹⁴⁴ |
| 2464. | L¹⁰⁹ | L¹¹⁰ | L¹⁴⁵ |
| 2465. | L¹⁰⁹ | L¹¹¹ | L¹⁴⁵ |
| 2466. | L¹⁰⁹ | L¹¹² | L¹⁴⁵ |
| 2467. | L¹⁰⁹ | L¹¹³ | L¹⁴⁵ |
| 2468. | L¹⁰⁹ | L¹¹⁴ | L¹⁴⁵ |
| 2469. | L¹⁰⁹ | L¹¹⁵ | L¹⁴⁵ |
| 2470. | L¹⁰⁹ | L¹¹⁶ | L¹⁴⁵ |
| 2471. | L¹⁰⁹ | L¹¹⁷ | L¹⁴⁵ |
| 2472. | L¹⁰⁹ | L¹¹⁸ | L¹⁴⁵ |
| 2473. | L¹⁰⁹ | L¹¹⁹ | L¹⁴⁵ |
| 2474. | L¹⁰⁹ | L¹³⁰ | L¹⁴⁵ |
| 2475. | L¹⁰⁹ | L¹³¹ | L¹⁴⁵ |

TABLE 1-continued

| Compound number | $L_1$ | $L_2$ | $L_3$ |
|---|---|---|---|
| 2476. | $L^{109}$ | $L^{132}$ | $L^{145}$ |
| 2477. | $L^{109}$ | $L^{133}$ | $L^{145}$ |
| 2478. | $L^{109}$ | $L^{134}$ | $L^{145}$ |
| 2479. | $L^{109}$ | $L^{140}$ | $L^{145}$ |
| 2480. | $L^{109}$ | $L^{141}$ | $L^{145}$ |
| 2481. | $L^{109}$ | $L^{159}$ | $L^{145}$ |
| 2482. | $L^{109}$ | $L^{160}$ | $L^{145}$ |
| 2483. | $L^{109}$ | $L^{110}$ | $L^{147}$ |
| 2484. | $L^{109}$ | $L^{111}$ | $L^{147}$ |
| 2485. | $L^{109}$ | $L^{112}$ | $L^{147}$ |
| 2486. | $L^{109}$ | $L^{113}$ | $L^{147}$ |
| 2487. | $L^{109}$ | $L^{114}$ | $L^{147}$ |
| 2488. | $L^{109}$ | $L^{115}$ | $L^{147}$ |
| 2489. | $L^{109}$ | $L^{116}$ | $L^{147}$ |
| 2490. | $L^{109}$ | $L^{117}$ | $L^{147}$ |
| 2491. | $L^{109}$ | $L^{118}$ | $L^{147}$ |
| 2492. | $L^{109}$ | $L^{119}$ | $L^{147}$ |
| 2493. | $L^{109}$ | $L^{130}$ | $L^{147}$ |
| 2494. | $L^{109}$ | $L^{131}$ | $L^{147}$ |
| 2495. | $L^{109}$ | $L^{132}$ | $L^{147}$ |
| 2496. | $L^{109}$ | $L^{133}$ | $L^{147}$ |
| 2497. | $L^{109}$ | $L^{134}$ | $L^{147}$ |
| 2498. | $L^{109}$ | $L^{140}$ | $L^{147}$ |
| 2499. | $L^{109}$ | $L^{141}$ | $L^{147}$ |
| 2500. | $L^{109}$ | $L^{159}$ | $L^{147}$ |
| 2501. | $L^{109}$ | $L^{160}$ | $L^{147}$ |
| 2502. | $L^{109}$ | $L^{110}$ | $L^{149}$ |
| 2503. | $L^{109}$ | $L^{111}$ | $L^{149}$ |
| 2504. | $L^{109}$ | $L^{112}$ | $L^{149}$ |
| 2505. | $L^{109}$ | $L^{113}$ | $L^{149}$ |
| 2506. | $L^{109}$ | $L^{114}$ | $L^{149}$ |
| 2507. | $L^{109}$ | $L^{115}$ | $L^{149}$ |
| 2508. | $L^{109}$ | $L^{116}$ | $L^{149}$ |
| 2509. | $L^{109}$ | $L^{117}$ | $L^{149}$ |
| 2510. | $L^{109}$ | $L^{118}$ | $L^{149}$ |
| 2511. | $L^{109}$ | $L^{119}$ | $L^{149}$ |
| 2512. | $L^{109}$ | $L^{130}$ | $L^{149}$ |
| 2513. | $L^{109}$ | $L^{131}$ | $L^{149}$ |
| 2514. | $L^{109}$ | $L^{132}$ | $L^{149}$ |
| 2515. | $L^{109}$ | $L^{133}$ | $L^{149}$ |
| 2516. | $L^{109}$ | $L^{134}$ | $L^{149}$ |
| 2517. | $L^{109}$ | $L^{140}$ | $L^{149}$ |
| 2518. | $L^{109}$ | $L^{141}$ | $L^{149}$ |
| 2519. | $L^{109}$ | $L^{159}$ | $L^{149}$ |
| 2520. | $L^{109}$ | $L^{160}$ | $L^{149}$ |
| 2521. | $L^{109}$ | $L^{110}$ | $L^{152}$ |
| 2522. | $L^{109}$ | $L^{111}$ | $L^{152}$ |
| 2523. | $L^{109}$ | $L^{112}$ | $L^{152}$ |
| 2524. | $L^{109}$ | $L^{113}$ | $L^{152}$ |
| 2525. | $L^{109}$ | $L^{114}$ | $L^{152}$ |
| 2526. | $L^{109}$ | $L^{115}$ | $L^{152}$ |
| 2527. | $L^{109}$ | $L^{116}$ | $L^{152}$ |
| 2528. | $L^{109}$ | $L^{117}$ | $L^{152}$ |
| 2529. | $L^{109}$ | $L^{118}$ | $L^{152}$ |
| 2530. | $L^{109}$ | $L^{119}$ | $L^{152}$ |
| 2531. | $L^{109}$ | $L^{130}$ | $L^{152}$ |
| 2532. | $L^{109}$ | $L^{131}$ | $L^{152}$ |
| 2533. | $L^{109}$ | $L^{132}$ | $L^{152}$ |
| 2534. | $L^{109}$ | $L^{133}$ | $L^{152}$ |
| 2535. | $L^{109}$ | $L^{134}$ | $L^{152}$ |
| 2536. | $L^{109}$ | $L^{140}$ | $L^{152}$ |
| 2537. | $L^{109}$ | $L^{141}$ | $L^{152}$ |
| 2538. | $L^{109}$ | $L^{159}$ | $L^{152}$ |
| 2539. | $L^{109}$ | $L^{160}$ | $L^{152}$ |
| 2540. | $L^{109}$ | $L^{110}$ | $L^{164}$ |
| 2541. | $L^{109}$ | $L^{111}$ | $L^{164}$ |
| 2542. | $L^{109}$ | $L^{112}$ | $L^{164}$ |
| 2543. | $L^{109}$ | $L^{113}$ | $L^{164}$ |
| 2544. | $L^{109}$ | $L^{114}$ | $L^{164}$ |
| 2545. | $L^{109}$ | $L^{115}$ | $L^{164}$ |
| 2546. | $L^{109}$ | $L^{116}$ | $L^{164}$ |
| 2547. | $L^{109}$ | $L^{117}$ | $L^{164}$ |
| 2548. | $L^{109}$ | $L^{118}$ | $L^{164}$ |
| 2549. | $L^{109}$ | $L^{119}$ | $L^{164}$ |
| 2550. | $L^{109}$ | $L^{130}$ | $L^{164}$ |
| 2551. | $L^{109}$ | $L^{131}$ | $L^{164}$ |
| 2552. | $L^{109}$ | $L^{132}$ | $L^{164}$ |
| 2553. | $L^{109}$ | $L^{133}$ | $L^{164}$ |
| 2554. | $L^{109}$ | $L^{134}$ | $L^{164}$ |
| 2555. | $L^{109}$ | $L^{140}$ | $L^{164}$ |
| 2556. | $L^{109}$ | $L^{141}$ | $L^{164}$ |
| 2557. | $L^{109}$ | $L^{159}$ | $L^{164}$ |
| 2558. | $L^{109}$ | $L^{160}$ | $L^{164}$ |
| 2559. | $L^{109}$ | $L^{110}$ | $L^{165}$ |
| 2560. | $L^{109}$ | $L^{111}$ | $L^{165}$ |
| 2561. | $L^{109}$ | $L^{112}$ | $L^{165}$ |
| 2562. | $L^{109}$ | $L^{113}$ | $L^{165}$ |
| 2563. | $L^{109}$ | $L^{114}$ | $L^{165}$ |
| 2564. | $L^{109}$ | $L^{115}$ | $L^{165}$ |
| 2565. | $L^{109}$ | $L^{116}$ | $L^{165}$ |
| 2566. | $L^{109}$ | $L^{117}$ | $L^{165}$ |
| 2567. | $L^{109}$ | $L^{118}$ | $L^{165}$ |
| 2568. | $L^{109}$ | $L^{119}$ | $L^{165}$ |
| 2569. | $L^{109}$ | $L^{130}$ | $L^{165}$ |
| 2570. | $L^{109}$ | $L^{131}$ | $L^{165}$ |
| 2571. | $L^{109}$ | $L^{132}$ | $L^{165}$ |
| 2572. | $L^{109}$ | $L^{133}$ | $L^{165}$ |
| 2573. | $L^{109}$ | $L^{134}$ | $L^{165}$ |
| 2574. | $L^{109}$ | $L^{140}$ | $L^{165}$ |
| 2575. | $L^{109}$ | $L^{141}$ | $L^{165}$ |
| 2576. | $L^{109}$ | $L^{159}$ | $L^{165}$ |
| 2577. | $L^{109}$ | $L^{160}$ | $L^{165}$ |
| 2578. | $L^{109}$ | $L^{110}$ | $L^{166}$ |
| 2579. | $L^{109}$ | $L^{111}$ | $L^{166}$ |
| 2580. | $L^{109}$ | $L^{112}$ | $L^{166}$ |
| 2581. | $L^{109}$ | $L^{113}$ | $L^{166}$ |
| 2582. | $L^{109}$ | $L^{114}$ | $L^{166}$ |
| 2583. | $L^{109}$ | $L^{115}$ | $L^{166}$ |
| 2584. | $L^{109}$ | $L^{116}$ | $L^{166}$ |
| 2585. | $L^{109}$ | $L^{117}$ | $L^{166}$ |
| 2586. | $L^{109}$ | $L^{118}$ | $L^{166}$ |
| 2587. | $L^{109}$ | $L^{119}$ | $L^{166}$ |
| 2588. | $L^{109}$ | $L^{130}$ | $L^{166}$ |
| 2589. | $L^{109}$ | $L^{131}$ | $L^{166}$ |
| 2590. | $L^{109}$ | $L^{132}$ | $L^{166}$ |
| 2591. | $L^{109}$ | $L^{133}$ | $L^{166}$ |
| 2592. | $L^{109}$ | $L^{134}$ | $L^{166}$ |
| 2593. | $L^{109}$ | $L^{140}$ | $L^{166}$ |
| 2594. | $L^{109}$ | $L^{141}$ | $L^{166}$ |
| 2595. | $L^{109}$ | $L^{159}$ | $L^{166}$ |
| 2596. | $L^{109}$ | $L^{160}$ | $L^{166}$ |
| 2597. | $L^{109}$ | $L^{110}$ | $L^{170}$ |
| 2598. | $L^{109}$ | $L^{111}$ | $L^{170}$ |
| 2599. | $L^{109}$ | $L^{112}$ | $L^{170}$ |
| 2600. | $L^{109}$ | $L^{113}$ | $L^{170}$ |
| 2601. | $L^{109}$ | $L^{114}$ | $L^{170}$ |
| 2602. | $L^{109}$ | $L^{115}$ | $L^{170}$ |
| 2603. | $L^{109}$ | $L^{116}$ | $L^{170}$ |
| 2604. | $L^{109}$ | $L^{117}$ | $L^{170}$ |
| 2605. | $L^{109}$ | $L^{118}$ | $L^{170}$ |
| 2606. | $L^{109}$ | $L^{119}$ | $L^{170}$ |
| 2607. | $L^{109}$ | $L^{130}$ | $L^{170}$ |
| 2608. | $L^{109}$ | $L^{131}$ | $L^{170}$ |
| 2609. | $L^{109}$ | $L^{132}$ | $L^{170}$ |
| 2610. | $L^{109}$ | $L^{133}$ | $L^{170}$ |
| 2611. | $L^{109}$ | $L^{134}$ | $L^{170}$ |
| 2612. | $L^{109}$ | $L^{140}$ | $L^{170}$ |
| 2613. | $L^{109}$ | $L^{141}$ | $L^{170}$ |
| 2614. | $L^{109}$ | $L^{159}$ | $L^{170}$ |
| 2615. | $L^{109}$ | $L^{160}$ | $L^{170}$ |
| 2616. | $L^{109}$ | $L^{110}$ | $L^{174}$ |
| 2617. | $L^{109}$ | $L^{111}$ | $L^{174}$ |
| 2618. | $L^{109}$ | $L^{112}$ | $L^{174}$ |
| 2619. | $L^{109}$ | $L^{113}$ | $L^{174}$ |
| 2620. | $L^{109}$ | $L^{114}$ | $L^{174}$ |
| 2621. | $L^{109}$ | $L^{115}$ | $L^{174}$ |
| 2622. | $L^{109}$ | $L^{116}$ | $L^{174}$ |
| 2623. | $L^{109}$ | $L^{117}$ | $L^{174}$ |
| 2624. | $L^{109}$ | $L^{118}$ | $L^{174}$ |
| 2625. | $L^{109}$ | $L^{119}$ | $L^{174}$ |
| 2626. | $L^{109}$ | $L^{130}$ | $L^{174}$ |
| 2627. | $L^{109}$ | $L^{131}$ | $L^{174}$ |
| 2628. | $L^{109}$ | $L^{132}$ | $L^{174}$ |
| 2629. | $L^{109}$ | $L^{133}$ | $L^{174}$ |

TABLE 1-continued

| Compound number | $L_1$ | $L_2$ | $L_3$ |
|---|---|---|---|
| 2630. | $L^{109}$ | $L^{134}$ | $L^{174}$ |
| 2631. | $L^{109}$ | $L^{140}$ | $L^{174}$ |
| 2632. | $L^{109}$ | $L^{141}$ | $L^{174}$ |
| 2633. | $L^{109}$ | $L^{159}$ | $L^{174}$ |
| 2634. | $L^{109}$ | $L^{160}$ | $L^{174}$ |
| 2635. | $L^{109}$ | $L^{110}$ | $L^{176}$ |
| 2636. | $L^{109}$ | $L^{111}$ | $L^{176}$ |
| 2637. | $L^{109}$ | $L^{112}$ | $L^{176}$ |
| 2638. | $L^{109}$ | $L^{113}$ | $L^{176}$ |
| 2639. | $L^{109}$ | $L^{114}$ | $L^{176}$ |
| 2640. | $L^{109}$ | $L^{115}$ | $L^{176}$ |
| 2641. | $L^{109}$ | $L^{116}$ | $L^{176}$ |
| 2642. | $L^{109}$ | $L^{117}$ | $L^{176}$ |
| 2643. | $L^{109}$ | $L^{118}$ | $L^{176}$ |
| 2644. | $L^{109}$ | $L^{119}$ | $L^{176}$ |
| 2645. | $L^{109}$ | $L^{130}$ | $L^{176}$ |
| 2646. | $L^{109}$ | $L^{131}$ | $L^{176}$ |
| 2647. | $L^{109}$ | $L^{132}$ | $L^{176}$ |
| 2648. | $L^{109}$ | $L^{133}$ | $L^{176}$ |
| 2649. | $L^{109}$ | $L^{134}$ | $L^{176}$ |
| 2650. | $L^{109}$ | $L^{140}$ | $L^{176}$ |
| 2651. | $L^{109}$ | $L^{141}$ | $L^{176}$ |
| 2652. | $L^{109}$ | $L^{159}$ | $L^{176}$ |
| 2653. | $L^{109}$ | $L^{160}$ | $L^{176}$ |
| 2654. | $L^{109}$ | $L^{110}$ | $L^{179}$ |
| 2655. | $L^{109}$ | $L^{111}$ | $L^{179}$ |
| 2656. | $L^{109}$ | $L^{112}$ | $L^{179}$ |
| 2657. | $L^{109}$ | $L^{113}$ | $L^{179}$ |
| 2658. | $L^{109}$ | $L^{114}$ | $L^{179}$ |
| 2659. | $L^{109}$ | $L^{115}$ | $L^{179}$ |
| 2660. | $L^{109}$ | $L^{116}$ | $L^{179}$ |
| 2661. | $L^{109}$ | $L^{117}$ | $L^{179}$ |
| 2662. | $L^{109}$ | $L^{118}$ | $L^{179}$ |
| 2663. | $L^{109}$ | $L^{119}$ | $L^{179}$ |
| 2664. | $L^{109}$ | $L^{130}$ | $L^{179}$ |
| 2665. | $L^{109}$ | $L^{131}$ | $L^{179}$ |
| 2666. | $L^{109}$ | $L^{132}$ | $L^{179}$ |
| 2667. | $L^{109}$ | $L^{133}$ | $L^{179}$ |
| 2668. | $L^{109}$ | $L^{134}$ | $L^{179}$ |
| 2669. | $L^{109}$ | $L^{140}$ | $L^{179}$ |
| 2670. | $L^{109}$ | $L^{141}$ | $L^{179}$ |
| 2671. | $L^{109}$ | $L^{159}$ | $L^{179}$ |
| 2672. | $L^{109}$ | $L^{160}$ | $L^{179}$ |
| 2673. | $L^{109}$ | $L^{110}$ | $L^{180}$ |
| 2674. | $L^{109}$ | $L^{111}$ | $L^{180}$ |
| 2675. | $L^{109}$ | $L^{112}$ | $L^{180}$ |
| 2676. | $L^{109}$ | $L^{113}$ | $L^{180}$ |
| 2677. | $L^{109}$ | $L^{114}$ | $L^{180}$ |
| 2678. | $L^{109}$ | $L^{115}$ | $L^{180}$ |
| 2679. | $L^{109}$ | $L^{116}$ | $L^{180}$ |
| 2680. | $L^{109}$ | $L^{117}$ | $L^{180}$ |
| 2681. | $L^{109}$ | $L^{118}$ | $L^{180}$ |
| 2682. | $L^{109}$ | $L^{119}$ | $L^{180}$ |
| 2683. | $L^{109}$ | $L^{130}$ | $L^{180}$ |
| 2684. | $L^{109}$ | $L^{131}$ | $L^{180}$ |
| 2685. | $L^{109}$ | $L^{132}$ | $L^{180}$ |
| 2686. | $L^{109}$ | $L^{133}$ | $L^{180}$ |
| 2687. | $L^{109}$ | $L^{134}$ | $L^{180}$ |
| 2688. | $L^{109}$ | $L^{140}$ | $L^{180}$ |
| 2689. | $L^{109}$ | $L^{141}$ | $L^{180}$ |
| 2690. | $L^{109}$ | $L^{159}$ | $L^{180}$ |
| 2691. | $L^{109}$ | $L^{160}$ | $L^{180}$ |
| 2692. | $L^{110}$ | $L^{111}$ | $L^{144}$ |
| 2693. | $L^{110}$ | $L^{112}$ | $L^{144}$ |
| 2694. | $L^{110}$ | $L^{113}$ | $L^{144}$ |
| 2695. | $L^{110}$ | $L^{114}$ | $L^{144}$ |
| 2696. | $L^{110}$ | $L^{115}$ | $L^{144}$ |
| 2697. | $L^{110}$ | $L^{116}$ | $L^{144}$ |
| 2698. | $L^{110}$ | $L^{117}$ | $L^{144}$ |
| 2699. | $L^{110}$ | $L^{118}$ | $L^{144}$ |
| 2700. | $L^{110}$ | $L^{119}$ | $L^{144}$ |
| 2701. | $L^{110}$ | $L^{130}$ | $L^{144}$ |
| 2702. | $L^{110}$ | $L^{131}$ | $L^{144}$ |
| 2703. | $L^{110}$ | $L^{132}$ | $L^{144}$ |
| 2704. | $L^{110}$ | $L^{133}$ | $L^{144}$ |
| 2705. | $L^{110}$ | $L^{134}$ | $L^{144}$ |
| 2706. | $L^{110}$ | $L^{140}$ | $L^{144}$ |
| 2707. | $L^{110}$ | $L^{141}$ | $L^{144}$ |
| 2708. | $L^{110}$ | $L^{159}$ | $L^{144}$ |
| 2709. | $L^{110}$ | $L^{160}$ | $L^{144}$ |
| 2710. | $L^{110}$ | $L^{110}$ | $L^{145}$ |
| 2711. | $L^{110}$ | $L^{112}$ | $L^{145}$ |
| 2712. | $L^{110}$ | $L^{113}$ | $L^{145}$ |
| 2713. | $L^{110}$ | $L^{114}$ | $L^{145}$ |
| 2714. | $L^{110}$ | $L^{115}$ | $L^{145}$ |
| 2715. | $L^{110}$ | $L^{116}$ | $L^{145}$ |
| 2716. | $L^{110}$ | $L^{117}$ | $L^{145}$ |
| 2717. | $L^{110}$ | $L^{118}$ | $L^{145}$ |
| 2718. | $L^{110}$ | $L^{119}$ | $L^{145}$ |
| 2719. | $L^{110}$ | $L^{130}$ | $L^{145}$ |
| 2720. | $L^{110}$ | $L^{131}$ | $L^{145}$ |
| 2721. | $L^{110}$ | $L^{132}$ | $L^{145}$ |
| 2722. | $L^{110}$ | $L^{133}$ | $L^{145}$ |
| 2723. | $L^{110}$ | $L^{134}$ | $L^{145}$ |
| 2724. | $L^{110}$ | $L^{140}$ | $L^{145}$ |
| 2725. | $L^{110}$ | $L^{141}$ | $L^{145}$ |
| 2726. | $L^{110}$ | $L^{159}$ | $L^{145}$ |
| 2727. | $L^{110}$ | $L^{160}$ | $L^{145}$ |
| 2728. | $L^{110}$ | $L^{111}$ | $L^{147}$ |
| 2729. | $L^{110}$ | $L^{112}$ | $L^{147}$ |
| 2730. | $L^{110}$ | $L^{113}$ | $L^{147}$ |
| 2731. | $L^{110}$ | $L^{114}$ | $L^{147}$ |
| 2732. | $L^{110}$ | $L^{115}$ | $L^{147}$ |
| 2733. | $L^{110}$ | $L^{116}$ | $L^{147}$ |
| 2734. | $L^{110}$ | $L^{117}$ | $L^{147}$ |
| 2735. | $L^{110}$ | $L^{118}$ | $L^{147}$ |
| 2736. | $L^{110}$ | $L^{119}$ | $L^{147}$ |
| 2737. | $L^{110}$ | $L^{130}$ | $L^{147}$ |
| 2738. | $L^{110}$ | $L^{131}$ | $L^{147}$ |
| 2739. | $L^{110}$ | $L^{132}$ | $L^{147}$ |
| 2740. | $L^{110}$ | $L^{133}$ | $L^{147}$ |
| 2741. | $L^{110}$ | $L^{134}$ | $L^{147}$ |
| 2742. | $L^{110}$ | $L^{140}$ | $L^{147}$ |
| 2743. | $L^{110}$ | $L^{141}$ | $L^{147}$ |
| 2744. | $L^{110}$ | $L^{159}$ | $L^{147}$ |
| 2745. | $L^{110}$ | $L^{160}$ | $L^{147}$ |
| 2746. | $L^{110}$ | $L^{111}$ | $L^{149}$ |
| 2747. | $L^{110}$ | $L^{112}$ | $L^{149}$ |
| 2748. | $L^{110}$ | $L^{113}$ | $L^{149}$ |
| 2749. | $L^{110}$ | $L^{114}$ | $L^{149}$ |
| 2750. | $L^{110}$ | $L^{115}$ | $L^{149}$ |
| 2751. | $L^{110}$ | $L^{116}$ | $L^{149}$ |
| 2752. | $L^{110}$ | $L^{117}$ | $L^{149}$ |
| 2753. | $L^{110}$ | $L^{118}$ | $L^{149}$ |
| 2754. | $L^{110}$ | $L^{119}$ | $L^{149}$ |
| 2755. | $L^{110}$ | $L^{130}$ | $L^{149}$ |
| 2756. | $L^{110}$ | $L^{131}$ | $L^{149}$ |
| 2757. | $L^{110}$ | $L^{132}$ | $L^{149}$ |
| 2758. | $L^{110}$ | $L^{133}$ | $L^{149}$ |
| 2759. | $L^{110}$ | $L^{134}$ | $L^{149}$ |
| 2760. | $L^{110}$ | $L^{140}$ | $L^{149}$ |
| 2761. | $L^{110}$ | $L^{141}$ | $L^{149}$ |
| 2762. | $L^{110}$ | $L^{159}$ | $L^{149}$ |
| 2763. | $L^{110}$ | $L^{160}$ | $L^{149}$ |
| 2764. | $L^{110}$ | $L^{111}$ | $L^{152}$ |
| 2765. | $L^{110}$ | $L^{112}$ | $L^{152}$ |
| 2766. | $L^{110}$ | $L^{113}$ | $L^{152}$ |
| 2767. | $L^{110}$ | $L^{114}$ | $L^{152}$ |
| 2768. | $L^{110}$ | $L^{115}$ | $L^{152}$ |
| 2769. | $L^{110}$ | $L^{116}$ | $L^{152}$ |
| 2770. | $L^{110}$ | $L^{117}$ | $L^{152}$ |
| 2771. | $L^{110}$ | $L^{118}$ | $L^{152}$ |
| 2772. | $L^{110}$ | $L^{119}$ | $L^{152}$ |
| 2773. | $L^{110}$ | $L^{130}$ | $L^{152}$ |
| 2774. | $L^{110}$ | $L^{131}$ | $L^{152}$ |
| 2775. | $L^{110}$ | $L^{132}$ | $L^{152}$ |
| 2776. | $L^{110}$ | $L^{133}$ | $L^{152}$ |
| 2777. | $L^{110}$ | $L^{134}$ | $L^{152}$ |
| 2778. | $L^{110}$ | $L^{140}$ | $L^{152}$ |
| 2779. | $L^{110}$ | $L^{141}$ | $L^{152}$ |
| 2780. | $L^{110}$ | $L^{159}$ | $L^{152}$ |
| 2781. | $L^{110}$ | $L^{160}$ | $L^{152}$ |
| 2782. | $L^{110}$ | $L^{111}$ | $L^{164}$ |
| 2783. | $L^{110}$ | $L^{112}$ | $L^{164}$ |

TABLE 1-continued

| Compound number | $L_1$ | $L_2$ | $L_3$ |
|---|---|---|---|
| 2784. | $L^{110}$ | $L^{113}$ | $L^{164}$ |
| 2785. | $L^{110}$ | $L^{114}$ | $L^{164}$ |
| 2786. | $L^{110}$ | $L^{115}$ | $L^{164}$ |
| 2787. | $L^{110}$ | $L^{116}$ | $L^{164}$ |
| 2788. | $L^{110}$ | $L^{117}$ | $L^{164}$ |
| 2789. | $L^{110}$ | $L^{118}$ | $L^{164}$ |
| 2790. | $L^{110}$ | $L^{119}$ | $L^{164}$ |
| 2791. | $L^{110}$ | $L^{130}$ | $L^{164}$ |
| 2792. | $L^{110}$ | $L^{131}$ | $L^{164}$ |
| 2793. | $L^{110}$ | $L^{132}$ | $L^{164}$ |
| 2794. | $L^{110}$ | $L^{133}$ | $L^{164}$ |
| 2795. | $L^{110}$ | $L^{134}$ | $L^{164}$ |
| 2796. | $L^{110}$ | $L^{140}$ | $L^{164}$ |
| 2797. | $L^{110}$ | $L^{141}$ | $L^{164}$ |
| 2798. | $L^{110}$ | $L^{159}$ | $L^{164}$ |
| 2799. | $L^{110}$ | $L^{160}$ | $L^{164}$ |
| 2800. | $L^{110}$ | $L^{111}$ | $L^{165}$ |
| 2801. | $L^{110}$ | $L^{112}$ | $L^{165}$ |
| 2802. | $L^{110}$ | $L^{113}$ | $L^{165}$ |
| 2803. | $L^{110}$ | $L^{114}$ | $L^{165}$ |
| 2804. | $L^{110}$ | $L^{115}$ | $L^{165}$ |
| 2805. | $L^{110}$ | $L^{116}$ | $L^{165}$ |
| 2806. | $L^{110}$ | $L^{117}$ | $L^{165}$ |
| 2807. | $L^{110}$ | $L^{118}$ | $L^{165}$ |
| 2808. | $L^{110}$ | $L^{119}$ | $L^{165}$ |
| 2809. | $L^{110}$ | $L^{130}$ | $L^{165}$ |
| 2810. | $L^{110}$ | $L^{131}$ | $L^{165}$ |
| 2811. | $L^{110}$ | $L^{132}$ | $L^{165}$ |
| 2812. | $L^{110}$ | $L^{133}$ | $L^{165}$ |
| 2813. | $L^{110}$ | $L^{134}$ | $L^{165}$ |
| 2814. | $L^{110}$ | $L^{140}$ | $L^{165}$ |
| 2815. | $L^{110}$ | $L^{141}$ | $L^{165}$ |
| 2816. | $L^{110}$ | $L^{159}$ | $L^{165}$ |
| 2817. | $L^{110}$ | $L^{160}$ | $L^{165}$ |
| 2818. | $L^{110}$ | $L^{111}$ | $L^{166}$ |
| 2819. | $L^{110}$ | $L^{112}$ | $L^{166}$ |
| 2820. | $L^{110}$ | $L^{113}$ | $L^{166}$ |
| 2821. | $L^{110}$ | $L^{114}$ | $L^{166}$ |
| 2822. | $L^{110}$ | $L^{115}$ | $L^{166}$ |
| 2823. | $L^{110}$ | $L^{116}$ | $L^{166}$ |
| 2824. | $L^{110}$ | $L^{117}$ | $L^{166}$ |
| 2825. | $L^{110}$ | $L^{118}$ | $L^{166}$ |
| 2826. | $L^{110}$ | $L^{119}$ | $L^{166}$ |
| 2827. | $L^{110}$ | $L^{130}$ | $L^{166}$ |
| 2828. | $L^{110}$ | $L^{131}$ | $L^{166}$ |
| 2829. | $L^{110}$ | $L^{132}$ | $L^{166}$ |
| 2830. | $L^{110}$ | $L^{133}$ | $L^{166}$ |
| 2831. | $L^{110}$ | $L^{134}$ | $L^{166}$ |
| 2832. | $L^{110}$ | $L^{140}$ | $L^{166}$ |
| 2833. | $L^{110}$ | $L^{141}$ | $L^{166}$ |
| 2834. | $L^{110}$ | $L^{159}$ | $L^{166}$ |
| 2835. | $L^{110}$ | $L^{160}$ | $L^{166}$ |
| 2836. | $L^{110}$ | $L^{111}$ | $L^{170}$ |
| 2837. | $L^{110}$ | $L^{112}$ | $L^{170}$ |
| 2838. | $L^{110}$ | $L^{113}$ | $L^{170}$ |
| 2839. | $L^{110}$ | $L^{114}$ | $L^{170}$ |
| 2840. | $L^{110}$ | $L^{115}$ | $L^{170}$ |
| 2841. | $L^{110}$ | $L^{116}$ | $L^{170}$ |
| 2842. | $L^{110}$ | $L^{117}$ | $L^{170}$ |
| 2843. | $L^{110}$ | $L^{118}$ | $L^{170}$ |
| 2844. | $L^{110}$ | $L^{119}$ | $L^{170}$ |
| 2845. | $L^{110}$ | $L^{130}$ | $L^{170}$ |
| 2846. | $L^{110}$ | $L^{131}$ | $L^{170}$ |
| 2847. | $L^{110}$ | $L^{132}$ | $L^{170}$ |
| 2848. | $L^{110}$ | $L^{133}$ | $L^{170}$ |
| 2849. | $L^{110}$ | $L^{134}$ | $L^{170}$ |
| 2850. | $L^{110}$ | $L^{140}$ | $L^{170}$ |
| 2851. | $L^{110}$ | $L^{141}$ | $L^{170}$ |
| 2852. | $L^{110}$ | $L^{159}$ | $L^{170}$ |
| 2853. | $L^{110}$ | $L^{160}$ | $L^{170}$ |
| 2854. | $L^{110}$ | $L^{111}$ | $L^{174}$ |
| 2855. | $L^{110}$ | $L^{112}$ | $L^{174}$ |
| 2856. | $L^{110}$ | $L^{113}$ | $L^{174}$ |
| 2857. | $L^{110}$ | $L^{114}$ | $L^{174}$ |
| 2858. | $L^{110}$ | $L^{115}$ | $L^{174}$ |
| 2859. | $L^{110}$ | $L^{116}$ | $L^{174}$ |
| 2860. | $L^{110}$ | $L^{117}$ | $L^{174}$ |
| 2861. | $L^{110}$ | $L^{118}$ | $L^{174}$ |
| 2862. | $L^{110}$ | $L^{119}$ | $L^{174}$ |
| 2863. | $L^{110}$ | $L^{130}$ | $L^{174}$ |
| 2864. | $L^{110}$ | $L^{131}$ | $L^{174}$ |
| 2865. | $L^{110}$ | $L^{132}$ | $L^{174}$ |
| 2866. | $L^{110}$ | $L^{133}$ | $L^{174}$ |
| 2867. | $L^{110}$ | $L^{134}$ | $L^{174}$ |
| 2868. | $L^{110}$ | $L^{140}$ | $L^{174}$ |
| 2869. | $L^{110}$ | $L^{141}$ | $L^{174}$ |
| 2870. | $L^{110}$ | $L^{159}$ | $L^{174}$ |
| 2871. | $L^{110}$ | $L^{160}$ | $L^{174}$ |
| 2872. | $L^{110}$ | $L^{111}$ | $L^{176}$ |
| 2873. | $L^{110}$ | $L^{112}$ | $L^{176}$ |
| 2874. | $L^{110}$ | $L^{113}$ | $L^{176}$ |
| 2875. | $L^{110}$ | $L^{114}$ | $L^{176}$ |
| 2876. | $L^{110}$ | $L^{115}$ | $L^{176}$ |
| 2877. | $L^{110}$ | $L^{116}$ | $L^{176}$ |
| 2878. | $L^{110}$ | $L^{117}$ | $L^{176}$ |
| 2879. | $L^{110}$ | $L^{118}$ | $L^{176}$ |
| 2880. | $L^{110}$ | $L^{119}$ | $L^{176}$ |
| 2881. | $L^{110}$ | $L^{130}$ | $L^{176}$ |
| 2882. | $L^{110}$ | $L^{131}$ | $L^{176}$ |
| 2883. | $L^{110}$ | $L^{132}$ | $L^{176}$ |
| 2884. | $L^{110}$ | $L^{133}$ | $L^{176}$ |
| 2885. | $L^{110}$ | $L^{134}$ | $L^{176}$ |
| 2886. | $L^{110}$ | $L^{140}$ | $L^{176}$ |
| 2887. | $L^{110}$ | $L^{141}$ | $L^{176}$ |
| 2888. | $L^{110}$ | $L^{159}$ | $L^{176}$ |
| 2889. | $L^{110}$ | $L^{160}$ | $L^{176}$ |
| 2890. | $L^{110}$ | $L^{111}$ | $L^{179}$ |
| 2891. | $L^{110}$ | $L^{112}$ | $L^{179}$ |
| 2892. | $L^{110}$ | $L^{113}$ | $L^{179}$ |
| 2893. | $L^{110}$ | $L^{114}$ | $L^{179}$ |
| 2894. | $L^{110}$ | $L^{115}$ | $L^{179}$ |
| 2895. | $L^{110}$ | $L^{116}$ | $L^{179}$ |
| 2896. | $L^{110}$ | $L^{117}$ | $L^{179}$ |
| 2897. | $L^{110}$ | $L^{118}$ | $L^{179}$ |
| 2898. | $L^{110}$ | $L^{119}$ | $L^{179}$ |
| 2899. | $L^{110}$ | $L^{130}$ | $L^{179}$ |
| 2900. | $L^{110}$ | $L^{131}$ | $L^{179}$ |
| 2901. | $L^{110}$ | $L^{132}$ | $L^{179}$ |
| 2902. | $L^{110}$ | $L^{133}$ | $L^{179}$ |
| 2903. | $L^{110}$ | $L^{134}$ | $L^{179}$ |
| 2904. | $L^{110}$ | $L^{140}$ | $L^{179}$ |
| 2905. | $L^{110}$ | $L^{141}$ | $L^{179}$ |
| 2906. | $L^{110}$ | $L^{159}$ | $L^{179}$ |
| 2907. | $L^{110}$ | $L^{160}$ | $L^{179}$ |
| 2908. | $L^{110}$ | $L^{111}$ | $L^{180}$ |
| 2909. | $L^{110}$ | $L^{112}$ | $L^{180}$ |
| 2910. | $L^{110}$ | $L^{113}$ | $L^{180}$ |
| 2911. | $L^{110}$ | $L^{114}$ | $L^{180}$ |
| 2912. | $L^{110}$ | $L^{115}$ | $L^{180}$ |
| 2913. | $L^{110}$ | $L^{116}$ | $L^{180}$ |
| 2914. | $L^{110}$ | $L^{117}$ | $L^{180}$ |
| 2915. | $L^{110}$ | $L^{118}$ | $L^{180}$ |
| 2916. | $L^{110}$ | $L^{119}$ | $L^{180}$ |
| 2917. | $L^{110}$ | $L^{130}$ | $L^{180}$ |
| 2918. | $L^{110}$ | $L^{131}$ | $L^{180}$ |
| 2919. | $L^{110}$ | $L^{132}$ | $L^{180}$ |
| 2920. | $L^{110}$ | $L^{133}$ | $L^{180}$ |
| 2921. | $L^{110}$ | $L^{134}$ | $L^{180}$ |
| 2922. | $L^{110}$ | $L^{135}$ | $L^{180}$ |
| 2923. | $L^{110}$ | $L^{141}$ | $L^{180}$ |
| 2924. | $L^{110}$ | $L^{159}$ | $L^{180}$ |
| 2925. | $L^{110}$ | $L^{160}$ | $L^{180}$ |
| 2926. | $L^{111}$ | $L^{112}$ | $L^{144}$ |
| 2927. | $L^{111}$ | $L^{113}$ | $L^{144}$ |
| 2928. | $L^{111}$ | $L^{114}$ | $L^{144}$ |
| 2929. | $L^{111}$ | $L^{115}$ | $L^{144}$ |
| 2930. | $L^{111}$ | $L^{116}$ | $L^{144}$ |
| 2931. | $L^{111}$ | $L^{117}$ | $L^{144}$ |
| 2932. | $L^{111}$ | $L^{118}$ | $L^{144}$ |
| 2933. | $L^{111}$ | $L^{119}$ | $L^{144}$ |
| 2934. | $L^{111}$ | $L^{130}$ | $L^{144}$ |
| 2935. | $L^{111}$ | $L^{131}$ | $L^{144}$ |
| 2936. | $L^{111}$ | $L^{132}$ | $L^{144}$ |
| 2937. | $L^{111}$ | $L^{133}$ | $L^{144}$ |

TABLE 1-continued

| Compound number | L₁ | L₂ | L₃ |
|---|---|---|---|
| 2938. | L¹¹¹ | L¹³⁴ | L¹⁴⁴ |
| 2939. | L¹¹¹ | L¹⁴⁰ | L¹⁴⁴ |
| 2940. | L¹¹¹ | L¹⁴¹ | L¹⁴⁴ |
| 2941. | L¹¹¹ | L¹⁵⁹ | L¹⁴⁴ |
| 2942. | L¹¹¹ | L¹⁶⁰ | L¹⁴⁴ |
| 2943. | L¹¹¹ | L¹¹² | L¹⁴⁵ |
| 2944. | L¹¹¹ | L¹¹³ | L¹⁴⁵ |
| 2945. | L¹¹¹ | L¹¹⁴ | L¹⁴⁵ |
| 2946. | L¹¹¹ | L¹¹⁵ | L¹⁴⁵ |
| 2947. | L¹¹¹ | L¹¹⁶ | L¹⁴⁵ |
| 2948. | L¹¹¹ | L¹¹⁷ | L¹⁴⁵ |
| 2949. | L¹¹¹ | L¹¹⁸ | L¹⁴⁵ |
| 2950. | L¹¹¹ | L¹¹⁹ | L¹⁴⁵ |
| 2951. | L¹¹¹ | L¹³⁰ | L¹⁴⁵ |
| 2952. | L¹¹¹ | L¹³¹ | L¹⁴⁵ |
| 2953. | L¹¹¹ | L¹³² | L¹⁴⁵ |
| 2954. | L¹¹¹ | L¹³³ | L¹⁴⁵ |
| 2955. | L¹¹¹ | L¹³⁴ | L¹⁴⁵ |
| 2956. | L¹¹¹ | L¹⁴⁰ | L¹⁴⁵ |
| 2957. | L¹¹¹ | L¹⁴¹ | L¹⁴⁵ |
| 2958. | L¹¹¹ | L¹⁵⁹ | L¹⁴⁵ |
| 2959. | L¹¹¹ | L¹⁶⁰ | L¹⁴⁵ |
| 2960. | L¹¹¹ | L¹¹² | L¹⁴⁷ |
| 2961. | L¹¹¹ | L¹¹³ | L¹⁴⁷ |
| 2962. | L¹¹¹ | L¹¹⁴ | L¹⁴⁷ |
| 2963. | L¹¹¹ | L¹¹⁵ | L¹⁴⁷ |
| 2964. | L¹¹¹ | L¹¹⁶ | L¹⁴⁷ |
| 2695. | L¹¹¹ | L¹¹⁷ | L¹⁴⁷ |
| 2696. | L¹¹¹ | L¹¹⁸ | L¹⁴⁷ |
| 2697. | L¹¹¹ | L¹¹⁹ | L¹⁴⁷ |
| 2698. | L¹¹¹ | L¹³⁰ | L¹⁴⁷ |
| 2699. | L¹¹¹ | L¹³¹ | L¹⁴⁷ |
| 2700. | L¹¹¹ | L¹³² | L¹⁴⁷ |
| 2701. | L¹¹¹ | L¹³³ | L¹⁴⁷ |
| 2702. | L¹¹¹ | L¹³⁴ | L¹⁴⁷ |
| 2703. | L¹¹¹ | L¹⁴⁰ | L¹⁴⁷ |
| 2704. | L¹¹¹ | L¹⁴¹ | L¹⁴⁷ |
| 2705. | L¹¹¹ | L¹⁵⁹ | L¹⁴⁷ |
| 2706. | L¹¹¹ | L¹⁶⁰ | L¹⁴⁷ |
| 2707. | L¹¹¹ | L¹¹² | L¹⁴⁹ |
| 2708. | L¹¹¹ | L¹¹³ | L¹⁴⁹ |
| 2709. | L¹¹¹ | L¹¹⁴ | L¹⁴⁹ |
| 2710. | L¹¹¹ | L¹¹⁵ | L¹⁴⁹ |
| 2711. | L¹¹¹ | L¹¹⁶ | L¹⁴⁹ |
| 2712. | L¹¹¹ | L¹¹⁷ | L¹⁴⁹ |
| 2713. | L¹¹¹ | L¹¹⁸ | L¹⁴⁹ |
| 2714. | L¹¹¹ | L¹¹⁹ | L¹⁴⁹ |
| 2715. | L¹¹¹ | L¹³⁰ | L¹⁴⁹ |
| 2716. | L¹¹¹ | L¹³¹ | L¹⁴⁹ |
| 2717. | L¹¹¹ | L¹³² | L¹⁴⁹ |
| 2718. | L¹¹¹ | L¹³³ | L¹⁴⁹ |
| 2719. | L¹¹¹ | L¹³⁴ | L¹⁴⁹ |
| 2720. | L¹¹¹ | L¹⁴⁰ | L¹⁴⁹ |
| 2721. | L¹¹¹ | L¹⁴¹ | L¹⁴⁹ |
| 2722. | L¹¹¹ | L¹⁵⁹ | L¹⁴⁹ |
| 2723. | L¹¹¹ | L¹⁶⁰ | L¹⁴⁹ |
| 2724. | L¹¹¹ | L¹¹² | L¹⁵² |
| 2725. | L¹¹¹ | L¹¹³ | L¹⁵² |
| 2726. | L¹¹¹ | L¹¹⁴ | L¹⁵² |
| 2727. | L¹¹¹ | L¹¹⁵ | L¹⁵² |
| 2728. | L¹¹¹ | L¹¹⁶ | L¹⁵² |
| 2729. | L¹¹¹ | L¹¹⁷ | L¹⁵² |
| 2730. | L¹¹¹ | L¹¹⁸ | L¹⁵² |
| 2731. | L¹¹¹ | L¹¹⁹ | L¹⁵² |
| 2732. | L¹¹¹ | L¹³⁰ | L¹⁵² |
| 2733. | L¹¹¹ | L¹³¹ | L¹⁵² |
| 2734. | L¹¹¹ | L¹³² | L¹⁵² |
| 2735. | L¹¹¹ | L¹³³ | L¹⁵² |
| 2736. | L¹¹¹ | L¹³⁴ | L¹⁵² |
| 2737. | L¹¹¹ | L¹⁴⁰ | L¹⁵² |
| 2738. | L¹¹¹ | L¹⁴¹ | L¹⁵² |
| 2739. | L¹¹¹ | L¹⁵⁹ | L¹⁵² |
| 2740. | L¹¹¹ | L¹⁶⁰ | L¹⁵² |
| 2741. | L¹¹¹ | L¹¹² | L¹⁶⁴ |
| 2742. | L¹¹¹ | L¹¹³ | L¹⁶⁴ |
| 2743. | L¹¹¹ | L¹¹⁴ | L¹⁶⁴ |
| 2744. | L¹¹¹ | L¹¹⁵ | L¹⁶⁴ |
| 2745. | L¹¹¹ | L¹¹⁶ | L¹⁶⁴ |
| 2746. | L¹¹¹ | L¹¹⁷ | L¹⁶⁴ |
| 2747. | L¹¹¹ | L¹¹⁸ | L¹⁶⁴ |
| 2748. | L¹¹¹ | L¹¹⁹ | L¹⁶⁴ |
| 2749. | L¹¹¹ | L¹³⁰ | L¹⁶⁴ |
| 2750. | L¹¹¹ | L¹³¹ | L¹⁶⁴ |
| 2751. | L¹¹¹ | L¹³² | L¹⁶⁴ |
| 2752. | L¹¹¹ | L¹³³ | L¹⁶⁴ |
| 2753. | L¹¹¹ | L¹³⁴ | L¹⁶⁴ |
| 2754. | L¹¹¹ | L¹⁴⁰ | L¹⁶⁴ |
| 2755. | L¹¹¹ | L¹⁴¹ | L¹⁶⁴ |
| 2756. | L¹¹¹ | L¹⁵⁹ | L¹⁶⁴ |
| 2757. | L¹¹¹ | L¹⁶⁰ | L¹⁶⁴ |
| 2758. | L¹¹¹ | L¹¹² | L¹⁶⁵ |
| 2759. | L¹¹¹ | L¹¹³ | L¹⁶⁵ |
| 2760. | L¹¹¹ | L¹¹⁴ | L¹⁶⁵ |
| 2761. | L¹¹¹ | L¹¹⁵ | L¹⁶⁵ |
| 2762. | L¹¹¹ | L¹¹⁶ | L¹⁶⁵ |
| 2763. | L¹¹¹ | L¹¹⁷ | L¹⁶⁵ |
| 2764. | L¹¹¹ | L¹¹⁸ | L¹⁶⁵ |
| 2765. | L¹¹¹ | L¹¹⁹ | L¹⁶⁵ |
| 2766. | L¹¹¹ | L¹³⁰ | L¹⁶⁵ |
| 2767. | L¹¹¹ | L¹³¹ | L¹⁶⁵ |
| 2768. | L¹¹¹ | L¹³² | L¹⁶⁵ |
| 2769. | L¹¹¹ | L¹³³ | L¹⁶⁵ |
| 2770. | L¹¹¹ | L¹³⁴ | L¹⁶⁵ |
| 2771. | L¹¹¹ | L¹⁴⁰ | L¹⁶⁵ |
| 2772. | L¹¹¹ | L¹⁴¹ | L¹⁶⁵ |
| 2773. | L¹¹¹ | L¹⁵⁹ | L¹⁶⁵ |
| 2774. | L¹¹¹ | L¹⁶⁰ | L¹⁶⁵ |
| 2775. | L¹¹¹ | L¹¹² | L¹⁶⁶ |
| 2776. | L¹¹¹ | L¹¹³ | L¹⁶⁶ |
| 2777. | L¹¹¹ | L¹¹⁴ | L¹⁶⁶ |
| 2778. | L¹¹¹ | L¹¹⁵ | L¹⁶⁶ |
| 2779. | L¹¹¹ | L¹¹⁶ | L¹⁶⁶ |
| 2780. | L¹¹¹ | L¹¹⁷ | L¹⁶⁶ |
| 2781. | L¹¹¹ | L¹¹⁸ | L¹⁶⁶ |
| 2782. | L¹¹¹ | L¹¹⁹ | L166 |
| 2783. | L¹¹¹ | L¹³⁰ | L¹⁶⁶ |
| 2784. | L¹¹¹ | L¹³¹ | L¹⁶⁶ |
| 2785. | L¹¹¹ | L¹³² | L¹⁶⁶ |
| 2786. | L¹¹¹ | L¹³³ | L¹⁶⁶ |
| 2787. | L¹¹¹ | L¹³⁴ | L¹⁶⁶ |
| 2788. | L¹¹¹ | L¹⁴⁰ | L¹⁶⁶ |
| 2789. | L¹¹¹ | L¹⁴¹ | L¹⁶⁶ |
| 2790. | L¹¹¹ | L¹⁵⁹ | L¹⁶⁶ |
| 2791. | L¹¹¹ | L¹⁶⁰ | L¹⁶⁶ |
| 2792. | L¹¹¹ | L¹¹² | L¹⁷⁰ |
| 2793. | L¹¹¹ | L¹¹³ | L¹⁷⁰ |
| 2794. | L¹¹¹ | L¹¹⁴ | L¹⁷⁰ |
| 2795. | L¹¹¹ | L¹¹⁵ | L¹⁷⁰ |
| 2796. | L¹¹¹ | L¹¹⁶ | L¹⁷⁰ |
| 2797. | L¹¹¹ | L¹¹⁷ | L¹⁷⁰ |
| 2798. | L¹¹¹ | L¹¹⁸ | L¹⁷⁰ |
| 2799. | L¹¹¹ | L¹¹⁹ | L¹⁷⁰ |
| 2800. | L¹¹¹ | L¹³⁰ | L¹⁷⁰ |
| 2801. | L¹¹¹ | L¹³¹ | L¹⁷⁰ |
| 2802. | L¹¹¹ | L¹³² | L¹⁷⁰ |
| 2803. | L¹¹¹ | L¹³³ | L¹⁷⁰ |
| 2804. | L¹¹¹ | L¹³⁴ | L¹⁷⁰ |
| 2805. | L¹¹¹ | L¹⁴⁰ | L¹⁷⁰ |
| 2806. | L¹¹¹ | L¹⁴¹ | L¹⁷⁰ |
| 2807. | L¹¹¹ | L¹⁷⁰ | L¹⁷⁰ |
| 2808. | L¹¹¹ | L¹⁶⁰ | L¹⁷⁰ |
| 2809. | L¹¹¹ | L¹¹² | L¹⁷⁴ |
| 2810. | L¹¹¹ | L¹¹³ | L¹⁷⁴ |
| 2811. | L¹¹¹ | L¹¹⁴ | L¹⁷⁴ |
| 2812. | L¹¹¹ | L¹¹⁵ | L¹⁷⁴ |
| 2813. | L¹¹¹ | L¹¹⁶ | L¹⁷⁴ |
| 2814. | L¹¹¹ | L¹¹⁷ | L¹⁷⁴ |
| 2815. | L¹¹¹ | L¹¹⁸ | L¹⁷⁴ |
| 2816. | L¹¹¹ | L¹¹⁹ | L¹⁷⁴ |
| 2817. | L¹¹¹ | L¹³⁰ | L¹⁷⁴ |
| 2818. | L¹¹¹ | L¹³¹ | L¹⁷⁴ |
| 2819. | L¹¹¹ | L¹³² | L¹⁷⁴ |
| 2820. | L¹¹¹ | L¹³³ | L¹⁷⁴ |
| 2821. | L¹¹¹ | L¹³⁴ | L¹⁷⁴ |

TABLE 1-continued

| Compound number | L₁ | L₂ | L₃ |
|---|---|---|---|
| 2822. | L¹¹¹ | L¹⁴⁰ | L¹⁷⁴ |
| 2823. | L¹¹¹ | L¹⁴¹ | L¹⁷⁴ |
| 2824. | L¹¹¹ | L¹⁵⁹ | L¹⁷⁴ |
| 2825. | L¹¹¹ | L¹⁶⁰ | L¹⁷⁴ |
| 2826. | L¹¹¹ | L¹¹² | L¹⁷⁶ |
| 2827. | L¹¹¹ | L¹¹³ | L¹⁷⁶ |
| 2828. | L¹¹¹ | L¹¹⁴ | L¹⁷⁶ |
| 2829. | L¹¹¹ | L¹¹⁵ | L¹⁷⁶ |
| 2830. | L¹¹¹ | L¹¹⁶ | L¹⁷⁶ |
| 2831. | L¹¹¹ | L¹¹⁷ | L¹⁷⁶ |
| 2832. | L¹¹¹ | L¹¹⁸ | L¹⁷⁶ |
| 2833. | L¹¹¹ | L¹¹⁹ | L¹⁷⁶ |
| 2834. | L¹¹¹ | L¹³⁰ | L¹⁷⁶ |
| 2835. | L¹¹¹ | L¹³¹ | L¹⁷⁶ |
| 2836. | L¹¹¹ | L¹³² | L¹⁷⁶ |
| 2837. | L¹¹¹ | L¹³³ | L¹⁷⁶ |
| 2838. | L¹¹¹ | L¹³⁴ | L¹⁷⁶ |
| 2839. | L¹¹¹ | L¹⁴⁰ | L¹⁷⁶ |
| 2840. | L¹¹¹ | L¹⁴¹ | L¹⁷⁶ |
| 2841. | L¹¹¹ | L¹⁵⁹ | L¹⁷⁶ |
| 2842. | L¹¹¹ | L¹⁶⁰ | L¹⁷⁶ |
| 2843. | L¹¹¹ | L¹¹² | L¹⁷⁹ |
| 2844. | L¹¹¹ | L¹¹³ | L¹⁷⁹ |
| 2845. | L¹¹¹ | L¹¹⁴ | L¹⁷⁹ |
| 2846. | L¹¹¹ | L¹¹⁵ | L¹⁷⁹ |
| 2847. | L¹¹¹ | L¹¹⁶ | L¹⁷⁹ |
| 2848. | L¹¹¹ | L¹¹⁷ | L¹⁷⁹ |
| 2849. | L¹¹¹ | L¹¹⁸ | L¹⁷⁹ |
| 2850. | L¹¹¹ | L¹¹⁹ | L¹⁷⁹ |
| 2851. | L¹¹¹ | L¹³⁰ | L¹⁷⁹ |
| 2852. | L¹¹¹ | L¹³¹ | L¹⁷⁹ |
| 2853. | L¹¹¹ | L¹³² | L¹⁷⁹ |
| 2854. | L¹¹¹ | L¹³³ | L¹⁷⁹ |
| 2855. | L¹¹¹ | L¹³⁴ | L¹⁷⁹ |
| 2856. | L¹¹¹ | L¹⁴⁰ | L¹⁷⁹ |
| 2857. | L¹¹¹ | L¹⁴¹ | L¹⁷⁹ |
| 2858. | L¹¹¹ | L¹⁵⁹ | L¹⁷⁹ |
| 2859. | L¹¹¹ | L¹⁶⁰ | L¹⁷⁹ |
| 2860. | L¹¹¹ | L¹¹² | L¹⁷⁹ |
| 2861. | L¹¹¹ | L¹¹³ | L¹⁸⁰ |
| 2862. | L¹¹¹ | L¹¹⁴ | L¹⁸⁰ |
| 2863. | L¹¹¹ | L¹¹⁵ | L¹⁸⁰ |
| 2864. | L¹¹¹ | L¹¹⁶ | L¹⁸⁰ |
| 2865. | L¹¹¹ | L¹¹⁷ | L¹⁸⁰ |
| 2866. | L¹¹¹ | L¹¹⁸ | L¹⁸⁰ |
| 2867. | L¹¹¹ | L¹¹⁹ | L¹⁸⁰ |
| 2868. | L¹¹¹ | L¹³⁰ | L¹⁸⁰ |
| 2869. | L¹¹¹ | L¹³¹ | L¹⁸⁰ |
| 2870. | L¹¹¹ | L¹³² | L¹⁸⁰ |
| 2871. | L¹¹¹ | L¹³³ | L¹⁸⁰ |
| 2872. | L¹¹¹ | L¹³⁴ | L¹⁸⁰ |
| 2873. | L¹¹¹ | L¹⁴⁰ | L¹⁸⁰ |
| 2874. | L¹¹¹ | L¹⁴¹ | L¹⁸⁰ |
| 2875. | L¹¹¹ | L¹⁵⁹ | L¹⁸⁰ |
| 2876. | L¹¹¹ | L¹⁶⁰ | L¹⁸⁰ |
| 2877. | L¹¹² | L¹¹³ | L¹⁴⁴ |
| 2878. | L¹¹² | L¹¹⁴ | L¹⁴⁴ |
| 2879. | L¹¹² | L¹¹⁵ | L¹⁴⁴ |
| 2880. | L¹¹² | L¹¹⁶ | L¹⁴⁴ |
| 2881. | L¹¹² | L¹¹⁷ | L¹⁴⁴ |
| 2882. | L¹¹² | L¹¹⁸ | L¹⁴⁴ |
| 2883. | L¹¹² | L¹¹⁹ | L¹⁴⁴ |
| 2884. | L¹¹² | L¹³⁰ | L¹⁴⁴ |
| 2885. | L¹¹² | L¹³¹ | L¹⁴⁴ |
| 2886. | L¹¹² | L¹³² | L¹⁴⁴ |
| 2887. | L¹¹² | L¹³³ | L¹⁴⁴ |
| 2888. | L¹¹² | L¹³⁴ | L¹⁴⁴ |
| 2889. | L¹¹² | L¹⁴⁰ | L¹⁴⁴ |
| 2890. | L¹¹² | L¹⁴¹ | L¹⁴⁴ |
| 2891. | L¹¹² | L¹⁵⁹ | L¹⁴⁴ |
| 2892. | L¹¹² | L¹⁶⁰ | L¹⁴⁴ |
| 2893. | L¹¹² | L¹¹³ | L¹⁴⁵ |
| 2894. | L¹¹² | L¹¹⁴ | L¹⁴⁵ |
| 2895. | L¹¹² | L¹¹⁵ | L¹⁴⁵ |
| 2896. | L¹¹² | L¹¹⁶ | L¹⁴⁵ |
| 2897. | L¹¹² | L¹¹⁷ | L¹⁴⁵ |
| 2898. | L¹¹² | L¹¹⁸ | L¹⁴⁵ |
| 2899. | L¹¹² | L¹¹⁹ | L¹⁴⁵ |
| 2900. | L¹¹² | L¹³⁰ | L¹⁴⁵ |
| 2901. | L¹¹² | L¹³¹ | L¹⁴⁵ |
| 2902. | L¹¹² | L¹³² | L¹⁴⁵ |
| 2903. | L¹¹² | L¹³³ | L¹⁴⁵ |
| 2904. | L¹¹² | L¹³⁴ | L¹⁴⁵ |
| 2905. | L¹¹² | L¹⁴⁰ | L¹⁴⁵ |
| 2906. | L¹¹² | L¹⁴¹ | L¹⁴⁵ |
| 2907. | L¹¹² | L¹⁵⁹ | L¹⁴⁵ |
| 2908. | L¹¹² | L¹⁶⁰ | L¹⁴⁵ |
| 2909. | L¹¹² | L¹¹³ | L¹⁴⁷ |
| 2910. | L¹¹² | L¹¹⁴ | L¹⁴⁷ |
| 2911. | L¹¹² | L¹¹⁵ | L¹⁴⁷ |
| 2912. | L¹¹² | L¹¹⁶ | L¹⁴⁷ |
| 2913. | L¹¹² | L¹¹⁷ | L¹⁴⁷ |
| 2914. | L¹¹² | L¹¹⁸ | L¹⁴⁷ |
| 2915. | L¹¹² | L¹¹⁹ | L¹⁴⁷ |
| 2916. | L¹¹² | L¹³⁰ | L¹⁴⁷ |
| 2917. | L¹¹² | L¹³¹ | L¹⁴⁷ |
| 2918. | L¹¹² | L¹³² | L¹⁴⁷ |
| 2919. | L¹¹² | L¹³³ | L¹⁴⁷ |
| 2920. | L¹¹² | L¹³⁴ | L¹⁴⁷ |
| 2921. | L¹¹² | L¹⁴⁰ | L¹⁴⁷ |
| 2922. | L¹¹² | L¹⁴¹ | L¹⁴⁷ |
| 2923. | L¹¹² | L¹⁵⁹ | L¹⁴⁷ |
| 2924. | L¹¹² | L¹⁶⁰ | L¹⁴⁷ |
| 2925. | L¹¹² | L¹¹³ | L¹⁴⁹ |
| 2926. | L¹¹² | L¹¹⁴ | L¹⁴⁹ |
| 2927. | L¹¹² | L¹¹⁵ | L¹⁴⁹ |
| 2928. | L¹¹² | L¹¹⁶ | L¹⁴⁹ |
| 2929. | L¹¹² | L¹¹⁷ | L¹⁴⁹ |
| 2930. | L¹¹² | L¹¹⁸ | L¹⁴⁹ |
| 2931. | L¹¹² | L¹¹⁹ | L¹⁴⁹ |
| 2932. | L¹¹² | L¹³⁰ | L¹⁴⁹ |
| 2933. | L¹¹² | L¹³¹ | L¹⁴⁹ |
| 2934. | L¹¹² | L¹³² | L¹⁴⁹ |
| 2935. | L¹¹² | L¹³³ | L¹⁴⁹ |
| 2936. | L¹¹² | L¹³⁴ | L¹⁴⁹ |
| 2937. | L¹¹² | L¹⁴⁰ | L¹⁴⁹ |
| 2938. | L¹¹² | L¹⁴¹ | L¹⁴⁹ |
| 2939. | L¹¹² | L¹⁵⁹ | L¹⁴⁹ |
| 2940. | L¹¹² | L¹⁶⁰ | L¹⁴⁹ |
| 2941. | L¹¹² | L¹¹³ | L¹⁵² |
| 2942. | L¹¹² | L¹¹⁴ | L¹⁵² |
| 2943. | L¹¹² | L¹¹⁵ | L¹⁵² |
| 2944. | L¹¹² | L¹¹⁶ | L¹⁵² |
| 2945. | L¹¹² | L¹¹⁷ | L¹⁵² |
| 2946. | L¹¹² | L¹¹⁸ | L¹⁵² |
| 2947. | L¹¹² | L¹¹⁹ | L¹⁵² |
| 2948. | L¹¹² | L¹³⁰ | L¹⁵² |
| 2949. | L¹¹² | L¹³¹ | L¹⁵² |
| 2950. | L¹¹² | L¹³² | L¹⁵² |
| 2951. | L¹¹² | L¹³³ | L¹⁵² |
| 2952. | L¹¹² | L¹³⁴ | L¹⁵² |
| 2953. | L¹¹² | L¹⁴⁰ | L¹⁵² |
| 2954. | L¹¹² | L¹⁴¹ | L¹⁵² |
| 2955. | L¹¹² | L¹⁵⁹ | L¹⁵² |
| 2956. | L¹¹² | L¹⁶⁰ | L¹⁵² |
| 2957. | L¹¹² | L¹¹³ | L¹⁶⁴ |
| 2958. | L¹¹² | L¹¹⁴ | L¹⁶⁴ |
| 2959. | L¹¹² | L¹¹⁵ | L¹⁶⁴ |
| 2960. | L¹¹² | L¹¹⁶ | L¹⁶⁴ |
| 2961. | L¹¹² | L¹¹⁷ | L¹⁶⁴ |
| 2962. | L¹¹² | L¹¹⁸ | L¹⁶⁴ |
| 2963. | L¹¹² | L¹¹⁹ | L¹⁶⁴ |
| 2964. | L¹¹² | L¹³⁰ | L¹⁶⁴ |
| 2965. | L¹¹² | L¹³¹ | L¹⁶⁴ |
| 2966. | L¹¹² | L¹³² | L¹⁶⁴ |
| 2967. | L¹¹² | L¹³³ | L¹⁶⁴ |
| 2968. | L¹¹² | L¹³⁴ | L¹⁶⁴ |
| 2969. | L¹¹² | L¹⁴⁰ | L¹⁶⁴ |
| 2970. | L¹¹² | L¹⁴¹ | L¹⁶⁴ |
| 2971. | L¹¹² | L¹⁵⁹ | L¹⁶⁴ |
| 2972. | L¹¹² | L¹⁶⁰ | L¹⁶⁴ |
| 2973. | L¹¹² | L¹¹³ | L¹⁶⁵ |
| 2974. | L¹¹² | L¹¹⁴ | L¹⁶⁵ |
| 2975. | L¹¹² | L¹¹⁵ | L¹⁶⁵ |

TABLE 1-continued

| Compound number | $L_1$ | $L_2$ | $L_3$ |
|---|---|---|---|
| 2976. | $L^{112}$ | $L^{116}$ | $L^{165}$ |
| 2977. | $L^{112}$ | $L^{117}$ | $L^{165}$ |
| 2978. | $L^{112}$ | $L^{118}$ | $L^{165}$ |
| 2979. | $L^{112}$ | $L^{119}$ | $L^{165}$ |
| 2980. | $L^{112}$ | $L^{130}$ | $L^{165}$ |
| 2981. | $L^{112}$ | $L^{131}$ | $L^{165}$ |
| 2982. | $L^{112}$ | $L^{132}$ | $L^{165}$ |
| 2983. | $L^{112}$ | $L^{133}$ | $L^{165}$ |
| 2984. | $L^{112}$ | $L^{134}$ | $L^{165}$ |
| 2985. | $L^{112}$ | $L^{140}$ | $L^{165}$ |
| 2986. | $L^{112}$ | $L^{141}$ | $L^{165}$ |
| 2987. | $L^{112}$ | $L^{159}$ | $L^{165}$ |
| 2988. | $L^{112}$ | $L^{160}$ | $L^{165}$ |
| 2989. | $L^{112}$ | $L^{113}$ | $L^{166}$ |
| 2990. | $L^{112}$ | $L^{114}$ | $L^{166}$ |
| 2991. | $L^{112}$ | $L^{115}$ | $L^{166}$ |
| 2992. | $L^{112}$ | $L^{116}$ | $L^{166}$ |
| 2993. | $L^{112}$ | $L^{117}$ | $L^{166}$ |
| 2994. | $L^{112}$ | $L^{118}$ | $L^{166}$ |
| 2995. | $L^{112}$ | $L^{119}$ | $L^{166}$ |
| 2996. | $L^{112}$ | $L^{130}$ | $L^{166}$ |
| 2997. | $L^{112}$ | $L^{131}$ | $L^{166}$ |
| 2998. | $L^{112}$ | $L^{132}$ | $L^{166}$ |
| 2999. | $L^{112}$ | $L^{133}$ | $L^{166}$ |
| 3000. | $L^{112}$ | $L^{134}$ | $L^{166}$ |
| 3001. | $L^{112}$ | $L^{140}$ | $L^{166}$ |
| 3002. | $L^{112}$ | $L^{141}$ | $L^{166}$ |
| 3003. | $L^{112}$ | $L^{159}$ | $L^{166}$ |
| 3004. | $L^{112}$ | $L^{160}$ | $L^{166}$ |
| 3005. | $L^{112}$ | $L^{113}$ | $L^{170}$ |
| 3006. | $L^{112}$ | $L^{114}$ | $L^{170}$ |
| 3007. | $L^{112}$ | $L^{115}$ | $L^{170}$ |
| 3008. | $L^{112}$ | $L^{116}$ | $L^{170}$ |
| 3009. | $L^{112}$ | $L^{117}$ | $L^{170}$ |
| 3010. | $L^{112}$ | $L^{118}$ | $L^{170}$ |
| 3011. | $L^{112}$ | $L^{119}$ | $L^{170}$ |
| 3012. | $L^{112}$ | $L^{130}$ | $L^{170}$ |
| 3013. | $L^{112}$ | $L^{131}$ | $L^{170}$ |
| 3014. | $L^{112}$ | $L^{132}$ | $L^{170}$ |
| 3015. | $L^{112}$ | $L^{133}$ | $L^{170}$ |
| 3016. | $L^{112}$ | $L^{134}$ | $L^{170}$ |
| 3017. | $L^{112}$ | $L^{140}$ | $L^{170}$ |
| 3018. | $L^{112}$ | $L^{141}$ | $L^{170}$ |
| 3019. | $L^{112}$ | $L^{159}$ | $L^{170}$ |
| 3020. | $L^{112}$ | $L^{160}$ | $L^{170}$ |
| 3021. | $L^{112}$ | $L^{113}$ | $L^{174}$ |
| 3022. | $L^{112}$ | $L^{114}$ | $L^{174}$ |
| 3023. | $L^{112}$ | $L^{115}$ | $L^{174}$ |
| 3024. | $L^{112}$ | $L^{116}$ | $L^{174}$ |
| 3025. | $L^{112}$ | $L^{117}$ | $L^{174}$ |
| 3026. | $L^{112}$ | $L^{118}$ | $L^{174}$ |
| 3027. | $L^{112}$ | $L^{119}$ | $L^{174}$ |
| 3028. | $L^{112}$ | $L^{130}$ | $L^{174}$ |
| 3029. | $L^{112}$ | $L^{131}$ | $L^{174}$ |
| 3030. | $L^{112}$ | $L^{132}$ | $L^{174}$ |
| 3031. | $L^{112}$ | $L^{133}$ | $L^{174}$ |
| 3032. | $L^{112}$ | $L^{134}$ | $L^{174}$ |
| 3033. | $L^{112}$ | $L^{140}$ | $L^{174}$ |
| 3034. | $L^{112}$ | $L^{141}$ | $L^{174}$ |
| 3035. | $L^{112}$ | $L^{159}$ | $L^{174}$ |
| 3036. | $L^{112}$ | $L^{160}$ | $L^{174}$ |
| 3037. | $L^{112}$ | $L^{113}$ | $L^{176}$ |
| 3038. | $L^{112}$ | $L^{114}$ | $L^{176}$ |
| 3039. | $L^{112}$ | $L^{115}$ | $L^{176}$ |
| 3040. | $L^{112}$ | $L^{116}$ | $L^{176}$ |
| 3041. | $L^{112}$ | $L^{117}$ | $L^{176}$ |
| 3042. | $L^{112}$ | $L^{118}$ | $L^{176}$ |
| 3043. | $L^{112}$ | $L^{119}$ | $L^{176}$ |
| 3044. | $L^{112}$ | $L^{130}$ | $L^{176}$ |
| 3045. | $L^{112}$ | $L^{131}$ | $L^{176}$ |
| 3046. | $L^{112}$ | $L^{132}$ | $L^{176}$ |
| 3047. | $L^{112}$ | $L^{133}$ | $L^{176}$ |
| 3048. | $L^{112}$ | $L^{134}$ | $L^{176}$ |
| 3049. | $L^{112}$ | $L^{140}$ | $L^{176}$ |
| 3050. | $L^{112}$ | $L^{141}$ | $L^{176}$ |
| 3051. | $L^{112}$ | $L^{159}$ | $L^{176}$ |
| 3052. | $L^{112}$ | $L^{160}$ | $L^{176}$ |
| 3053. | $L^{112}$ | $L^{113}$ | $L^{179}$ |
| 3054. | $L^{112}$ | $L^{114}$ | $L^{179}$ |
| 3055. | $L^{112}$ | $L^{115}$ | $L^{179}$ |
| 3056. | $L^{112}$ | $L^{116}$ | $L^{179}$ |
| 3057. | $L^{112}$ | $L^{117}$ | $L^{179}$ |
| 3058. | $L^{112}$ | $L^{118}$ | $L^{179}$ |
| 3059. | $L^{112}$ | $L^{119}$ | $L^{179}$ |
| 3060. | $L^{112}$ | $L^{130}$ | $L^{179}$ |
| 3061. | $L^{112}$ | $L^{131}$ | $L^{179}$ |
| 3062. | $L^{112}$ | $L^{132}$ | $L^{179}$ |
| 3063. | $L^{112}$ | $L^{133}$ | $L^{179}$ |
| 3064. | $L^{112}$ | $L^{134}$ | $L^{179}$ |
| 3065. | $L^{112}$ | $L^{140}$ | $L^{179}$ |
| 3066. | $L^{112}$ | $L^{141}$ | $L^{179}$ |
| 3067. | $L^{112}$ | $L^{159}$ | $L^{179}$ |
| 3068. | $L^{112}$ | $L^{160}$ | $L^{179}$ |
| 3069. | $L^{112}$ | $L^{113}$ | $L^{180}$ |
| 3070. | $L^{112}$ | $L^{114}$ | $L^{180}$ |
| 3071. | $L^{112}$ | $L^{115}$ | $L^{180}$ |
| 3072. | $L^{112}$ | $L^{116}$ | $L^{180}$ |
| 3073. | $L^{112}$ | $L^{117}$ | $L^{180}$ |
| 3074. | $L^{112}$ | $L^{118}$ | $L^{180}$ |
| 3075. | $L^{112}$ | $L^{119}$ | $L^{180}$ |
| 3076. | $L^{112}$ | $L^{130}$ | $L^{180}$ |
| 3077. | $L^{112}$ | $L^{131}$ | $L^{180}$ |
| 3078. | $L^{112}$ | $L^{132}$ | $L^{180}$ |
| 3079. | $L^{112}$ | $L^{133}$ | $L^{180}$ |
| 3080. | $L^{112}$ | $L^{134}$ | $L^{180}$ |
| 3081. | $L^{112}$ | $L^{140}$ | $L^{180}$ |
| 3082. | $L^{112}$ | $L^{141}$ | $L^{180}$ |
| 3083. | $L^{112}$ | $L^{159}$ | $L^{180}$ |
| 3084. | $L^{112}$ | $L^{160}$ | $L^{180}$ |
| 3085. | $L^{113}$ | $L^{114}$ | $L^{144}$ |
| 3086. | $L^{113}$ | $L^{115}$ | $L^{144}$ |
| 3087. | $L^{113}$ | $L^{116}$ | $L^{144}$ |
| 3088. | $L^{113}$ | $L^{117}$ | $L^{144}$ |
| 3089. | $L^{113}$ | $L^{118}$ | $L^{144}$ |
| 3090. | $L^{113}$ | $L^{119}$ | $L^{144}$ |
| 3091. | $L^{113}$ | $L^{130}$ | $L^{144}$ |
| 3092. | $L^{113}$ | $L^{131}$ | $L^{144}$ |
| 3093. | $L^{113}$ | $L^{132}$ | $L^{144}$ |
| 3094. | $L^{113}$ | $L^{133}$ | $L^{144}$ |
| 3095. | $L^{113}$ | $L^{134}$ | $L^{144}$ |
| 3096. | $L^{113}$ | $L^{140}$ | $L^{144}$ |
| 3097. | $L^{113}$ | $L^{141}$ | $L^{144}$ |
| 3098. | $L^{113}$ | $L^{159}$ | $L^{144}$ |
| 3099. | $L^{113}$ | $L^{160}$ | $L^{144}$ |
| 3100. | $L^{113}$ | $L^{114}$ | $L^{145}$ |
| 3101. | $L^{113}$ | $L^{115}$ | $L^{145}$ |
| 3102. | $L^{113}$ | $L^{116}$ | $L^{145}$ |
| 3103. | $L^{113}$ | $L^{117}$ | $L^{145}$ |
| 3104. | $L^{113}$ | $L^{118}$ | $L^{145}$ |
| 3105. | $L^{113}$ | $L^{119}$ | $L^{145}$ |
| 3106. | $L^{113}$ | $L^{130}$ | $L^{145}$ |
| 3107. | $L^{113}$ | $L^{131}$ | $L^{145}$ |
| 3108. | $L^{113}$ | $L^{132}$ | $L^{145}$ |
| 3109. | $L^{113}$ | $L^{133}$ | $L^{145}$ |
| 3110. | $L^{113}$ | $L^{134}$ | $L^{145}$ |
| 3111. | $L^{113}$ | $L^{140}$ | $L^{145}$ |
| 3112. | $L^{113}$ | $L^{141}$ | $L^{145}$ |
| 3113. | $L^{113}$ | $L^{159}$ | $L^{145}$ |
| 3114. | $L^{113}$ | $L^{160}$ | $L^{145}$ |
| 3115. | $L^{113}$ | $L^{114}$ | $L^{147}$ |
| 3116. | $L^{113}$ | $L^{115}$ | $L^{147}$ |
| 3117. | $L^{113}$ | $L^{116}$ | $L^{147}$ |
| 3118. | $L^{113}$ | $L^{117}$ | $L^{147}$ |
| 3119. | $L^{113}$ | $L^{118}$ | $L^{147}$ |
| 3120. | $L^{113}$ | $L^{119}$ | $L^{147}$ |
| 3121. | $L^{113}$ | $L^{130}$ | $L^{147}$ |
| 3122. | $L^{113}$ | $L^{131}$ | $L^{147}$ |
| 3123. | $L^{113}$ | $L^{132}$ | $L^{147}$ |
| 3124. | $L^{113}$ | $L^{133}$ | $L^{147}$ |
| 3125. | $L^{113}$ | $L^{134}$ | $L^{147}$ |
| 3126. | $L^{113}$ | $L^{140}$ | $L^{147}$ |
| 3127. | $L^{113}$ | $L^{141}$ | $L^{147}$ |
| 3128. | $L^{113}$ | $L^{159}$ | $L^{147}$ |
| 3129. | $L^{113}$ | $L^{160}$ | $L^{147}$ |

TABLE 1-continued

| Compound number | L₁ | L₂ | L₃ |
|---|---|---|---|
| 3130. | L¹¹³ | L¹¹⁴ | L¹⁴⁹ |
| 3131. | L¹¹³ | L¹¹⁵ | L¹⁴⁹ |
| 3132. | L¹¹³ | L¹¹⁶ | L¹⁴⁹ |
| 3133. | L¹¹³ | L¹¹⁷ | L¹⁴⁹ |
| 3134. | L¹¹³ | L¹¹⁸ | L¹⁴⁹ |
| 3135. | L¹¹³ | L¹¹⁹ | L¹⁴⁹ |
| 3136. | L¹¹³ | L¹³⁰ | L¹⁴⁹ |
| 3137. | L¹¹³ | L¹³¹ | L¹⁴⁹ |
| 3138. | L¹¹³ | L¹³² | L¹⁴⁹ |
| 3139. | L¹¹³ | L¹³³ | L¹⁴⁹ |
| 3140. | L¹¹³ | L¹³⁴ | L¹⁴⁹ |
| 3141. | L¹¹³ | L¹⁴⁰ | L¹⁴⁹ |
| 3142. | L¹¹³ | L¹⁴¹ | L¹⁴⁹ |
| 3143. | L¹¹³ | L¹⁵⁹ | L¹⁴⁹ |
| 3144. | L¹¹³ | L¹⁶⁰ | L¹⁴⁹ |
| 3145. | L¹¹³ | L¹¹⁴ | L¹⁵² |
| 3146. | L¹¹³ | L¹¹⁵ | L¹⁵² |
| 3147. | L¹¹³ | L¹¹⁶ | L¹⁵² |
| 3148. | L¹¹³ | L¹¹⁷ | L¹⁵² |
| 3149. | L¹¹³ | L¹¹⁸ | L¹⁵² |
| 3150. | L¹¹³ | L¹¹⁹ | L¹⁵² |
| 3151. | L¹¹³ | L¹³⁰ | L¹⁵² |
| 3152. | L¹¹³ | L¹³¹ | L¹⁵² |
| 3153. | L¹¹³ | L¹³² | L¹⁵² |
| 3154. | L¹¹³ | L¹³³ | L¹⁵² |
| 3155. | L¹¹³ | L¹³⁴ | L¹⁵² |
| 3156. | L¹¹³ | L¹⁴⁰ | L¹⁵² |
| 3157. | L¹¹³ | L¹⁴¹ | L¹⁵² |
| 3158. | L¹¹³ | L¹⁵⁹ | L¹⁵² |
| 3159. | L¹¹³ | L¹⁶⁰ | L¹⁵² |
| 3160. | L¹¹³ | L¹¹⁴ | L¹⁶⁴ |
| 3161. | L¹¹³ | L¹¹⁵ | L¹⁶⁴ |
| 3162. | L¹¹³ | L¹¹⁶ | L¹⁶⁴ |
| 3163. | L¹¹³ | L¹¹⁷ | L¹⁶⁴ |
| 3164. | L¹¹³ | L¹¹⁸ | L¹⁶⁴ |
| 3165. | L¹¹³ | L¹¹⁹ | L¹⁶⁴ |
| 3166. | L¹¹³ | L¹³⁰ | L¹⁶⁴ |
| 3167. | L¹¹³ | L¹³¹ | L¹⁶⁴ |
| 3168. | L¹¹³ | L¹³² | L¹⁶⁴ |
| 3169. | L¹¹³ | L¹³³ | L¹⁶⁴ |
| 3170. | L¹¹³ | L¹³⁴ | L¹⁶⁴ |
| 3171. | L¹¹³ | L¹⁴⁰ | L¹⁶⁴ |
| 3172. | L¹¹³ | L¹⁴¹ | L¹⁶⁴ |
| 3173. | L¹¹³ | L¹⁵⁹ | L¹⁶⁴ |
| 3174. | L¹¹³ | L¹⁶⁰ | L¹⁶⁴ |
| 3175. | L¹¹³ | L¹¹⁴ | L¹⁶⁵ |
| 3176. | L¹¹³ | L¹¹⁵ | L¹⁶⁵ |
| 3177. | L¹¹³ | L¹¹⁶ | L¹⁶⁵ |
| 3178. | L¹¹³ | L¹¹⁷ | L¹⁶⁵ |
| 3179. | L¹¹³ | L¹¹⁸ | L¹⁶⁵ |
| 3180. | L¹¹³ | L¹¹⁹ | L¹⁶⁵ |
| 3181. | L¹¹³ | L¹³⁰ | L¹⁶⁵ |
| 3182. | L¹¹³ | L¹³¹ | L¹⁶⁵ |
| 3183. | L¹¹³ | L¹³² | L¹⁶⁵ |
| 3184. | L¹¹³ | L¹³³ | L¹⁶⁵ |
| 3185. | L¹¹³ | L¹³⁴ | L¹⁶⁵ |
| 3186. | L¹¹³ | L¹⁴⁰ | L¹⁶⁵ |
| 3187. | L¹¹³ | L¹⁴¹ | L¹⁶⁵ |
| 3188. | L¹¹³ | L¹⁵⁹ | L¹⁶⁵ |
| 3189. | L¹¹³ | L¹⁶⁰ | L¹⁶⁵ |
| 3190. | L¹¹³ | L¹¹⁴ | L¹⁶⁶ |
| 3191. | L¹¹³ | L¹¹⁵ | L¹⁶⁶ |
| 3192. | L¹¹³ | L¹¹⁶ | L¹⁶⁶ |
| 3193. | L¹¹³ | L¹¹⁷ | L¹⁶⁶ |
| 3194. | L¹¹³ | L¹¹⁸ | L¹⁶⁶ |
| 3195. | L¹¹³ | L¹¹⁹ | L¹⁶⁶ |
| 3196. | L¹¹³ | L¹³⁰ | L¹⁶⁶ |
| 3197. | L¹¹³ | L¹³¹ | L¹⁶⁶ |
| 3198. | L¹¹³ | L¹³² | L¹⁶⁶ |
| 3199. | L¹¹³ | L¹³³ | L¹⁶⁶ |
| 3200. | L¹¹³ | L¹³⁴ | L¹⁶⁶ |
| 3201. | L¹¹³ | L¹⁴⁰ | L¹⁶⁶ |
| 3202. | L¹¹³ | L¹⁴¹ | L¹⁶⁶ |
| 3203. | L¹¹³ | L¹⁵⁹ | L¹⁶⁶ |
| 3204. | L¹¹³ | L¹⁶⁰ | L¹⁶⁶ |
| 3205. | L¹¹³ | L¹¹⁴ | L¹⁷⁰ |
| 3206. | L¹¹³ | L¹¹⁵ | L¹⁷⁰ |
| 3207. | L¹¹³ | L¹¹⁶ | L¹⁷⁰ |
| 3208. | L¹¹³ | L¹¹⁷ | L¹⁷⁰ |
| 3209. | L¹¹³ | L¹¹⁸ | L¹⁷⁰ |
| 3210. | L¹¹³ | L¹¹⁹ | L¹⁷⁰ |
| 3211. | L¹¹³ | L¹³⁰ | L¹⁷⁰ |
| 3212. | L¹¹³ | L¹³¹ | L¹⁷⁰ |
| 3213. | L¹¹³ | L¹³² | L¹⁷⁰ |
| 3214. | L¹¹³ | L¹³³ | L¹⁷⁰ |
| 3215. | L¹¹³ | L¹³⁴ | L¹⁷⁰ |
| 3216. | L¹¹³ | L¹⁴⁰ | L¹⁷⁰ |
| 3217. | L¹¹³ | L¹⁴¹ | L¹⁷⁰ |
| 3218. | L¹¹³ | L¹⁵⁹ | L¹⁷⁰ |
| 3219. | L¹¹³ | L¹⁶⁰ | L¹⁷⁰ |
| 3220. | L¹¹³ | L¹¹⁴ | L¹⁷⁴ |
| 3221. | L¹¹³ | L¹¹⁵ | L¹⁷⁴ |
| 3222. | L¹¹³ | L¹¹⁶ | L¹⁷⁴ |
| 3223. | L¹¹³ | L¹¹⁷ | L¹⁷⁴ |
| 3224. | L¹¹³ | L¹¹⁸ | L¹⁷⁴ |
| 3225. | L¹¹³ | L¹¹⁹ | L¹⁷⁴ |
| 3226. | L¹¹³ | L¹³⁰ | L¹⁷⁴ |
| 3227. | L¹¹³ | L¹³¹ | L¹⁷⁴ |
| 3228. | L¹¹³ | L¹³² | L¹⁷⁴ |
| 3229. | L¹¹³ | L¹³³ | L¹⁷⁴ |
| 3230. | L¹¹³ | L¹³⁴ | L¹⁷⁴ |
| 3231. | L¹¹³ | L¹⁴⁰ | L¹⁷⁴ |
| 3232. | L¹¹³ | L¹⁴¹ | L¹⁷⁴ |
| 3233. | L¹¹³ | L¹⁵⁹ | L¹⁷⁴ |
| 3234. | L¹¹³ | L¹⁶⁰ | L¹⁷⁴ |
| 3235. | L¹¹³ | L¹¹⁴ | L¹⁷⁶ |
| 3236. | L¹¹³ | L¹¹⁵ | L¹⁷⁶ |
| 3237. | L¹¹³ | L¹¹⁶ | L¹⁷⁶ |
| 3238. | L¹¹³ | L¹¹⁷ | L¹⁷⁶ |
| 3239. | L¹¹³ | L¹¹⁸ | L¹⁷⁶ |
| 3240. | L¹¹³ | L¹¹⁹ | L¹⁷⁶ |
| 3241. | L¹¹³ | L¹³⁰ | L¹⁷⁶ |
| 3242. | L¹¹³ | L¹³¹ | L¹⁷⁶ |
| 3243. | L¹¹³ | L¹³² | L¹⁷⁶ |
| 3244. | L¹¹³ | L¹³³ | L¹⁷⁶ |
| 3245. | L¹¹³ | L¹³⁴ | L¹⁷⁶ |
| 3246. | L¹¹³ | L¹⁴⁰ | L¹⁷⁶ |
| 3247. | L¹¹³ | L¹⁴¹ | L¹⁷⁶ |
| 3248. | L¹¹³ | L¹⁵⁹ | L¹⁷⁶ |
| 3249. | L¹¹³ | L¹⁶⁰ | L¹⁷⁶ |
| 3250. | L¹¹³ | L¹¹⁴ | L¹⁷⁹ |
| 3251. | L¹¹³ | L¹¹⁵ | L¹⁷⁹ |
| 3252. | L¹¹³ | L¹¹⁶ | L¹⁷⁹ |
| 3253. | L¹¹³ | L¹¹⁷ | L¹⁷⁹ |
| 3254. | L¹¹³ | L¹¹⁸ | L¹⁷⁹ |
| 3255. | L¹¹³ | L¹¹⁹ | L¹⁷⁹ |
| 3256. | L¹¹³ | L¹³⁰ | L¹⁷⁹ |
| 3257. | L¹¹³ | L¹³¹ | L¹⁷⁹ |
| 3258. | L¹¹³ | L¹³² | L¹⁷⁹ |
| 3259. | L¹¹³ | L¹³³ | L¹⁷⁹ |
| 3260. | L¹¹³ | L¹³⁴ | L¹⁷⁹ |
| 3261. | L¹¹³ | L¹⁴⁰ | L¹⁷⁹ |
| 3262. | L¹¹³ | L¹⁴¹ | L¹⁷⁹ |
| 3263. | L¹¹³ | L¹⁵⁹ | L¹⁷⁹ |
| 3264. | L¹¹³ | L¹⁶⁰ | L¹⁷⁹ |
| 3265. | L¹¹³ | L¹¹⁴ | L¹⁸⁰ |
| 3266. | L¹¹³ | L¹¹⁵ | L¹⁸⁰ |
| 3267. | L¹¹³ | L¹¹⁶ | L¹⁸⁰ |
| 3268. | L¹¹³ | L¹¹⁷ | L¹⁸⁰ |
| 3269. | L¹¹³ | L¹¹⁸ | L¹⁸⁰ |
| 3270. | L¹¹³ | L¹¹⁹ | L¹⁸⁰ |
| 3271. | L¹¹³ | L¹³⁰ | L¹⁸⁰ |
| 3272. | L¹¹³ | L¹³¹ | L¹⁸⁰ |
| 3273. | L¹¹³ | L¹³² | L¹⁸⁰ |
| 3274. | L¹¹³ | L¹³³ | L¹⁸⁰ |
| 3275. | L¹¹³ | L¹³⁴ | L¹⁸⁰ |
| 3276. | L¹¹³ | L¹⁴⁰ | L¹⁸⁰ |
| 3277. | L¹¹³ | L¹⁴¹ | L¹⁸⁰ |
| 3278. | L¹¹³ | L¹⁵⁹ | L¹⁸⁰ |
| 3279. | L¹¹³ | L¹⁶⁰ | L¹⁸⁰ |
| 3280. | L¹¹⁴ | L¹¹⁵ | L¹⁴⁴ |
| 3281. | L¹¹⁴ | L¹¹⁶ | L¹⁴⁴ |
| 3282. | L¹¹⁴ | L¹¹⁷ | L¹⁴⁴ |
| 3283. | L¹¹⁴ | L¹¹⁸ | L¹⁴⁴ |

TABLE 1-continued

| Compound number | $L_1$ | $L_2$ | $L_3$ |
|---|---|---|---|
| 3284. | $L^{114}$ | $L^{119}$ | $L^{144}$ |
| 3285. | $L^{114}$ | $L^{130}$ | $L^{144}$ |
| 3286. | $L^{114}$ | $L^{131}$ | $L^{144}$ |
| 3287. | $L^{114}$ | $L^{132}$ | $L^{144}$ |
| 3288. | $L^{114}$ | $L^{133}$ | $L^{144}$ |
| 3289. | $L^{114}$ | $L^{134}$ | $L^{144}$ |
| 3290. | $L^{114}$ | $L^{140}$ | $L^{144}$ |
| 3291. | $L^{114}$ | $L^{141}$ | $L^{144}$ |
| 3292. | $L^{114}$ | $L^{159}$ | $L^{144}$ |
| 3293. | $L^{114}$ | $L^{160}$ | $L^{144}$ |
| 3294. | $L^{114}$ | $L^{115}$ | $L^{145}$ |
| 3295. | $L^{114}$ | $L^{116}$ | $L^{145}$ |
| 3296. | $L^{114}$ | $L^{117}$ | $L^{145}$ |
| 3297. | $L^{114}$ | $L^{118}$ | $L^{145}$ |
| 3298. | $L^{114}$ | $L^{119}$ | $L^{145}$ |
| 3299. | $L^{114}$ | $L^{130}$ | $L^{145}$ |
| 3300. | $L^{114}$ | $L^{131}$ | $L^{145}$ |
| 3301. | $L^{114}$ | $L^{132}$ | $L^{145}$ |
| 3302. | $L^{114}$ | $L^{133}$ | $L^{145}$ |
| 3303. | $L^{114}$ | $L^{134}$ | $L^{145}$ |
| 3304. | $L^{114}$ | $L^{140}$ | $L^{145}$ |
| 3305. | $L^{114}$ | $L^{141}$ | $L^{145}$ |
| 3306. | $L^{114}$ | $L^{159}$ | $L^{145}$ |
| 3307. | $L^{114}$ | $L^{160}$ | $L^{145}$ |
| 3308. | $L^{114}$ | $L^{115}$ | $L^{147}$ |
| 3309. | $L^{114}$ | $L^{116}$ | $L^{147}$ |
| 3310. | $L^{114}$ | $L^{117}$ | $L^{147}$ |
| 3311. | $L^{114}$ | $L^{118}$ | $L^{147}$ |
| 3312. | $L^{114}$ | $L^{119}$ | $L^{147}$ |
| 3313. | $L^{114}$ | $L^{130}$ | $L^{147}$ |
| 3314. | $L^{114}$ | $L^{131}$ | $L^{147}$ |
| 3315. | $L^{114}$ | $L^{132}$ | $L^{147}$ |
| 3316. | $L^{114}$ | $L^{133}$ | $L^{147}$ |
| 3317. | $L^{114}$ | $L^{134}$ | $L^{147}$ |
| 3318. | $L^{114}$ | $L^{140}$ | $L^{147}$ |
| 3319. | $L^{114}$ | $L^{141}$ | $L^{147}$ |
| 3320. | $L^{114}$ | $L^{159}$ | $L^{147}$ |
| 3321. | $L^{114}$ | $L^{160}$ | $L^{147}$ |
| 3322. | $L^{114}$ | $L^{115}$ | $L^{149}$ |
| 3323. | $L^{114}$ | $L^{116}$ | $L^{149}$ |
| 3324. | $L^{114}$ | $L^{117}$ | $L^{149}$ |
| 3325. | $L^{114}$ | $L^{118}$ | $L^{149}$ |
| 3326. | $L^{114}$ | $L^{119}$ | $L^{149}$ |
| 3327. | $L^{114}$ | $L^{130}$ | $L^{149}$ |
| 3328. | $L^{114}$ | $L^{131}$ | $L^{149}$ |
| 3329. | $L^{114}$ | $L^{132}$ | $L^{149}$ |
| 3330. | $L^{114}$ | $L^{133}$ | $L^{149}$ |
| 3331. | $L^{114}$ | $L^{134}$ | $L^{149}$ |
| 3332. | $L^{114}$ | $L^{140}$ | $L^{149}$ |
| 3333. | $L^{114}$ | $L^{141}$ | $L^{149}$ |
| 3334. | $L^{114}$ | $L^{159}$ | $L^{149}$ |
| 3335. | $L^{114}$ | $L^{160}$ | $L^{149}$ |
| 3336. | $L^{114}$ | $L^{115}$ | $L^{152}$ |
| 3337. | $L^{114}$ | $L^{116}$ | $L^{152}$ |
| 3338. | $L^{114}$ | $L^{117}$ | $L^{152}$ |
| 3339. | $L^{114}$ | $L^{118}$ | $L^{152}$ |
| 3340. | $L^{114}$ | $L^{119}$ | $L^{152}$ |
| 3341. | $L^{114}$ | $L^{130}$ | $L^{152}$ |
| 3342. | $L^{114}$ | $L^{131}$ | $L^{152}$ |
| 3343. | $L^{114}$ | $L^{132}$ | $L^{152}$ |
| 3344. | $L^{114}$ | $L^{133}$ | $L^{152}$ |
| 3345. | $L^{114}$ | $L^{134}$ | $L^{152}$ |
| 3346. | $L^{114}$ | $L^{140}$ | $L^{152}$ |
| 3347. | $L^{114}$ | $L^{141}$ | $L^{152}$ |
| 3348. | $L^{114}$ | $L^{159}$ | $L^{152}$ |
| 3349. | $L^{114}$ | $L^{160}$ | $L^{152}$ |
| 3350. | $L^{114}$ | $L^{115}$ | $L^{164}$ |
| 3351. | $L^{114}$ | $L^{116}$ | $L^{164}$ |
| 3352. | $L^{114}$ | $L^{117}$ | $L^{164}$ |
| 3353. | $L^{114}$ | $L^{118}$ | $L^{164}$ |
| 3354. | $L^{114}$ | $L^{119}$ | $L^{164}$ |
| 3355. | $L^{114}$ | $L^{130}$ | $L^{164}$ |
| 3356. | $L^{114}$ | $L^{131}$ | $L^{164}$ |
| 3357. | $L^{114}$ | $L^{132}$ | $L^{164}$ |
| 3358. | $L^{114}$ | $L^{133}$ | $L^{164}$ |
| 3359. | $L^{114}$ | $L^{134}$ | $L^{164}$ |
| 3360. | $L^{114}$ | $L^{140}$ | $L^{164}$ |
| 3361. | $L^{114}$ | $L^{141}$ | $L^{164}$ |
| 3362. | $L^{114}$ | $L^{159}$ | $L^{164}$ |
| 3363. | $L^{114}$ | $L^{160}$ | $L^{164}$ |
| 3364. | $L^{114}$ | $L^{115}$ | $L^{165}$ |
| 3365. | $L^{114}$ | $L^{116}$ | $L^{165}$ |
| 3366. | $L^{114}$ | $L^{117}$ | $L^{165}$ |
| 3367. | $L^{114}$ | $L^{118}$ | $L^{165}$ |
| 3368. | $L^{114}$ | $L^{119}$ | $L^{165}$ |
| 3369. | $L^{114}$ | $L^{130}$ | $L^{165}$ |
| 3370. | $L^{114}$ | $L^{131}$ | $L^{165}$ |
| 3371. | $L^{114}$ | $L^{132}$ | $L^{165}$ |
| 3372. | $L^{114}$ | $L^{133}$ | $L^{165}$ |
| 3373. | $L^{114}$ | $L^{134}$ | $L^{165}$ |
| 3374. | $L^{114}$ | $L^{140}$ | $L^{165}$ |
| 3375. | $L^{114}$ | $L^{141}$ | $L^{165}$ |
| 3376. | $L^{114}$ | $L^{159}$ | $L^{165}$ |
| 3377. | $L^{114}$ | $L^{160}$ | $L^{165}$ |
| 3378. | $L^{114}$ | $L^{115}$ | $L^{166}$ |
| 3379. | $L^{114}$ | $L^{116}$ | $L^{166}$ |
| 3380. | $L^{114}$ | $L^{117}$ | $L^{166}$ |
| 3381. | $L^{114}$ | $L^{118}$ | $L^{166}$ |
| 3382. | $L^{114}$ | $L^{119}$ | $L^{166}$ |
| 3383. | $L^{114}$ | $L^{130}$ | $L^{166}$ |
| 3384. | $L^{114}$ | $L^{131}$ | $L^{166}$ |
| 3385. | $L^{114}$ | $L^{132}$ | $L^{166}$ |
| 3386. | $L^{114}$ | $L^{133}$ | $L^{166}$ |
| 3387. | $L^{114}$ | $L^{134}$ | $L^{166}$ |
| 3388. | $L^{114}$ | $L^{140}$ | $L^{166}$ |
| 3389. | $L^{114}$ | $L^{141}$ | $L^{166}$ |
| 3390. | $L^{114}$ | $L^{159}$ | $L^{166}$ |
| 3391. | $L^{114}$ | $L^{160}$ | $L^{166}$ |
| 3392. | $L^{114}$ | $L^{115}$ | $L^{170}$ |
| 3393. | $L^{114}$ | $L^{116}$ | $L^{170}$ |
| 3394. | $L^{114}$ | $L^{117}$ | $L^{170}$ |
| 3395. | $L^{114}$ | $L^{118}$ | $L^{170}$ |
| 3396. | $L^{114}$ | $L^{119}$ | $L^{170}$ |
| 3397. | $L^{114}$ | $L^{130}$ | $L^{170}$ |
| 3398. | $L^{114}$ | $L^{131}$ | $L^{170}$ |
| 3399. | $L^{114}$ | $L^{132}$ | $L^{170}$ |
| 3400. | $L^{114}$ | $L^{133}$ | $L^{170}$ |
| 3401. | $L^{114}$ | $L^{134}$ | $L^{170}$ |
| 3402. | $L^{114}$ | $L^{140}$ | $L^{170}$ |
| 3403. | $L^{114}$ | $L^{141}$ | $L^{170}$ |
| 3404. | $L^{114}$ | $L^{159}$ | $L^{170}$ |
| 3405. | $L^{114}$ | $L^{160}$ | $L^{170}$ |
| 3406. | $L^{114}$ | $L^{115}$ | $L^{174}$ |
| 3407. | $L^{114}$ | $L^{116}$ | $L^{174}$ |
| 3408. | $L^{114}$ | $L^{117}$ | $L^{174}$ |
| 3409. | $L^{114}$ | $L^{118}$ | $L^{174}$ |
| 3410. | $L^{114}$ | $L^{119}$ | $L^{174}$ |
| 3411. | $L^{114}$ | $L^{130}$ | $L^{174}$ |
| 3412. | $L^{114}$ | $L^{131}$ | $L^{174}$ |
| 3413. | $L^{114}$ | $L^{132}$ | $L^{174}$ |
| 3414. | $L^{114}$ | $L^{133}$ | $L^{174}$ |
| 3415. | $L^{114}$ | $L^{134}$ | $L^{174}$ |
| 3416. | $L^{114}$ | $L^{140}$ | $L^{174}$ |
| 3417. | $L^{114}$ | $L^{141}$ | $L^{174}$ |
| 3418. | $L^{114}$ | $L^{159}$ | $L^{174}$ |
| 3419. | $L^{114}$ | $L^{160}$ | $L^{174}$ |
| 3420. | $L^{114}$ | $L^{115}$ | $L^{176}$ |
| 3421. | $L^{114}$ | $L^{116}$ | $L^{176}$ |
| 3422. | $L^{114}$ | $L^{117}$ | $L^{176}$ |
| 3423. | $L^{114}$ | $L^{118}$ | $L^{176}$ |
| 3424. | $L^{114}$ | $L^{119}$ | $L^{176}$ |
| 3425. | $L^{114}$ | $L^{130}$ | $L^{176}$ |
| 3426. | $L^{114}$ | $L^{131}$ | $L^{176}$ |
| 3427. | $L^{114}$ | $L^{132}$ | $L^{176}$ |
| 3428. | $L^{114}$ | $L^{133}$ | $L^{176}$ |
| 3429. | $L^{114}$ | $L^{134}$ | $L^{176}$ |
| 3430. | $L^{114}$ | $L^{140}$ | $L^{176}$ |
| 3431. | $L^{114}$ | $L^{141}$ | $L^{176}$ |
| 3432. | $L^{114}$ | $L^{159}$ | $L^{176}$ |
| 3433. | $L^{114}$ | $L^{160}$ | $L^{176}$ |
| 3434. | $L^{114}$ | $L^{115}$ | $L^{179}$ |
| 3435. | $L^{114}$ | $L^{116}$ | $L^{179}$ |
| 3436. | $L^{114}$ | $L^{117}$ | $L^{179}$ |
| 3437. | $L^{114}$ | $L^{118}$ | $L^{179}$ |

TABLE 1-continued

| Compound number | L₁ | L₂ | L₃ |
|---|---|---|---|
| 3438. | $L^{114}$ | $L^{119}$ | $L^{179}$ |
| 3439. | $L^{114}$ | $L^{130}$ | $L^{179}$ |
| 3440. | $L^{114}$ | $L^{131}$ | $L^{179}$ |
| 3441. | $L^{114}$ | $L^{132}$ | $L^{179}$ |
| 3442. | $L^{114}$ | $L^{133}$ | $L^{179}$ |
| 3443. | $L^{114}$ | $L^{134}$ | $L^{179}$ |
| 3444. | $L^{114}$ | $L^{140}$ | $L^{179}$ |
| 3445. | $L^{114}$ | $L^{141}$ | $L^{179}$ |
| 3446. | $L^{114}$ | $L^{159}$ | $L^{179}$ |
| 3447. | $L^{114}$ | $L^{160}$ | $L^{179}$ |
| 3448. | $L^{114}$ | $L^{115}$ | $L^{180}$ |
| 3449. | $L^{114}$ | $L^{116}$ | $L^{180}$ |
| 3450. | $L^{114}$ | $L^{117}$ | $L^{180}$ |
| 3451. | $L^{114}$ | $L^{118}$ | $L^{180}$ |
| 3452. | $L^{114}$ | $L^{119}$ | $L^{180}$ |
| 3453. | $L^{114}$ | $L^{130}$ | $L^{180}$ |
| 3454. | $L^{114}$ | $L^{131}$ | $L^{180}$ |
| 3455. | $L^{114}$ | $L^{132}$ | $L^{180}$ |
| 3456. | $L^{114}$ | $L^{133}$ | $L^{180}$ |
| 3457. | $L^{114}$ | $L^{134}$ | $L^{180}$ |
| 3458. | $L^{114}$ | $L^{140}$ | $L^{180}$ |
| 3459. | $L^{114}$ | $L^{141}$ | $L^{180}$ |
| 3460. | $L^{114}$ | $L^{159}$ | $L^{180}$ |
| 3461. | $L^{114}$ | $L^{160}$ | $L^{180}$ |
| 3462. | $L^{115}$ | $L^{116}$ | $L^{144}$ |
| 3463. | $L^{115}$ | $L^{117}$ | $L^{144}$ |
| 3464. | $L^{115}$ | $L^{118}$ | $L^{144}$ |
| 3465. | $L^{115}$ | $L^{119}$ | $L^{144}$ |
| 3466. | $L^{115}$ | $L^{130}$ | $L^{144}$ |
| 3467. | $L^{115}$ | $L^{131}$ | $L^{144}$ |
| 3468. | $L^{115}$ | $L^{132}$ | $L^{144}$ |
| 3469. | $L^{115}$ | $L^{133}$ | $L^{144}$ |
| 3470. | $L^{115}$ | $L^{134}$ | $L^{144}$ |
| 3471. | $L^{115}$ | $L^{140}$ | $L^{144}$ |
| 3472. | $L^{115}$ | $L^{141}$ | $L^{144}$ |
| 3473. | $L^{115}$ | $L^{159}$ | $L^{144}$ |
| 3474. | $L^{115}$ | $L^{160}$ | $L^{144}$ |
| 3475. | $L^{115}$ | $L^{116}$ | $L^{145}$ |
| 3476. | $L^{115}$ | $L^{117}$ | $L^{145}$ |
| 3477. | $L^{115}$ | $L^{118}$ | $L^{145}$ |
| 3478. | $L^{115}$ | $L^{119}$ | $L^{145}$ |
| 3479. | $L^{115}$ | $L^{130}$ | $L^{145}$ |
| 3480. | $L^{115}$ | $L^{131}$ | $L^{145}$ |
| 3481. | $L^{115}$ | $L^{132}$ | $L^{145}$ |
| 3482. | $L^{115}$ | $L^{133}$ | $L^{145}$ |
| 3483. | $L^{115}$ | $L^{134}$ | $L^{145}$ |
| 3484. | $L^{115}$ | $L^{140}$ | $L^{145}$ |
| 3485. | $L^{115}$ | $L^{141}$ | $L^{145}$ |
| 3486. | $L^{115}$ | $L^{159}$ | $L^{145}$ |
| 3487. | $L^{115}$ | $L^{160}$ | $L^{145}$ |
| 3488. | $L^{115}$ | $L^{116}$ | $L^{147}$ |
| 3489. | $L^{115}$ | $L^{117}$ | $L^{147}$ |
| 3490. | $L^{115}$ | $L^{118}$ | $L^{147}$ |
| 3491. | $L^{115}$ | $L^{119}$ | $L^{147}$ |
| 3492. | $L^{115}$ | $L^{130}$ | $L^{147}$ |
| 3493. | $L^{115}$ | $L^{131}$ | $L^{147}$ |
| 3494. | $L^{115}$ | $L^{132}$ | $L^{147}$ |
| 3495. | $L^{115}$ | $L^{133}$ | $L^{147}$ |
| 3496. | $L^{115}$ | $L^{134}$ | $L^{147}$ |
| 3497. | $L^{115}$ | $L^{140}$ | $L^{147}$ |
| 3498. | $L^{115}$ | $L^{141}$ | $L^{147}$ |
| 3499. | $L^{115}$ | $L^{159}$ | $L^{147}$ |
| 3500. | $L^{115}$ | $L^{160}$ | $L^{147}$ |
| 3501. | $L^{115}$ | $L^{116}$ | $L^{149}$ |
| 3502. | $L^{115}$ | $L^{117}$ | $L^{149}$ |
| 3503. | $L^{115}$ | $L^{118}$ | $L^{149}$ |
| 3504. | $L^{115}$ | $L^{119}$ | $L^{149}$ |
| 3505. | $L^{115}$ | $L^{130}$ | $L^{149}$ |
| 3506. | $L^{115}$ | $L^{131}$ | $L^{149}$ |
| 3507. | $L^{115}$ | $L^{132}$ | $L^{149}$ |
| 3508. | $L^{115}$ | $L^{133}$ | $L^{149}$ |
| 3509. | $L^{115}$ | $L^{134}$ | $L^{149}$ |
| 3510. | $L^{115}$ | $L^{140}$ | $L^{149}$ |
| 3511. | $L^{115}$ | $L^{141}$ | $L^{149}$ |
| 3512. | $L^{115}$ | $L^{159}$ | $L^{149}$ |
| 3513. | $L^{115}$ | $L^{160}$ | $L^{149}$ |
| 3514. | $L^{115}$ | $L^{116}$ | $L^{152}$ |
| 3515. | $L^{115}$ | $L^{117}$ | $L^{152}$ |
| 3516. | $L^{115}$ | $L^{118}$ | $L^{152}$ |
| 3517. | $L^{115}$ | $L^{119}$ | $L^{152}$ |
| 3518. | $L^{115}$ | $L^{130}$ | $L^{152}$ |
| 3519. | $L^{115}$ | $L^{131}$ | $L^{152}$ |
| 3520. | $L^{115}$ | $L^{132}$ | $L^{152}$ |
| 3521. | $L^{115}$ | $L^{133}$ | $L^{152}$ |
| 3522. | $L^{115}$ | $L^{134}$ | $L^{152}$ |
| 3523. | $L^{115}$ | $L^{140}$ | $L^{152}$ |
| 3524. | $L^{115}$ | $L^{141}$ | $L^{152}$ |
| 3525. | $L^{115}$ | $L^{159}$ | $L^{152}$ |
| 3526. | $L^{115}$ | $L^{160}$ | $L^{152}$ |
| 3527. | $L^{115}$ | $L^{116}$ | $L^{164}$ |
| 3528. | $L^{115}$ | $L^{117}$ | $L^{164}$ |
| 3529. | $L^{115}$ | $L^{118}$ | $L^{164}$ |
| 3530. | $L^{115}$ | $L^{119}$ | $L^{164}$ |
| 3531. | $L^{115}$ | $L^{130}$ | $L^{164}$ |
| 3532. | $L^{115}$ | $L^{131}$ | $L^{164}$ |
| 3533. | $L^{115}$ | $L^{132}$ | $L^{164}$ |
| 3534. | $L^{115}$ | $L^{133}$ | $L^{164}$ |
| 3535. | $L^{115}$ | $L^{134}$ | $L^{164}$ |
| 3536. | $L^{115}$ | $L^{140}$ | $L^{164}$ |
| 3537. | $L^{115}$ | $L^{141}$ | $L^{164}$ |
| 3538. | $L^{115}$ | $L^{159}$ | $L^{164}$ |
| 3539. | $L^{115}$ | $L^{160}$ | $L^{164}$ |
| 3540. | $L^{115}$ | $L^{116}$ | $L^{165}$ |
| 3541. | $L^{115}$ | $L^{117}$ | $L^{165}$ |
| 3542. | $L^{115}$ | $L^{118}$ | $L^{165}$ |
| 3543. | $L^{115}$ | $L^{119}$ | $L^{165}$ |
| 3544. | $L^{115}$ | $L^{130}$ | $L^{165}$ |
| 3545. | $L^{115}$ | $L^{131}$ | $L^{165}$ |
| 3546. | $L^{115}$ | $L^{132}$ | $L^{165}$ |
| 3547. | $L^{115}$ | $L^{133}$ | $L^{165}$ |
| 3548. | $L^{115}$ | $L^{134}$ | $L^{165}$ |
| 3549. | $L^{115}$ | $L^{140}$ | $L^{165}$ |
| 3550. | $L^{115}$ | $L^{141}$ | $L^{165}$ |
| 3551. | $L^{115}$ | $L^{159}$ | $L^{165}$ |
| 3552. | $L^{115}$ | $L^{160}$ | $L^{165}$ |
| 3553. | $L^{115}$ | $L^{116}$ | $L^{166}$ |
| 3554. | $L^{115}$ | $L^{117}$ | $L^{166}$ |
| 3555. | $L^{115}$ | $L^{118}$ | $L^{166}$ |
| 3556. | $L^{115}$ | $L^{119}$ | $L^{166}$ |
| 3557. | $L^{115}$ | $L^{130}$ | $L^{166}$ |
| 3558. | $L^{115}$ | $L^{131}$ | $L^{166}$ |
| 3559. | $L^{115}$ | $L^{132}$ | $L^{166}$ |
| 3560. | $L^{115}$ | $L^{133}$ | $L^{166}$ |
| 3561. | $L^{115}$ | $L^{134}$ | $L^{166}$ |
| 3562. | $L^{115}$ | $L^{140}$ | $L^{166}$ |
| 3563. | $L^{115}$ | $L^{141}$ | $L^{166}$ |
| 3564. | $L^{115}$ | $L^{159}$ | $L^{166}$ |
| 3565. | $L^{115}$ | $L^{160}$ | $L^{166}$ |
| 3566. | $L^{115}$ | $L^{116}$ | $L^{170}$ |
| 3567. | $L^{115}$ | $L^{117}$ | $L^{170}$ |
| 3568. | $L^{115}$ | $L^{118}$ | $L^{170}$ |
| 3569. | $L^{115}$ | $L^{119}$ | $L^{170}$ |
| 3570. | $L^{115}$ | $L^{130}$ | $L^{170}$ |
| 3571. | $L^{115}$ | $L^{131}$ | $L^{170}$ |
| 3572. | $L^{115}$ | $L^{132}$ | $L^{170}$ |
| 3573. | $L^{115}$ | $L^{133}$ | $L^{170}$ |
| 3574. | $L^{115}$ | $L^{134}$ | $L^{170}$ |
| 3575. | $L^{115}$ | $L^{140}$ | $L^{170}$ |
| 3576. | $L^{115}$ | $L^{141}$ | $L^{170}$ |
| 3577. | $L^{115}$ | $L^{159}$ | $L^{170}$ |
| 3578. | $L^{115}$ | $L^{160}$ | $L^{170}$ |
| 3579. | $L^{115}$ | $L^{116}$ | $L^{174}$ |
| 3580. | $L^{115}$ | $L^{117}$ | $L^{174}$ |
| 3581. | $L^{115}$ | $L^{118}$ | $L^{174}$ |
| 3582. | $L^{115}$ | $L^{119}$ | $L^{174}$ |
| 3583. | $L^{115}$ | $L^{130}$ | $L^{174}$ |
| 3584. | $L^{115}$ | $L^{131}$ | $L^{174}$ |
| 3585. | $L^{115}$ | $L^{132}$ | $L^{174}$ |
| 3586. | $L^{115}$ | $L^{133}$ | $L^{174}$ |
| 3587. | $L^{115}$ | $L^{134}$ | $L^{174}$ |
| 3588. | $L^{115}$ | $L^{140}$ | $L^{174}$ |
| 3589. | $L^{115}$ | $L^{141}$ | $L^{174}$ |
| 3590. | $L^{115}$ | $L^{159}$ | $L^{174}$ |
| 3591. | $L^{115}$ | $L^{160}$ | $L^{174}$ |

TABLE 1-continued

| Compound number | $L_1$ | $L_2$ | $L_3$ |
|---|---|---|---|
| 3592. | $L^{115}$ | $L^{116}$ | $L^{176}$ |
| 3593. | $L^{115}$ | $L^{117}$ | $L^{176}$ |
| 3594. | $L^{115}$ | $L^{118}$ | $L^{176}$ |
| 3595. | $L^{115}$ | $L^{119}$ | $L^{176}$ |
| 3596. | $L^{115}$ | $L^{130}$ | $L^{176}$ |
| 3597. | $L^{115}$ | $L^{131}$ | $L^{176}$ |
| 3598. | $L^{115}$ | $L^{132}$ | $L^{176}$ |
| 3599. | $L^{115}$ | $L^{133}$ | $L^{176}$ |
| 3600. | $L^{115}$ | $L^{134}$ | $L^{176}$ |
| 3601. | $L^{115}$ | $L^{140}$ | $L^{176}$ |
| 3602. | $L^{115}$ | $L^{141}$ | $L^{176}$ |
| 3603. | $L^{115}$ | $L^{159}$ | $L^{176}$ |
| 3604. | $L^{115}$ | $L^{160}$ | $L^{176}$ |
| 3605. | $L^{115}$ | $L^{116}$ | $L^{179}$ |
| 3606. | $L^{115}$ | $L^{117}$ | $L^{179}$ |
| 3607. | $L^{115}$ | $L^{118}$ | $L^{179}$ |
| 3608. | $L^{115}$ | $L^{119}$ | $L^{179}$ |
| 3609. | $L^{115}$ | $L^{130}$ | $L^{179}$ |
| 3610. | $L^{115}$ | $L^{131}$ | $L^{179}$ |
| 3611. | $L^{115}$ | $L^{132}$ | $L^{179}$ |
| 3612. | $L^{115}$ | $L^{133}$ | $L^{179}$ |
| 3613. | $L^{115}$ | $L^{134}$ | $L^{179}$ |
| 3614. | $L^{115}$ | $L^{140}$ | $L^{179}$ |
| 3615. | $L^{115}$ | $L^{141}$ | $L^{179}$ |
| 3616. | $L^{115}$ | $L^{159}$ | $L^{179}$ |
| 3617. | $L^{115}$ | $L^{160}$ | $L^{179}$ |
| 3618. | $L^{115}$ | $L^{116}$ | $L^{180}$ |
| 3619. | $L^{115}$ | $L^{117}$ | $L^{180}$ |
| 3620. | $L^{115}$ | $L^{118}$ | $L^{180}$ |
| 3621. | $L^{115}$ | $L^{119}$ | $L^{180}$ |
| 3622. | $L^{115}$ | $L^{130}$ | $L^{180}$ |
| 3623. | $L^{115}$ | $L^{131}$ | $L^{180}$ |
| 3624. | $L^{115}$ | $L^{132}$ | $L^{180}$ |
| 3625. | $L^{115}$ | $L^{133}$ | $L^{180}$ |
| 3626. | $L^{115}$ | $L^{134}$ | $L^{180}$ |
| 3627. | $L^{115}$ | $L^{140}$ | $L^{180}$ |
| 3628. | $L^{115}$ | $L^{141}$ | $L^{180}$ |
| 3629. | $L^{115}$ | $L^{159}$ | $L^{180}$ |
| 3630. | $L^{115}$ | $L^{160}$ | $L^{180}$ |
| 3631. | $L^{116}$ | $L^{117}$ | $L^{144}$ |
| 3632. | $L^{116}$ | $L^{118}$ | $L^{144}$ |
| 3633. | $L^{116}$ | $L^{119}$ | $L^{144}$ |
| 3634. | $L^{116}$ | $L^{130}$ | $L^{144}$ |
| 3635. | $L^{115}$ | $L^{131}$ | $L^{144}$ |
| 3636. | $L^{116}$ | $L^{132}$ | $L^{144}$ |
| 3637. | $L^{116}$ | $L^{133}$ | $L^{144}$ |
| 3638. | $L^{116}$ | $L^{134}$ | $L^{144}$ |
| 3639. | $L^{116}$ | $L^{140}$ | $L^{144}$ |
| 3640. | $L^{116}$ | $L^{141}$ | $L^{144}$ |
| 3641. | $L^{116}$ | $L^{159}$ | $L^{144}$ |
| 3642. | $L^{116}$ | $L^{160}$ | $L^{144}$ |
| 3643. | $L^{116}$ | $L^{117}$ | $L^{145}$ |
| 3644. | $L^{116}$ | $L^{118}$ | $L^{145}$ |
| 3645. | $L^{116}$ | $L^{119}$ | $L^{145}$ |
| 3646. | $L^{116}$ | $L^{130}$ | $L^{145}$ |
| 3647. | $L^{116}$ | $L^{131}$ | $L^{145}$ |
| 3648. | $L^{116}$ | $L^{132}$ | $L^{145}$ |
| 3649. | $L^{116}$ | $L^{133}$ | $L^{145}$ |
| 3650. | $L^{116}$ | $L^{134}$ | $L^{145}$ |
| 3651. | $L^{116}$ | $L^{140}$ | $L^{145}$ |
| 3652. | $L^{116}$ | $L^{141}$ | $L^{145}$ |
| 3653. | $L^{116}$ | $L^{159}$ | $L^{145}$ |
| 3654. | $L^{116}$ | $L^{160}$ | $L^{145}$ |
| 3655. | $L^{116}$ | $L^{117}$ | $L^{147}$ |
| 3656. | $L^{116}$ | $L^{118}$ | $L^{147}$ |
| 3657. | $L^{116}$ | $L^{119}$ | $L^{147}$ |
| 3658. | $L^{116}$ | $L^{130}$ | $L^{147}$ |
| 3659. | $L^{116}$ | $L^{131}$ | $L^{147}$ |
| 3660. | $L^{116}$ | $L^{132}$ | $L^{147}$ |
| 3661. | $L^{116}$ | $L^{133}$ | $L^{147}$ |
| 3662. | $L^{116}$ | $L^{134}$ | $L^{147}$ |
| 3663. | $L^{116}$ | $L^{140}$ | $L^{147}$ |
| 3664. | $L^{116}$ | $L^{141}$ | $L^{147}$ |
| 3665. | $L^{116}$ | $L^{159}$ | $L^{147}$ |
| 3666. | $L^{116}$ | $L^{160}$ | $L^{147}$ |
| 3667. | $L^{116}$ | $L^{117}$ | $L^{149}$ |
| 3668. | $L^{116}$ | $L^{118}$ | $L^{149}$ |
| 3669. | $L^{116}$ | $L^{119}$ | $L^{149}$ |
| 3670. | $L^{116}$ | $L^{130}$ | $L^{149}$ |
| 3671. | $L^{116}$ | $L^{131}$ | $L^{149}$ |
| 3672. | $L^{116}$ | $L^{132}$ | $L^{149}$ |
| 3673. | $L^{116}$ | $L^{133}$ | $L^{149}$ |
| 3674. | $L^{116}$ | $L^{134}$ | $L^{149}$ |
| 3675. | $L^{116}$ | $L^{140}$ | $L^{149}$ |
| 3676. | $L^{116}$ | $L^{141}$ | $L^{149}$ |
| 3677. | $L^{116}$ | $L^{159}$ | $L^{149}$ |
| 3678. | $L^{116}$ | $L^{160}$ | $L^{149}$ |
| 3679. | $L^{116}$ | $L^{117}$ | $L^{152}$ |
| 3680. | $L^{116}$ | $L^{118}$ | $L^{152}$ |
| 3681. | $L^{116}$ | $L^{119}$ | $L^{152}$ |
| 3682. | $L^{116}$ | $L^{130}$ | $L^{152}$ |
| 3683. | $L^{116}$ | $L^{131}$ | $L^{152}$ |
| 3684. | $L^{116}$ | $L^{132}$ | $L^{152}$ |
| 3685. | $L^{116}$ | $L^{133}$ | $L^{152}$ |
| 3686. | $L^{116}$ | $L^{134}$ | $L^{152}$ |
| 3687. | $L^{116}$ | $L^{140}$ | $L^{152}$ |
| 3688. | $L^{116}$ | $L^{141}$ | $L^{152}$ |
| 3689. | $L^{116}$ | $L^{159}$ | $L^{152}$ |
| 3690. | $L^{116}$ | $L^{160}$ | $L^{152}$ |
| 3691. | $L^{116}$ | $L^{117}$ | $L^{164}$ |
| 3692. | $L^{116}$ | $L^{118}$ | $L^{164}$ |
| 3693. | $L^{116}$ | $L^{119}$ | $L^{164}$ |
| 3694. | $L^{116}$ | $L^{130}$ | $L^{164}$ |
| 3695. | $L^{116}$ | $L^{131}$ | $L^{164}$ |
| 3696. | $L^{116}$ | $L^{132}$ | $L^{164}$ |
| 3697. | $L^{116}$ | $L^{133}$ | $L^{164}$ |
| 3698. | $L^{116}$ | $L^{134}$ | $L^{164}$ |
| 3699. | $L^{116}$ | $L^{140}$ | $L^{164}$ |
| 3700. | $L^{116}$ | $L^{141}$ | $L^{164}$ |
| 3701. | $L^{116}$ | $L^{159}$ | $L^{164}$ |
| 3702. | $L^{116}$ | $L^{160}$ | $L^{164}$ |
| 3703. | $L^{116}$ | $L^{117}$ | $L^{165}$ |
| 3704. | $L^{116}$ | $L^{118}$ | $L^{165}$ |
| 3705. | $L^{116}$ | $L^{119}$ | $L^{164}$ |
| 3706. | $L^{116}$ | $L^{130}$ | $L^{164}$ |
| 3707. | $L^{116}$ | $L^{131}$ | $L^{165}$ |
| 3708. | $L^{116}$ | $L^{132}$ | $L^{165}$ |
| 3709. | $L^{116}$ | $L^{133}$ | $L^{165}$ |
| 3710. | $L^{116}$ | $L^{134}$ | $L^{165}$ |
| 3711. | $L^{116}$ | $L^{140}$ | $L^{165}$ |
| 3712. | $L^{116}$ | $L^{141}$ | $L^{165}$ |
| 3713. | $L^{116}$ | $L^{159}$ | $L^{165}$ |
| 3714. | $L^{116}$ | $L^{160}$ | $L^{165}$ |
| 3715. | $L^{116}$ | $L^{117}$ | $L^{166}$ |
| 3716. | $L^{116}$ | $L^{118}$ | $L^{166}$ |
| 3717. | $L^{116}$ | $L^{119}$ | $L^{166}$ |
| 3718. | $L^{116}$ | $L^{130}$ | $L^{166}$ |
| 3719. | $L^{116}$ | $L^{131}$ | $L^{166}$ |
| 3720. | $L^{116}$ | $L^{132}$ | $L^{166}$ |
| 3721. | $L^{116}$ | $L^{133}$ | $L^{166}$ |
| 3722. | $L^{116}$ | $L^{134}$ | $L^{166}$ |
| 3723. | $L^{116}$ | $L^{140}$ | $L^{166}$ |
| 3724. | $L^{116}$ | $L^{141}$ | $L^{166}$ |
| 3725. | $L^{116}$ | $L^{159}$ | $L^{166}$ |
| 3726. | $L^{116}$ | $L^{160}$ | $L^{166}$ |
| 3727. | $L^{116}$ | $L^{117}$ | $L^{170}$ |
| 3728. | $L^{116}$ | $L^{118}$ | $L^{170}$ |
| 3729. | $L^{116}$ | $L^{119}$ | $L^{170}$ |
| 3730. | $L^{116}$ | $L^{130}$ | $L^{170}$ |
| 3731. | $L^{116}$ | $L^{131}$ | $L^{170}$ |
| 3732. | $L^{116}$ | $L^{132}$ | $L^{170}$ |
| 3733. | $L^{116}$ | $L^{133}$ | $L^{170}$ |
| 3734. | $L^{116}$ | $L^{134}$ | $L^{170}$ |
| 3735. | $L^{116}$ | $L^{140}$ | $L^{170}$ |
| 3736. | $L^{116}$ | $L^{141}$ | $L^{170}$ |
| 3737. | $L^{116}$ | $L^{159}$ | $L^{170}$ |
| 3738. | $L^{116}$ | $L^{160}$ | $L^{170}$ |
| 3739. | $L^{116}$ | $L^{117}$ | $L^{174}$ |
| 3740. | $L^{116}$ | $L^{118}$ | $L^{174}$ |
| 3741. | $L^{116}$ | $L^{119}$ | $L^{174}$ |
| 3742. | $L^{116}$ | $L^{130}$ | $L^{174}$ |
| 3743. | $L^{116}$ | $L^{131}$ | $L^{174}$ |
| 3744. | $L^{116}$ | $L^{132}$ | $L^{174}$ |
| 3745. | $L^{116}$ | $L^{133}$ | $L^{174}$ |

TABLE 1-continued

| Compound number | $L_1$ | $L_2$ | $L_3$ |
|---|---|---|---|
| 3746. | $L^{116}$ | $L^{134}$ | $L^{174}$ |
| 3747. | $L^{116}$ | $L^{140}$ | $L^{174}$ |
| 3748. | $L^{116}$ | $L^{141}$ | $L^{174}$ |
| 3749. | $L^{116}$ | $L^{159}$ | $L^{174}$ |
| 3750. | $L^{116}$ | $L^{160}$ | $L^{174}$ |
| 3751. | $L^{116}$ | $L^{117}$ | $L^{176}$ |
| 3752. | $L^{116}$ | $L^{118}$ | $L^{176}$ |
| 3753. | $L^{116}$ | $L^{119}$ | $L^{176}$ |
| 3754. | $L^{116}$ | $L^{130}$ | $L^{176}$ |
| 3755. | $L^{116}$ | $L^{131}$ | $L^{176}$ |
| 3756. | $L^{116}$ | $L^{132}$ | $L^{176}$ |
| 3757. | $L^{116}$ | $L^{133}$ | $L^{176}$ |
| 3758. | $L^{116}$ | $L^{134}$ | $L^{176}$ |
| 3759. | $L^{116}$ | $L^{140}$ | $L^{176}$ |
| 3760. | $L^{116}$ | $L^{141}$ | $L^{176}$ |
| 3761. | $L^{116}$ | $L^{159}$ | $L^{176}$ |
| 3762. | $L^{116}$ | $L^{160}$ | $L^{176}$ |
| 3763. | $L^{116}$ | $L^{117}$ | $L^{179}$ |
| 3764. | $L^{116}$ | $L^{118}$ | $L^{179}$ |
| 3765. | $L^{116}$ | $L^{119}$ | $L^{179}$ |
| 3766. | $L^{116}$ | $L^{130}$ | $L^{179}$ |
| 3767. | $L^{116}$ | $L^{131}$ | $L^{179}$ |
| 3768. | $L^{116}$ | $L^{132}$ | $L^{179}$ |
| 3769. | $L^{116}$ | $L^{133}$ | $L^{179}$ |
| 3770. | $L^{116}$ | $L^{134}$ | $L^{179}$ |
| 3771. | $L^{116}$ | $L^{140}$ | $L^{179}$ |
| 3772. | $L^{116}$ | $L^{141}$ | $L^{179}$ |
| 3773. | $L^{116}$ | $L^{159}$ | $L^{179}$ |
| 3774. | $L^{116}$ | $L^{160}$ | $L^{179}$ |
| 3775. | $L^{116}$ | $L^{117}$ | $L^{180}$ |
| 3776. | $L^{116}$ | $L^{118}$ | $L^{180}$ |
| 3777. | $L^{116}$ | $L^{119}$ | $L^{180}$ |
| 3778. | $L^{116}$ | $L^{130}$ | $L^{180}$ |
| 3779. | $L^{116}$ | $L^{131}$ | $L^{180}$ |
| 3780. | $L^{116}$ | $L^{132}$ | $L^{180}$ |
| 3781. | $L^{116}$ | $L^{133}$ | $L^{180}$ |
| 3782. | $L^{116}$ | $L^{134}$ | $L^{180}$ |
| 3783. | $L^{116}$ | $L^{140}$ | $L^{180}$ |
| 3784. | $L^{116}$ | $L^{141}$ | $L^{180}$ |
| 3785. | $L^{116}$ | $L^{159}$ | $L^{180}$ |
| 3786. | $L^{116}$ | $L^{160}$ | $L^{180}$ |
| 3787. | $L^{116}$ | $L^{118}$ | $L^{144}$ |
| 3788. | $L^{116}$ | $L^{119}$ | $L^{144}$ |
| 3789. | $L^{116}$ | $L^{130}$ | $L^{144}$ |
| 3790. | $L^{117}$ | $L^{131}$ | $L^{144}$ |
| 3791. | $L^{117}$ | $L^{132}$ | $L^{144}$ |
| 3792. | $L^{117}$ | $L^{133}$ | $L^{144}$ |
| 3793. | $L^{117}$ | $L^{134}$ | $L^{144}$ |
| 3794. | $L^{117}$ | $L^{140}$ | $L^{144}$ |
| 3795. | $L^{117}$ | $L^{141}$ | $L^{144}$ |
| 3796. | $L^{117}$ | $L^{159}$ | $L^{144}$ |
| 3797. | $L^{117}$ | $L^{160}$ | $L^{144}$ |
| 3798. | $L^{117}$ | $L^{118}$ | $L^{145}$ |
| 3799. | $L^{117}$ | $L^{119}$ | $L^{145}$ |
| 3800. | $L^{117}$ | $L^{130}$ | $L^{145}$ |
| 3801. | $L^{117}$ | $L^{131}$ | $L^{145}$ |
| 3802. | $L^{117}$ | $L^{132}$ | $L^{145}$ |
| 3803. | $L^{117}$ | $L^{133}$ | $L^{145}$ |
| 3804. | $L^{117}$ | $L^{134}$ | $L^{145}$ |
| 3805. | $L^{117}$ | $L^{140}$ | $L^{145}$ |
| 3806. | $L^{117}$ | $L^{141}$ | $L^{145}$ |
| 3807. | $L^{117}$ | $L^{159}$ | $L^{145}$ |
| 3808. | $L^{117}$ | $L^{160}$ | $L^{145}$ |
| 3809. | $L^{117}$ | $L^{118}$ | $L^{147}$ |
| 3810. | $L^{117}$ | $L^{119}$ | $L^{147}$ |
| 3811. | $L^{117}$ | $L^{130}$ | $L^{147}$ |
| 3812. | $L^{117}$ | $L^{131}$ | $L^{147}$ |
| 3813. | $L^{117}$ | $L^{132}$ | $L^{147}$ |
| 3814. | $L^{117}$ | $L^{133}$ | $L^{147}$ |
| 3815. | $L^{117}$ | $L^{134}$ | $L^{147}$ |
| 3816. | $L^{117}$ | $L^{140}$ | $L^{147}$ |
| 3817. | $L^{117}$ | $L^{141}$ | $L^{147}$ |
| 3818. | $L^{117}$ | $L^{159}$ | $L^{147}$ |
| 3819. | $L^{117}$ | $L^{160}$ | $L^{147}$ |
| 3820. | $L^{117}$ | $L^{118}$ | $L^{149}$ |
| 3821. | $L^{117}$ | $L^{119}$ | $L^{149}$ |
| 3822. | $L^{117}$ | $L^{130}$ | $L^{149}$ |
| 3823. | $L^{117}$ | $L^{131}$ | $L^{149}$ |
| 3824. | $L^{117}$ | $L^{132}$ | $L^{149}$ |
| 3825. | $L^{117}$ | $L^{133}$ | $L^{149}$ |
| 3826. | $L^{117}$ | $L^{134}$ | $L^{149}$ |
| 3827. | $L^{117}$ | $L^{140}$ | $L^{149}$ |
| 3828. | $L^{117}$ | $L^{141}$ | $L^{149}$ |
| 3829. | $L^{117}$ | $L^{159}$ | $L^{149}$ |
| 3830. | $L^{117}$ | $L^{160}$ | $L^{149}$ |
| 3831. | $L^{117}$ | $L^{118}$ | $L^{152}$ |
| 3832. | $L^{117}$ | $L^{119}$ | $L^{152}$ |
| 3833. | $L^{117}$ | $L^{130}$ | $L^{152}$ |
| 3834. | $L^{117}$ | $L^{131}$ | $L^{152}$ |
| 3835. | $L^{117}$ | $L^{132}$ | $L^{152}$ |
| 3836. | $L^{117}$ | $L^{133}$ | $L^{152}$ |
| 3837. | $L^{117}$ | $L^{134}$ | $L^{152}$ |
| 3838. | $L^{117}$ | $L^{140}$ | $L^{152}$ |
| 3839. | $L^{117}$ | $L^{141}$ | $L^{152}$ |
| 3840. | $L^{117}$ | $L^{159}$ | $L^{152}$ |
| 3841. | $L^{117}$ | $L^{160}$ | $L^{152}$ |
| 3842. | $L^{117}$ | $L^{118}$ | $L^{164}$ |
| 3843. | $L^{117}$ | $L^{119}$ | $L^{164}$ |
| 3844. | $L^{117}$ | $L^{130}$ | $L^{164}$ |
| 3845. | $L^{117}$ | $L^{131}$ | $L^{164}$ |
| 3846. | $L^{117}$ | $L^{132}$ | $L^{164}$ |
| 3847. | $L^{117}$ | $L^{133}$ | $L^{164}$ |
| 3848. | $L^{117}$ | $L^{134}$ | $L^{164}$ |
| 3849. | $L^{117}$ | $L^{140}$ | $L^{164}$ |
| 3850. | $L^{117}$ | $L^{141}$ | $L^{164}$ |
| 3851. | $L^{117}$ | $L^{159}$ | $L^{164}$ |
| 3852. | $L^{117}$ | $L^{160}$ | $L^{164}$ |
| 3853. | $L^{117}$ | $L^{118}$ | $L^{165}$ |
| 3854. | $L^{117}$ | $L^{119}$ | $L^{165}$ |
| 3855. | $L^{117}$ | $L^{130}$ | $L^{165}$ |
| 3856. | $L^{117}$ | $L^{131}$ | $L^{165}$ |
| 3857. | $L^{117}$ | $L^{132}$ | $L^{165}$ |
| 3858. | $L^{117}$ | $L^{133}$ | $L^{165}$ |
| 3859. | $L^{117}$ | $L^{134}$ | $L^{165}$ |
| 3860. | $L^{117}$ | $L^{140}$ | $L^{165}$ |
| 3861. | $L^{117}$ | $L^{141}$ | $L^{165}$ |
| 3862. | $L^{117}$ | $L^{159}$ | $L^{165}$ |
| 3863. | $L^{117}$ | $L^{160}$ | $L^{165}$ |
| 3864. | $L^{117}$ | $L^{118}$ | $L^{166}$ |
| 3865. | $L^{117}$ | $L^{119}$ | $L^{166}$ |
| 3866. | $L^{117}$ | $L^{130}$ | $L^{166}$ |
| 3867. | $L^{117}$ | $L^{131}$ | $L^{166}$ |
| 3868. | $L^{117}$ | $L^{132}$ | $L^{166}$ |
| 3869. | $L^{117}$ | $L^{133}$ | $L^{166}$ |
| 3870. | $L^{117}$ | $L^{134}$ | $L^{166}$ |
| 3871. | $L^{117}$ | $L^{140}$ | $L^{166}$ |
| 3872. | $L^{117}$ | $L^{141}$ | $L^{166}$ |
| 3873. | $L^{117}$ | $L^{159}$ | $L^{166}$ |
| 3874. | $L^{117}$ | $L^{160}$ | $L^{166}$ |
| 3875. | $L^{117}$ | $L^{118}$ | $L^{170}$ |
| 3876. | $L^{117}$ | $L^{119}$ | $L^{170}$ |
| 3877. | $L^{117}$ | $L^{130}$ | $L^{170}$ |
| 3878. | $L^{117}$ | $L^{131}$ | $L^{170}$ |
| 3879. | $L^{117}$ | $L^{132}$ | $L^{170}$ |
| 3880. | $L^{117}$ | $L^{133}$ | $L^{170}$ |
| 3881. | $L^{117}$ | $L^{134}$ | $L^{170}$ |
| 3882. | $L^{117}$ | $L^{140}$ | $L^{170}$ |
| 3883. | $L^{117}$ | $L^{141}$ | $L^{170}$ |
| 3884. | $L^{117}$ | $L^{159}$ | $L^{170}$ |
| 3885. | $L^{117}$ | $L^{160}$ | $L^{170}$ |
| 3886. | $L^{117}$ | $L^{118}$ | $L^{174}$ |
| 3887. | $L^{117}$ | $L^{119}$ | $L^{174}$ |
| 3888. | $L^{117}$ | $L^{130}$ | $L^{174}$ |
| 3889. | $L^{117}$ | $L^{131}$ | $L^{174}$ |
| 3890. | $L^{117}$ | $L^{132}$ | $L^{174}$ |
| 3891. | $L^{117}$ | $L^{133}$ | $L^{174}$ |
| 3892. | $L^{117}$ | $L^{134}$ | $L^{174}$ |
| 3893. | $L^{117}$ | $L^{140}$ | $L^{174}$ |
| 3894. | $L^{117}$ | $L^{141}$ | $L^{174}$ |
| 3895. | $L^{117}$ | $L^{159}$ | $L^{174}$ |
| 3896. | $L^{117}$ | $L^{160}$ | $L^{174}$ |
| 3897. | $L^{117}$ | $L^{118}$ | $L^{176}$ |
| 3898. | $L^{117}$ | $L^{119}$ | $L^{176}$ |
| 3899. | $L^{117}$ | $L^{130}$ | $L^{176}$ |

TABLE 1-continued

| Compound number | $L_1$ | $L_2$ | $L_3$ |
|---|---|---|---|
| 3900. | $L^{117}$ | $L^{131}$ | $L^{176}$ |
| 3901. | $L^{117}$ | $L^{132}$ | $L^{176}$ |
| 3902. | $L^{117}$ | $L^{133}$ | $L^{176}$ |
| 3903. | $L^{117}$ | $L^{134}$ | $L^{176}$ |
| 3904. | $L^{117}$ | $L^{140}$ | $L^{176}$ |
| 3905. | $L^{117}$ | $L^{141}$ | $L^{176}$ |
| 3906. | $L^{117}$ | $L^{159}$ | $L^{176}$ |
| 3907. | $L^{117}$ | $L^{160}$ | $L^{176}$ |
| 3908. | $L^{117}$ | $L^{118}$ | $L^{179}$ |
| 3909. | $L^{117}$ | $L^{119}$ | $L^{179}$ |
| 3910. | $L^{117}$ | $L^{130}$ | $L^{179}$ |
| 3911. | $L^{117}$ | $L^{131}$ | $L^{179}$ |
| 3912. | $L^{117}$ | $L^{132}$ | $L^{179}$ |
| 3913. | $L^{117}$ | $L^{133}$ | $L^{179}$ |
| 3914. | $L^{117}$ | $L^{134}$ | $L^{179}$ |
| 3915. | $L^{117}$ | $L^{140}$ | $L^{179}$ |
| 3916. | $L^{117}$ | $L^{141}$ | $L^{179}$ |
| 3917. | $L^{117}$ | $L^{159}$ | $L^{179}$ |
| 3918. | $L^{117}$ | $L^{160}$ | $L^{179}$ |
| 3919. | $L^{117}$ | $L^{118}$ | $L^{180}$ |
| 3920. | $L^{117}$ | $L^{119}$ | $L^{180}$ |
| 3921. | $L^{117}$ | $L^{130}$ | $L^{180}$ |
| 3922. | $L^{117}$ | $L^{131}$ | $L^{180}$ |
| 3923. | $L^{117}$ | $L^{132}$ | $L^{180}$ |
| 3924. | $L^{117}$ | $L^{133}$ | $L^{180}$ |
| 3925. | $L^{117}$ | $L^{134}$ | $L^{180}$ |
| 3926. | $L^{117}$ | $L^{140}$ | $L^{180}$ |
| 3927. | $L^{117}$ | $L^{141}$ | $L^{180}$ |
| 3928. | $L^{117}$ | $L^{159}$ | $L^{180}$ |
| 3929. | $L^{117}$ | $L^{160}$ | $L^{180}$ |
| 3930. | $L^{118}$ | $L^{119}$ | $L^{144}$ |
| 3931. | $L^{118}$ | $L^{130}$ | $L^{144}$ |
| 3932. | $L^{118}$ | $L^{131}$ | $L^{144}$ |
| 3933. | $L^{118}$ | $L^{132}$ | $L^{144}$ |
| 3934. | $L^{118}$ | $L^{133}$ | $L^{144}$ |
| 3935. | $L^{118}$ | $L^{134}$ | $L^{144}$ |
| 3936. | $L^{118}$ | $L^{140}$ | $L^{144}$ |
| 3937. | $L^{118}$ | $L^{141}$ | $L^{144}$ |
| 3938. | $L^{118}$ | $L^{159}$ | $L^{144}$ |
| 3939. | $L^{118}$ | $L^{160}$ | $L^{144}$ |
| 3940. | $L^{118}$ | $L^{119}$ | $L^{145}$ |
| 3941. | $L^{118}$ | $L^{130}$ | $L^{145}$ |
| 3942. | $L^{118}$ | $L^{131}$ | $L^{145}$ |
| 3943. | $L^{118}$ | $L^{132}$ | $L^{145}$ |
| 3944. | $L^{118}$ | $L^{133}$ | $L^{145}$ |
| 3945. | $L^{118}$ | $L^{134}$ | $L^{145}$ |
| 3946. | $L^{118}$ | $L^{140}$ | $L^{145}$ |
| 3947. | $L^{118}$ | $L^{141}$ | $L^{145}$ |
| 3948. | $L^{118}$ | $L^{159}$ | $L^{145}$ |
| 3949. | $L^{118}$ | $L^{160}$ | $L^{145}$ |
| 3950. | $L^{118}$ | $L^{119}$ | $L^{147}$ |
| 3951. | $L^{118}$ | $L^{130}$ | $L^{147}$ |
| 3952. | $L^{118}$ | $L^{131}$ | $L^{147}$ |
| 3953. | $L^{118}$ | $L^{132}$ | $L^{147}$ |
| 3954. | $L^{118}$ | $L^{133}$ | $L^{147}$ |
| 3955. | $L^{118}$ | $L^{134}$ | $L^{147}$ |
| 3956. | $L^{118}$ | $L^{140}$ | $L^{147}$ |
| 3957. | $L^{118}$ | $L^{141}$ | $L^{147}$ |
| 3958. | $L^{118}$ | $L^{159}$ | $L^{147}$ |
| 3959. | $L^{118}$ | $L^{160}$ | $L^{147}$ |
| 3960. | $L^{118}$ | $L^{119}$ | $L^{149}$ |
| 3961. | $L^{118}$ | $L^{130}$ | $L^{149}$ |
| 3962. | $L^{118}$ | $L^{131}$ | $L^{149}$ |
| 3963. | $L^{118}$ | $L^{132}$ | $L^{149}$ |
| 3964. | $L^{118}$ | $L^{133}$ | $L^{149}$ |
| 3965. | $L^{118}$ | $L^{134}$ | $L^{149}$ |
| 3966. | $L^{118}$ | $L^{140}$ | $L^{149}$ |
| 3967. | $L^{118}$ | $L^{141}$ | $L^{149}$ |
| 3968. | $L^{118}$ | $L^{159}$ | $L^{149}$ |
| 3969. | $L^{118}$ | $L^{160}$ | $L^{149}$ |
| 3970. | $L^{118}$ | $L^{119}$ | $L^{152}$ |
| 3971. | $L^{118}$ | $L^{130}$ | $L^{152}$ |
| 3972. | $L^{118}$ | $L^{131}$ | $L^{152}$ |
| 3973. | $L^{118}$ | $L^{132}$ | $L^{152}$ |
| 3974. | $L^{118}$ | $L^{133}$ | $L^{152}$ |
| 3975. | $L^{118}$ | $L^{134}$ | $L^{152}$ |
| 3976. | $L^{118}$ | $L^{140}$ | $L^{152}$ |
| 3977. | $L^{118}$ | $L^{141}$ | $L^{152}$ |
| 3978. | $L^{118}$ | $L^{159}$ | $L^{152}$ |
| 3979. | $L^{118}$ | $L^{160}$ | $L^{152}$ |
| 3980. | $L^{118}$ | $L^{119}$ | $L^{164}$ |
| 3981. | $L^{118}$ | $L^{130}$ | $L^{164}$ |
| 3982. | $L^{118}$ | $L^{131}$ | $L^{164}$ |
| 3983. | $L^{118}$ | $L^{132}$ | $L^{164}$ |
| 3984. | $L^{118}$ | $L^{133}$ | $L^{164}$ |
| 3985. | $L^{118}$ | $L^{134}$ | $L^{164}$ |
| 3986. | $L^{118}$ | $L^{140}$ | $L^{164}$ |
| 3987. | $L^{118}$ | $L^{141}$ | $L^{164}$ |
| 3988. | $L^{118}$ | $L^{159}$ | $L^{164}$ |
| 3989. | $L^{118}$ | $L^{160}$ | $L^{164}$ |
| 3990. | $L^{118}$ | $L^{119}$ | $L^{165}$ |
| 3991. | $L^{118}$ | $L^{130}$ | $L^{165}$ |
| 3992. | $L^{118}$ | $L^{131}$ | $L^{165}$ |
| 3993. | $L^{118}$ | $L^{132}$ | $L^{165}$ |
| 3994. | $L^{118}$ | $L^{133}$ | $L^{165}$ |
| 3995. | $L^{118}$ | $L^{134}$ | $L^{165}$ |
| 3996. | $L^{118}$ | $L^{140}$ | $L^{165}$ |
| 3997. | $L^{118}$ | $L^{141}$ | $L^{165}$ |
| 3998. | $L^{118}$ | $L^{159}$ | $L^{165}$ |
| 3999. | $L^{118}$ | $L^{160}$ | $L^{165}$ |
| 4000. | $L^{118}$ | $L^{119}$ | $L^{166}$ |
| 4001. | $L^{118}$ | $L^{130}$ | $L^{166}$ |
| 4002. | $L^{118}$ | $L^{131}$ | $L^{166}$ |
| 4003. | $L^{118}$ | $L^{132}$ | $L^{166}$ |
| 4004. | $L^{118}$ | $L^{133}$ | $L^{166}$ |
| 4005. | $L^{118}$ | $L^{134}$ | $L^{166}$ |
| 4006. | $L^{118}$ | $L^{140}$ | $L^{166}$ |
| 4007. | $L^{118}$ | $L^{141}$ | $L^{166}$ |
| 4008. | $L^{118}$ | $L^{159}$ | $L^{166}$ |
| 4009. | $L^{118}$ | $L^{160}$ | $L^{166}$ |
| 4010. | $L^{118}$ | $L^{119}$ | $L^{170}$ |
| 4011. | $L^{118}$ | $L^{130}$ | $L^{170}$ |
| 4012. | $L^{118}$ | $L^{131}$ | $L^{170}$ |
| 4013. | $L^{118}$ | $L^{132}$ | $L^{170}$ |
| 4014. | $L^{118}$ | $L^{133}$ | $L^{170}$ |
| 4015. | $L^{118}$ | $L^{134}$ | $L^{170}$ |
| 4016. | $L^{118}$ | $L^{140}$ | $L^{170}$ |
| 4017. | $L^{118}$ | $L^{141}$ | $L^{170}$ |
| 4018. | $L^{118}$ | $L^{159}$ | $L^{170}$ |
| 4019. | $L^{118}$ | $L^{160}$ | $L^{170}$ |
| 4020. | $L^{118}$ | $L^{119}$ | $L^{174}$ |
| 4021. | $L^{118}$ | $L^{130}$ | $L^{174}$ |
| 4022. | $L^{118}$ | $L^{131}$ | $L^{174}$ |
| 4023. | $L^{118}$ | $L^{132}$ | $L^{174}$ |
| 4024. | $L^{118}$ | $L^{133}$ | $L^{174}$ |
| 4025. | $L^{118}$ | $L^{134}$ | $L^{174}$ |
| 4026. | $L^{118}$ | $L^{140}$ | $L^{174}$ |
| 4027. | $L^{118}$ | $L^{141}$ | $L^{174}$ |
| 4028. | $L^{118}$ | $L^{159}$ | $L^{174}$ |
| 4029. | $L^{118}$ | $L^{160}$ | $L^{174}$ |
| 4030. | $L^{118}$ | $L^{119}$ | $L^{176}$ |
| 4031. | $L^{118}$ | $L^{130}$ | $L^{176}$ |
| 4032. | $L^{118}$ | $L^{131}$ | $L^{176}$ |
| 4033. | $L^{118}$ | $L^{132}$ | $L^{176}$ |
| 4034. | $L^{118}$ | $L^{133}$ | $L^{176}$ |
| 4035. | $L^{118}$ | $L^{134}$ | $L^{176}$ |
| 4036. | $L^{118}$ | $L^{140}$ | $L^{176}$ |
| 4037. | $L^{118}$ | $L^{141}$ | $L^{176}$ |
| 4038. | $L^{118}$ | $L^{159}$ | $L^{176}$ |
| 4039. | $L^{118}$ | $L^{160}$ | $L^{176}$ |
| 4040. | $L^{118}$ | $L^{119}$ | $L^{179}$ |
| 4041. | $L^{118}$ | $L^{130}$ | $L^{179}$ |
| 4042. | $L^{118}$ | $L^{131}$ | $L^{179}$ |
| 4043. | $L^{118}$ | $L^{132}$ | $L^{179}$ |
| 4044. | $L^{118}$ | $L^{133}$ | $L^{179}$ |
| 4045. | $L^{118}$ | $L^{134}$ | $L^{179}$ |
| 4046. | $L^{118}$ | $L^{140}$ | $L^{179}$ |
| 4047. | $L^{118}$ | $L^{141}$ | $L^{179}$ |
| 4048. | $L^{118}$ | $L^{159}$ | $L^{179}$ |
| 4049. | $L^{118}$ | $L^{160}$ | $L^{179}$ |
| 4050. | $L^{118}$ | $L^{119}$ | $L^{180}$ |
| 4051. | $L^{118}$ | $L^{130}$ | $L^{180}$ |
| 4052. | $L^{118}$ | $L^{131}$ | $L^{180}$ |
| 4053. | $L^{118}$ | $L^{132}$ | $L^{180}$ |

TABLE 1-continued

| Compound number | $L_1$ | $L_2$ | $L_3$ |
|---|---|---|---|
| 4054. | $L^{118}$ | $L^{133}$ | $L^{180}$ |
| 4055. | $L^{118}$ | $L^{134}$ | $L^{180}$ |
| 4056. | $L^{118}$ | $L^{140}$ | $L^{180}$ |
| 4057. | $L^{118}$ | $L^{141}$ | $L^{180}$ |
| 4058. | $L^{118}$ | $L^{159}$ | $L^{180}$ |
| 4059. | $L^{118}$ | $L^{160}$ | $L^{180}$ |
| 4060. | $L^{119}$ | $L^{130}$ | $L^{144}$ |
| 4061. | $L^{119}$ | $L^{131}$ | $L^{144}$ |
| 4062. | $L^{119}$ | $L^{132}$ | $L^{144}$ |
| 4063. | $L^{119}$ | $L^{133}$ | $L^{144}$ |
| 4064. | $L^{119}$ | $L^{134}$ | $L^{144}$ |
| 4065. | $L^{119}$ | $L^{140}$ | $L^{144}$ |
| 4066. | $L^{119}$ | $L^{141}$ | $L^{144}$ |
| 4067. | $L^{119}$ | $L^{159}$ | $L^{144}$ |
| 4068. | $L^{119}$ | $L^{160}$ | $L^{144}$ |
| 4069. | $L^{119}$ | $L^{130}$ | $L^{145}$ |
| 4070. | $L^{119}$ | $L^{131}$ | $L^{145}$ |
| 4071. | $L^{119}$ | $L^{132}$ | $L^{145}$ |
| 4072. | $L^{119}$ | $L^{133}$ | $L^{145}$ |
| 4073. | $L^{119}$ | $L^{134}$ | $L^{145}$ |
| 4074. | $L^{119}$ | $L^{140}$ | $L^{145}$ |
| 4075. | $L^{119}$ | $L^{141}$ | $L^{145}$ |
| 4076. | $L^{119}$ | $L^{159}$ | $L^{145}$ |
| 4077. | $L^{119}$ | $L^{160}$ | $L^{145}$ |
| 4078. | $L^{119}$ | $L^{130}$ | $L^{147}$ |
| 4079. | $L^{119}$ | $L^{131}$ | $L^{147}$ |
| 4080. | $L^{119}$ | $L^{132}$ | $L^{147}$ |
| 4081. | $L^{119}$ | $L^{133}$ | $L^{147}$ |
| 4082. | $L^{119}$ | $L^{134}$ | $L^{147}$ |
| 4083. | $L^{119}$ | $L^{140}$ | $L^{147}$ |
| 4084. | $L^{119}$ | $L^{141}$ | $L^{147}$ |
| 4085. | $L^{119}$ | $L^{159}$ | $L^{147}$ |
| 4086. | $L^{119}$ | $L^{160}$ | $L^{147}$ |
| 4087. | $L^{119}$ | $L^{130}$ | $L^{149}$ |
| 4088. | $L^{119}$ | $L^{131}$ | $L^{149}$ |
| 4089. | $L^{119}$ | $L^{132}$ | $L^{149}$ |
| 4090. | $L^{119}$ | $L^{133}$ | $L^{149}$ |
| 4091. | $L^{119}$ | $L^{134}$ | $L^{149}$ |
| 4092. | $L^{119}$ | $L^{140}$ | $L^{149}$ |
| 4093. | $L^{119}$ | $L^{141}$ | $L^{149}$ |
| 4094. | $L^{119}$ | $L^{159}$ | $L^{149}$ |
| 4095. | $L^{119}$ | $L^{160}$ | $L^{149}$ |
| 4096. | $L^{119}$ | $L^{130}$ | $L^{152}$ |
| 4097. | $L^{119}$ | $L^{131}$ | $L^{152}$ |
| 4098. | $L^{119}$ | $L^{132}$ | $L^{152}$ |
| 4099. | $L^{119}$ | $L^{133}$ | $L^{152}$ |
| 4100. | $L^{119}$ | $L^{134}$ | $L^{152}$ |
| 4101. | $L^{119}$ | $L^{140}$ | $L^{152}$ |
| 4102. | $L^{119}$ | $L^{141}$ | $L^{152}$ |
| 4103. | $L^{119}$ | $L^{159}$ | $L^{152}$ |
| 4104. | $L^{119}$ | $L^{160}$ | $L^{152}$ |
| 4105. | $L^{119}$ | $L^{130}$ | $L^{164}$ |
| 4106. | $L^{119}$ | $L^{131}$ | $L^{164}$ |
| 4107. | $L^{119}$ | $L^{132}$ | $L^{164}$ |
| 4108. | $L^{119}$ | $L^{133}$ | $L^{164}$ |
| 4109. | $L^{119}$ | $L^{134}$ | $L^{164}$ |
| 4110. | $L^{119}$ | $L^{140}$ | $L^{164}$ |
| 4111. | $L^{119}$ | $L^{141}$ | $L^{164}$ |
| 4112. | $L^{119}$ | $L^{159}$ | $L^{164}$ |
| 4113. | $L^{119}$ | $L^{160}$ | $L^{164}$ |
| 4114. | $L^{119}$ | $L^{130}$ | $L^{165}$ |
| 4115. | $L^{119}$ | $L^{131}$ | $L^{165}$ |
| 4116. | $L^{119}$ | $L^{132}$ | $L^{165}$ |
| 4117. | $L^{119}$ | $L^{133}$ | $L^{165}$ |
| 4118. | $L^{119}$ | $L^{134}$ | $L^{165}$ |
| 4119. | $L^{119}$ | $L^{140}$ | $L^{165}$ |
| 4120. | $L^{119}$ | $L^{141}$ | $L^{165}$ |
| 4121. | $L^{119}$ | $L^{159}$ | $L^{165}$ |
| 4122. | $L^{119}$ | $L^{160}$ | $L^{165}$ |
| 4123. | $L^{119}$ | $L^{130}$ | $L^{166}$ |
| 4124. | $L^{119}$ | $L^{131}$ | $L^{166}$ |
| 4125. | $L^{119}$ | $L^{132}$ | $L^{166}$ |
| 4126. | $L^{119}$ | $L^{133}$ | $L^{166}$ |
| 4127. | $L^{119}$ | $L^{134}$ | $L^{166}$ |
| 4128. | $L^{119}$ | $L^{140}$ | $L^{166}$ |
| 4129. | $L^{119}$ | $L^{141}$ | $L^{166}$ |
| 4130. | $L^{119}$ | $L^{159}$ | $L^{166}$ |
| 4131. | $L^{119}$ | $L^{160}$ | $L^{166}$ |
| 4132. | $L^{119}$ | $L^{130}$ | $L^{170}$ |
| 4133. | $L^{119}$ | $L^{131}$ | $L^{170}$ |
| 4134. | $L^{119}$ | $L^{132}$ | $L^{170}$ |
| 4135. | $L^{119}$ | $L^{133}$ | $L^{170}$ |
| 4136. | $L^{119}$ | $L^{134}$ | $L^{170}$ |
| 4137. | $L^{119}$ | $L^{140}$ | $L^{170}$ |
| 4138. | $L^{119}$ | $L^{141}$ | $L^{170}$ |
| 4139. | $L^{119}$ | $L^{159}$ | $L^{170}$ |
| 4140. | $L^{119}$ | $L^{160}$ | $L^{170}$ |
| 4141. | $L^{119}$ | $L^{130}$ | $L^{174}$ |
| 4142. | $L^{119}$ | $L^{131}$ | $L^{174}$ |
| 4143. | $L^{119}$ | $L^{132}$ | $L^{174}$ |
| 4144. | $L^{119}$ | $L^{133}$ | $L^{174}$ |
| 4145. | $L^{119}$ | $L^{134}$ | $L^{174}$ |
| 4146. | $L^{119}$ | $L^{140}$ | $L^{174}$ |
| 4147. | $L^{119}$ | $L^{141}$ | $L^{174}$ |
| 4148. | $L^{119}$ | $L^{159}$ | $L^{174}$ |
| 4149. | $L^{119}$ | $L^{160}$ | $L^{174}$ |
| 4150. | $L^{119}$ | $L^{130}$ | $L^{176}$ |
| 4151. | $L^{119}$ | $L^{131}$ | $L^{176}$ |
| 4152. | $L^{119}$ | $L^{132}$ | $L^{176}$ |
| 4153. | $L^{119}$ | $L^{133}$ | $L^{176}$ |
| 4154. | $L^{119}$ | $L^{134}$ | $L^{176}$ |
| 4155. | $L^{119}$ | $L^{140}$ | $L^{176}$ |
| 4156. | $L^{119}$ | $L^{141}$ | $L^{176}$ |
| 4157. | $L^{119}$ | $L^{159}$ | $L^{176}$ |
| 4158. | $L^{119}$ | $L^{160}$ | $L^{170}$ |
| 4159. | $L^{119}$ | $L^{130}$ | $L^{179}$ |
| 4160. | $L^{119}$ | $L^{131}$ | $L^{179}$ |
| 4161. | $L^{119}$ | $L^{132}$ | $L^{179}$ |
| 4162. | $L^{119}$ | $L^{133}$ | $L^{179}$ |
| 4163. | $L^{119}$ | $L^{134}$ | $L^{179}$ |
| 4164. | $L^{119}$ | $L^{140}$ | $L^{179}$ |
| 4165. | $L^{119}$ | $L^{141}$ | $L^{179}$ |
| 4166. | $L^{119}$ | $L^{159}$ | $L^{179}$ |
| 4167. | $L^{119}$ | $L^{160}$ | $L^{179}$ |
| 4168. | $L^{119}$ | $L^{130}$ | $L^{180}$ |
| 4169. | $L^{119}$ | $L^{131}$ | $L^{180}$ |
| 4170. | $L^{119}$ | $L^{132}$ | $L^{180}$ |
| 4171. | $L^{119}$ | $L^{133}$ | $L^{180}$ |
| 4172. | $L^{119}$ | $L^{134}$ | $L^{180}$ |
| 4173. | $L^{119}$ | $L^{140}$ | $L^{180}$ |
| 4174. | $L^{119}$ | $L^{141}$ | $L^{180}$ |
| 4175. | $L^{119}$ | $L^{159}$ | $L^{180}$ |
| 4176. | $L^{119}$ | $L^{160}$ | $L^{180}$ |

According to one embodiment, the following Table 2 lists a group of preferred compounds:

TABLE 2

| Compound number | L₁ | L₂ | L₃ | Compound number | L₁ | L₂ | L₃ | Compound number | L₁ | L₂ | L₃ |
|---|---|---|---|---|---|---|---|---|---|---|---|
| 136 | $L^{101}$ | $L^{102}$ | $L^{164}$ | 190 | $L^{101}$ | $L^{102}$ | $L^{166}$ | 28 | $L^{101}$ | $L^{102}$ | $L^{145}$ |
| 137 | $L^{101}$ | $L^{103}$ | $L^{164}$ | 191 | $L^{101}$ | $L^{103}$ | $L^{166}$ | 29 | $L^{101}$ | $L^{103}$ | $L^{145}$ |
| 138 | $L^{101}$ | $L^{104}$ | $L^{164}$ | 192 | $L^{101}$ | $L^{104}$ | $L^{166}$ | 30 | $L^{101}$ | $L^{104}$ | $L^{145}$ |
| 139 | $L^{101}$ | $L^{105}$ | $L^{164}$ | 193 | $L^{101}$ | $L^{105}$ | $L^{166}$ | 31 | $L^{101}$ | $L^{105}$ | $L^{145}$ |
| 140 | $L^{101}$ | $L^{106}$ | $L^{164}$ | 194 | $L^{101}$ | $L^{106}$ | $L^{166}$ | 32 | $L^{101}$ | $L^{106}$ | $L^{145}$ |
| 141 | $L^{101}$ | $L^{107}$ | $L^{164}$ | 195 | $L^{101}$ | $L^{107}$ | $L^{166}$ | 33 | $L^{101}$ | $L^{107}$ | $L^{145}$ |
| 142 | $L^{101}$ | $L^{108}$ | $L^{164}$ | 196 | $L^{101}$ | $L^{108}$ | $L^{166}$ | 34 | $L^{101}$ | $L^{108}$ | $L^{145}$ |
| 143 | $L^{101}$ | $L^{109}$ | $L^{164}$ | 197 | $L^{101}$ | $L^{109}$ | $L^{166}$ | 35 | $L^{101}$ | $L^{109}$ | $L^{145}$ |
| 144 | $L^{101}$ | $L^{110}$ | $L^{164}$ | 198 | $L^{101}$ | $L^{110}$ | $L^{166}$ | 36 | $L^{101}$ | $L^{110}$ | $L^{145}$ |
| 145 | $L^{101}$ | $L^{111}$ | $L^{164}$ | 199 | $L^{101}$ | $L^{111}$ | $L^{166}$ | 37 | $L^{101}$ | $L^{111}$ | $L^{145}$ |
| 146 | $L^{101}$ | $L^{112}$ | $L^{164}$ | 200 | $L^{101}$ | $L^{112}$ | $L^{166}$ | 38 | $L^{101}$ | $L^{112}$ | $L^{145}$ |
| 147 | $L^{101}$ | $L^{113}$ | $L^{164}$ | 201 | $L^{101}$ | $L^{113}$ | $L^{166}$ | 39 | $L^{101}$ | $L^{113}$ | $L^{145}$ |
| 148 | $L^{101}$ | $L^{114}$ | $L^{164}$ | 202 | $L^{101}$ | $L^{114}$ | $L^{166}$ | 40 | $L^{101}$ | $L^{114}$ | $L^{145}$ |
| 149 | $L^{101}$ | $L^{115}$ | $L^{164}$ | 203 | $L^{101}$ | $L^{115}$ | $L^{166}$ | 41 | $L^{101}$ | $L^{115}$ | $L^{145}$ |
| 150 | $L^{101}$ | $L^{116}$ | $L^{164}$ | 204 | $L^{101}$ | $L^{116}$ | $L^{166}$ | 42 | $L^{101}$ | $L^{116}$ | $L^{145}$ |
| 2809 | $L^{111}$ | $L^{112}$ | $L^{174}$ | 205 | $L^{101}$ | $L^{117}$ | $L^{166}$ | 43 | $L^{101}$ | $L^{117}$ | $L^{145}$ |
| 2810 | $L^{111}$ | $L^{113}$ | $L^{174}$ | 206 | $L^{101}$ | $L^{118}$ | $L^{166}$ | 44 | $L^{101}$ | $L^{118}$ | $L^{145}$ |
| 2811 | $L^{111}$ | $L^{114}$ | $L^{174}$ | 207 | $L^{101}$ | $L^{119}$ | $L^{166}$ | 45 | $L^{101}$ | $L^{119}$ | $L^{145}$ |
| 2812 | $L^{111}$ | $L^{115}$ | $L^{174}$ | 208 | $L^{101}$ | $L^{130}$ | $L^{166}$ | 46 | $L^{101}$ | $L^{130}$ | $L^{145}$ |
| 2813 | $L^{111}$ | $L^{116}$ | $L^{174}$ | 209 | $L^{101}$ | $L^{131}$ | $L^{166}$ | 47 | $L^{101}$ | $L^{131}$ | $L^{145}$ |
| 2814 | $L^{111}$ | $L^{117}$ | $L^{174}$ | 210 | $L^{101}$ | $L^{132}$ | $L^{166}$ | 48 | $L^{101}$ | $L^{132}$ | $L^{145}$ |
| 2815 | $L^{111}$ | $L^{118}$ | $L^{174}$ | 211 | $L^{101}$ | $L^{133}$ | $L^{166}$ | 49 | $L^{101}$ | $L^{133}$ | $L^{145}$ |
| 2816 | $L^{111}$ | $L^{119}$ | $L^{174}$ | 212 | $L^{101}$ | $L^{134}$ | $L^{166}$ | 50 | $L^{101}$ | $L^{134}$ | $L^{145}$ |
| 2817 | $L^{111}$ | $L^{130}$ | $L^{174}$ | 213 | $L^{101}$ | $L^{140}$ | $L^{166}$ | 51 | $L^{101}$ | $L^{140}$ | $L^{145}$ |
| 2818 | $L^{111}$ | $L^{131}$ | $L^{174}$ | 214 | $L^{101}$ | $L^{141}$ | $L^{166}$ | 52 | $L^{101}$ | $L^{141}$ | $L^{145}$ |
| 2819 | $L^{111}$ | $L^{132}$ | $L^{174}$ | 215 | $L^{101}$ | $L^{159}$ | $L^{166}$ | 53 | $L^{101}$ | $L^{159}$ | $L^{145}$ |
| 2820 | $L^{111}$ | $L^{133}$ | $L^{174}$ | 216 | $L^{101}$ | $L^{160}$ | $L^{166}$ | 54 | $L^{101}$ | $L^{160}$ | $L^{145}$ |

One example of the inventive synthetic method is shown below:

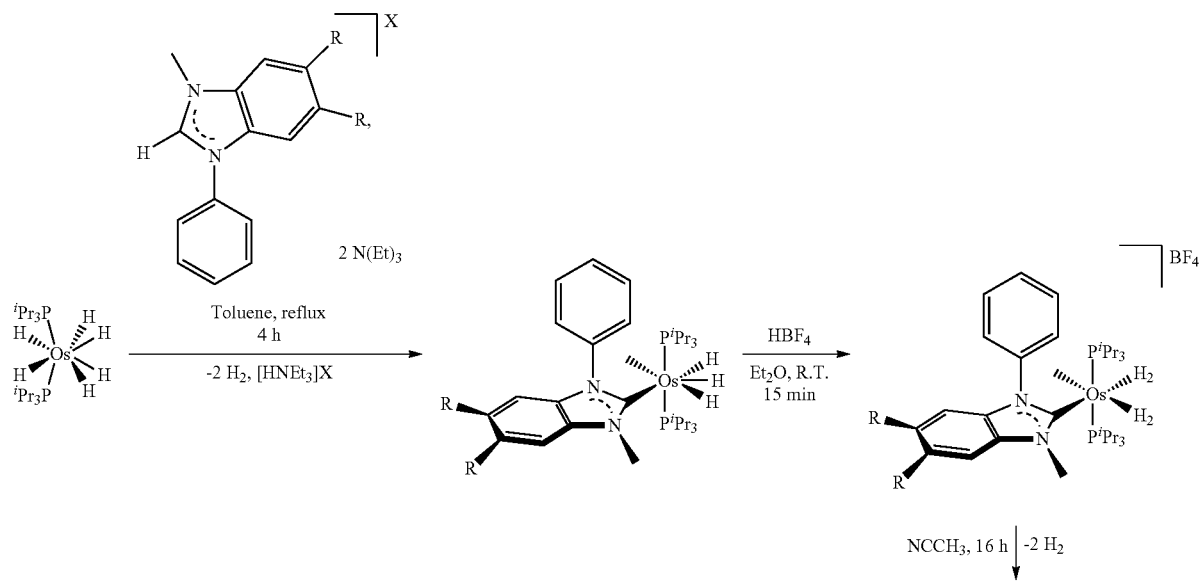

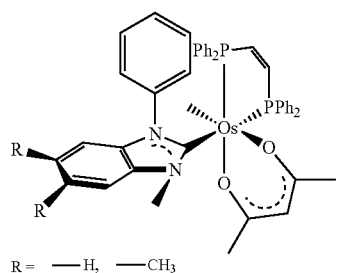 + 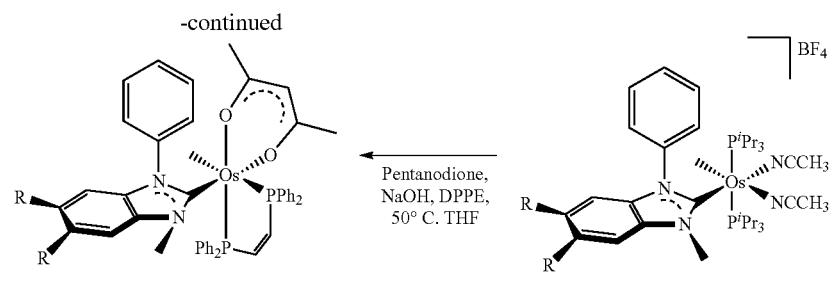

R = —H, —CH₃ where

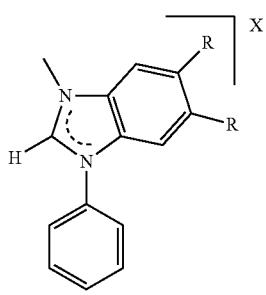

is the precursor of ligand L¹ with X being a counter ion; cis-1,2-bis(diphenylphosphino)ethylene ((z)-Bdppe)(DPPE) is the ligand L²; and Pentanodione is the ligand L³.

In describing the novel synthesis method, all reactions were carried out with rigorous exclusion of air using Schlenk-tube techniques. Solvents, except acetonitrile that was dried and distilled under argon, were obtained oxygen- and water-free from an MBraun solvent purification apparatus. ¹H, ³¹P{¹H}, ¹⁹F and ¹³C{¹H}NMR spectra were recorded on Bruker 300 ARX, Bruker Avance 300 MHz, and Bruker Avance 400 MHz instruments. Chemical shifts (expressed in parts per million) are referenced to residual solvent peaks (¹H, ¹³C {¹H}) or external 85% H₃PO₄ (³¹P{¹H}), or external CFCl₃ (¹⁹F). Coupling constants J and N are given in hertz. Attenuated total reflection infrared spectra (ATR-IR) of solid samples were run on a Perkin-Elmer Spectrum 100 FT-IR spectrometer. C, H, and N analyses were carried out in a Perkin-Elmer 2400 CHNS/O analyzer. High-resolution electrospray mass spectra were acquired using a MicroTOF-Q hybrid quadrupole time-of-flight spectrometer (Bruker Daltonics, Bremen, Germany). OsH₆(P^iPr₃)₂ was prepared by the method published in Aracama, M.; Esteruelas, M. A.; Lahoz, F. J.; López, J. A.; Meyer, U.; Oro, L. A.; Werner, H. *Inorg. Chem.* 1991, 30, 288.

Preparation of Trihydride-Bi2

Toluene (40 mL) and NEt₃ (120 μl, 0.86 mmol) were added to a mixture of the osmium precursor, OsH₆(P^iPr₃)₂ (400 mg, 0.78 mmol) and a precursor of ligand L¹, 1-phenyl-3-methyl-1-H-benzimidazolium tetrafluoroborate-Bi2 (229.2 mg, 0.78 mmol). The resulting mixture was refluxed for 4 hours and then the brownish-yellow solution was extracted and concentrated under vacuum to 1 mL. MeOH was added (8 mL), affording a white powder which was filtered and washed with MeOH (2×4 mL) at 195 K and dried in vacuo.

Experimental data for trihydride-Bi2: Yield: 76.4% 426.0 mg. Analytical Calculation for C₃₂H₅₆N₂OsP₂ was C, 53.31%; H, 7.83%; N, 3.89%. Found: C, 53.01%; H, 8.14%; N, 3.91%. HRMS (electrospray, m/z): calculated for C₃₂H₅₁N₂OsP₂ [M-5H]⁺: 719.3295. Found: 719.3281. IR (cm⁻¹): υ(Os—H) 2044 (m). ¹H NMR (400 MHz, C₆D₆, 293 K): δ 8.66 (d, J_{H-H}=7.2, 1H, CH Ph), 7.91-7.88 (m, 2H, CH Ph, CH Bzm), 7.24 (ddd, J_{H-H}=7.2, J_{H-H}=7.2, J_{H-H}=1.0, 1H, CH Ph), 7.10 (ddd, J_{H-H}=7.2, J_{H-H}=7.2, J_{H-H}=1.0, 1H, CH Ph), 7.05-6.99 (m, 2H, CH Bzm), 6.91 (m, 1H, CH Bzm), 3.92 (s, 3H, N—CH₃), 1.79 (m, 6H, PCH), 0.96 (dvt, N=12.5, J=6.9, 18H, PCH(CH₃)₂) 0.83 (dvt, N=12.5, J=6.9, 18H, PCH(CH₃)₂), −8.18 (br, 1H, Os—H), −9.94 (br, 2H, Os—H). T_{1(min)} (ms, OsH, 400 MHz, CD₂Cl₂): 118.2±10 (213 K). ¹³C{¹H}-APT NMR, HMBC and HSQC (100.6 MHz, C₆D₆, 293 K): δ 206.3 (t, J_{C-P}=5.4, NCN Bzm), 157.9 (t, J_{C-P}=6.7, Os—C Ph), 148.9 (s, N—C Ph), 148.0 (s, C—H Ph), 137.5 (s, C Bzm), 133.6 (s, C Bzm), 124.3 (s, C—H Ph), 122.1 (s, C—H Bzm), 121.3 (s, C—H Bzm), 119.8 (s, C—H Ph), 112.5 (s, C—H Bzm), 110.4 (s, C—H Ph), 109.1 (s, C—H Bzm), 36.6 (s, N—CH₃ Bzm), 27.9 (dvt, N=25.0, P—CH), 19.9 (s, PCH(CH₃)₂), 19.8 (s, PCH(CH₃)₂). ³¹P{¹H}NMR (162.0 MHz, C₆D₆, 293 K): δ 25.7 (s).

Preparation of Trihydride-Bi3

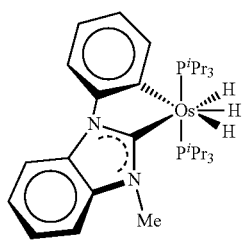

Toluene (40 mL) and NEt₃ (120 μl, 0.86 mmol) were added to a mixture of OsH₆(P^iPr₃)₂ (400 mg, 0.78 mmol) and 1-phenyl-3-methyl-1-H,-5,6-dimethyl-benzimidazolium tetrafluoroborate (Bi3, 250.9 mg, 0.78 mmol). The resulting mixture was refluxed for 4 hours and then the solution was extracted and concentrated under vacuum to 1 mL. MeOH was added (8 mL) and the resulting white powder was filtered and washed with MeOH (3×3 mL).

Experimental data for trihydride-Bi3: Yield: 84% 490.7 mg. Analytical Calculation for $C_{34}H_{60}N_2OsP_2 \cdot CH_3OH$: C, 53.82%; H, 8.26%; N, 3.59%. Found: C, 53.99%; H, 8.51%; N, 3.67%. HRMS (electrospray, m/z): calculated for $C_{34}H_{55}OsP_2N_2[M-H]^+$: 745.3452. Found: 745.3460. IR: (cm$^{-1}$) υ(Os—H) 2049 (m), υ(Os—H) 2027 (m). $^1$H NMR (400 MHz, $C_6D_6$, 293 K): δ 8.67 (d, $J_{H-H}$=7.5, 1H, CH Ph), 8.02 (dd, $J_{H-H}$=7.5, $J_{H-H}$=0.8, 1H, CH Ph), 7.88 (s, 1H, H Bzm), 7.24 (ddd, $J_{H-H}$=7.5, $J_{H-H}$=7.5, $J_{H-H}$=1.1, 1H, CH Ph), 7.10 (ddd, $J_{H-H}$=7.5, $J_{H-H}$=7.5, $J_{H-H}$=0.8, 1H, CH Ph), 6.80 (s, 1H, CH Bzm), 3.96 (s, 3H, N—CH$_3$), 2.13 and 2.12 (both s, each 3H, —CH$_3$ Bzm), 1.84 (m, 6H, P—CH), 0.99 (dvt, N=12.5, J=6.9, 18H, PCH(CH$_3$)$_2$), 0.87 (dvt, N=12.5, J=6.9, 18H, PCH(CH$_3$)$_2$), −8.21 (br, 1H, Os—H), −9.96 (br, 2H, Os—H). $T_{1(min)}$ (ms, OsH, 400 MHz, $CD_2Cl_2$): 115.0±11 (233 K). $^{13}C\{^1H\}$-APT NMR, HMBC and HSQC (100.6 MHz, $C_6D_6$, 293 K): δ 204.9 (t, $J_{C-P}$=5.6, NCN Bzm), 157.7 (t, $J_{C-P}$=6.7, Os—C Ph), 149.2 (s, N—C Ph), 148.0 (s, C—H Ph), 136.2 (s, C Bzm), 132.3 (s, C Bzm), 130.3 (s, C Bzm), 129.6 (s, C Bzm), 124.2 (s, C—H Ph), 119.8 (s, C—H Ph), 112.3 (s, C—H Ph), 111.6 (s, C—H Bzm), 110.2 (s, C—H Bzm), 36.8 (s, NCH$_3$), 28.1 (dvt, N=24.8, P—CH), 20.2 and 20.1 (both s, —CH$_3$ Bzm), 20.0 (s, PCH(CH$_3$)$_2$), 19.8 (s, PCH(CH$_3$)$_2$). $^{31}P\{^1H\}$NMR (162.0 MHz, $C_6D_6$, 293 K): δ 25.6 (s).

Preparation of Bisdihydrogen-Bi2

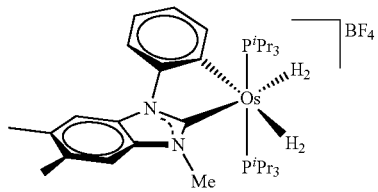

A yellow solution of trihydride-Bi2 (353.5 mg, 0.490 mmol) in Et$_2$O (15 mL) was treated with HBF$_4$.Et$_2$O (87.4 μl, 0.539 mmol). The mixture was stirred for 20 minutes and the resulting brown oily product was stirred at low temperature (196 K) for 4 hours affording a white powder. The product was filtered and washed with Et$_2$O (3×3 mL).

Experimental data for Bisdihydrogen-Bi2: Yield: 403.3 mg (83.3%). Analytical Calculation for $C_{32}H_{57}BF_4N_2OsP_2$: C, 47.52%; H, 7.01%; N, 3.35%. Found: C, 47.37%; H, 6.87%; N, 3.42%. HRMS (electrospray, m/z): calculated for $C_{32}H_{51}N_2OsP_2$ [M-6H]$^+$: 717.3138. Found: 717.3309. IR: (cm$^{-1}$) υ(B—F) 1034 (br, vs). $^1$H NMR (300 MHz, $CD_2Cl_2$, 223 K) δ 8.10 (m, 1H, CH Bzm), 7.98 (d, $J_{H-H}$=7.6, 1H, CH Ph), 7.90 (d, $J_{H-H}$=7.6, 1H, CH Ph), 7.54 (m, 1H, CH Bzm), 7.45-7.42 (m, 2H, CH Bzm), 7.30 (dd, $J_{H-H}$=7.6, $J_{H-H}$=7.6, 1H, CH Ph), 7.01 (dd, $J_{H-H}$=7.6, $J_{H-H}$=7.6, 1H, CH Ph), 3.96 (s, 3H, N—CH$_3$), 1.80 (m, 6H, P—CH), 0.86 (dvt, N=13.7, J=6.8, 18H, PCH(CH$_3$)$_2$), 0.81 (dvt, N=13.1, J=6.5, 18H, PCH(CH$_3$)$_2$), −6.74 (br, 4H, Os—H$_2$). $T_{1(min)}$ (ms, OsH, 400 MHz, $CD_2Cl_2$): 12.0±2 (193 K). $^{13}C\{^1H\}$-APT NMR, HMBC and HSQC (75 MHz, $CD_2Cl_2$, 293 K): δ 188.6 (t, $J_{C-P}$=5.6, NCN Bzm), 148.2 (Br, Os—C Ph), 144.8 (s, C—H Ph), 135.2 (s, C Bzm), 131.1 (s, C Bzm), 126.0 (s, C—H Ph), 124.4 (s, C—H Ph), 123.9 (s, C Bzm), 123.5 (s, C Bzm), 113.8 (s, C—H Bzm), 111.5 (s, C—H Bzm), 111.0 (s, C—H Bzm), 36.6 (s, N—CH$_3$), 25.4 (dvt, $J_{P-C}$=13.9 Hz, P—CH), 19.3 (s, PCH(CH$_3$)$_2$), 18.7 (s, PCH(CH$_3$)$_2$). $^{31}P\{^1H\}$NMR (121.0 MHz, $CCl_2D_2$, 293 K): δ 14.9 (s). $^{19}F\{^1H\}$NMR (282.4 MHz, $C_6D_6$, 293 K): δ −153.3 (s).

Preparation of Bisdihydrogen-Bi3

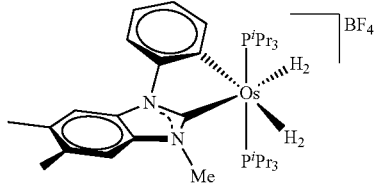

A yellow solution of trihydride-Bi3 (100.0 mg, 0.134 mmol) in Et$_2$O (5 mL) was treated with HBF$_4$.Et$_2$O (20.0 μl, 0.147 mmol). The mixture was stirred for 20 minutes and the resulting brown oily product was stirred at low temperature (196 K) for 4 hours affording a white powder. The product was filtered and washed with Et$_2$O (3×2 mL).

Experimental data for Bisdihydrogen-Bi3: Yield: 98.3 mg (88%). Analytical Calculation for $C_{34}H_{61}BF_4N_2OsP_2$: C, 48.8%; H, 7.35%; N, 3.35%. Found: C, 48.65%; H, 7.51%; N, 3.14%. HRMS (electrospray, m/z): calculated for $C_{34}H_{55}N_2OsP_2$ [M-6H]$^+$: 745.3583. Found: 745.3452. IR: (cm$^{-1}$) υ(B—F) 1048 (vs), υ(B—F) 1034 (vs). $^1$H NMR (300 MHz, $CD_2Cl_2$, 223 K): δ 7.98 (d, $J_{H-H}$=7.5, 1H, C—H Ph), 7.89 (d, $J_{H-H}$=7.5, 1H, C—H Ph), 7.85 (s, 1H, C—H Bzm), 7.34-7.25 (m, 2H, C—H Bzm and C—H Ph), 7.00 (dd, $J_{H-H}$=7.5, $J_{H-H}$=7.5, 1H, C—H Ph), 3.90 (s, 3H, N—CH$_3$), 2.42 and 2.38 (both s, each 3H, —CH$_3$ Bzm), 1.80 (m, 6H, P—CH), 0.99 (dvt, N=14.0, J=7.0, 18H, PCH(CH$_3$)$_2$), 0.78 (dvt, N=14.0, J=7.0, 18H, PCH(CH$_3$)$_2$), −6.78 (br, 4H, Os—H$_2$). $T_{1(min)}$ (ms, OsH, 400 MHz, $CD_2Cl_2$): 14.2±1 (193 K). $^{13}C\{^1H\}$-APT NMR, HMBC and HSQC (75 MHz, $CD_2Cl_2$, 223 K): δ 187.0 (t, $J_{C-P}$=7.7, NCN Bzm), 148.6 (t, J=1.6 Hz, Os—C Ph), 145.1 (s, C—H Ph), 134.0 (s, C Bzm), 133.5 (s, C Bzm), 133.2 (s, C Bzm), 129.8 (s, C Bzm), 126.1 (s, C—H Ph), 125.0 (s, C—H Ph), 114.1 (s, C—H Ph), 112.3 (s, C—H Bzm), 111.4 (s, C—H Bzm), 36.7 (s, N—CH$_3$) 25.8 (dvt, $J_{P-C}$=27.8 Hz, P—CH), 20.7 and 20.4 (both s, —CH$_3$ Bzm), 19.6 (s, PCH(CH$_3$)$_2$), 18.9 (s, PCH (CH$_3$)$_2$). $^{31}P\{^1H\}$NMR (121.0 MHz, $CCl_2D_2$, 293 K): δ 15.2 (s). $^{19}F\{^1H\}$NMR (282.4 MHz, $C_6D_6$, 293 K): δ −153.3 (s).

Preparation of Bisacetonitrile-Bi2

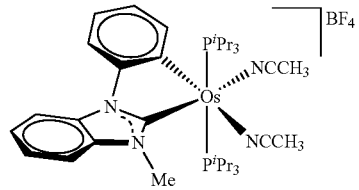

A yellow solution of bishydrogen-Bi2 (315.0 mg, 0.376 mmol) in NCCH$_3$ (20 mL) was stirred for 20 h under a flow of argon. The greenish-yellow solution was concentrated under vacuum to dryness and the resulting oily product was stirred in Et$_2$O (8 mL) at 196 K. The resulting green solid was washed with Et$_2$O (2×4 mL).

Experimental data for Bisacetonitrile-Bi2: Yield: 291.8 mg (84.7%). HRMS (electrospray, m/z): calculated for $C_{32}H_{51}N_2OsP_2$ [M-2H-2(NCCH$_3$)]$^+$: 717.3138. Found: 717.3351. IR: υ(CN, NCCH$_3$) 2253 (w), υ(BF) 1049 (vs), υ(B—F) 1029 (vs). $^1$H NMR (400 MHz, $CD_2Cl_2$) δ 7.96 (m, 1H, C—H Bzm), 7.80 (d, $J_{H-H}$=7.3, 1H, C—H Ph), 7.64 (d, $J_{H-H}$=7.3, 1H, C—H Ph), 7.34 (m, 1H, C—H Bzm), 7.31-7.27 (m, 2H, C—H Bzm), 6.93 (dd, $J_{H-H}$=7.3, $J_{H-H}$=7.3, 1H, C—H Ph), 6.84 (dd, $J_{H-H}$=7.3, $J_{H-H}$=7.3, 1H, C—H Ph), 4.07 (s, 3H, N—CH$_3$), 2.74 and 2.69 (both s, each 3H, NCCH$_3$), 2.14-2.09 (m, 6H, P—CH), 0.94 (dvt, N=12.6, J=6.8, 18H, PCH(CH$_3$)$_2$), 0.89 (dvt, N=12.6, J=6.8, 18H, PCH(CH$_3$)$_2$). $^{13}$C{$^1$H}-APT NMR, HMBC and HSQC (101 MHz, CD$_2$Cl$_2$) δ 188.2 (t, $J_{C-P}$=7.6, NCN Bzm), 151.4 (s, C Ph), 146.6 (t, $J_{C-P}$=7.7 Hz, Os—C Ph), 139.4 (s, C—H Ph), 137.5 (s, C Bzm), 133.4 (s, C Bzm), 124.8 and 123.6 (both s, NCCH$_3$), 123.4 (br, C—H Ph and C—H Bzm), 122.4 (s, C—H Bzm), 120.6 (s, C—H Ph), 112.1 (s, C—H Ph), 110.4 (s, C—H Bzm), 109.6 (s, C—H Bzm), 35.2 (s, N—CH$_3$), 25.1 (dvt, N=22.4, P—CH), 19.6 (s, PCH(CH$_3$)$_2$), 19.5 (s, PCH (CH$_3$)$_2$), 5.4 and 5.3 (both s, NCCH$_3$). $^{31}$P{$^1$H}NMR (121.0 MHz, C$_6$D$_6$, 293 K): δ −10.2 (s). $^{19}$F{$^1$H}NMR (162.0 MHz, C$_6$D$_6$, 293 K): δ −153.3 (s).

Preparation of Bisacetonitrile-Bi3

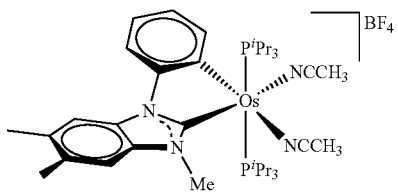

A yellow solution of bishydrogen-Bi3 (421.8 mg, 0.504 mmol) in NCCH$_3$ (20 mL) was stirred for 20 h under a flow of argon. The greenish-yellow solution was concentrated under vacuum to ca. 1 mL and Et$_2$O (8 mL) was added. The resulting palish green solid was washed with Et$_2$O (3×2 mL).

Experimental data for Bisacetonitrile-Bi3: Yield: 411.2 mg (89.2%). Analytical Calculation for C$_{38}$H$_{63}$BF$_4$N$_4$OsP$_2$: C, 49.89; H, 6.94; N, 6.12. Found: C, 49.85; H, 6.95; N, 5.99. HRMS (electrospray, m/z): calculated for C$_{34}$H$_{55}$N$_2$OsP$_2$ [M-2H-2NCCH$_3$]$^+$: 745.3452. Found: 745.3489 IR: (cm$^{-1}$) υ(CN, NCCH$_3$) 2245 (w), υ(BF) 1054 (vs), υ(B—F) 1036 (vs), υ(B—F) 1025 (vs). $^1$H NMR (400 MHz, CD$_2$Cl$_2$, 298 K): δ 7.77 (d, $J_{H-H}$=7.3, 1H, C—H Ph), 7.74 (s, 1H, C—H Bzm), 7.62 (d, $J_{H-H}$=7.3, 1H, C—H Ph), 7.1 (s, 1H, C—H Bzm), 6.91 (dd, $J_{H-H}$=7.3, $J_{H-H}$=7.3, 1H, C—H Ph), 6.81 (dd, $J_{H-H}$=7.3, $J_{H-H}$=7.3, 1H, C—H Ph), 4.02 (s, 3H, N—CH$_3$), 2.73 and 2.69 (both s, each 3H, NCCH$_3$), 2.43 and 2.39 (both s, each 3H, —CH$_3$ Bzm), 2.1 (m, 6H, P—CH), 0.93 (dvt, N=12.8, J=6.5, 18H, PCH(CH$_3$)$_2$), 0.89 (dvt, N=12.8, J=6.5, 18H, PCH(CH$_3$)$_2$). $^{13}$C{$^1$H}-APT NMR, HMBC and HSQC (75 MHz, CD$_2$Cl$_2$) δ 186.4 (t, $J_{C-P}$=7.7, NCN Bzm), 151.6 (s, C Ph), 146.6 (t, $J_{C-P}$=7.7 Hz, Os—C Ph), 139.3 (s, C—H Ph), 136.0 (s, C Bzm), 132.1 (s, C Bzm), 131.8 (s, C Bzm), 131.3 (s, C Bzm), 124.5 and 123.4 (both s, NCCH$_3$), 123.1 (s, C—H Ph), 120.5 (s, C—H Ph), 111.9 (s, C—H Ph), 111.3 (s, C—H Bzm), 110.3 (s, C—H Bzm), 35.1 (s, N—CH$_3$), 25.0 (t, $J_{P-C}$=22.4, PCH), 20.6 and 20.4 (both s, —CH$_3$ Bzm), 19.5 (s, PCH(CH$_3$)$_2$), 19.4 (s, PCH(CH$_3$)$_2$), 5.4 and 5.3 (both s, NCCH$_3$). $^{31}$P{$^1$H}NMR (121.0 MHz, C$_6$D$_6$, 293 K): δ −10.1 (s). $^{19}$F{$^1$H}NMR (162.0 MHz, C$_6$D$_6$, 293 K): δ −148.2 (s).

Preparation of the Osmium Complex Compound 428

KOH (2.2 mL, 0.259 M in MeOH) was added to a solution of complex bisacetonitrile-Bi2 (300 mg, 0.338 mmol), ligand L$^2$; cis-1,2-bis(diphenylphosphino)ethylene ((z)-Bdppe) (134.0 mg, 0.338 mmol) and ligand L$^3$; pentanodione (58 µL, 0.58 mmol) in THF (15 mL). The resulting red solution was stirred at 323 K for 5 hours and then the solvent was concentrated under vacuum to dryness. CH$_2$Cl$_2$ was added and the resulting orange solution was extracted and concentrated to dryness under vacuum. The resulting yellow solid was washed with pentane (150 mL) affording a yellow powder Compound 428-1. The resulting yellowish-orange pentane solution was extracted and concentrated to dryness under vacuum affording an orange solid which was purified by chromatography (silicagel 230-400 mesh and pentane/methylene chloride 1/1 as eluent) yielding complex Compound 428-2.

Experimental Data for Compound 428-1:

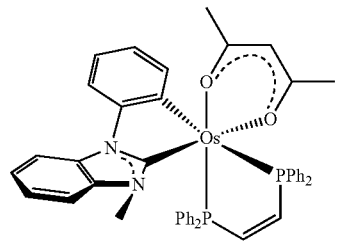

Figure 3:
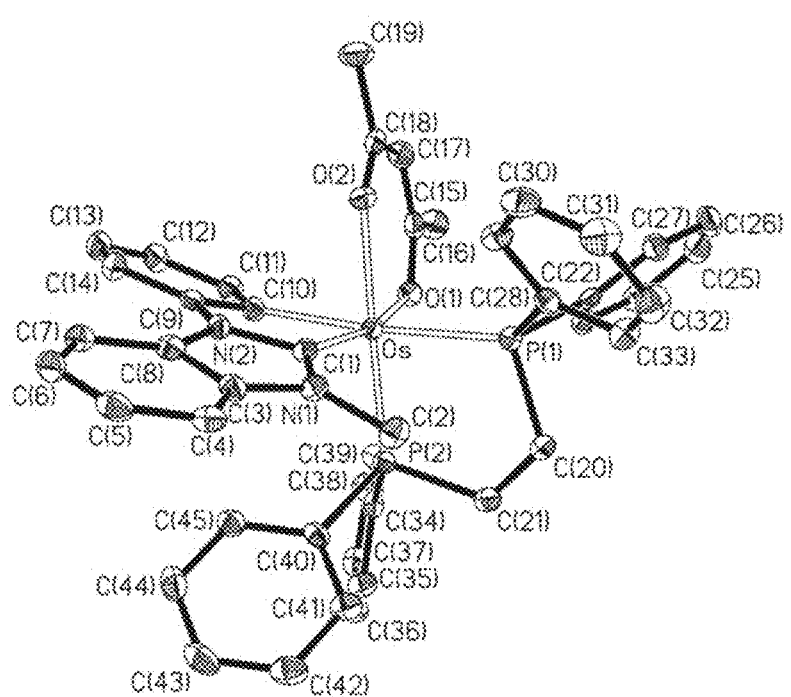
FIG. 3 shows molecular diagram of an osmium tribidentate complex, trisbidentatecomplex-Bi2 (1), disclosed herein with X-ray diffraction analysis characterization.

Yield: 104.0 mg (34.5%). HRMS (electrospray, m/z): calculated for C$_{45}$H$_{40}$N$_2$O$_2$OsP$_2$ [M]$^+$: 894.2177. Found: 894.2379. IR: (cm$^{-1}$) υ(CO) 1580 (m), υ(CO) 1518 (m). $^1$H NMR (300 MHz, CD$_2$Cl$_2$, 298 K): δ 8.19-6.45 (30H, 22C—H (z)-Bdppe+4C—H Bzm+4C—H Ph), 4.73 (s, 1H, C—H Acac), 2.64 (s, 3H, N—CH$_3$), 1.50 and 1.24 (both s, each 3H, —CH$_3$ Acac). $^{13}$C{$^1$H}-APT NMR, HMBC and HSQC (75 MHz, CD$_2$Cl$_2$): δ 189.6 (dd, $J_{C-P}$=9.5, $J_{C-P}$=1.6, NCN Bzm), 182.7 (s, CO Acac), 181.2 (s, CO Acac), 164.6 (dd, $J_{P-C}$=85.4, $J_{P-C}$=7.0, C—Os Ph), 154.6 (dd, $J_{P-C}$=45.5, $J_{P-C}$=32.5, C—H ethylene (z)-Bdppe), 151.0 (d, $J_{P-C}$=6.7, C Ph), 150.6 (dd, $J_{P-C}$=35.9, $J_{P-C}$=21.8, C—H ethylene (z)-Bdppe), 139.3 (d, $J_{P-C}$=33.1, C (z)-Bdppe), 138.7 (dd, $J_{P-C}$=57.2, $J_{P-C}$=2.6, C (z)-Bdppe), 137.9 (dd, $J_{P-C}$=30.6, $J_{P-C}$=1.5, C (z)-Bdppe), 137.3 (s, C Bzm), 137.3 (d, $J_{P-C}$=42.8, C (z)-Bdppe), 135.4 (s, C—H Ph), 134.3 (d, $J_{P-C}$=10.4, C—H (z)-Bdppe), 133.6 (s, C Bzm), 132.7 (d, $J_{P-C}$=10.0, C—H (z)-Bdppe), 130.5 (d, $J_{P-C}$=1.7, C—H (z)-Bdppe), 129.6 (d, $J_{P-C}$=9.3, C—H (z)-Bdppe), 129.6 (br, C—H (z)-Bdppe), 129.0 (d, $J_{P-C}$=9.0, C—H (z)-Bdppe), 128.3 (d, $J_{P-C}$=2.0, C—H (z)-Bdppe), 128.2 (d, $J_{P-C}$=0.6, C—H (z)-Bdppe). 128.0 (d, $J_{P-C}$=9.6, C—H (z)-Bdppe), 127.8 (d, $J_{P-C}$=7.9, C—H (z)-Bdppe), 127.5 (d, $J_{P-C}$=9.7, C—H (z)-Bdppe), 123.1 (d, $J_{P-C}$=4.9, C—H Ph), 121.9 (s, C—H Ph), 121.7 (s, C—H Bzm), 120.9 (s, C—H Bzm), 112.2 (d, $J_{P-C}$=2.6, C—H Ph), 109.6 (s, C—H Bzm), 108.2 (s, C—H Bzm), 101.2 (s, C—H Acac), 34.9 (d, $J_{P-C}$=4.7, N—CH$_3$), 27.7 (br, 2 CH$_3$ Acac). $^{31}$P{$^1$H}NMR (121.0 MHz, CD$_2$Cl$_2$, 293 K): δ 42.7 (d, $J_{P-P}$=18.5), 26.5 (d. $J_{P-P}$=18.5). This complex has been characterized by X-ray diffraction analysis. The resulting X-ray molecular structure is shown in FIG. 3. Selected bond lengths (Å) and angles (°) are: Os—P(1)=2.325(1), Os—P(2)=2.233(1), Os—C(1)=1.998(3), Os—C(10)=2.100(3), Os—O(1)=2.137(2), Os—O(2)=2.150(2), P(1)-Os—P(2)=83.65(3), C(1)-Os—C(10)=78.6(1), O(1)-Os—O(2)=86.19(9).

Experimental Data for Compound 428-2:

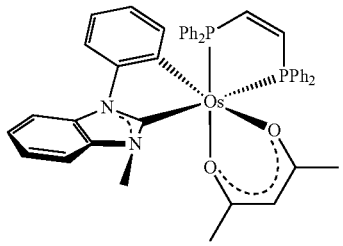

Yield 74 mg (24.6%). HRMS (electrospray, m/z): calculated for $C_{45}H_{41}N_2O_2OsP_2$ [M]$^+$: 894.2208. Found: 894.2177 IR: (cm$^{-1}$) υ(CO) 1578 (m), υ(CO) 1512(m). $^1$H NMR (300 MHz, CD$_2$Cl$_2$, 298 K): δ 8.12 (m, 2H, C—H Ph (z)-Bdppe), 7.92 (m, 2H, C—H Ph (z)-Bdppe), 7.84-7.08 (15H, 2C—H ethylene (z)-Bdppe, 9C—H Ph (z)-Bdppe, 4C—H Bzm), 6.98 (dd, J=7.8, J=1.0, 1H, C—H Ph), 6.89 (m, 2H, C—H Ph (z)-Bdppe), 6.75 (m, 1H, C—H Ph (z)-Bdppe), 6.66 (d, $J_{H-H}$=7.4, 1H, C—H Ph), 6.48 (ddd, $J_{H-H}$=7.6, $J_{H-H}$=7.6, $J_{H-H}$=1.4, 1H, C—H Ph), 6.34 (m, 2H, C—H Ph (z)-Bdppe), 6.19 (dd, $J_{H-H}$=7.4, $J_{H-H}$=7.4, $J_{H-H}$=1.1, 1H, C—H Ph), 6.06 (m, 2H, C—H Ph (z)-Bdppe), 5.04 (s, 1H, C—H Acac), 3.92 (s, 3H, N—CH$_3$), 1.60 and 1.20 (both s, each 3H, —CH$_3$ Acac). $^{13}$C$\{^1$H$\}$-APT NMR, HMBC and HSQC (75 MHz, CD$_2$Cl$_2$) δ 196.8 (dd, $J_{P-C}$=104.1, $J_{P-C}$=8.7, NCN Bzm), 184.2 (s, CO Acac), 183.4 (s, CO Acac), 153.8 (dd, $J_{P-C}$=45.9, $J_{P-C}$=28.4, C—H ethylene (z)-Bdppe), 152.6 (d, $J_{P-C}$=2.2, C Ph), 147.7 (dd, $J_{P-C}$=41.9, $J_{P-C}$=23.4, C—H ethylene (z)-Bdppe), 145.4 (dd, $J_{P-C}$=8.3, $J_{P-C}$=4.3, C—Os Ph), 144.4 (d, $J_{P-C}$=6.3, C—H Ph), 140.9 (d, $J_{P-C}$=42.6, C Ph (z)-Bdppe), 139.2 (d, $J_{P-C}$=35.3, C Ph (z) Bdppe), 137.8, (d, $J_{P-C}$=35.3, C Bzm), 137 (m, C Ph (z)-Bdppe), 136.2 (d, $J_{P-C}$=11.2, C—H Ph (z)-Bdppe), 135.2 (dd, $J_{P-C}$=34.3, $J_{P-C}$=2.4, C Ph (z)-Bdppe), 135.1 (d, $J_{P-C}$=11.0, C—H Bdppe), 133.8 (d, $J_{P-C}$=2.3C Bzm), 132.6 (d, $J_{P-C}$=10.4, C—H Ph (z)-Bdppe), 130.5 ($J_{P-C}$=1.6, C—H Ph (z)-Bdppe), 129.7-129.5 (m, 2C Ph (z)-Bdppe), 128.6 (d, $J_{P-C}$=9.1, C—H Ph (z)-Bdppe), 128.2 (s, C—H Ph (z)-Bdppe), 127.8 (d, $J_{P-C}$=9.5, C—H Ph (z)-Bdppe), 127.8 (d, $J_{P-C}$=8.1, C—H Ph (z)-Bdppe), 127.4 (d, $J_{P-C}$=2.0, C—H Ph (z)-Bdppe), 126.9 (d, $J_{P-C}$=9.7, C—H Ph (z)-Bdppe), 122.8 (s, C—H Bzm), 122.7 (s, C—H Ph), 121.7 (s, C—H Bzm), 118.9 (s, C—H Ph), 111.6 (s, C—H Ph), 111.0 (s, C—H Bzm), 109.5 (s, C—H Bzm), 101.9 (s, C—H Acac), 32.1 (s, N—CH$_3$), 28.1 (d, $J_{P-C}$=4.2, —CH$_3$ Acac), 27.6 (s, —CH$_3$ Acac). $^{31}$P$\{^1$H$\}$NMR (121.0 MHz, CD$_2$Cl$_2$, 293 K): δ 48.4 (d, $J_{P-P}$=10.9), 30.6 (d. $J_{P-P}$=10.9).

Preparation of Compound 1085:

KOH (4.3 mL, 0.259 M in MeOH) was added to a solution of complex bisacetonitrile-Bi3 (600 mg, 0.656 mmol), cis-1,2-bis(diphenylphosphino)ethylene ((z)-Bdppe) (259.9 mg, 0.657 mmol) and pentanodione (115 μL, 1.12 mmol) in THF (24 mL). The resulting red solution was stirred at 323 K for 3 h and then the solvent was concentrated under vacuum to dryness. CH$_2$Cl$_2$ was added and the resulting orange solution was extracted and concentrated to dryness under vacuum. The resulting ochre solid was washed with pentane (200 mL) affording a yellow powder (Compound 1085-1). The resulting orange pentane solution was extracted and concentrated to dryness under vacuum affording an orange solid which was purified by chromatography yielding Compound 1085-2.

Experimental Data for Compound 1085-1:

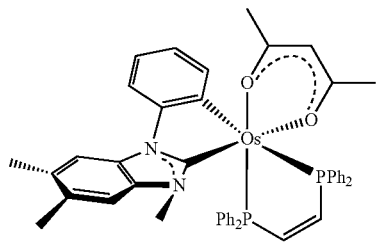

Yield: 245.2 mg (40.6%). HRMS (electrospray, m/z): calcd for $C_{47}H_{44}N_2O_2OsP_2$ [M]$^+$: 922.2506. found: 922.2491). IR: (cm$^{-1}$) υ(CO) 1581 (m), υ(CO) 1520 (m). $^1$H NMR (300 MHz, CD$_2$Cl$_2$, 298 K): δ 8.18-6.38 (28H, 22C—H (z)-Bdppe, C—H$_2$ Bzm, 4C—H Ph), 4.75 (s, 1H, C—H Acac), 2.57 (s, 3H, N—CH$_3$), 2.35 and 2.22 (both s, each 3H, —CH$_3$ Bzm), 1.50 and 1.23 (both s, each 3H, —CH$_3$ Acac). $^{13}$C$\{^1$H$\}$-APT NMR, HMBC and HSQC (75 MHz, CD$_2$Cl$_2$): δ 188.2 (dd, $J_{C-P}$=10.1, $J_{C-P}$=1.5, NCN Bzm), 182.7 (s, CO Acac), 181.2 (s, CO Acac), 164.8 (dd, $J_{P-C}$=85.5, $J_{P-C}$=6.9, C—Os Ph), 154.8 (dd, $J_{P-C}$=45.3, $J_{P-C}$=32.7, C—H ethylene (z)-Bdppe), 151.3 (d, $J_{P-C}$=2.2, C Ph), 150.6 (dd, $J_{P-C}$=35.9, $J_{P-C}$=21.9, C—H ethylene (z)-Bdppe), 139.5 (d, $J_{P-C}$=32.8, C (z)-Bdppe), 139.0 (dd, $J_{P-C}$=57.2, $J_{P-C}$=2.5, C (z)-Bdppe), 138.1 (dd, $J_{P-C}$=30.3, $J_{P-C}$=1.5, C (z)-Bdppe), 137.6 (d, $J_{P-C}$=42.8, C (z)-Bdppe), 135.8 (s, C Bzm), 135.5 (s, C—H Ph), 134.3 (d, $J_{P-C}$=10.4, C—H (z)-Bdppe), 132.7 (d, $J_{P-C}$=10.0, C—H (z)-Bdppe), 132.2 (s, C Bzm), 130.4 (d, $J_{P-C}$=1.4, C—H (z)-Bdppe), 130.1 (s, C Bzm), 129.8 (d, $J_{P-C}$=9.7, C—H (z)-Bdppe), 129.5 (d, $J_{P-C}$=1.9, C—H (z)-Bdppe), 129.4 (s, C Bzm), 129.0 (d, $J_{P-C}$=9.1, C—H (z)-Bdppe), 128.4 (d, $J_{P-C}$=2.0, C—H (z)-Bdppe), 128.1 (d, $J_{P-C}$=1.0, C—H (z)-Bdppe), 128.0 (d, $J_{P-C}$=10.0, C—H (z)-Bdppe), 127.9 (d, $J_{P-C}$=8.3C—H (z)-Bdppe), 127.6 (s, $J_{P-C}$=9.7, C—H (z)-Bdppe), 122.8 (d, $J_{P-C}$=5.0, C—H Ph), 121.8 (s, C—H Ph), 112.0 (d, $J_{P-C}$=2.6, C—H Ph), 110.8 (s, C—H Bzm), 109.1 (s, C—H Bzm), 101.1 (s, C—H Acac), 34.83 (d, $J_{P-C}$=5.0, N—CH$_3$), 27.7 and 27.6 (both s, —CH$_3$ Acac)), 20.49 and 20.19 (both s, —CH$_3$ Bzm). $^{31}$P$\{^1$H$\}$NMR (121.0 MHz, CD$_2$Cl$_2$, 293 K): δ 42.7 (d, $J_{P-P}$=18.1), 26.6 (d. $J_{P-P}$=18.1).

Experimental Data for Compound 1085-2:

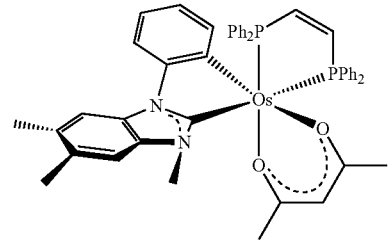

Figure 4:
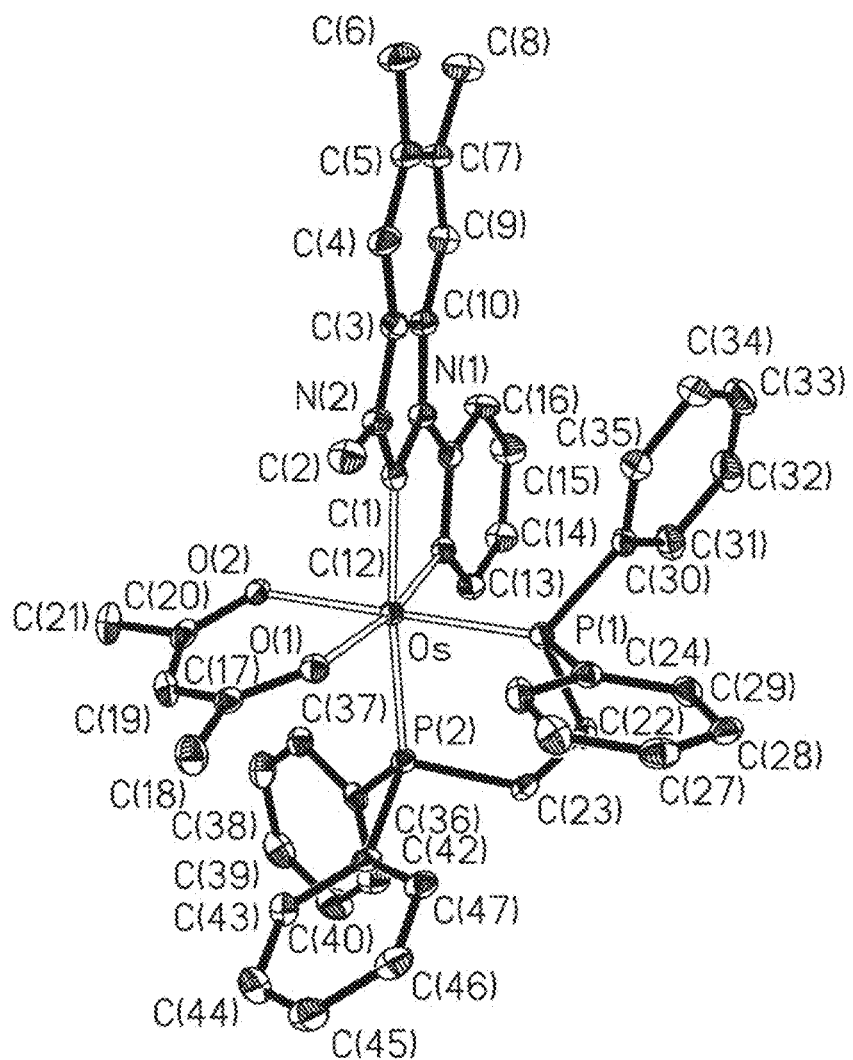
FIG. 4 shows molecular diagram of another osmium tribidentate complex, trisbidentatecomplex-Bi3 (2), disclosed herein with X-ray diffraction analysis characterization.

Yield: 153.7 mg (25.4%). HRMS (electrospray, m/z): calculated for $C_{47}H_{44}O_2OsN_2P_2$[M]$^+$: 922.2506. Found: 922.2491 IR: (cm$^{-1}$) υ(CO) 1581 (m), υ(CO) 1515 (m). $^1$H NMR (300 MHz, CD$_2$Cl$_2$, 298 K): δ 8.11 (m, 2H, C—H Ph (z)-Bdppe), 7.91 (m, 2H, C—H Ph (z)-Bdppe), 7.73 (ddd, $J_{H-P}$=46.8, $J_{H-P}$=8.7 Hz, $J_{H-H}$=8.7 Hz, 1H, C—H ethylene (z)-Bdppe), 7.57-7.04 (12H, 1C—H ethylene (z)-Bdppe, 9C—H Ph (z)-Bdppe, 2C—H Bzm), 6.96 (d, J=7.4, 1H, C—H Ph), 6.89 (m, 2H, C—H Ph (z)-Bdppe), 6.76 (m, 1H, C—H Ph (z)-Bdppe), 6.62 (d, $J_{H-H}$=7.4, 1H, C—H Ph), 6.45 (dd, $J_{H-H}$=7.4, $J_{H-H}$=7.4, 1H, C—H Ph), 6.36 (m, 2H, C—H Ph (z)-Bdppe), 6.15 (dd, $J_{H-H}$=7.4, $J_{H-H}$=7.4, 1H, C—H Ph), 6.07 (m, 2H, C—H Ph (z)-Bdppe), 5.02 (s, 1H, C—H Acac), 3.87 (s, 3H, N—CH$_3$), 2.40 and 2.36 (both s, each 3H, —CH$_3$ Bzm), 1.59 and 1.19 (both s, each 3H, —CH$_3$ Acac). $^{13}$C$\{^1$H$\}$-APT NMR, HMBC and HSQC (75 MHz, CD$_2$Cl$_2$) δ 195.6 (dd, $J_{P-C}$=103.6, $J_{P-C}$=7.7, NCN Bzm), 184.1 (s, CO Acac), 183.3 (s, CO Acac), 153.8 (dd, $J_{P-C}$=45.7, $J_{P-C}$=28.5, C—H ethylene (z)-Bdppe), 152.8 (d, $J_{P-C}$=1.9, C Ph), 147.8 (dd, $J_{P-C}$=41.7, $J_{P-C}$=23.2, C—H ethylene (z)-Bdppe), 145.2 (dd, $J_{P-C}$=7.2, $J_{P-C}$=3.5, C—Os Ph), 144.4 (d, $J_{P-C}$=6.2, C—H Ph), 141.1 (d, $J_{P-C}$=42.5, C Ph (z)-Bdppe), 139.4 (d, $J_{P-C}$=35.0, C Ph (z) Bdppe), 137.1, 136.4 and 133.5 (3C, C Bzm, 2C Ph (z)-Bdppe), 136.2 (d, $J_{P-C}$=11.2, C—H Ph (z)-Bdppe), 135.1 (d, $J_{P-C}$=10.9, C—H Ph (z)-Bdppe), 132.6 (d, $J_{P-C}$=10.3, C—H Ph (z)-Bdppe), 132.3 (d, $J_{P-C}$=2.4, C Bzm), 131.4 and 130.5 (both s, C Bzm), 130.4 (d, $J_{P-C}$=1.6, C—H Ph (z)-Bdppe), 129.7 (d, $J_{P-C}$=9.1, C—H Ph (z)-Bdppe), 129.6 (d, $J_{P-C}$=0.6, C—H Ph (z)-Bdppe), 128.6 (d, $J_{P-C}$=9.0, C—H Ph (z)-Bdppe), 128.2 (s, C—H Ph (z)-Bdppe), 127.8 (d, $J_{P-C}$=9.4, C—H Ph (z)-Bdppe), 127.7 (d, $J_{P-C}$=8.1, C—H Ph (z)-Bdppe), 127.3 (s, C—H Ph (z)-Bdppe), 126.9 (d, $J_{P-C}$=9.6, C—H Ph (z)-Bdppe), 122.4 (s, C—H Ph), 118.8 (s, C—H Ph), 111.9 (s, C—H Bzm), 111.4 (s, C—H Ph), 110.2 (s, C—H Bzm), 101.9 (s, C—H Acac), 32.0 (s, N—CH$_3$), 28.0 (d, $J_{P-C}$=3.9, —CH$_3$ Acac), 27.6 (s, —CH$_3$ Acac), 20.7 and 20.5 (both s, —CH$_3$ Bzm). $^{31}$P{$^{1}$H}NMR (121.0 MHz, CD$_2$Cl$_2$, 293 K): δ 48.5 (d, $J_{P-P}$=10.9), 30.7 (d. $J_{P-P}$=10.9). This complex has been characterized by X-ray diffraction analysis. The X-ray molecular structure is shown in FIG. 4. Selected bond lengths (A) and angles (°) are: Os—P(1)=2.2270(7), Os—P(2)=2.3155(7), Os—C(1)=2.049(3), Os—C(12)=2.066(3), Os—O(1)=2.178(1), Os—O(2)=2.150(2), P(1)-Os—P(2)=83.24(3), C(1)-Os—C(12)=78.3(1), O(1)-Os—O(2)=84.57(7).

According to one aspect of the present disclosure, a compound having the formula Os(L$^1$)(L$^2$)(L$^3$) is disclosed wherein L$^1$, L$^2$ and L$^3$ are independently a bidentate ligand; and wherein each of L$^1$, L$^2$ and L$^3$ is different from each other. In one embodiment of the compound, the ligands L$^1$, L$^2$ and L$^3$ are independently selected from the group of ligands LIST-A as defined above. According to another embodiment of the compound, the ligands L$^1$, L$^2$ and L$^3$ are independently selected from the group of ligands LIST-B as defined above. According to another embodiment of the compound, the ligands L$^1$, L$^2$ and L$^3$ are independently selected from the group of ligands LIST-C as defined above. According to another embodiment of the compound, the ligands L$^1$, L$^2$ and L$^3$ are independently selected from the group of ligands LIST-D as defined above.

According to another aspect of the present disclosure, the compound having the formula Os(L$^1$)(L$^2$)(L$^3$) is selected from the group consisting of Compounds 1 to 4176 defined in Table 1 provided above. Table 2 provides a group of preferred compounds.

According to another aspect of the present disclosure, a first device comprising a first organic light emitting device is disclosed. The first organic light emitting device comprises an anode; a cathode; and an organic layer disposed between the anode and the cathode. The organic layer comprises a compound having the formula Os(L$^1$)(L$^2$)(L$^3$), wherein L$^1$, L$^2$ and L$^3$ are independently a bidentate ligand, and wherein each of L$^1$, L$^2$ and L$^3$ is different from each other.

In an embodiment of the first device, the ligands L$^1$, L$^2$ and L$^3$ in the compound having the formula Os(L$^1$)(L$^2$)(L$^3$) are independently selected from the group of ligands LIST-A as defined above. According to another embodiment of the first device, the ligands L$^1$, L$^2$ and L$^3$ in the compound having the formula Os(L$^1$)(L$^2$)(L$^3$) are independently selected from the group of ligands LIST-B as defined above. According to another embodiment of the first device, the ligands L$^1$, L$^2$ and L$^3$ in the compound having the formula Os(L$^1$)(L$^2$)(L$^3$) are independently selected from the group of ligands LIST-C as defined above. According to another embodiment of the first device, the ligands L$^1$, L$^2$ and L$^3$ in the compound having the formula Os(L$^1$)(L$^2$)(L$^3$) are independently selected from the group of ligands LIST-D as defined above.

The first device can be a consumer product. The first device can be an organic light emitting device. The first device can comprise a light panel.

In another embodiment of the first device, the organic layer is an emissive layer and the compound is an emissive dopant. In another embodiment, the compound is a non-emissive dopant in the emissive layer.

In another embodiment of the first device, the organic layer further comprises a host material. The host material can comprise a triphenylene containing benzo-fused thiophene or benzo-fused furan; wherein any substituent in the host material is an unfused substituent independently selected from the group consisting of C$_n$H$_{2n+1}$, OC$_n$H$_{2n+1}$, OAr$_1$, N(C$_n$H$_{2n+1}$)$_2$, N(Ar$_1$)(Ar$_2$), CH=CH—C$_n$H$_{2n+1}$, C≡C—C$_n$H$_{2n+1}$, Ar$_1$, Ar$_1$—Ar$_2$, C$_n$H$_{2n}$—Ar$_1$, or no substitution;

wherein n is from 1 to 10; and wherein Ar$_1$ and Ar$_2$ are independently selected from the group consisting of benzene, biphenyl, naphthalene, triphenylene, carbazole, and heteroaromatic analogs thereof.

In another embodiment, the host material comprises at least one chemical group selected from the group consisting of carbazole, dibenzothiphene, dibenzofuran, dibenzoselenophene, azacarbazole, aza-dibenzothiophene, aza-dibenzofuran, and aza-dibenzoselenophene.

In another embodiment, the host material is selected from the group consisting of

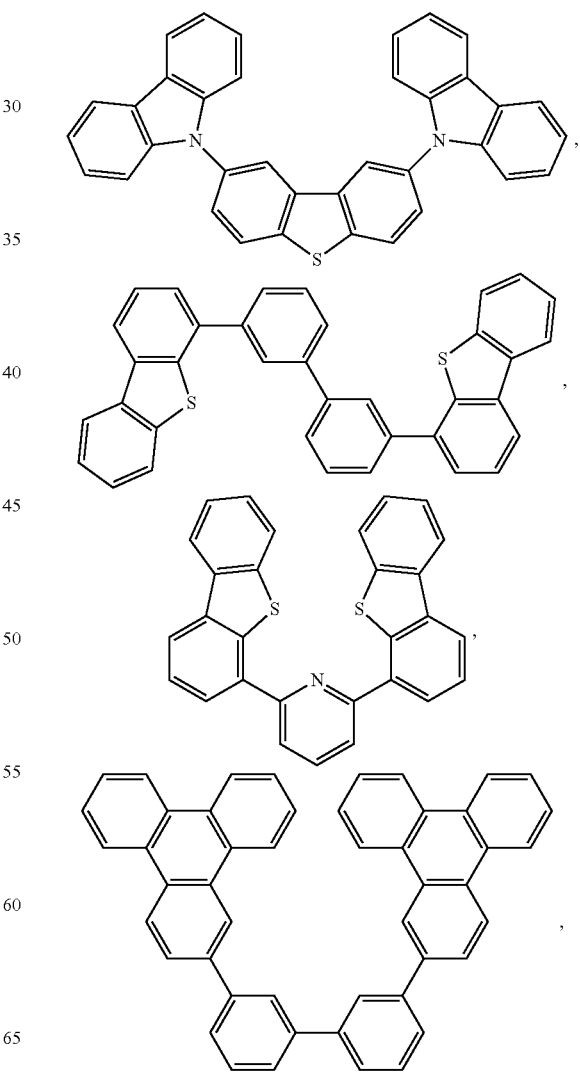

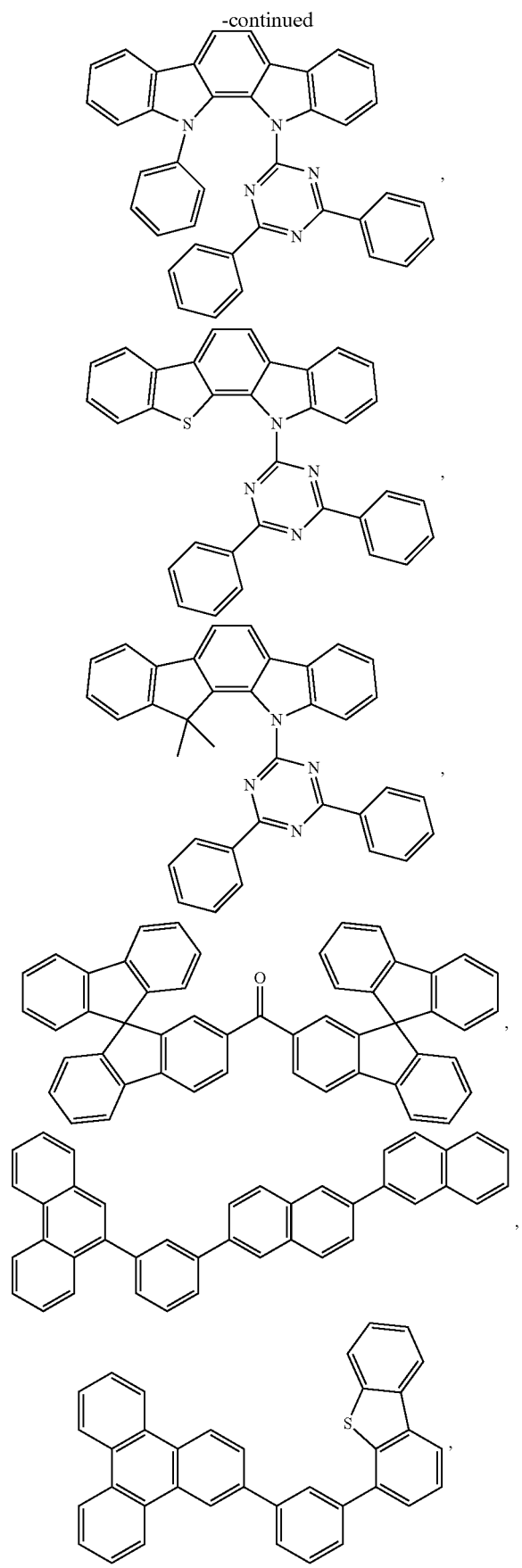

and combinations thereof.

In yet another embodiment, the host material comprises a metal complex.

According to another aspect of the present disclosure, a novel formulation is disclosed. The formulation comprises a compound having a structure according to the formula $Os(L^1)(L^2)(L^3)$, wherein $L^1$, $L^2$ and $L^3$ are independently a bidentate ligand, and wherein each of $L^1$, $L^2$ and $L^3$ is different from each other.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoOx; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

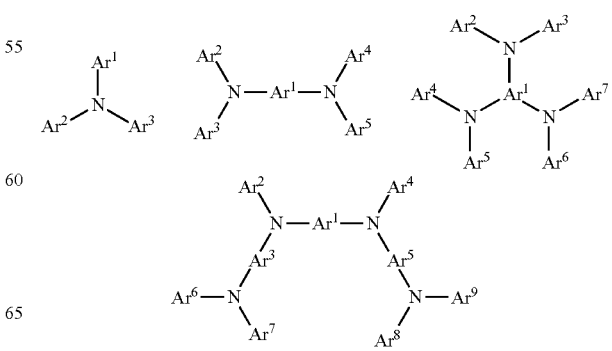

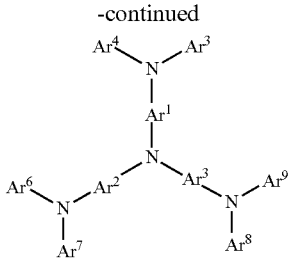

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

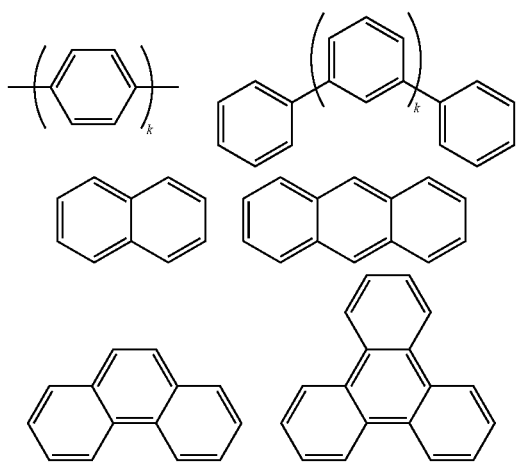

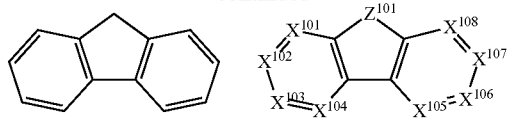

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

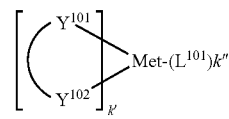

wherein Met is a metal, which can have an atomic weight greater than 40; $(Y^{101}-Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}-Y^{102})$ is a 2-phenylpyridine derivative. In another aspect, $(Y^{101}-Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

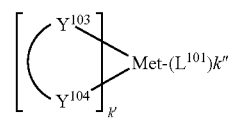

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

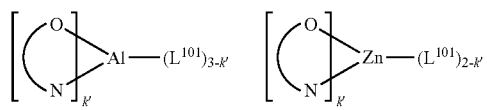

wherein (O—N) is a bidentate ligand, having metal coordinated to atoms O and N.

In another aspect, Met is selected from Ir and Pt. In a further aspect, ($Y^{103}$—$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

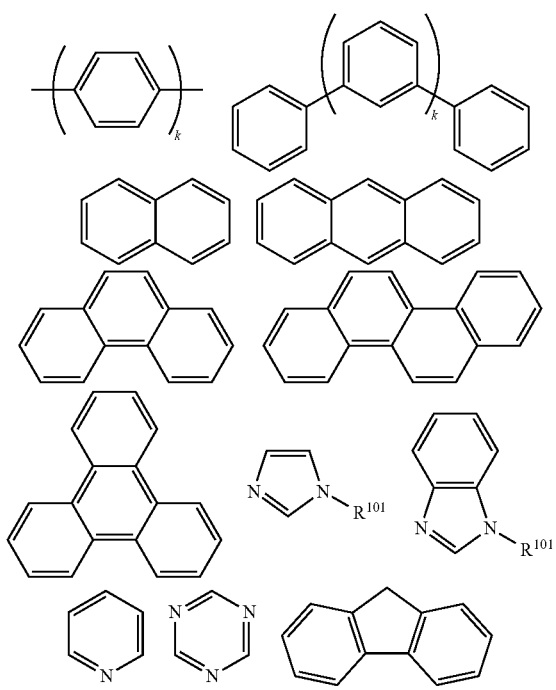

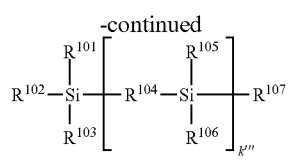

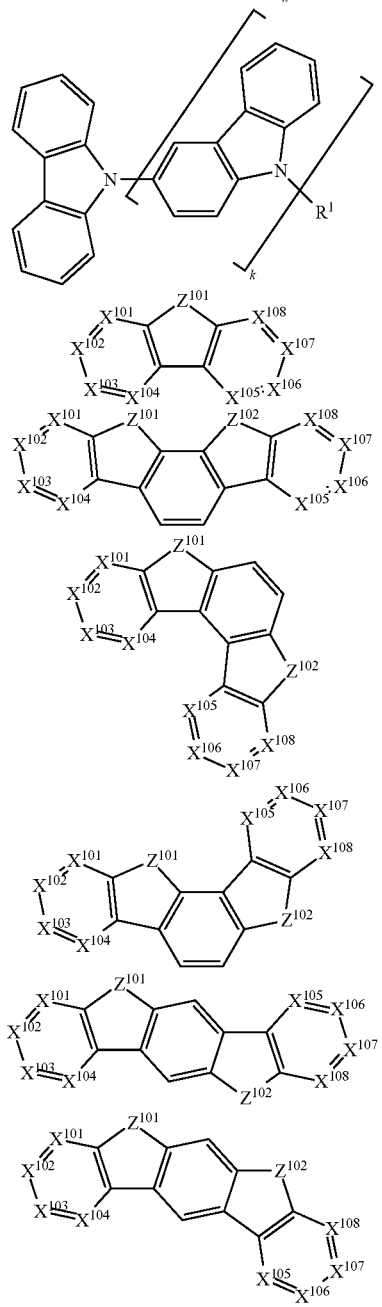

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

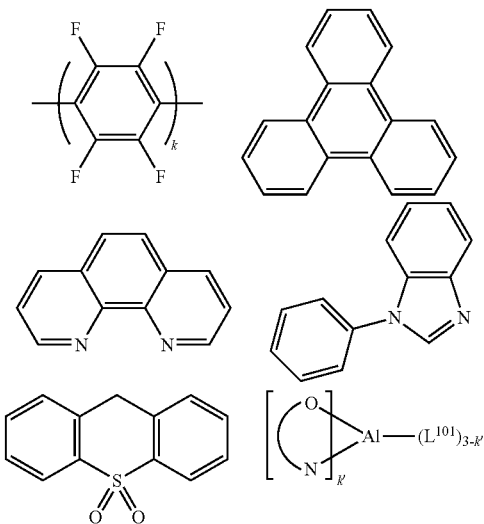

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

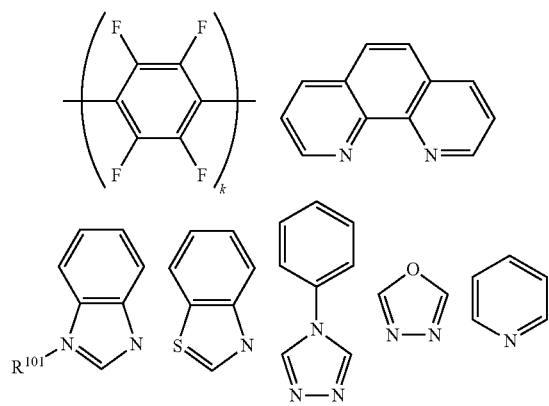

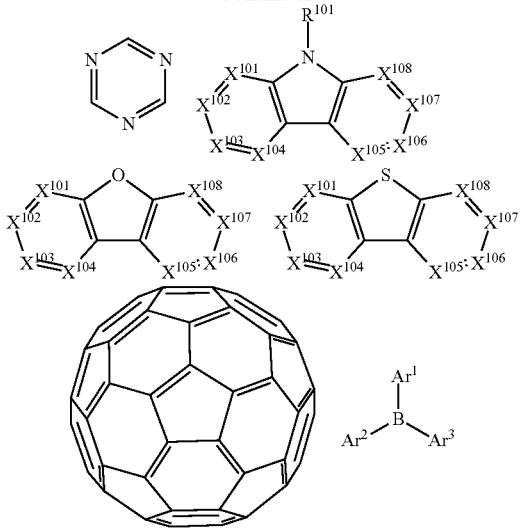

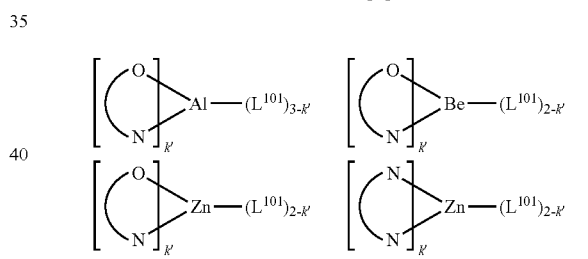

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

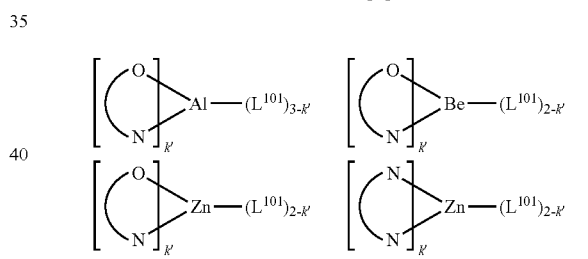

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 3 below. Table 3 lists non-limiting classes of materials, non-limiting examples of compounds for each class, and references that disclose the materials.

TABLE 3

| MATERIAL | EXAMPLES OF MATERIAL | PUBLICATIONS |
| --- | --- | --- |
| Hole injection materials | | |
| Phthalocyanine and porphryin compounds | (Cu phthalocyanine structure) | Appl. Phys. Lett. 69, 2160 (1996) |
| Starburst triarylamines | (starburst triarylamine structure) | J. Lumin. 72-74, 985 (1997) |
| CF$_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polypthiophene) | (PEDOT:PSS structure) | Synth. Met. 87, 171 (1997) WO2007002683 |
| Phosphonic acid and silane SAMs | (N(C$_6$H$_4$SiCl$_3$)$_3$ structure) | US20030162053 |

TABLE 3-continued
| MATERIAL | EXAMPLES OF MATERIAL | PUBLICATIONS |
|---|---|---|
| Triarylamine or polythiophene polymers with conductivity dopants | 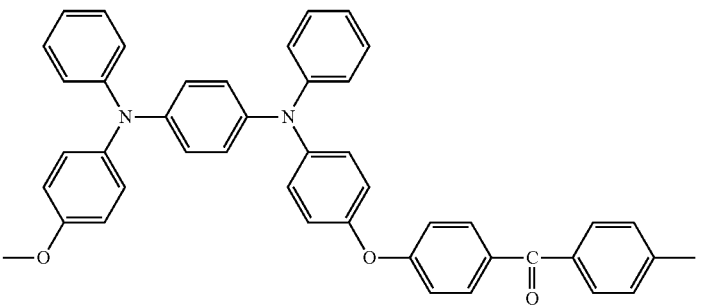 and 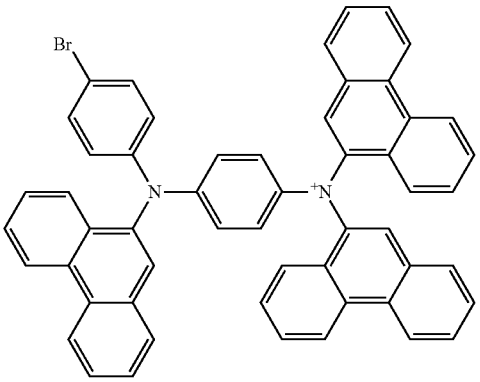 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | EP1725079A1 |
| Organic compounds with conductive inorganic compounds, such as molybdenum and tungsten oxides | 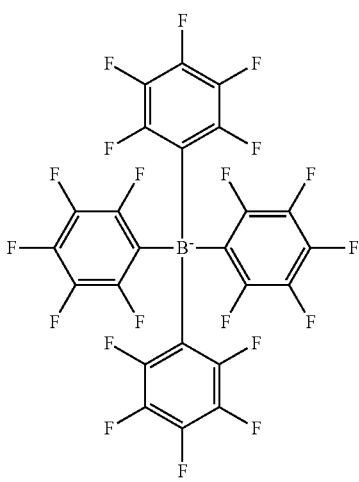 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] + MoO$_x$ | US20050123751 SID Symposium Digest, 37, 923 (2006) WO2009018009 |

TABLE 3-continued

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 3-continued
| MATERIAL | EXAMPLES OF MATERIAL | PUBLICATIONS |
| --- | --- | --- |
| Hole transporting materials | | |
| Triarylamines (e.g., TPD, α-NPD) | 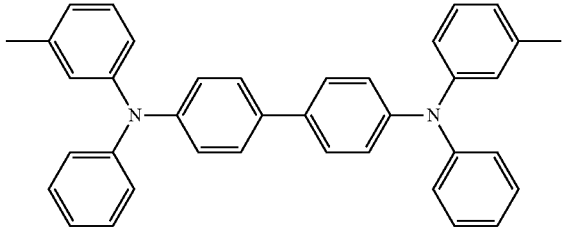 | Appl. Phys. Lett. 51, 913 (1987) |
| | 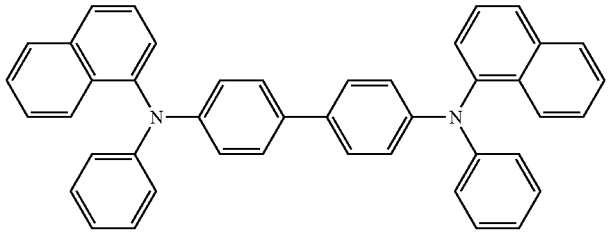 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 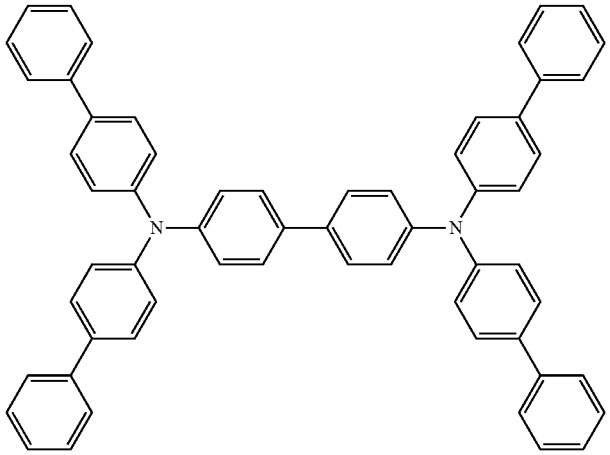 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 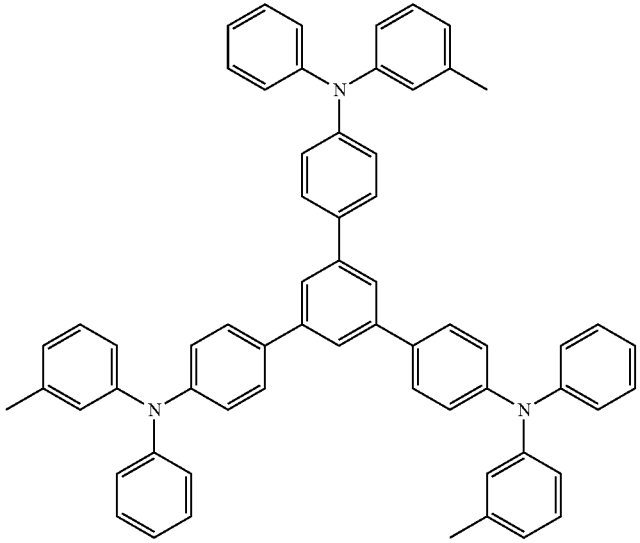 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 3-continued

| MATERIAL | EXAMPLES OF MATERIAL | PUBLICATIONS |
| --- | --- | --- |
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 3-continued
| MATERIAL | EXAMPLES OF MATERIAL | PUBLICATIONS |
|---|---|---|
| Triarylamine with (di)benzothiophene/ (di)benzofuran | 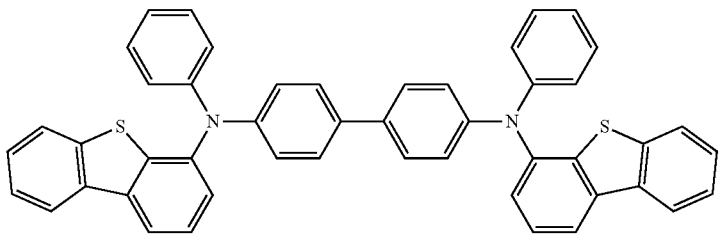 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 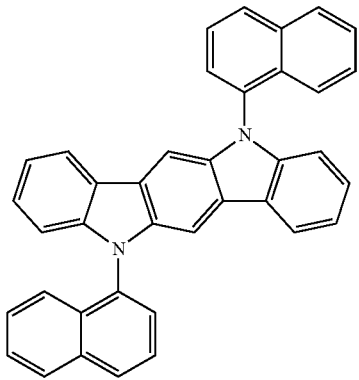 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 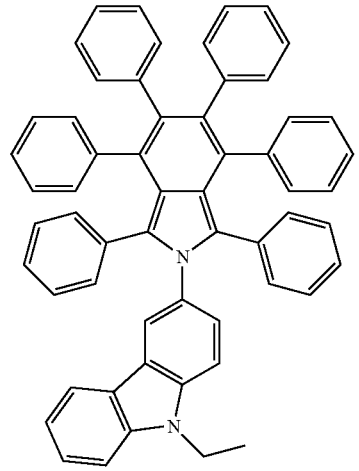 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 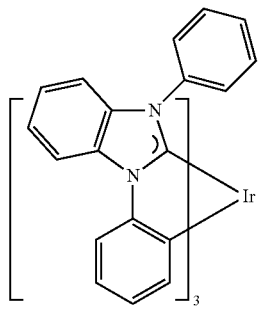 | US20080018221 |

TABLE 3-continued

| MATERIAL | EXAMPLES OF MATERIAL | PUBLICATIONS |
| --- | --- | --- |
| Phosphorescent OLED host materials Red hosts | | |
| Arylcarbazoles | | Appl. Phys. Lett. 78, 1622 (2001) |
| Metal 8-hydroxyquinolates (e.g., Alq₃, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 3-continued

| MATERIAL | EXAMPLES OF MATERIAL | PUBLICATIONS |
|---|---|---|
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
|---|---|---|
| Arylcarbazoles | | Appl. Phys. Lett. 78, 1622 (2001) |
| | | US20030175553 |
| | | WO2001039234 |

| MATERIAL | EXAMPLES OF MATERIAL | PUBLICATIONS |
|---|---|---|
| Aryltriphenylene compounds | 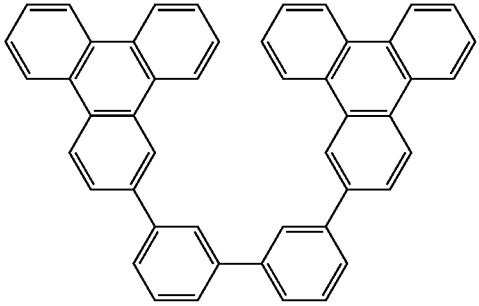 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 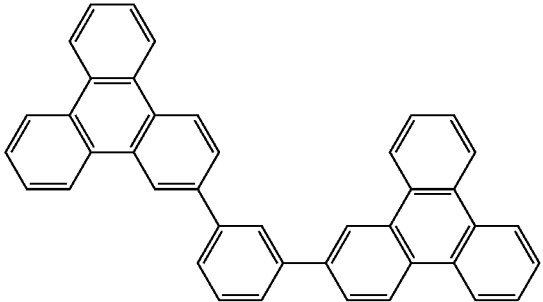 [SMILES: c1cc(-c2ccc3c4ccccc4c4ccccc4c3c2)cc(-c2ccc3c4ccccc4c4ccccc4c3c2)c1] | US20060280965 |
| | 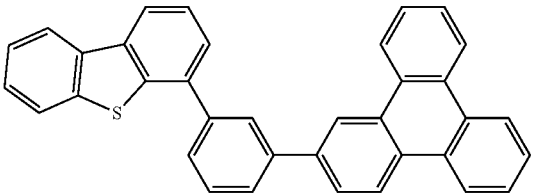 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 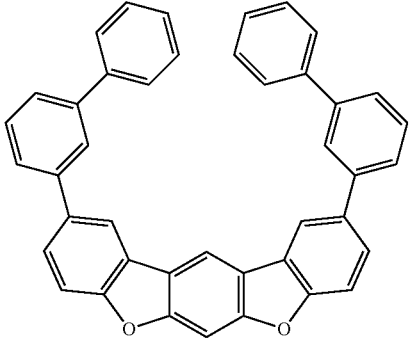 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 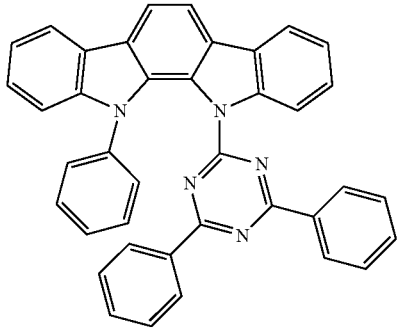 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 3-continued

| MATERIAL | EXAMPLES OF MATERIAL | PUBLICATIONS |
|---|---|---|
| | | WO2010107244 |
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |

TABLE 3-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 3-continued

| MATERIAL | EXAMPLES OF MATERIAL | PUBLICATIONS |
| --- | --- | --- |
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 3-continued

| MATERIAL | EXAMPLES OF MATERIAL | PUBLICATIONS |
|---|---|---|
| Metal phenoxypyridine compounds | | WO2005030900 |
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 3-continued
| MATERIAL | EXAMPLES OF MATERIAL | PUBLICATIONS |
|---|---|---|
| | 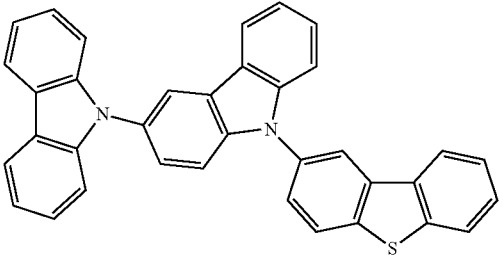 [SMILES: c1ccc2c(c1)sc1ccc(-n3c4ccccc4c4cc(-n5c6ccccc6c6ccccc65)ccc43)cc12] | WO2009086028 |
| | 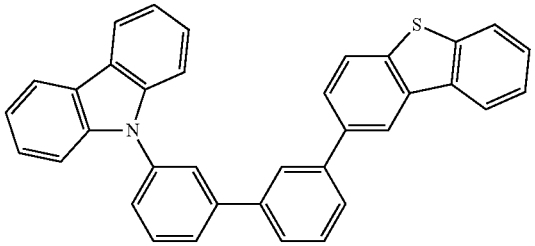 [SMILES: c1cc(-c2cccc(-n3c4ccccc4c4ccccc43)c2)cc(-c2ccc3sc4ccccc4c3c2)c1] | US20090030202, US20090017330 |
| | 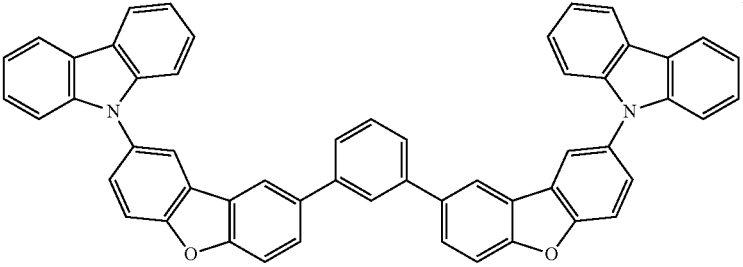 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 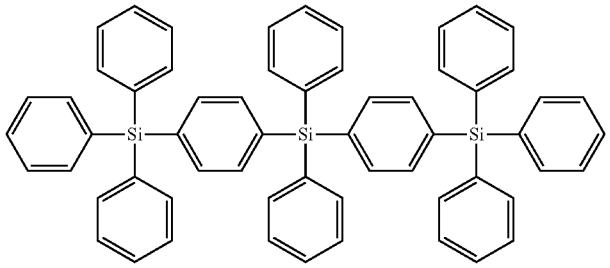 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 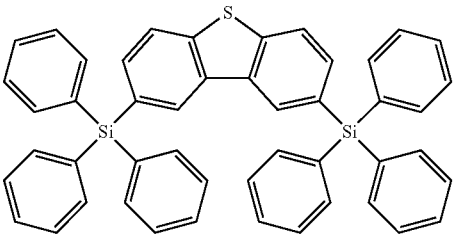 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 3-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE 3-continued

| MATERIAL | EXAMPLES OF MATERIAL | PUBLICATIONS |
|---|---|---|
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

TABLE 3-continued
| MATERIAL | EXAMPLES OF MATERIAL | PUBLICATIONS |
|---|---|---|
| | 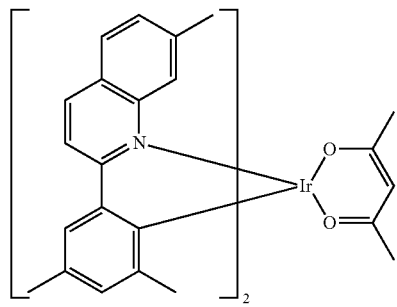 | US20060202194 |
| | 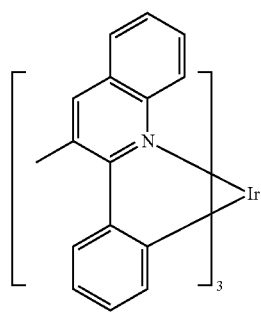 | US20070087321 |
| | 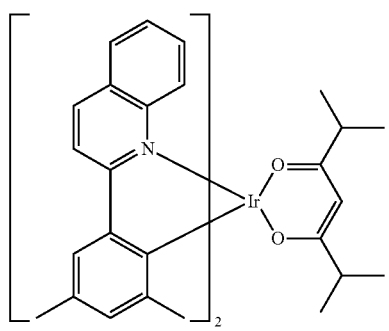 | US20080261076<br>US20100090591 |
| | 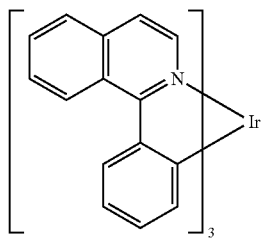 | US20070087321 |
| | 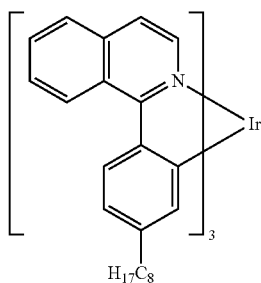 | Adv. Mater. 19, 739 (2007) |

TABLE 3-continued

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE 3-continued
| MATERIAL | EXAMPLES OF MATERIAL | PUBLICATIONS |
| --- | --- | --- |
| Osminum(III) complexes | 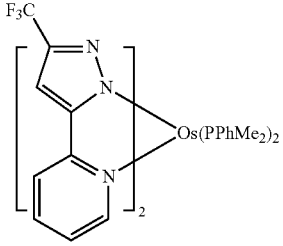 | Chem. Mater. 17, 3532 (2005) |
| Ruthenium(II) complexes | 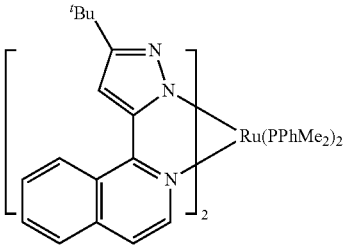 | Adv. Mater. 17, 1059 (2005) |
| Rhenium (I), (II), and (III) complexes | 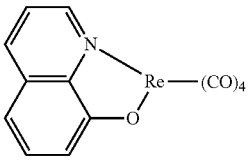 | US20050244673 |
Green dopants
| | | |
| --- | --- | --- |
| Iridium(III) organometallic complexes | 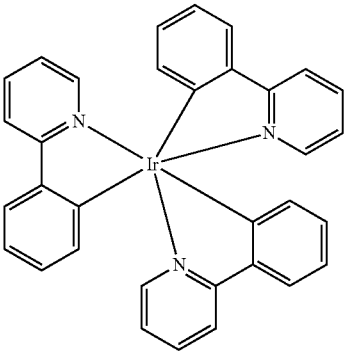<br>and its derivatives | Inorg. Chem. 40, 1704 (2001) |
| | 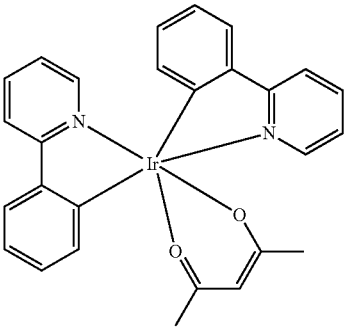 | US20020034656 |

TABLE 3-continued
| MATERIAL | EXAMPLES OF MATERIAL | PUBLICATIONS |
|---|---|---|
| | 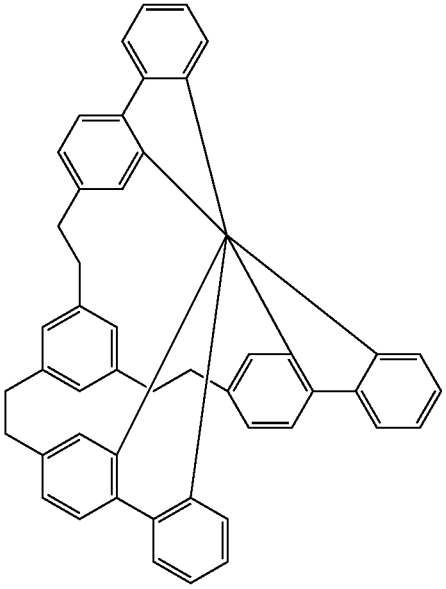 | U.S. Pat. No. 7,332,232 |
| | 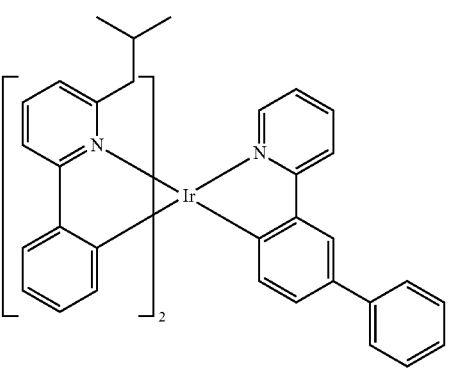 | US20090108737 |
| | 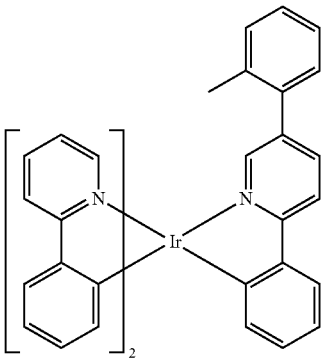 | WO2010028151 |

TABLE 3-continued
| MATERIAL | EXAMPLES OF MATERIAL | PUBLICATIONS |
|---|---|---|
| | 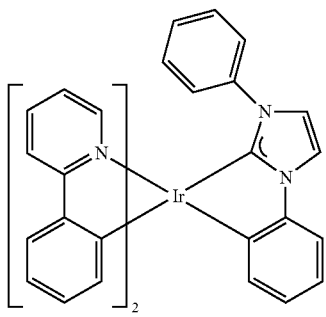 | EP1841834B |
| | 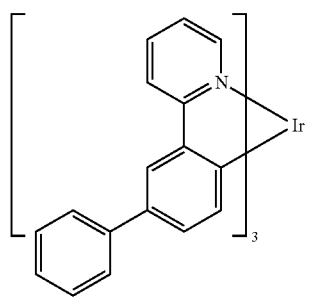 | US20060127696 |
| | 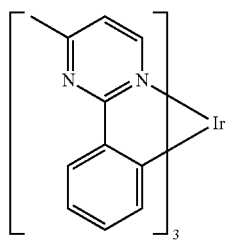 | US20090039776 |
| | 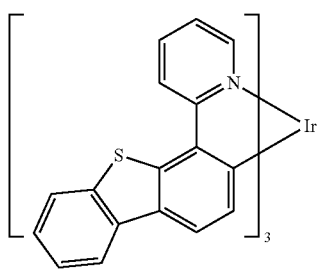 | U.S. Pat. No. 6,921,915 |
| | 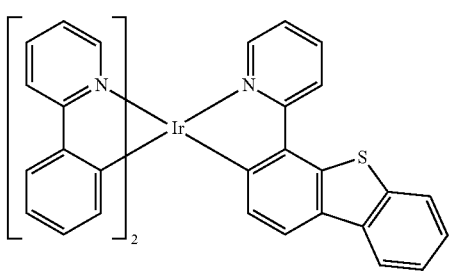 | US20100244004 |

TABLE 3-continued
| MATERIAL | EXAMPLES OF MATERIAL | PUBLICATIONS |
|---|---|---|
| | 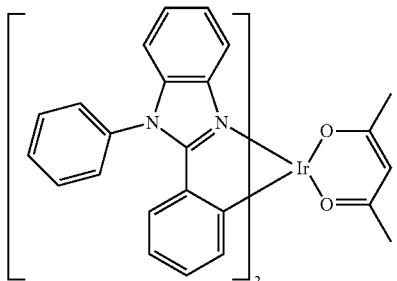 | U.S. Pat. No. 6,687,266 |
| | 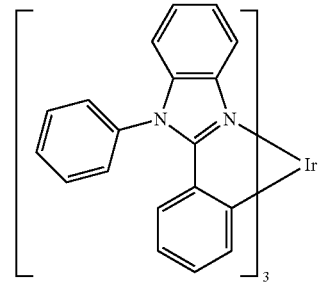 | Chem. Mater. 16, 2480 (2004) |
| | 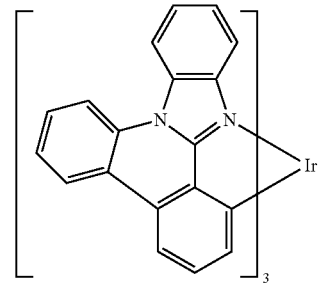 | US20070190359 |
| | 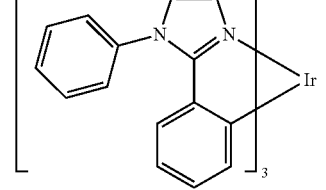 | US 20060008670 JP2007123392 |
| | 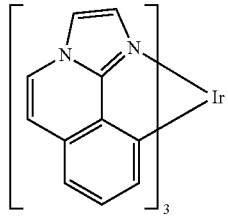 | WO2010086089, WO2011044988 |
| | 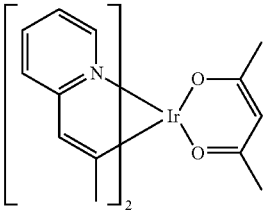 | Adv. Mater. 16, 2003 (2004) |

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 3-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 3-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 3-continued

| MATERIAL | EXAMPLES OF MATERIAL | PUBLICATIONS |
| --- | --- | --- |
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |
| Deuterated organometallic complexes | | US20030138657 |

TABLE 3-continued
| MATERIAL | EXAMPLES OF MATERIAL | PUBLICATIONS |
|---|---|---|
| Organometallic complexes with two or more metal centers | 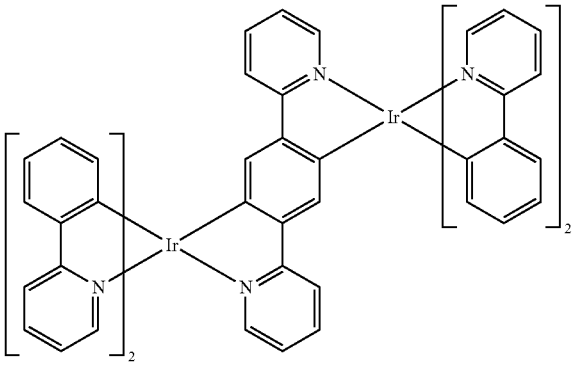 | US20030152802 |
| | 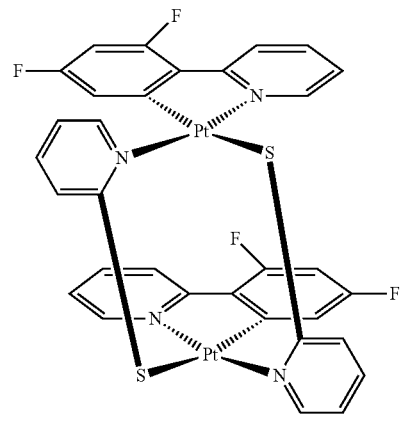 | U.S. Pat. No. 7,090,928 |
| Blue dopants | | |
| Iridium(III) organometallic complexes | 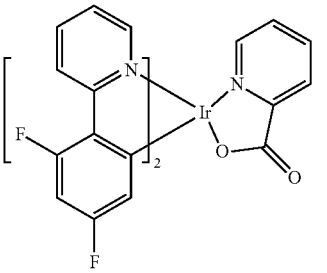 | WO2002002714 |
| | 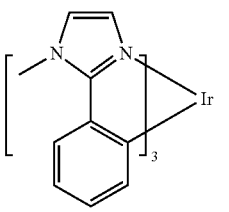 | WO2006009024 |
| | 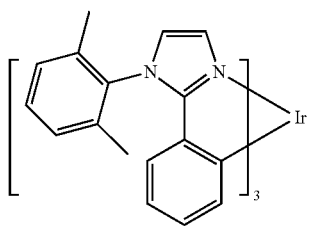 | US20060251923<br>US20110057559<br>US20110204333 |

TABLE 3-continued
| MATERIAL | EXAMPLES OF MATERIAL | PUBLICATIONS |
|---|---|---|
| | 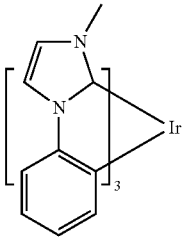 | U.S. Pat. No. 7,393,599, WO2006056418, US20050260441, WO2005019373 |
| | 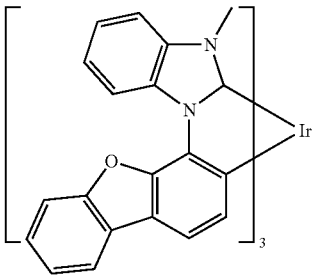 | U.S. Pat. No. 7,534,505 |
| | 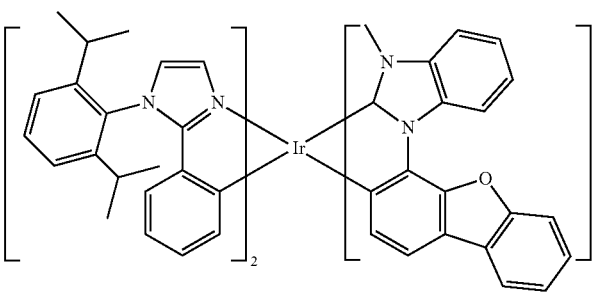 | WO2011051404 |
| | 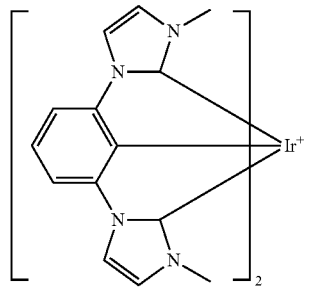 | U.S. Pat. No. 7,445,855 |
| | 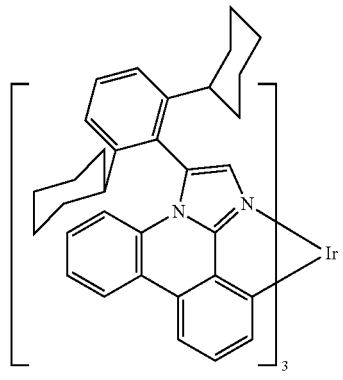 | US20070190359, US20080297033 US20100148663 |

TABLE 3-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 4542 (2008) |
| | | Chem. Mater. 18, 5119 (2006) |
| | | Inorg. Chem. 46, 4308 (2007) |

| MATERIAL | EXAMPLES OF MATERIAL | PUBLICATIONS |
|---|---|---|
| | 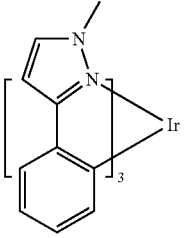 | WO2005123873 |
| | 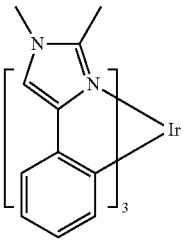 | WO2005123873 |
| | 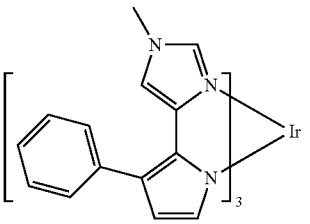 | WO2007004380 |
| | 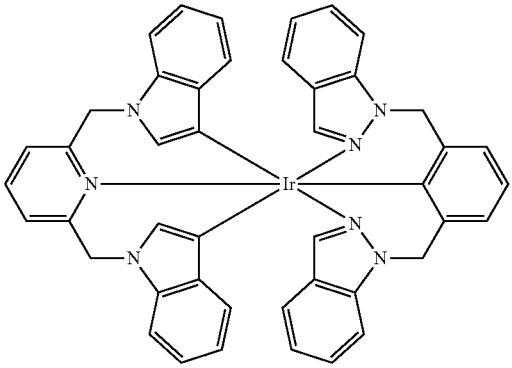 | WO2006082742 |
| Osmium(II) complexes | 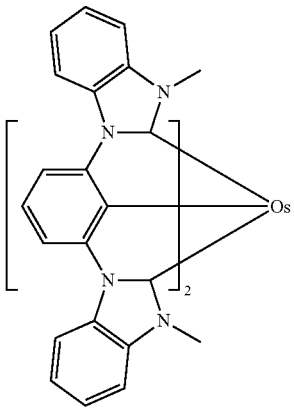 | U.S. Pat. No. 7,279,704 |

| MATERIAL | EXAMPLES OF MATERIAL | PUBLICATIONS |
|---|---|---|
| | 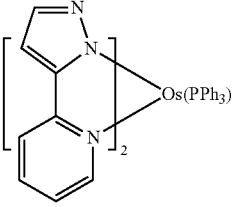 | Organometallics 23, 3745 (2004) |
| Gold complexes | 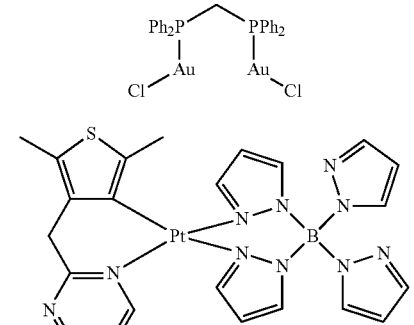 | Appl. Phys. Lett. 74, 1361 (1999) |
| Platinum(II) complexes | 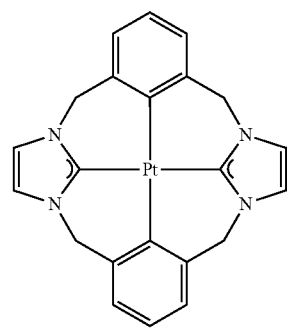 | WO2006098120, WO2006103874 |
| Pt tetradentate complexes with at least one metal-carbene bond | 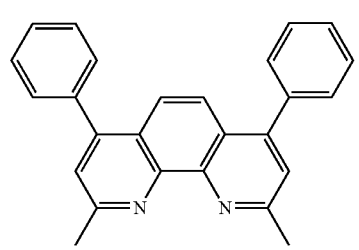 [SMILES: Cc1cc(-c2ccccc2)c2ccc3c(-c4ccccc4)cc(C)nc3c2n1] | U.S. Pat. No. 7,655,323 |
| Exciton/hole blocking layer materials | | |
| Bathocuprine compounds (e.g., BCP, BPhen) | 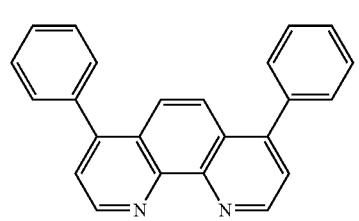 | Appl. Phys. Lett. 75, 4 (1999) |
| | 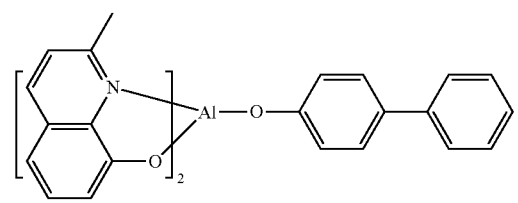 | Appl. Phys. Lett. 79, 449 (2001) |
| Metal 8-hydroxyquinolates (e.g., BAlq) | | Appl. Phys. Lett. 81, 162 (2002) |

TABLE 3-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 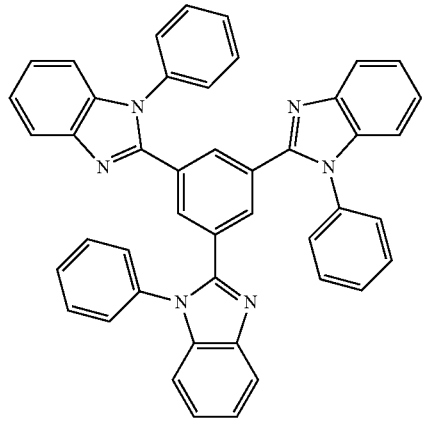 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 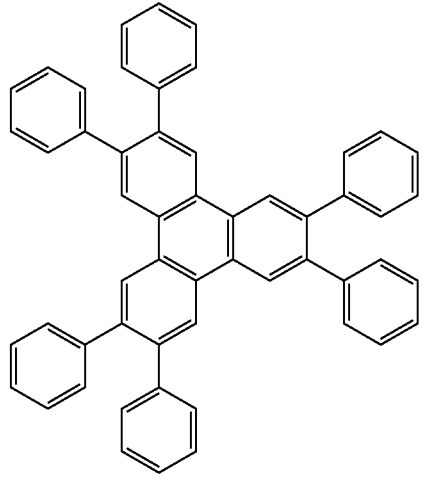 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 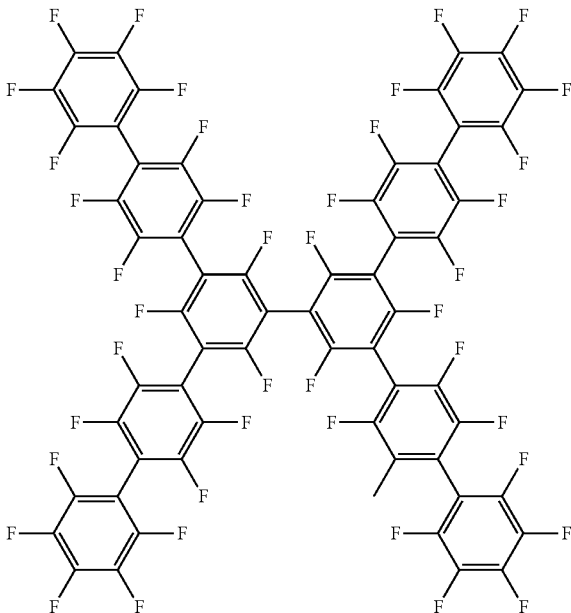 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 3-continued

| MATERIAL | EXAMPLES OF MATERIAL | PUBLICATIONS |
| --- | --- | --- |
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE 3-continued
| MATERIAL | EXAMPLES OF MATERIAL | PUBLICATIONS |
|---|---|---|
| Aza triphenylene derivatives | 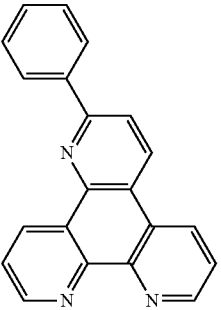 [SMILES: c1ccc(-c2ccc3c4cccnc4c4ncccc4c3n2)cc1] | US20090115316 |
| Anthracene-benzothiazole compounds | 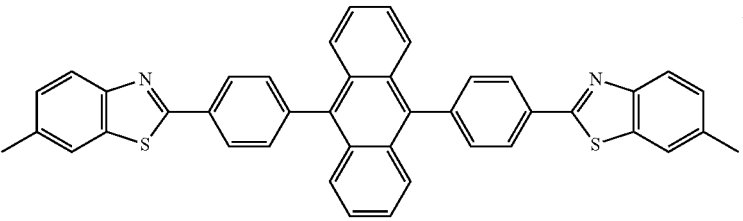 | Appl. Phys. Lett. 89, 063504 (2006) |
| Metal 8-hydroxyquinolates (e.g., Alq$_3$, Zrq$_4$) | 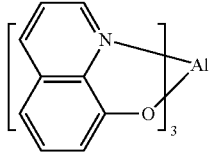 | Appl. Phys. Lett. 51, 913 (1987) U.S. Pat. No. 7,230,107 |
| Metal hydroxybenoquinolates | 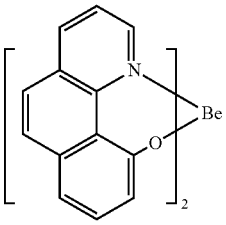 | Chem. Lett. 5, 905 (1993) |
| Bathocuprine compounds such as BCP, BPhen, etc | 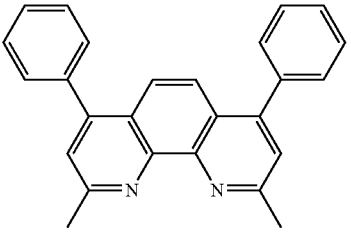 [SMILES: Cc1cc(-c2ccccc2)c2ccc3c(-c4ccccc4)cc(C)nc3c2n1] | Appl. Phys. Lett. 91, 263503 (2007) |
| | 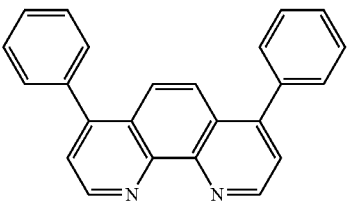 [SMILES: c1ccc(-c2ccnc3c2ccc2c(-c4ccccc4)ccnc23)cc1] | Appl. Phys. Lett. 79, 449 (2001) |

TABLE 3-continued

| MATERIAL | EXAMPLES OF MATERIAL | PUBLICATIONS |
| --- | --- | --- |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |

TABLE 3-continued

| MATERIAL | EXAMPLES OF MATERIAL | PUBLICATIONS |
| --- | --- | --- |
| Fullerene (e.g., C60) | 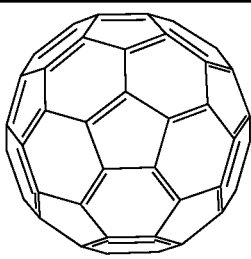 | US20090101870 |
| Triazine complexes | 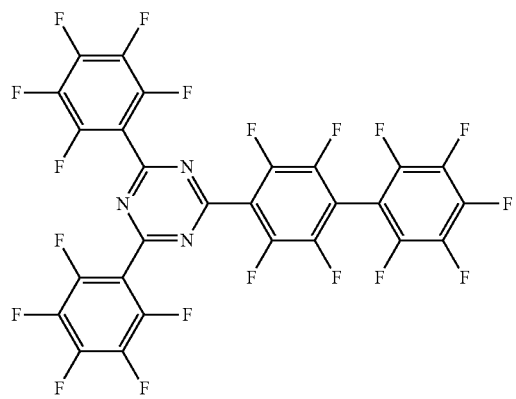 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 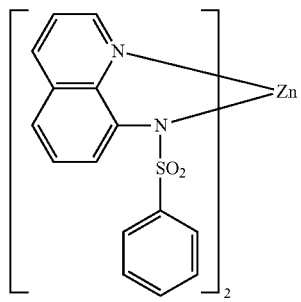 | U.S. Pat. No. 6,528,187 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A method of making a compound having the formula $Os(L^1)(L^2)(L^3)$, wherein each of $L^1$, $L^2$, and $L^3$ is independently a bidentate ligand, said method comprising:

(a) reacting a precursor of ligand $L^1$ with an osmium precursor to form a first intermediate product that has the ligand $L^1$ coordinated to the osmium, wherein the osmium precursor has the formula $OsH_x(PR_3)_y$, wherein x is an integer from 2 to 6 and y is an integer from 2 to 5, and R is selected from the group consisting of aryl, alkyl and cycloalkyl;

(b) reacting the first intermediate product with a reducing agent to form a Os(II) second intermediate product;

(c) reacting the second intermediate product with a coordinating solvent to form a third intermediate product; and (d) reacting a mixture of precursors of ligands $L^2$ and $L^3$ with said third intermediate product;

wherein $L^1$ is

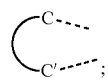

wherein one of $L^2$ and $L^3$ is

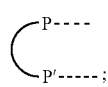

wherein the other of $L^2$ and $L^3$ is

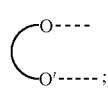

and
wherein C is a monoanionic carbon coordinating atom, C' is a neutral carbene coordinating atom, P and P' are each a neutral phosphorus coordinating atom, O is a monoanionic oxygen coordinating atom, and O' is a neutral oxygen coordinating atom.

2. A compound having the formula $Os(L^1)(L^2)(L^3)$:
wherein $L^1$, $L^2$ and $L^3$ are independently a bidentate ligand;
wherein $L^1$ is

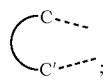

wherein one of $L^2$ and $L^3$ is

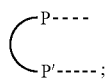

wherein the other of $L^2$ and $L^3$ is

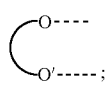

and
wherein C is a monoanionic carbon coordinating atom, C' is a neutral carbene coordinating atom, P and P' are each a neutral phosphorus coordinating atom, O is a monoanionic oxygen coordinating atom, and O' is a neutral oxygen coordinating atom.

3. A first device comprising a first organic light emitting device, the first organic light emitting device comprising:
an anode;
a cathode; and
an organic layer, disposed between the anode and the cathode, comprising a compound having the formula $Os(L^1)(L^2)(L^3)$,
wherein $L^1$, $L^2$ and $L^3$ are independently a bidentate ligand, wherein $L^1$ is

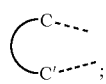

wherein one of $L^2$ and $L^3$ is

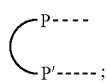

wherein the other of $L^2$ and $L^3$ is

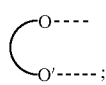

and
wherein C is a monoanionic carbon coordinating atom, C' is a neutral carbene coordinating atom, P and P' are each a neutral phosphorus coordinating atom, O is a monoanionic oxygen coordinating atom, and O' is a neutral oxygen coordinating atom.

4. The first device of claim 3, wherein the first device is a consumer product.

5. The first device of claim 3, wherein the first device is an organic light emitting device.

6. The first device of claim 3, wherein the first device comprises a light panel.

7. The first device of claim 3, wherein the organic layer is an emissive layer and the compound is an emissive dopant.

8. The first device of claim 3, wherein the organic layer is an emissive layer and the compound is a non-emissive dopant.

9. The first device of claim 3, wherein the organic layer further comprises a host material.

10. The compound of claim 2, wherein $L^1$ is

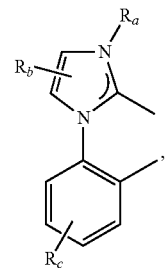

wherein $L^3$ is

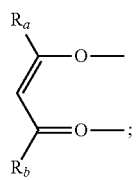

wherein $R_a$, $R_b$ and $R_c$ are each independently no substitutions, up to the maximum possible substitutions;

wherein $R_a$, $R_b$, and $R_c$, are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of $R_a$, $R_b$, and $R_c$ are optionally joined to form a fused ring and may be further substituted; and wherein the dash lines show the connection points to osmium.

11. The compound of claim 2, wherein $L^1$ is selected from the group consisting of:
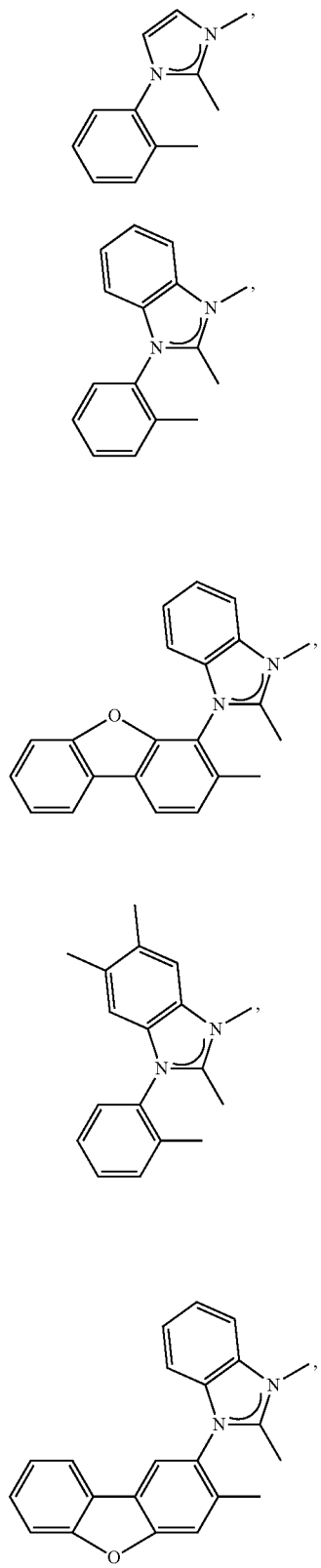
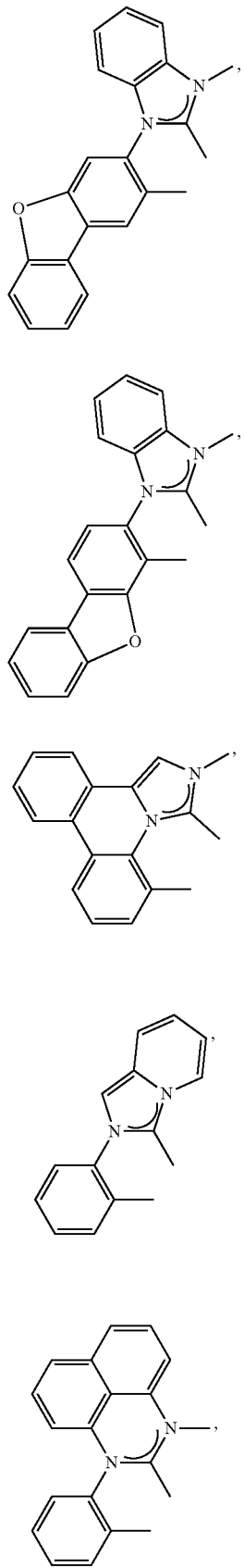

L¹¹¹
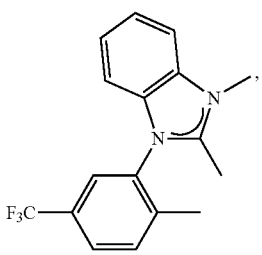

L¹¹²
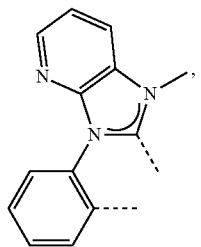

L¹¹³
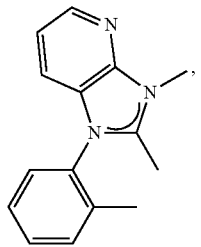

L¹¹⁴
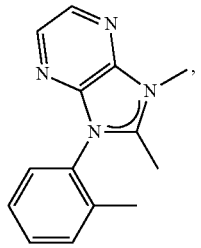

L¹¹⁵
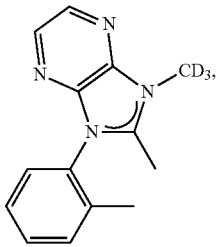

L¹¹⁶
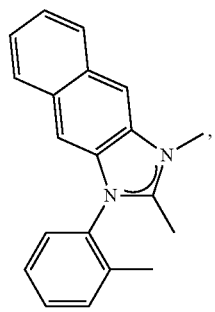

L¹¹⁷
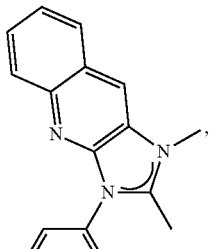

L¹¹⁸
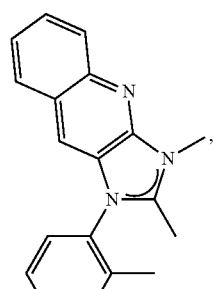

L¹¹⁹
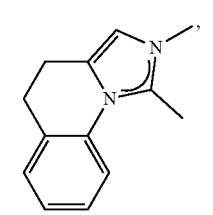

wherein the dash lines show the connection points to osmium.

12. The compound of claim 11, wherein the compound is selected from the group consisting of:

| Compound number | $L_1$ | $L_2$ | $L_3$ |
|---|---|---|---|
| 26. | $L^{101}$ | $L^{159}$ | $L^{144}$ |
| 53. | $L^{101}$ | $L^{159}$ | $L^{145}$ |
| 80. | $L^{101}$ | $L^{159}$ | $L^{147}$ |
| 376. | $L^{102}$ | $L^{159}$ | $L^{144}$ |
| 402. | $L^{102}$ | $L^{159}$ | $L^{145}$ |
| 428. | $L^{102}$ | $L^{159}$ | $L^{147}$ |
| 713. | $L^{103}$ | $L^{159}$ | $L^{144}$ |
| 738. | $L^{103}$ | $L^{159}$ | $L^{145}$ |
| 763. | $L^{103}$ | $L^{159}$ | $L^{147}$ |
| 1037. | $L^{104}$ | $L^{159}$ | $L^{144}$ |
| 1061. | $L^{104}$ | $L^{159}$ | $L^{145}$ |
| 1085. | $L^{104}$ | $L^{159}$ | $L^{147}$ |
| 1348. | $L^{105}$ | $L^{159}$ | $L^{144}$ |
| 1371. | $L^{105}$ | $L^{159}$ | $L^{145}$ |
| 1394. | $L^{105}$ | $L^{159}$ | $L^{147}$ |
| 1646. | $L^{106}$ | $L^{159}$ | $L^{144}$ |
| 1668. | $L^{106}$ | $L^{159}$ | $L^{145}$ |
| 1690. | $L^{106}$ | $L^{159}$ | $L^{147}$ |
| 1931. | $L^{107}$ | $L^{159}$ | $L^{144}$ |
| 1952. | $L^{107}$ | $L^{159}$ | $L^{145}$ |
| 1973. | $L^{107}$ | $L^{159}$ | $L^{147}$ |
| 2203. | $L^{108}$ | $L^{159}$ | $L^{144}$ |
| 2223. | $L^{108}$ | $L^{159}$ | $L^{145}$ |
| 2243. | $L^{108}$ | $L^{159}$ | $L^{147}$ |
| 2462. | $L^{109}$ | $L^{159}$ | $L^{144}$ |
| 2481. | $L^{109}$ | $L^{159}$ | $L^{145}$ |
| 2500. | $L^{109}$ | $L^{159}$ | $L^{147}$ |

-continued

| Compound number | L₁ | L₂ | L₃ |
|---|---|---|---|
| 2708. | L¹¹⁰ | L¹⁵⁹ | L¹⁴⁴ |
| 2726. | L¹¹⁰ | L¹⁵⁹ | L¹⁴⁵ |
| 2744. | L¹¹⁰ | L¹⁵⁹ | L¹⁴⁷ |
| 2941. | L¹¹¹ | L¹⁵⁹ | L¹⁴⁴ |
| 2958. | L¹¹¹ | L¹⁵⁹ | L¹⁴⁵ |
| 2705. | L¹¹¹ | L¹⁵⁹ | L¹⁴⁷ |
| 2891. | L¹¹² | L¹⁵⁹ | L¹⁴⁴ |
| 2907. | L¹¹² | L¹⁵⁹ | L¹⁴⁵ |
| 2923. | L¹¹² | L¹⁵⁹ | L¹⁴⁷ |
| 3098. | L¹¹³ | L¹⁵⁹ | L¹⁴⁴ |
| 3113. | L¹¹³ | L¹⁵⁹ | L¹⁴⁵ |
| 3128. | L¹¹³ | L¹⁵⁹ | L¹⁴⁷ |
| 3292. | L¹¹⁴ | L¹⁵⁹ | L¹⁴⁴ |
| 3306. | L¹¹⁴ | L¹⁵⁹ | L¹⁴⁵ |
| 3320. | L¹¹⁴ | L¹⁵⁹ | L¹⁴⁷ |
| 3473. | L¹¹⁵ | L¹⁵⁹ | L¹⁴⁴ |
| 3486. | L¹¹⁵ | L¹⁵⁹ | L¹⁴⁵ |
| 3499. | L¹¹⁵ | L¹⁵⁹ | L¹⁴⁷ |
| 3653. | L¹¹⁶ | L¹⁵⁹ | L¹⁴⁵ |
| 3665. | L¹¹⁶ | L¹⁵⁹ | L¹⁴⁷ |
| 3796. | L¹¹⁷ | L¹⁵⁹ | L¹⁴⁴ |
| 3807. | L¹¹⁷ | L¹⁵⁹ | L¹⁴⁵ |
| 3818. | L¹¹⁷ | L¹⁵⁹ | L¹⁴⁷ |
| 3938. | L¹¹⁸ | L¹⁵⁹ | L¹⁴⁴ |
| 3948. | L¹¹⁸ | L¹⁵⁹ | L¹⁴⁵ |
| 3958. | L¹¹⁸ | L¹⁵⁹ | L¹⁴⁷ |
| 4067. | L¹¹⁹ | L¹⁵⁹ | L¹⁴⁴ |
| 4076. | L¹¹⁹ | L¹⁵⁹ | L¹⁴⁵ |
| 4085. | L¹¹⁹ | L¹⁵⁹ | L¹⁴⁷ | wherein $L^{144}$ to $L^{145}$, $L^{147}$, and $L^{159}$ have the following meanings:

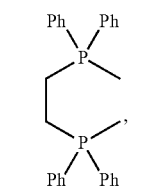

L¹⁴⁴

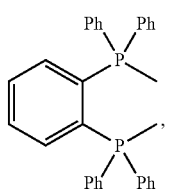

L¹⁴⁵

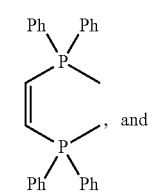

L¹⁴⁷

, and

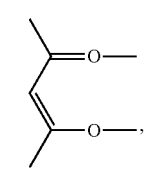

L¹⁵⁹ wherein the dash lines show the connection points to osmium.

13. The compound of claim 2, wherein $L^2$ s elected from the group consisting of:

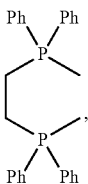

L¹⁴⁴

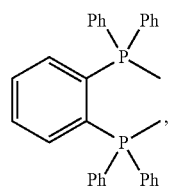

L¹⁴⁵

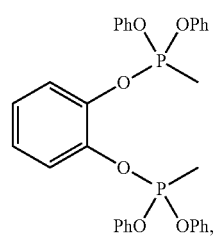

L¹⁴⁶

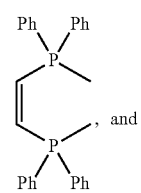

L¹⁴⁷

, and

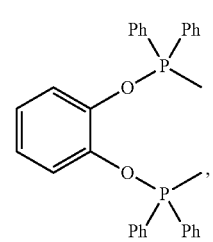

L¹⁴⁸ wherein the dash lines show the connection points to osmium.

14. The first device of claim 3, wherein $L^1$ is

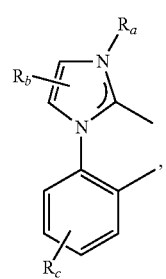

and wherein L³ is

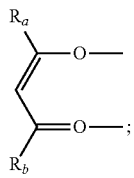

wherein $R_a$, $R_b$ and $R_c$ are each independently no substitutions, up to the maximum possible substitutions;

wherein $R_a$, $R_b$, and $R_c$, are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein two adjacent substituents of $R_a$, $R_b$, and $R_c$ are optionally joined to form a fused ring and may be further substituted; and wherein the dash lines show the connection points to osmium.

15. The first device of claim 3, wherein L¹ is selected from the group consisting of:

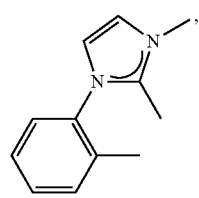

L¹⁰¹

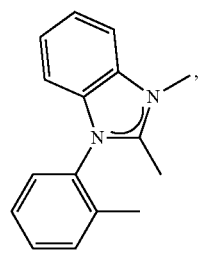

L¹⁰²

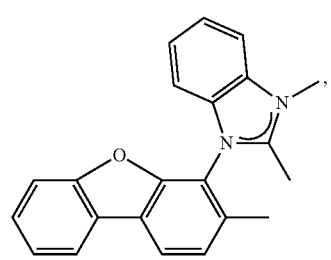

L¹⁰³

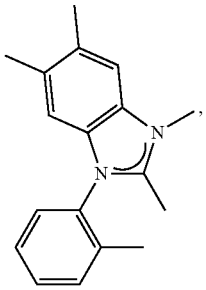

L¹⁰⁴

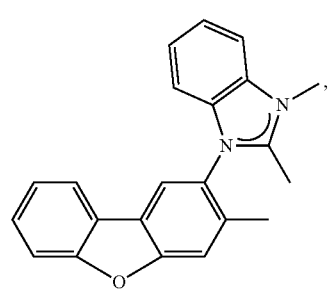

L¹⁰⁵

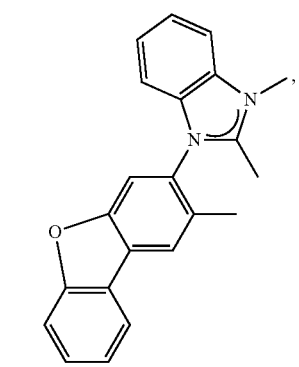

L¹⁰⁶

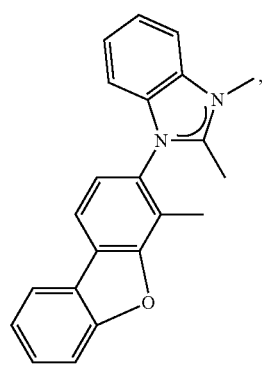

L¹⁰⁷

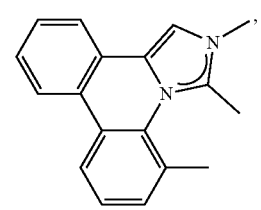

L¹⁰⁸

187
-continued
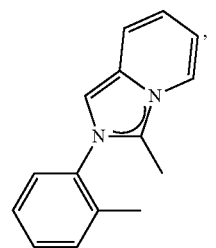
L[109]
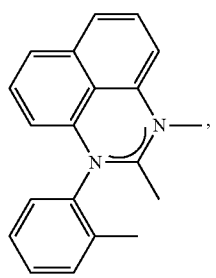
L[110]
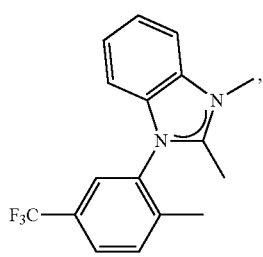
L[111]
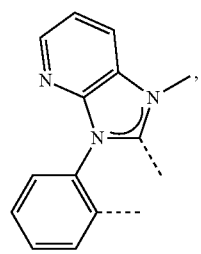
L[112]
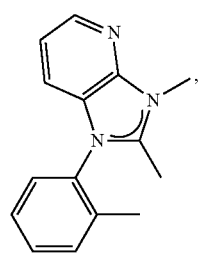
L[113]
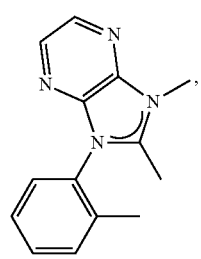
L[114]
188
-continued
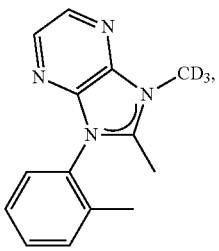
L[115]
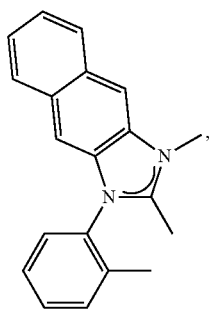
L[116]
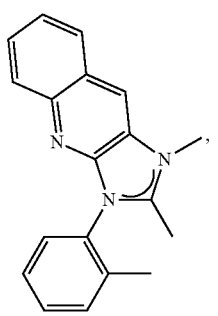
L[117]
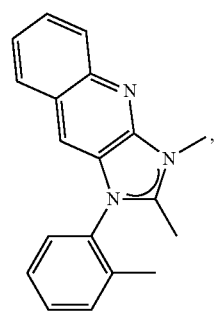
L[118]
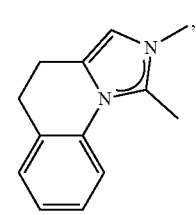
L[119]
wherein the dash lines show the connection points to osmium.

16. The first device of claim 15, wherein the compound is selected from the group consisting of:

| Compound number | $L_1$ | $L_2$ | $L_3$ |
|---|---|---|---|
| 26. | $L^{101}$ | $L^{159}$ | $L^{144}$ |
| 53. | $L^{101}$ | $L^{159}$ | $L^{145}$ |
| 80. | $L^{101}$ | $L^{159}$ | $L^{147}$ |
| 376. | $L^{102}$ | $L^{159}$ | $L^{144}$ |
| 402. | $L^{102}$ | $L^{159}$ | $L^{145}$ |
| 428. | $L^{102}$ | $L^{159}$ | $L^{147}$ |
| 713. | $L^{103}$ | $L^{159}$ | $L^{144}$ |
| 738. | $L^{103}$ | $L^{159}$ | $L^{145}$ |
| 763. | $L^{103}$ | $L^{159}$ | $L^{147}$ |
| 1037. | $L^{104}$ | $L^{159}$ | $L^{144}$ |
| 1061. | $L^{104}$ | $L^{159}$ | $L^{145}$ |
| 1085. | $L^{104}$ | $L^{159}$ | $L^{147}$ |
| 1348. | $L^{105}$ | $L^{159}$ | $L^{144}$ |
| 1371. | $L^{105}$ | $L^{159}$ | $L^{145}$ |
| 1394. | $L^{105}$ | $L^{159}$ | $L^{147}$ |
| 1646. | $L^{106}$ | $L^{159}$ | $L^{144}$ |
| 1668. | $L^{106}$ | $L^{159}$ | $L^{145}$ |
| 1690. | $L^{106}$ | $L^{159}$ | $L^{147}$ |
| 1931. | $L^{107}$ | $L^{159}$ | $L^{144}$ |
| 1952. | $L^{107}$ | $L^{159}$ | $L^{145}$ |
| 1973. | $L^{107}$ | $L^{159}$ | $L^{147}$ |
| 2203. | $L^{108}$ | $L^{159}$ | $L^{144}$ |
| 2223. | $L^{108}$ | $L^{159}$ | $L^{145}$ |
| 2243. | $L^{108}$ | $L^{159}$ | $L^{147}$ |
| 2462. | $L^{109}$ | $L^{159}$ | $L^{144}$ |
| 2481. | $L^{109}$ | $L^{159}$ | $L^{145}$ |
| 2500. | $L^{109}$ | $L^{159}$ | $L^{147}$ |
| 2708. | $L^{110}$ | $L^{159}$ | $L^{144}$ |
| 2726. | $L^{110}$ | $L^{159}$ | $L^{145}$ |
| 2744. | $L^{110}$ | $L^{159}$ | $L^{147}$ |
| 2941. | $L^{111}$ | $L^{159}$ | $L^{144}$ |
| 2958. | $L^{111}$ | $L^{159}$ | $L^{145}$ |
| 2705. | $L^{111}$ | $L^{159}$ | $L^{147}$ |
| 2891. | $L^{112}$ | $L^{159}$ | $L^{144}$ |
| 2907. | $L^{112}$ | $L^{159}$ | $L^{145}$ |
| 2923. | $L^{112}$ | $L^{159}$ | $L^{147}$ |
| 3098. | $L^{113}$ | $L^{159}$ | $L^{144}$ |
| 3113. | $L^{113}$ | $L^{159}$ | $L^{145}$ |
| 3128. | $L^{113}$ | $L^{159}$ | $L^{147}$ |
| 3292. | $L^{114}$ | $L^{159}$ | $L^{144}$ |
| 3306. | $L^{114}$ | $L^{159}$ | $L^{145}$ |
| 3320. | $L^{114}$ | $L^{159}$ | $L^{147}$ |
| 3473. | $L^{115}$ | $L^{159}$ | $L^{144}$ |
| 3486. | $L^{115}$ | $L^{159}$ | $L^{145}$ |
| 3499. | $L^{115}$ | $L^{159}$ | $L^{147}$ |
| 3653. | $L^{116}$ | $L^{159}$ | $L^{145}$ |
| 3665. | $L^{116}$ | $L^{159}$ | $L^{147}$ |
| 3796. | $L^{117}$ | $L^{159}$ | $L^{144}$ |
| 3807. | $L^{117}$ | $L^{159}$ | $L^{145}$ |
| 3818. | $L^{117}$ | $L^{159}$ | $L^{147}$ |
| 3938. | $L^{118}$ | $L^{159}$ | $L^{144}$ |
| 3948. | $L^{118}$ | $L^{159}$ | $L^{145}$ |
| 3958. | $L^{118}$ | $L^{159}$ | $L^{147}$ |
| 4067. | $L^{119}$ | $L^{159}$ | $L^{144}$ |
| 4076. | $L^{119}$ | $L^{159}$ | $L^{145}$ |
| 4085. | $L^{119}$ | $L^{159}$ | $L^{147}$ | wherein $L^{144}$ to $L^{145}$, $L^{147}$, and $L^{159}$ have the following meanings:

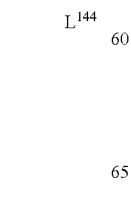
$L^{144}$

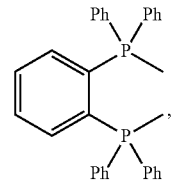
$L^{145}$

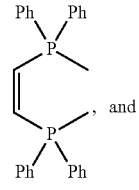
$L^{147}$

, and

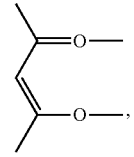
$L^{159}$ wherein the dash lines show the connection points to osmium.

17. The first device of claim 3, wherein $L^2$ is selected from the group consisting of:

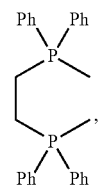
$L^{144}$

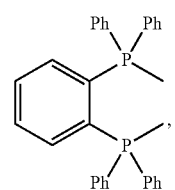
$L^{145}$

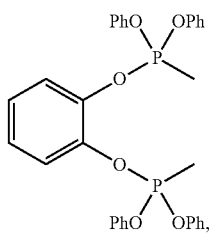
$L^{146}$

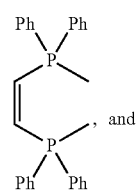
$L^{147}$

, and

-continued
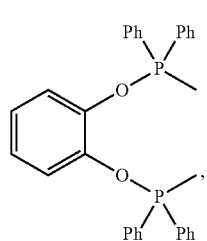
L^{148}
wherein the dash lines show the connection points to osmium.
* * * * *